(12) United States Patent
Ramseier et al.

US009109229B2

(10) Patent No.: US 9,109,229 B2
(45) Date of Patent: *Aug. 18, 2015

(54) PROCESS FOR IMPROVED PROTEIN EXPRESSION BY STRAIN ENGINEERING

(71) Applicant: Pfenex Inc., San Diego, CA (US)

(72) Inventors: Thomas M. Ramseier, Newton, MA (US); Hongfan Jin, San Diego, CA (US); Charles H. Squires, Poway, CA (US)

(73) Assignee: Pfenex Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/071,273

(22) Filed: Nov. 4, 2013

(65) Prior Publication Data

US 2014/0162279 A1   Jun. 12, 2014

Related U.S. Application Data

(63) Continuation of application No. 11/189,375, filed on Jul. 26, 2005, now Pat. No. 8,603,824.

(60) Provisional application No. 60/591,489, filed on Jul. 26, 2004.

(51) Int. Cl.
| | |
|---|---|
| *C12N 15/67* | (2006.01) |
| *C12N 15/63* | (2006.01) |
| *C12N 15/65* | (2006.01) |
| *C12N 15/52* | (2006.01) |
| *C12N 15/70* | (2006.01) |
| *C12N 15/74* | (2006.01) |
| *C12N 15/78* | (2006.01) |
| *C12P 21/02* | (2006.01) |

(52) U.S. Cl.
CPC ............. *C12N 15/63* (2013.01); *C12N 15/70* (2013.01); *C12N 15/74* (2013.01); *C12N 15/78* (2013.01); *C12P 21/02* (2013.01)

(58) Field of Classification Search
CPC ........ C12N 15/63; C12N 15/00; C12N 15/64; C12N 15/01; C12P 21/00
See application file for complete search history.

(56) References Cited

U.S. PATENT DOCUMENTS

| | | | |
|---|---|---|---|
| 3,844,893 A | 10/1974 | Hitzman | |
| 3,878,093 A | 4/1975 | Kanani et al. | |
| 4,169,010 A | 9/1979 | Marwil | |
| 4,432,895 A | 2/1984 | Tarnowski | |
| 4,511,503 A | 4/1985 | Olson et al. | |
| 4,551,433 A | 11/1985 | DeBoer | |
| 4,595,658 A | 6/1986 | Zinder et al. | |
| 4,637,980 A | 1/1987 | Auerbach et al. | |
| 4,680,260 A | 7/1987 | Debabov et al. | |
| 4,680,264 A | 7/1987 | Puhler et al. | |
| 4,695,455 A | 9/1987 | Barnes et al. | |
| 4,695,462 A | 9/1987 | Barnes et al. | |
| 4,755,465 A | 7/1988 | Gray et al. | |
| 4,861,595 A | 8/1989 | Barnes et al. | |
| 4,888,274 A | 12/1989 | Radding et al. | |
| 4,963,495 A | 10/1990 | Chang et al. | |
| 5,023,171 A | 6/1991 | Ho et al. | |
| 5,043,430 A | 8/1991 | Yoshikawa | |
| 5,055,294 A | 10/1991 | Gilroy | |
| 5,082,783 A | 1/1992 | Ernst et al. | |
| 5,084,559 A | 1/1992 | Profy | |
| 5,085,862 A | 2/1992 | Klein et al. | |
| 5,128,130 A | 7/1992 | Gilroy et al. | |
| 5,151,350 A | 9/1992 | Colbert et al. | |
| 5,165,927 A | 11/1992 | Kaslow | |
| 5,169,760 A | 12/1992 | Wilcox | |
| 5,169,772 A | 12/1992 | Zimmerman et al. | |
| 5,173,616 A | 12/1992 | Hinooka | |
| 5,232,840 A | 8/1993 | Olins | |
| 5,264,365 A | 11/1993 | Georgiou et al. | |
| 5,281,532 A | 1/1994 | Rammler et al. | |
| 5,292,507 A | 3/1994 | Charley | |
| 5,292,658 A | 3/1994 | Cormier et al. | |
| 5,348,867 A | 9/1994 | Georgiou et al. | |
| 5,399,684 A | 3/1995 | Davie et al. | |
| 5,418,155 A | 5/1995 | Cormier et al. | |
| 5,441,934 A | 8/1995 | Krapcho et al. | |
| 5,508,192 A | 4/1996 | Georgiou et al. | |

(Continued)

FOREIGN PATENT DOCUMENTS

| | | |
|---|---|---|
| EP | 0121352 | 10/1984 |
| EP | 0155189 | 9/1985 |

(Continued)

OTHER PUBLICATIONS

Abdullah et al., "System-48" high-throughput cloning and protein expression analysis," Methods Mol Biol 498:117-127 (2009).
Ada, Gordon, et al., Overview of Host Defense Mechanisms with Special Reference to Viral Infections, Gamma Interferon in Antiviral Defense, 1997, Chapter 1, pp. 1-18, R.G. Landes Group.
Ahn Jung Hoon, et al., Homologous Expression of the Lipase and ABC Transporter Gene Cluster, tliDEFA, Enhances Lipase Secretion in *Pseudomonas* spp., Appl. Environ. Microbiol., Dec. 2001, pp. 5506-5511, vol. 67, No. 12, American Society for Microbiology.
Akao, et al., "Unique synthetic peptides stimulating streptolysin S production in streptococci," 1999, J. Biochem. 125(1):27-30.

(Continued)

*Primary Examiner* — Maria Marvich
(74) *Attorney, Agent, or Firm* — Wilson Sonsini Goodrich & Rosati

(57) ABSTRACT

This invention is a process for improving the production levels of recombinant proteins or peptides or improving the level of active recombinant proteins or peptides expressed in host cells. The invention is a process of comparing two genetic profiles of a cell that expresses a recombinant protein and modifying the cell to change the expression of a gene product that is upregulated in response to the recombinant protein expression. The process can improve protein production or can improve protein quality, for example, by increasing solubility of a recombinant protein.

30 Claims, 15 Drawing Sheets

(56) References Cited

U.S. PATENT DOCUMENTS

| | | |
|---|---|---|
| 5,527,883 A | 6/1996 | Thompson et al. |
| 5,552,302 A | 9/1996 | Lewis et al. |
| 5,558,862 A | 9/1996 | Corbin et al. |
| 5,559,015 A | 9/1996 | Capage et al. |
| 5,571,694 A | 11/1996 | Makoff et al. |
| 5,591,828 A | 1/1997 | Bosslet et al. |
| 5,595,898 A | 1/1997 | Robinson et al. |
| 5,610,044 A | 3/1997 | Lam et al. |
| 5,621,074 A | 4/1997 | Bjorn et al. |
| 5,622,846 A | 4/1997 | Kiener et al. |
| 5,641,671 A | 6/1997 | Bos et al. |
| 5,641,870 A | 6/1997 | Rinderknecht et al. |
| 5,643,774 A | 7/1997 | Ligon et al. |
| 5,662,898 A | 9/1997 | Ligon et al. |
| 5,677,127 A | 10/1997 | Hogan et al. |
| 5,683,888 A | 11/1997 | Campbell |
| 5,686,282 A | 11/1997 | Lam et al. |
| 5,686,283 A | 11/1997 | Gaffney et al. |
| 5,698,425 A | 12/1997 | Ligon et al. |
| 5,698,435 A | 12/1997 | Robinson et al. |
| 5,710,031 A | 1/1998 | Gaffney et al. |
| 5,728,574 A | 3/1998 | Legg |
| 5,731,280 A | 3/1998 | Nielsen et al. |
| 5,736,379 A | 4/1998 | Davie et al. |
| 5,741,663 A | 4/1998 | Russell |
| 5,741,668 A | 4/1998 | Ward et al. |
| 5,756,087 A | 5/1998 | Ligon et al. |
| 5,757,051 A | 5/1998 | Wu et al. |
| 5,766,926 A | 6/1998 | Blanchette et al. |
| 5,773,600 A | 6/1998 | Burnette, III |
| 5,776,730 A | 7/1998 | Stuart |
| 5,777,079 A | 7/1998 | Tsien et al. |
| 5,795,759 A | 8/1998 | Rosazza et al. |
| 5,804,387 A | 9/1998 | Cormack et al. |
| 5,824,472 A | 10/1998 | Betlach et al. |
| 5,834,250 A | 11/1998 | Wells et al. |
| 5,840,554 A | 11/1998 | Thompson et al. |
| 5,869,038 A | 2/1999 | Leifert et al. |
| 5,874,304 A | 2/1999 | Zolotukhin et al. |
| 5,876,995 A | 3/1999 | Bryan |
| 5,891,688 A | 4/1999 | Gaffney et al. |
| 5,914,233 A | 6/1999 | Mundy et al. |
| 5,914,254 A | 6/1999 | Mascarenhas et al. |
| 5,919,445 A | 7/1999 | Chao |
| 5,922,576 A | 7/1999 | He et al. |
| 5,925,558 A | 7/1999 | Tsien et al. |
| 5,932,435 A | 8/1999 | Atkins et al. |
| 5,942,387 A | 8/1999 | Hollinshead |
| 5,948,681 A | 9/1999 | Scanlin et al. |
| 5,948,889 A | 9/1999 | de Boer et al. |
| 5,952,208 A | 9/1999 | Darzins et al. |
| 5,952,236 A | 9/1999 | Thompson et al. |
| 5,955,348 A | 9/1999 | Ligon et al. |
| 5,958,713 A | 9/1999 | Thastrup et al. |
| 5,968,738 A | 10/1999 | Anderson et al. |
| 5,968,773 A | 10/1999 | Heddle et al. |
| 5,968,779 A | 10/1999 | Campfield et al. |
| 5,985,577 A | 11/1999 | Bulinski |
| 5,989,808 A | 11/1999 | Young et al. |
| 5,993,778 A | 11/1999 | Firestein et al. |
| 5,994,071 A | 11/1999 | Ross et al. |
| 5,994,077 A | 11/1999 | Valdivia et al. |
| 6,001,557 A | 12/1999 | Wilson et al. |
| 6,013,447 A | 1/2000 | Nilsen et al. |
| 6,015,557 A | 1/2000 | Tobinick et al. |
| 6,020,192 A | 2/2000 | Muzyczka et al. |
| 6,025,192 A | 2/2000 | Beach et al. |
| 6,027,881 A | 2/2000 | Pavlakis et al. |
| 6,037,133 A | 3/2000 | Li |
| 6,040,138 A | 3/2000 | Lockhart et al. |
| 6,051,383 A | 4/2000 | Thomashow et al. |
| 6,054,321 A | 4/2000 | Tsien et al. |
| 6,060,247 A | 5/2000 | Miller et al. |
| 6,066,476 A | 5/2000 | Tsien et al. |
| 6,071,738 A | 6/2000 | Johnson et al. |
| 6,077,707 A | 6/2000 | Tsien et al. |
| 6,080,576 A | 6/2000 | Zambrowicz et al. |
| 6,083,690 A | 7/2000 | Harris et al. |
| 6,090,919 A | 7/2000 | Cormack et al. |
| 6,093,808 A | 7/2000 | Li |
| 6,096,717 A | 8/2000 | Jarvik |
| 6,096,865 A | 8/2000 | Michaels |
| 6,110,711 A | 8/2000 | Serafini et al. |
| 6,117,670 A | 9/2000 | Ligon et al. |
| 6,121,247 A | 9/2000 | Huang et al. |
| 6,124,128 A | 9/2000 | Tsien et al. |
| 6,130,313 A | 10/2000 | Li et al. |
| 6,133,429 A | 10/2000 | Davis et al. |
| 6,136,538 A | 10/2000 | Olivo et al. |
| 6,136,539 A | 10/2000 | Basbaum et al. |
| 6,136,566 A | 10/2000 | Sands et al. |
| 6,140,132 A | 10/2000 | Tsien et al. |
| 6,146,826 A | 11/2000 | Chalfie et al. |
| 6,150,176 A | 11/2000 | Tsien et al. |
| 6,153,409 A | 11/2000 | Bentley et al. |
| 6,156,313 A | 12/2000 | Burton et al. |
| 6,156,552 A | 12/2000 | Okkels et al. |
| 6,172,188 B1 | 1/2001 | Thastrup et al. |
| 6,180,343 B1 | 1/2001 | Anderson et al. |
| 6,184,440 B1 | 2/2001 | Shoseyov et al. |
| 6,194,194 B1 | 2/2001 | Molloy |
| 6,197,928 B1 | 3/2001 | Tsien et al. |
| 6,203,986 B1 | 3/2001 | Singer et al. |
| 6,204,023 B1 | 3/2001 | Robinson et al. |
| 6,210,910 B1 | 4/2001 | Walt et al. |
| 6,210,922 B1 | 4/2001 | Cote et al. |
| 6,214,563 B1 | 4/2001 | Negulescu et al. |
| 6,214,567 B1 | 4/2001 | Allen-Hoffmann et al. |
| 6,218,185 B1 | 4/2001 | Shirk et al. |
| 6,221,612 B1 | 4/2001 | Knapp et al. |
| 6,225,082 B1 | 5/2001 | Carson et al. |
| 6,228,639 B1 | 5/2001 | Gaitanaris |
| 6,232,107 B1 | 5/2001 | Bryan et al. |
| 6,246,543 B1 | 6/2001 | Baumgart et al. |
| 6,248,550 B1 | 6/2001 | Tsien et al. |
| 6,248,558 B1 | 6/2001 | Lin et al. |
| 6,251,384 B1 | 6/2001 | Tan et al. |
| 6,251,582 B1 | 6/2001 | Littman et al. |
| 6,251,602 B1 | 6/2001 | Young et al. |
| 6,251,677 B1 | 6/2001 | Wilson et al. |
| 6,255,071 B1 | 7/2001 | Beach et al. |
| 6,255,558 B1 | 7/2001 | Haseloff et al. |
| 6,258,560 B1 | 7/2001 | Leung et al. |
| 6,261,760 B1 | 7/2001 | Fielding et al. |
| 6,261,776 B1 | 7/2001 | Pirrung et al. |
| 6,265,548 B1 | 7/2001 | Pavlakis et al. |
| 6,268,201 B1 | 7/2001 | Alland et al. |
| 6,268,549 B1 | 7/2001 | Sailland et al. |
| 6,270,958 B1 | 8/2001 | Olivo et al. |
| 6,274,354 B1 | 8/2001 | Wilson et al. |
| 6,277,625 B1 | 8/2001 | Huang et al. |
| 6,280,934 B1 | 8/2001 | Madden et al. |
| 6,284,496 B1 | 9/2001 | Litman et al. |
| 6,284,519 B1 | 9/2001 | Young et al. |
| 6,291,175 B1 | 9/2001 | Sevigny et al. |
| 6,291,177 B1 | 9/2001 | Madden et al. |
| 6,303,373 B1 | 10/2001 | Bogan et al. |
| 6,316,181 B1 | 11/2001 | Fillmore et al. |
| 6,319,669 B1 | 11/2001 | Tsien et al. |
| 6,329,172 B1 | 12/2001 | Rhee et al. |
| 6,344,316 B1 | 2/2002 | Lockhart et al. |
| 6,372,225 B1 | 4/2002 | Matsuda |
| 6,403,957 B1 | 6/2002 | Fodor et al. |
| 6,410,229 B1 | 6/2002 | Lockhart et al. |
| 6,420,108 B2 | 7/2002 | Mack et al. |
| 6,447,770 B1 | 9/2002 | Raaijmakers et al. |
| 6,451,536 B1 | 9/2002 | Fodor et al. |
| 6,495,357 B1 | 12/2002 | Fuglsang et al. |
| 6,506,559 B1 | 1/2003 | Fire et al. |
| 6,509,181 B1 | 1/2003 | Danielsen et al. |
| 6,524,827 B2 | 2/2003 | Moller et al. |
| 6,528,298 B1 | 3/2003 | Svendsen et al. |
| 6,532,462 B2 | 3/2003 | Balaban |
| 6,551,784 B2 | 4/2003 | Fodor et al. |

(56) References Cited

U.S. PATENT DOCUMENTS

| | | |
|---|---|---|
| 6,558,939 B1 | 5/2003 | Norregaard-Madsen et al. |
| 6,567,540 B2 | 5/2003 | Balaban et al. |
| 6,573,099 B2 | 6/2003 | Graham |
| 6,576,424 B2 | 6/2003 | Fodor et al. |
| 6,600,031 B1 | 7/2003 | Fodor et al. |
| 6,607,885 B1 | 8/2003 | Larossa et al. |
| 6,608,018 B1 | 8/2003 | Shinohara |
| 6,617,143 B1 | 9/2003 | Fukuyama |
| 6,642,030 B1 | 11/2003 | English et al. |
| 6,673,580 B2 | 1/2004 | Koren et al. |
| 6,687,692 B1 | 2/2004 | Balaban et al. |
| 6,696,561 B1 | 2/2004 | Pompujus et al. |
| 6,800,738 B1 | 10/2004 | Carter et al. |
| 6,979,556 B2 | 12/2005 | Simmons et al. |
| 7,112,324 B1 | 9/2006 | Dorken et al. |
| 7,175,840 B2 | 2/2007 | Kim et al. |
| 7,189,389 B2 | 3/2007 | Yanai et al. |
| 7,217,796 B2 | 5/2007 | Wang et al. |
| 7,235,641 B2 | 6/2007 | Kufer et al. |
| 7,270,993 B2 | 9/2007 | Smit et al. |
| 7,338,794 B2 | 3/2008 | Gaertner et al. |
| 7,381,804 B2 | 6/2008 | Osslund |
| 7,399,463 B2 | 7/2008 | Shirley et al. |
| 7,411,050 B2 | 8/2008 | Anderson |
| 7,416,849 B2 | 8/2008 | Allen et al. |
| 7,427,596 B2 | 9/2008 | Keyt et al. |
| 7,439,063 B2 | 10/2008 | Digicaylioglu et al. |
| 7,439,323 B2 | 10/2008 | Bielicki |
| 7,445,772 B2 | 11/2008 | West et al. |
| 7,452,971 B2 | 11/2008 | Vitetta et al. |
| 7,459,540 B1 | 12/2008 | Thomason et al. |
| 7,491,697 B2 | 2/2009 | Beals et al. |
| 7,504,237 B2 | 3/2009 | Jensen et al. |
| 7,524,931 B2 | 4/2009 | Van Den Hazel et al. |
| 7,537,771 B2 | 5/2009 | Williamson et al. |
| 7,544,519 B2 | 6/2009 | Hsu et al. |
| 7,547,821 B2 | 6/2009 | Moloney et al. |
| 7,553,940 B2 | 6/2009 | Fares et al. |
| 7,553,941 B2 | 6/2009 | Fares et al. |
| 7,556,817 B2 | 7/2009 | Steward et al. |
| 7,560,112 B2 | 7/2009 | Chen et al. |
| 7,563,443 B2 | 7/2009 | Grant et al. |
| 7,566,566 B2 | 7/2009 | Alitalo et al. |
| 7,566,769 B2 | 7/2009 | Browning et al. |
| 7,575,923 B2 | 8/2009 | Dorken et al. |
| 7,576,190 B2 | 8/2009 | Glaesner et al. |
| 7,582,607 B2 | 9/2009 | Frye et al. |
| 7,585,942 B2 | 9/2009 | Harrison et al. |
| 7,618,799 B2 | 11/2009 | Coleman et al. |
| 7,985,564 B2 | 7/2011 | Retallack et al. |
| 8,288,127 B2 | 10/2012 | Schneider et al. |
| 8,603,824 B2 * | 12/2013 | Ramseier et al. ............ 435/69.1 |
| 8,927,205 B2 | 1/2015 | Pfizenmaier et al. |
| 2003/0013150 A1 | 1/2003 | Manosroi et al. |
| 2003/0044906 A1 | 3/2003 | Habermann et al. |
| 2003/0064435 A1 | 4/2003 | Weiner et al. |
| 2003/0108923 A1 | 6/2003 | Tuschl et al. |
| 2003/0114409 A1 | 6/2003 | Mello et al. |
| 2003/0157069 A1 | 8/2003 | Lyman et al. |
| 2003/0180937 A1 | 9/2003 | Georgiou et al. |
| 2004/0028705 A1 | 2/2004 | Ballard et al. |
| 2004/0138127 A1 | 7/2004 | Davidson et al. |
| 2004/0143854 A1 | 7/2004 | Klebl et al. |
| 2004/0146484 A1 | 7/2004 | Gaertner et al. |
| 2004/0157289 A1 | 8/2004 | Salerno et al. |
| 2004/0180378 A1 | 9/2004 | Tozer et al. |
| 2005/0186666 A1 | 8/2005 | Schneider et al. |
| 2005/0214321 A1 | 9/2005 | Rasochova et al. |
| 2006/0008877 A1 | 1/2006 | Retallack et al. |
| 2006/0040352 A1 | 2/2006 | Retallack et al. |
| 2006/0062784 A1 | 3/2006 | Grant et al. |
| 2006/0115470 A1 | 6/2006 | Silence et al. |
| 2006/0149041 A1 | 7/2006 | Silence |
| 2006/0193852 A1 | 8/2006 | Dorken et al. |
| 2006/0211088 A1 | 9/2006 | Hermans et al. |
| 2006/0234346 A1 | 10/2006 | Retallack et al. |
| 2006/0246477 A1 | 11/2006 | Hermans et al. |
| 2007/0077249 A1 | 4/2007 | Silence et al. |
| 2007/0123479 A1 | 5/2007 | Kufer et al. |
| 2007/0178082 A1 | 8/2007 | Silence et al. |
| 2007/0224205 A1 | 9/2007 | Powell et al. |
| 2007/0237769 A1 | 10/2007 | Silence et al. |
| 2007/0269422 A1 | 11/2007 | Beirnaert et al. |
| 2008/0096223 A1 | 4/2008 | De Groot et al. |
| 2008/0107601 A1 | 5/2008 | Lauwereys et al. |
| 2008/0107673 A1 | 5/2008 | Ballard et al. |
| 2008/0193974 A1 | 8/2008 | Coleman et al. |
| 2008/0267949 A1 | 10/2008 | Revets et al. |
| 2008/0269070 A1 | 10/2008 | Ramseier et al. |
| 2009/0022721 A1 | 1/2009 | Silence et al. |
| 2009/0028880 A1 | 1/2009 | Beirnaert et al. |
| 2009/0062143 A1 | 3/2009 | Ramseier et al. |
| 2009/0074770 A1 | 3/2009 | Lasters et al. |
| 2009/0148438 A1 | 6/2009 | Nuttal et al. |
| 2009/0191186 A1 | 7/2009 | Bebbington et al. |
| 2009/0226432 A1 | 9/2009 | Lutterbuse et al. |
| 2009/0226444 A1 | 9/2009 | Rau et al. |
| 2009/0238829 A1 | 9/2009 | Silence et al. |
| 2009/0252681 A1 | 10/2009 | Laeremans et al. |
| 2010/0137162 A1 | 6/2010 | Retallack et al. |

FOREIGN PATENT DOCUMENTS

| | | |
|---|---|---|
| EP | 0177343 A1 | 4/1986 |
| EP | 0288451 A2 | 10/1988 |
| EP | 0207459 B1 | 3/1991 |
| EP | 1709170 | 10/2006 |
| JP | 2001-299360 A | 10/2001 |
| KR | 10-2003-0074654 | 9/2003 |
| WO | WO-87-05937 | 10/1987 |
| WO | WO-87-05938 | 10/1987 |
| WO | WO-89-10971 | 11/1989 |
| WO | WO-90-03438 | 4/1990 |
| WO | WO-92-15673 | 9/1992 |
| WO | WO-93-11161 | 6/1993 |
| WO | WO-95-03395 | 2/1995 |
| WO | WO-95-07463 | 3/1995 |
| WO | WO 95/15388 | 6/1995 |
| WO | WO-96-17943 | 6/1996 |
| WO | WO-97-22687 A1 | 6/1997 |
| WO | WO-98-14605 | 4/1998 |
| WO | WO-98-24919 | 6/1998 |
| WO | WO-98-26277 | 6/1998 |
| WO | WO-99-09834 | 3/1999 |
| WO | WO-99-15650 | 4/1999 |
| WO | WO-99-49019 | 9/1999 |
| WO | WO-99-53035 | 10/1999 |
| WO | WO-00-15761 | 3/2000 |
| WO | WO-00-29604 | 5/2000 |
| WO | WO-00-59537 | 10/2000 |
| WO | WO-01-21662 | 3/2001 |
| WO | WO-01-27258 | 4/2001 |
| WO | WO-01-32844 A1 | 5/2001 |
| WO | WO-02-14551 | 2/2002 |
| WO | WO-02-16940 | 2/2002 |
| WO | WO-02-40696 | 5/2002 |
| WO | WO-02-48376 A2 | 6/2002 |
| WO | WO-02-068660 | 9/2002 |
| WO | WO-03-006477 | 1/2003 |
| WO | WO-03-012052 | 2/2003 |
| WO | WO-03-023015 | 3/2003 |
| WO | WO-03-056022 | 7/2003 |
| WO | WO-03-064435 | 8/2003 |
| WO | WO-03-064621 | 8/2003 |
| WO | WO 03/068926 | 8/2003 |
| WO | WO-03-068926 A2 | 8/2003 |
| WO | WO-03-070966 | 8/2003 |
| WO | WO-03-079007 | 9/2003 |
| WO | WO-03-089455 A2 | 10/2003 |
| WO | WO-2004-005221 A2 | 1/2004 |
| WO | WO-2004-006657 | 1/2004 |
| WO | WO-2004-011628 | 2/2004 |
| WO | WO-2004-055206 | 7/2004 |
| WO | WO 2004/055206 | 7/2004 |

(56) References Cited

FOREIGN PATENT DOCUMENTS

| WO | WO-2004-087864 | 10/2004 |
|---|---|---|
| WO | WO-2005-014639 A2 | 2/2005 |
| WO | WO-2005-052151 | 6/2005 |
| WO | WO-2005-069913 | 8/2005 |
| WO | WO-2005-089093 | 9/2005 |
| WO | WO 2005/103077 | 11/2005 |
| WO | WO-2005-115622 | 12/2005 |
| WO | WO-2006-014899 | 2/2006 |
| WO | WO-2006-059701 | 6/2006 |
| WO | WO-2006-066001 | 6/2006 |
| WO | WO-2008-017906 | 2/2008 |
| WO | WO-2008-094986 | 8/2008 |
| WO | WO-2008-134461 | 11/2008 |

OTHER PUBLICATIONS

Akao, et al., "Purification and Characterization of a Peptide Essential for Formation of Streptolysin S by *Streptococcus pyogenes*," 1992, Infection and Immunity 60(11):4777-4780.
Altschul, Stephen F., et al., Basic Alignment Search Tool, J. Mol. Biol., 1990, pp. 403-410, vol. 215.
Ames, et al., "Simple, Rapid, and Quantitive Release of Periplasmic Proteins by Chloroform," 1984, J. Bacteriol., 160(3): 1181-1183.
Amitani et al., "Purification and Characterization of Factors Produced by *Aspergillus fumigatus* Which Affect Human Ciliated Respiratory Epithelium," 1995, Infection and Immunity 63(9):3266-3271.
Andersen, D.C., et al., "Production technologies for monoclonal antibodies and their fragments," Current Opinion in Biotechnology, London, GB, vol. 15, No. 5, Oct. 1, 2004, pp. 456-462.
Anderson, et al., "A homologue of the TNF receptor and its ligand enhance T-cell growth and dendritic-cell function," 1997, Nature 390 (6656), 175-179.
Anderson, Kevin P., et al., Enhancement of a Secondary Antibody Response to Vesicular Stomatitis Virus G Protein by IFN-γ Treatment at Primary Immunization. The Journal of Immunology, 1988, pp. 3599-3604, vol. 140, No. 10, The American Association of Immunologists.
Appa Rao, et al., "High-Level expression of ovine growth hormone in *Escherichia coli*: single-step purification and characterization," Protein Expr Purif, 1997, vol. 1, No. 2, pp. 201-208.
Aricescu et al., "A time—and cost-efficient system for high-level protein production in mammalian cells," 2006, Acta Cryst D62:1243-1250.
Aricescu et al., "Eukaryotic expression: developments for structural proteomics," Acta Cryst D62:1114-1124 (2006).
Ariga, et al.,"Release of Thermophilic α-amylase from Transformed *Escherichia coli* by Addition of Glycine," 1989, J. Ferm. Bioeng., 68:243-246.
Arthur, et al., High Level expression of interleukin-1beta in a recombinant *Escherichia coli* strain for use in a controlled bioreactor, Journal of Biotechnology, Elsevier Science Publishers, 1990, vol. 13, No. 1, pp. 29-46.
Asami, et al., "Synchronized disruption of *Escherichia coli* cells by T4 Phage Infection." 1997, J. Ferment and Bioeng., 83: pp. 511-516.
AU Patent Application 2005206951 Office Action issued Jan. 16, 2009.
AU Patent Application 2005269527 Office Action issued Nov. 3, 2010.
AU Patent Application 2008245696 Office Action issued Oct. 24, 2012.
Babiuk, L.A., et al., Symposium Immunobiology of Cytokines and Their Application in Disease Prevention in Dairy Cattle, J. Dairy Sci., 1991, vol. 74, pp. 4385-4398, Veterinary Infectious Disease Organization.
Bagdasarian, M. and Timmis, K., "Host: Vector Systems for Gene Cloning in *Pseudomonas*." 1982, Curr. Topics Microbial. Immunol., pp. 47-67, vol. 96.
Bagdasarian, M., et al., Specific-purpose plasmid cloning vectors II. Broad host range, high copy number, RSF1010-derived vectors, and a host-vector system for gene cloning in *Pseudomonas*, 1981, Gene, pp. 237-247, vol. 16, Elsevier/North-Holland Biomedical Press.
Bahia et al., "Optimisation of insect cell growth in deep-well blocks: development of a high-throughput insect cell expression screen," 2005, Protein Expression and Purification 39:61-70.
Baldwin et al., "Subunit Vaccine against the Seven Serotypes of Botulism," 2008, Infection and Immunity 76(3):1314-1318.
Baldwin, G.S., Comparison of Transferrin Sequences From Different Species. 1993, Comp. Biocherm Physiol., vol. 106B. No. 1, Pergamon Press Ltd., pp. 203-218.
Baneyx, F. and G. Georgiou, "Construction and Characterization of *Escherichia coli* Strains Deficient in Multiple Secreted Proteases: Protease III Degrades High-Molecular-Weight Substrates In Vivo," 1991, J. Bacteriol., pp. 2696-2703, vol. 173, No. 8.
Baneyx, Francois, "Recombinant protein expression in *Escherichia coli*," 1999, Curr. Op. Biotech. 10:411-421.
Bardwell, et al., "Pathways of Disulfide Bond Formation in Proteins in Vivo," 1994, Phosphate Microorg. Chapter 45, pp. 270-275.
Bebbington and Yarranton, "Antibodies for the treatment of bacterial infections: current experience and future prospects," 2008, Curr Op Biotech 19(6):613-619.
Bellini, et al., "Production processes of recombinant IL-1beta from *Bacillus subtilis*: comparison between intracellular and exocellular expression," Journal of Biotechnology, Elsevier Science, 1991, vol. 18, No. 3, pp. 177-192.
Benoist & Chambon, "In vivo sequence requirements of the SV40 early promoter region," 1981, Nature 290:304-310.
Berrow, N.S. et al., "Recombinant protein expression and solubility screening in *Escherichia coli*: a comparative study." 2006, Biological Crystallography. 62: 1218-1226.
Blattner, et al., "The Complete Genome Sequence for *Escherichia coli* K-12." 1997, Science 277 (5331): 1453-74.
Boettner, et al., "High-throughput screening for expression of heterologous proteins in the yeast *Pichia pastoris*," 2002, J Biotech 99:51-62.
Bohnsack, R.N. "Site-directed mutagenesis using positive antibiotic selection." 1996, Meth. Mol. Biol. 57,1-12.
Brosius Jurgen, "Toxicity of an overproduced foreign gene product in *Escherichia coli* and its use in plasmid vectors for the selection of transcription terminators." 1984, Gene 27(2): 161-72.
Broxmeyer, H.E., Monocyte-Macrophage-Derived Acidic Isoferritins: Nomal Feedback Regulators of Granulocyte-Macrophage Progenitor Cells In Vitro, Blood, 1982, pp. 595-607, vol. 60, American Society of Hematology.
Butte, A. "The use and analysis of microarray data." 2002, Nat Rev Drug Discov 1:951-60.
Buzzi, et al., "CRM197: reduction of atherosclerosis stenoses in carotids of three elderly patients," Therapy 4(3):293-298 (2007).
Calvete, et al., "The disulfide bond pattern of catrocollastatin C, a disintegrin-like/cysteine-rich protein isolated from *Crotalus atrox* venom," Protein Science, 2000, 9:1365-1373.
Carrier, M.I., et al., Expression of Human IL-1B in *Salmonella typhimurium* a Model System for the Delivery of Recombinant Therapeutic Proteins in Vivo, The Journal of Immunology, 1992, pp. 1176-1181, vol. 148, No. 4, The American Association of Immunologists.
Carter et al., "High Level *Escherichia coli* expression and production of a bivalent humanized antibody fragment." 1992, Bio/Technology, 10: 163-167.
Casavant, et al., "Use of a site-specific recombination-based biosensor for detecting bioavailable toluene and related compounds on roots." Environmental Microbiology, Apr. 2003, pp. 238-249, vol. 5, No. 4, Society for Applied Microbiology.
Cerretti, Douglas Pat., et al., Cloning, Sequence, and Expression of Bovine Interferon- γ, The Journal of Immunology, 1986, pp. 4561-4564, vol. 136, No. 12, The American Association of Immunologists.
Chalfie, et al., "Green fluorescent protein as a marker for gene expression." 1994, Science 263(5148):802-805.
Chang and Cohen "Construction and Characterization of Amplifiable Multiopy DNA Cloning Vehicles Derived from the P15A Cryptic Miniplasmid." 1978, Journal of Bacteriology, vol. 134, No. 3, p. 1141-1156.

(56) References Cited

OTHER PUBLICATIONS

Chew, et al., "Production of Recombinant Proteins. Novel Microbial and Eucaryotic Expression Systems," 2005, G. Gellissen, Weinheim, Wiley-VCH: 45-66.

Chiou et al., "Cobra venom cardiotoxin (cytotoxin) isoforms and neurotoxin: Comparative potency of protein kinase C inhibition and cancer cell cytotoxicity and modes of enzyme inhibition," 1993, Biochemistry, 32 (8), pp. 2062-2067.

Cho, Won-Kyung, et al., "Production and In Vitro Refolding of a Single-Chain Antibody Specific for Human Plasma Apolipoprotein A-I". Journal of Biotechnology, 2000, pp. 169-178, vol. 77, Elsevier Science B.V.

Choi et al., "Enhanced Production of Insulin-Like Growth Factor I Fusion Protein in *Escherichia coli* by Coexpression of the Down-Regulated Genes Identified by Tanscriptome Profiling," 2003, App. Envir. Microbio 69, pp. 4737-4742.

Clark-Curtiss, Josephine, et al., "Analysis of Recombinant DNA Using *Escherichia coli* Minicells." Methods in Enzymology, 1983, vol. 101, pp. 347-362, Academic Press, Inc.

CN200580032245 Office Action dated Apr. 12, 2012.

CN200880022208 Secord Office Action dated Jul. 16, 2012.

Cosman, "A Family of Ligands for the TNF Receptor Superfamily," Stem Cells, 1994: 12:440-455.

Dabora and Cooney, "Intracellular lytic enzyme systems and their use for disruption of *Escherichia coli*." 1990, Advances in Biochemical Engineering/Biotechnology, vol. 43, A. Fiechter, ed. (Springer-Verlag: Berlin), pp. 11-30.

Damasceno, et al., "Cooverexpression of chaperones for enhanced secretion of a single-chain antibody fragment in *Pichia pastoris*," 2007, Appl Microbiol Biotechnol 74:381-389.

Dammeyer et al., "Efficient production of soluble recombinant single chain Fv fragments by a *Pseudomonas putida* strain KT2440 cell factory." 2011, Microbial Cell Factories, vol. 10, pp. 1-8.

Davis and ES Mingioli "Mutants of *Escherichia coli* Requiring Methionin or Vitamin B12." (1950) J. Bact. 60:17-28.

Davis, Bernard D., et al., Mutants of *Escherichia coli* Requiring Methionine or Vitamin B12, 1950, J. Bact., pp. 1728, vol. 60.

De Marco, Ario, et al., Native folding of aggregation-prone recombinant proteins in *Escherichia coli* by osmolytes, plasmid- or benzyl alcohol-overexpressed molecular chaperones, 2005, Cell Stress and Chaperones, 10(4), pp. 329-339, Cell Stress Society International.

Deng, W.P. and Nickoloff, J.A., "Site-directed mutagenesis of virtually any plasmid by eliminating a unique site," 1992, Anal. Biochem. 200, 81.

Dolinski, et al., "Peptidyl-prolyl isomerases—an overview of the cyclophilin, FKBP and parvulin families in Guidebook to Molecular Chaperones and Protein-Folding Catalysts." (1997) Gething M-J Ed. Oxford University Press Inc. New York. pp. 359-369.

Doudoroff, M., et al., Gram-Negative Aerobic Rods and Cocci, 1974, Bergey's Manual of Determinative Bacteriology, edited by Buchanan and Gibbons, pp. 217-289.

Duetz and Witholt, "Oxygen transfer by orbital shaking of square vessels and deepwell microtiter plates of various dimensions," 2004, Biochem Eng J 17:181-185.

Duetz, et al., "Methods for Intense Aeration, Growth, Storage, and Replication of Bacterial Strains in Microtiter Plates," 2000, Appl Env Microbiol 66(6):2641-2646.

Dulebohn, D., "Trans-Translation: The tmRNA-Mediated Surveillance Mechanism for Ribosome Rescue, Directed Protein Degradation, and Nonstop mRNA Decay," Biochemistry, 2007, 46 (16): 4681-4693.

Edmond, et al., "Optimized and Automated Protocols for High-Throughput Screening of Amylosucrase Libraries," 2007, J Biomol Screen 12:715-723.

Elbashir, et al., "Duplexes of 21-nucleotide RNAs mediate RNA interference in cultured mammalian cells," 2001, Nature 411(6836): 494-8.

Elbashir, et al., "RNA interference is mediated by 21- and 22-nucleotide RNAs," 2001, Genes & Development 15(2):188-200.

EP12198545 Extended European Search Report dated Jun. 14, 2013.

Espejo, A., "Protein-domain microarrays Processes," 2004, Mol Biol., 264:173-81.

Eymann, C., et al., "*Bacillis subtilis* Functional Genomics: Global Characterization of the Stringent Response by Proteome and Transcriptome Analysis," 2002, J Bacteriol 184(9), pp. 2500-2520.

Fang, et al., "Development of a high-throughput yeast two-hybrid screening system to study protein-protein interactions in plants," 2002, Mol Genet Genomics 267:142-153.

Fathallah-Shaykh, H.M., "Microarrays: applications and pitfalls," 2005, Arch. Neurol. 62(11):1669-1672.

Fire,A., et al. "Potent and specific genetic interference by double-stranded RNA in *Caenorhabdtis elegans*,." 1998, Nature 391:806-11.

Fischer and Montal, "Crucial Role of the Disulfide Bridge between Botulinum Neurotoxin Light and Heavy Chains in Protease Translocation across Membranes," 2007, Biol Chem 282(40):29604-29611.

Fleer et al., "High-level secretion of correctly processed recombinant human interleukin-1 beta in *Kluyveromyces lactis*." Gene, Elsevier, 1991, vol. 107, No. 2, pp. 285-295.

Foss, FM, 2001, "Interleukin-2 fusion toxin: targeted therapy for cutaneous T cell lymphoma," Ann N Y Acad Sci. 941:166-76.

Fox, L.K., et al., The Effect of Interferon-γ Intramammary Administration on Mammary Phagocyte Function, J. Vet. Med., 1990, pp. 28-30. Paul Parey Scientific Publishers.

Fransen, Lucie, et al., Recombinant Tumor Necrosis Factor: Species Specificity for a Variety of Human and Murine Transformed Cell Lines, Cellular Immunology, 1986, vol. 100, Academic Press, Inc., pp. 260-267.

French et al., "Development of a simple method for the recovery of recombinant proteins from the *Escherichia coli* periplasm." 1996, Enzyme and Microb. Tech., 19: 332-338.

Friedman, Robert M., et al., Interferon with Special Emphasis on the Immune System, Advances in Immunology, pp. 97-140, 1983, vol. 34, Academic Press Inc.

Frishman, Dmitrij, et al., Starts of bacterial genes: estimating the reliability of computer predictions, Gene, 1999, vol. 234, Elsevier Science B.V., pp. 257-265.

Furlong and Sundstrom, "Immobilized cell bioreactors for producing immobilized protein bioadsorbers," 1989, Developments in Industrial Microbiology, vol. 30, pp. 141-148.

Gaertner, Frank H., CellCap: An Encapsulation System for Insecticidal Biotoxin Proteins, Advanced Engineered Pesticides, 1993, pp. 73-83, Marcel Dekker, New York.

Gaertner, Frank H., et al., Amended recombinant cells (ARCs(TM)): An economical and surprisingly effective production and delivery vehicle for recombinant bovine IFN-γ, Journal of Controlled Release, Oct. 2005, vol. 107, Elsevier B.V., pp. 189-202.

Gardiner et al., "Bioinformatic and expression analysis of the putative gliotoxin biosynthetic gene cluster of *Aspergillus fumigatus*," 2005, FEMS Microbiol. Lett. 248(2):241-248.

Gardy, et al., 2005 PSORTb v.2.0 expanded prediction of bacterial protein subcellular localization and insights gained from comparative proteome analysis. Bioinformatics 21(5): 617-623.

Gellison, ed. Production of Recombinant Proteins, Novel Microbial and Eukaryotic Expression Systems, Wiley-VCH 2005, pp. 47-48.

Gene Ontology Consortium 2004, The Gene Ontology (GO) database and informatics resource, Nucleic Acids Research 32: D258-D261.

Georgiou, et al., "Preparative expression of secreted proteins in bacteria: status report and future prospects," 2005, Current Opinion in Biotechnology, vol. 16, pp. 538-545.

Georgopoulos, Costa, "Toothpicks, Serendipity and the Emergence of the *Escherichia coli* DnaK (Hsp70) and GroEL (Hsp60) 2006, Chaperone Machines," Genetics 174:1699-1707.

Giannini, G., et al., "The amino-acid sequence of two non-toxic mutants of diphtheria toxin: CRM45 and CRM197," 1984, Nucl Acids Res 12(10):4063-4069.

Gill, et al., "Genomic Analysis of High-Cell-Density Recombinant *Escherichia coli* Fermentation and "Cell Conditioning" for Improving Recombinant Protein Yield," 2001, Biotech. Bioengin 72, pp. 85-95.

Gillette, W.K., et al., Pooled ORF Expression Technology (POET), Molecular and Cellular Proteomics, 4: 1657-1652 (2005).

(56) References Cited

OTHER PUBLICATIONS

Goeddel, et al., "Expression in *Escherichia coli* of chemically synthesized genes for human insulin," Jan. 1979, Proc. Nat. Acad. Sci. USA, vol. 76, No. 1, pp. 106-110.
Gonzalez Barrios, et al., "Autoinducer 2 Controls Biofilm Formation in *Escherichia coli* through a Novel Motility Quorum-Sensing Regulator (MqsR, B3022)," 2006, J Bacteriol 188:305-316.
Gottesman S., et al. "The ClpXP and ClpAP proteases degrade proteins with carboxyl-terminal peptide tails added by the SsrA-tagging system," 1998, Genes Dev 12, pp. 1338-1347.
Gottesman Susan, "Proteases and their Targets in *Escherichia coli*," 1996, Annu. Rev. Genet 30, pp. 465-506.
Gough, R.E., et al., Further Studies on the Adjuvant Effect of an Interferon Inducer (BRL 5907) on Newcastle Disease and Avian Influenza Inactivated Vaccines, Research in Veterinary Science, 1975, vol. 19, pp. 185-188.
Graslund, S. et al., Protein production and purification, Nature Methods, 5:135-146 (2008).
Graupner, S. & Wackernagel, W., "A broad-host-range expression vector series including a Ptac test plasmid and its application in the expression of the *dod* gene of *Serratia marcescens* (coding for ribulose-5-phosphate 3-epimerase) in *Pseudomonas stutzeri*," 2000, Biomolecular Engineering, vol. 17, Elsevier Science B.V., pp. 11-16.
Gray, et al, "Structure of the human immune interferon gene." (1982) Nature 298:859-63.
Gray, et al. "*Pseudomonas aeruginosa* Secretes and Correctly Processes Human Growth Hormone." (Bio/Technology, Feb. 1984, pp. 161-165).
Greenfield, L., et al., "Nucleotide sequence of the structural gene for diphtheria toxin carried by corynebacteriophage beta," 1983, Proc. Natl. Acad. Sci. USA, 80(22):6853-6857.
Gresser, Ion, et al., Anti-Tumor Effects of Interferon in Mice Injected with Interferon Sensitive and Interferon-Resistant Friend Leukemia Cells. VI. Adjuvant Therapy After Surgery in the Inhibition of Liver and Spleen Metastases, Int. J. Cancer, 1987, vol. 39, Alan R. Liss, Inc., pp. 789-792.
Gruss, P., et al., "Simian virus 40 tandem repeated sequences as an element of the early promoter," 1981, Proc. Nat. Acad. Sci. USA 78:943-947.
Gubler, U., et al., "Recombinant Human Interleukin 1-Alpha Purification and Biological Characterization," Journal of Immunology, 1986, vol. 136, No. 7, pp. 2492-2497.
Guzman, M., et al., "Tight Regulation, Modulation and High-Level Expression by Vectors Containing the Arabinose PBAD Promoter," 1995, Journal of Bacteriology 177(14):4121-30.
Gygi, et al., "Quantitative analysis of complex protein mixtures using isotope-coded affinity tags," Nat. Biotech, Oct. 1999, 17:994-999.
Halling, K., et al., "Genomic cloning and characterization of a ricin gene from *Ricinus communis*," 1985, Nucl Acids Res 13(22):8019-8033.
Hamilton, et al., "New Method for generating deletions and gene replacements in *Escherichia coli*," 1989, Journal of Bacteriology 171(9): 4617-4622.
Han, et al., "Engineering *Escherichia coli* for Increased Productivity of Serine-Rich Proteins Based on Proteome Profiling," 2003, Applied Env. Microbiol. 69(10):5772-5781.
Hancock and I. Poxton, "Isolation and Purification of Cell Walls," 1988, Bacterial Cell Surface Techniques, Chapter 3, p. 55, John Wiley & Sons Ltd.
Hayase N., et al., "Secretion of Human Epidermal Growth Factor (EGF) in Autotrophic Culture by a Recombinant Hydrogen-Utilizing Bacterium, *Pseudomonas psedollava*, Carrying Broad-Host-Range EGF Secretion Vector pKSEGF2." Applied and Environmental Microbiology, Sep. 1994, pp. 3336-3342, vol. 60, No. 9, American Society for Microbiology.
Heffron, F., et al., "Translocation of a plasmid DNA sequence which mediates ampicillin resistance: Molecular nature and specificity of Insertion," Sep. 1975, Proc. Nat. Acad. Sci., vol. 72, No. 9, pp. 3623-3627.

Heim and Tsien, "Engineering green fluorescent protein for improved brightness, longer wavelengths and fluorescence resonance energy transfer," 1996, Curr. Biol.6:178-182.
Herman, C., et al., "Degradation of carboxy-terminal-tagged cytoplasmic proteins by the *Escherichia coli* protease HflB (FtsH)," 1998, Genes Dev 12, pp. 1348-1355.
Hochuli, Erich, "Purification of Recombinant Proteins with Metal Chelate Absorbent," 1990, Genetic Engineering, vol. 12, pp. 87-91.
Hockney, Robert C., "Recent developments in heterologous protein production in *Escherichia coli*," 1994, Trends BioTechnology, 12, pp. 456-463.
Holliday, R., "A Mechanism for Gene Conversion in Fungi," Genet Res. 5:282, 1964.
Holliger, et al., "Diabodies": small bivalent and bispecific antibody fragments, 1993, Proc. Natl. Acad. Sci. USA, 90:6444-6448.
Holtwick, R., et al., "A novel rolling-circle-replicating plasmid from *Pseudomonas putida* P8: molecular characterization and use as a vector," 2001, Microbiology, vol. 147, Pt. 2, pp. 337-344.
Holz, et al., "A micro-scale process for high-throughput expression of cDNAs in the yeast *Saccharomyces cerevisiae*," 2002, Protein Expression and Purification 25:372-378.
Horton, et al., "Gene splicing by overlap extension: tailor-made genes using the polymerase chain reaction," 1990, BioTechniques 8(5): 528-30, 532, 534-5.
Hsieh, et al., "Pairing of homologous DNA sequences by proteins: evidence for three-stranded DNA," 1990, Genes & Development 4: 1951-1963.
Hsiung et al., "Use of Bacteriocin Release Protein in *E. coli* for Excretion of Human Growth Hormone into the Culture Medium," 1989, Bio/Technology 7:267-71.
Hsu, et al., "Engineering the Assembly Pathway of the Baculovirus-Insect Cell Expression System," 1994, Annals New York Academy of Sciences 721:208-217.
Ikehata, O., et al., Primary structure of nitrile hydratase deduced from the nucleotide sequence of a *Rhodococcus* species and its expression in *Escherichia coli*, 1989, Eur. J. Biochem, pp. 563-570, vol. 181.
Ishii, T., et al., Elastase gene expression in non-elastase-producing *Pseudomonas aeruginosa* strains using novel shuttle vector systems, 1994, FEMS Microbiology Letters, vol. 116, Federation of European Microbiological Societies, pp. 307-314.
Jarvis, et al., "Influence of Different Signal Peptides and Prosequences on Expression and Secretion of Human Tissue Plasminogen Activator in the Baculovirus System," 1993, J Biol Chem 268:pp. 16754-16762.
Jeong K.J. and Lee S.Y., "Excretion of Human β-Endorphin into Culture Medium by Using Outer Membrane Protein F as a Fusion Partner in Recombinant *Escherichia coli*," 2002, Appl. Environ. Microbio 68: vol. 10, pp. 4979-4985.
Jin, H., et al., "Soluble periplasmic production of human granulocyte colony-stimulating factor (G-CSF) in *Pseudomonas fluorescens*," 2011, Protein Expression and Purification, vol. 78, No. 1, pp. 69-77.
Jones, Jonathan D.G., et al., An Efficient Mobilizable Cosmic Vector, pRK7813, and its Use in a Rapid Method for Markler Exchange in *Pseudomonas fluorescens* Strain HV37a, Gene, 1987, Elsevier Science Publishers B.V., pp. 299-306.
Joseph-Liazun et al., "Human recombinant interleukin-1β isolated from *Escherichia coli* by simple osmotic shock," 1990, Gene 86:291-295.
Kabir, et al., "Gene expression patterns for metabolic pathway in *pgi* knockout *Escherichia coli* with and without *phb* genes based on RT-PCR," 2003, J. Biotech. 105(1-2):11-31.
Kaster, K.R. et al., "Analysis of a bacterial hygromycin B resistance gene by transcriptional and translational fusions and by DNA sequencing," 1983, Nucleic Acids Res. (19):6895-911.
Keown, et al., "Methods for Introducing DNA into Mammalian Cells," Processes in Enzymology, 1990, vol. 185, pp. 527-537.
Khoury, G. and Gruss, P., "Enhancer Elements," 1983, Cell, vol. 33:313-314.
Kim, W., et al., "Glycosyltransferase—a specific marker for the discrimination of *Bacillus anthracis* from the *Bacillus cereus* group," 2008, J. Med Microbiol 57:279-286.

(56) References Cited

OTHER PUBLICATIONS

Knight Jr., E., Antiviral and Cell Growth Inhibitory Activities Reside in the Same Glycoprotein of Human Fibroblast Interferon, Nature, 1976, vol. 262, Nature Publishing Group, pp. 302-303.

Knight, et al., Construction and initial characterization of a mouse-human chimeric anti-TNF antibody, Mol Immunol. Nov. 1993;30(16):1443-53.

Kodama, T., et al., "The Initial Phosphate Burst in ATP Hydrolysis by Myosin and Subfragment-1 as Studied by a Modified Malachite Green Method for Determination of Inorganic Phosphate," 1986, J. Biochem., vol. 99, pp. 1465-1472.

Korean Patent Application 10-2006-7014191 Office Action dated Sep. 8, 2011 (English Translation only).

Korean Patent Application 10-2007-7004418 Exam Report dated Dec. 22, 2011.

Korean Patent Application 10-2007-7004418 Exam Report dated Nov. 26, 2012.

Korean Patent Application 10-2007-7004418 Exam Report dated Jun. 25, 2013.

Korean Patent Application 10-2013-7002343 Office Action dated Feb. 25, 2014.

Kumar, et al., "The highly efficient productions of full-length and mutant rat brain calcium-binding proteins (calbindins-28K) in a bacterial expression system," Arch Biochem Biophys, 1994, vol. 308, No. 1, pp. 311-317.

Kunkel, T.A., et al., Rapid and efficient site-specific mutagenesis without phenotypic selection, 1987, Meth. Enzymol 154, p. 367.

Kunkel, Thomas A., "Rapid and efficient site-specific mutagenesis without phenotypic selection," 1985, Proc. Natl. Acad. Sci. USA, vol. 82, pp. 488-492.

Landry, T., et al., "Safety evaluation of an α-amylase enzyme preparation derived from the archaeal order *Thermococcales* as expressed in *Pseudomonas fluorescens* biovar I," 2003, Regulatory Toxicology and Pharmacology, vol. 37, pp. 149-168, see whole article, particularly pp. 151-152.

Larsen, et al., "Expression of *Candida antarctica* lipase B in *Pichia pastoris* and various *Escherichia coli* systems," 2008, Protein Expression and Purification 62:90-97.

Lawn, R., et al., "The sequence of human serum albumin cDNA and its expression in *E. coli*," 1981, Nucleic Acids Research, vol. 9, No. 22, IRL Press Limited, London, pp. 6103-6114.

Lee et al., "Global Analyses of Transcriptomes and Proteomes of a Parent Strain and an L-Threonine-Overproducing Mutant Strain," 2003, J. Bacteriol. 185(18):5442-5451.

Lee, M.H., "Bacterial Expression and in Vitro Refolding of a Single-Chain Fv Antibody Specific for Human Plasma Apolipoprotein B-100," 2002, Protein Expression and Purification, vol. 25, Elsevier Science USA, pp. 166-173.

Lee, S., et al.,"Effect of Overproduction of Heat Shock Chaperones GroESL and DnaK on Human Procollagenase Production in *Escherichia coli*," 1992, Journal of Biological Chemistry, vol. 267, No. 5, pp. 2849-2852.

Lewis, M.K. and Thompson, D.V., "Efficient site directed in vitro mutagenesis using ampicillin selection," 1990, Nucl. Acids Res. 18, No. 12, pp. 3439-3443.

Lloubes, R. et al., "Colincin A lysis protein promotes extracellular release of active human growth hormone accumulated in *Escherichia coli* cytoplasm," 1993, Biochimie 75, pp. 451-458.

Lockhart, et al., "Expression monitoring by hybridization to high-density oligonucleotide arrays," 1996, Nat Biotechnol 14:1675-80.

Lofthouse, S.A., et al., Cytokines as Adjuvants for Ruminant Vaccines, International Journal of Parasitology, 1996, vol. 26, No. 8/9, Elsevier Science, pp. 835-842.

Lombardo, et al, "*Escherichia coli* PapD in Guidebook to Molecular Chaperones and Protein Folding Catalysts," Gething M-J Ed. Oxford University Press Inc. New York, 1997, pp. 463-465.

Lombillo, Vivian A., Antibodies to the Kinesin Motor Domain and CENP-E Inhibit Microtubule Depolymerization-dependent Motion of Chromosomes In Vitro, 1995, The Journal of Cell Biology, vol. 128, Nos. 1 & 2, The Rockefeller University Press, pp. 107-115.

Lopez, et al., "Homologous recombination intermediates between two duplex DNA catalysed by human cell extracts," 1987, Nucleic Acids Res. 15:5643-5655.

Lundell et al., "Cytoplasmic and periplasmic expression of a highly basic protein, human interleukin 4, in *Escherichia coli*," 1990, J. Indust. Microbio. 5: pp. 215-228.

Lushnikov, A.A., et al., "Shuttle Vector for *Escherichia coli, Pseudomonas putida*, and *Pseudomonas aeruginosa*," 1985, Basic Life Sci., vol. 30, pp. 657-662.

MacBeath, G. & Schreiber, SL, "Printing proteins as microarrays for high-throughput function determination," 2000, Science 289:1760-1763.

Magnan, et al., SOLpro: accurate sequence-based prediction of protein solubility, 2009, Bioinformatics 25(17): 2200-2207.

Makarenkova, et al., "Dendritic cells and natural killer cells interact via multiple TNF family molecules," J Leukocyte Biol 77:408-413 (2005).

Manduchi, E., et al., "Comparison of different labeling processes for two-channel high-density microarray experiments," 2002, Physiol Genomics 10:169-79.

Manoil, Colin, "Tagging Exported Proteins Using *Escherichia coli* Alkaline Phosphatase Gene Fusions," 2000, Methods in Enzymol, 326: 35-47.

Martineau, Pierre, et al., Expression of an Antibody Fragment at High Levels in the Bacterial Cytoplasm, J. Mol. Biol., 1998, Academic Press, pp. 117-127.

McCarthy, et al., "Translational Control of Prokaryotic Gene Expression," 1990, Trends in Genetics 6:78-85.

Menne, et al., "A comparison of signal sequence prediction methods using a t test set of signal peptides," 2000, Bioinformatics, vol. 16, No. 8, pp. 741-742.

Messing et al., "Genetic Engineering of Plants: An Agricultural Perspective," 1983, Edited by Kosuge et al., eds., pp. 211-227.

Mezghani-Abdelmoula, et al., "Invasive Behavior and Depolarization Effect of *Pseudomonas fluorescens* on Rat Cerebellar Granule Neurons," African Journal of Clinical and Experimental Microbiology, Jan. 2005, pp. 1-13.

Michalski, Wojtek, et al., Recombinant Chicken IFN-γ Expressed in *Escherichia coli*: Analysis of C-Terminal Truncation and Effect on Biologic Activity, Journal of Interferon and Cytokine Research, 1999, vol. 19, Mary Ann Liebert, Inc., pp. 383-392.

Miksch, G., et al, "The kil gene of the ColE1 plasmid of *Escherichia coli* controlled by a growth-phase-dependent promoter mediates the secretion of a heterologous periplasmic protein during the stationary phase," 1997, Arch. Microbiol. 167:143-150.

Missiakas, D., et al., "Identification and characterization of HsIV HsIU (ClpQ ClpY) proteins involved in overall proteolysis of misfolded proteins in *Escherichia coli*," 1996, Embo J. 15:6899-909.

Mitamura, et al., "Diphtheria Toxin Binds to the Epidermal Growth Factor (EGF)-like Domain of Human Heparin-binding EGF-like Growth Factor/Diphtheria Toxin Receptor and Inhibits Specifically Its Mitogenic Activity," J Biol Chem 270(3):1015-1019 (1995).

Montgomerie et al., "Improving the accuracy of protein secondary structure prediction using structural alignment," BMC Bioinformatics 7:301 (2006).

Morrison, D.A., Transformation in *Escherichia coli*: Cryogenic Preservation of Competent Cells, Journal of Bacteriology, Oct. 1977, vol. 132, No. I, American Society for Microbiology, pp. 349-351.

Mukhija, Reema, et al., High-Level Production and One-Step Purification of Biologically Active Human Growth Hormone in *Escherichia coli*, Gene, 1995, vol. 165, Elsevier Science B.V., pp. 303-306.

Mukhopadhyay, Pradip, et al., "Construction of a Stable Shuttle Vector for High-Frequency Transformation in *Pseudomonas syringae* pv. *Syringae*," Journal of Bacteriology, Jan. 1990, vol. 172, No. 1, American Society for Microbiology, pp. 477-480.

Mulder et al., "InterPro, progress and status in 2005," Nucleic Acids Res., 2005, 33, Database Issue: D201-5.

Naamati et al., "ClanTox: a classifier of short animal toxins," 2009, Nucleic Acids Research 37, Web Server issue W363-W368; doi:10.1093/nar/gkp299.

(56) References Cited

OTHER PUBLICATIONS

Nagahari, Kenji, et al., "RSF1010 Plasmid as a Potentially Useful Vector in *Pseudomonas* Species," Journal of Bacteriology, Mar. 1978, vol. 133, No. 3, American Society for Microbiology, pp. 1527-1529.
Nagahira, et al., Humanization of a mouse neutralizing monoclonal antibody against tumor necrosis factor-alpha (TNF-alpha), J Immunol Methods, Jan. 1, 1999;222(1-2):83-92.
Naglak and Wang, "Recovery of a foreign protein from the periplasm of *Escherichia coli* by chemical permeabilization," 1990, Enzyme Microb. Technol., 12: 603-611.
Nakamaye, K. and Eckstein F., "Inhibition of restriction endonuclease Nci I cleavage by phosphorothioate groups and its application to oligonucleotide-directed mutagenesis," 1986, Nucl. Acids Res. 14, 9679-98.
Nakashima, Nobutaka, et al., "Cell-free protein synthesis using cell extract of *Pseudomonas fluorescens* and CspA promoter," Biochemical and Biophysical Research Communications, Jun. 2004, vol. 319, No. 2., Elsevier, pp. 671-676.
Nedospasov, et al., "Tandem arrangement of genes coding for tumor necrosis factor (TNF-alpha) and lymphotoxin (TNF-beta) in the human genome," 1986, Cold Spring Harb. Symp. Quant. Biol. 51 Pt 1, pp. 611-624.
Needleman, Saul B., et al., "A General Method Applicable to the Search for Similarities in the Amino Acid Sequence of Two Proteins," J. Mol. Biol., 1970, vol. 48, pp. 443-453.
Neu and Heppel, "The release of enzymes from *Escherichia coli* by osmotic shock and during the formation of spheroplasts," (1965) J. Biol. Chem., 240:3685-3692.
Neu and Heppel, "The Release of Ribonuclease into the Medium when *Escherichia coli* Cells are converted to Spheroplasts," 1964, J. Biol. Chem 239: 3893-3900.
Nielsen, Iienrik, et al., Short Communication—"Identification of Prokaryotic and Eukaryotic Signal Peptides and Prediction of their Cleavage Sites," Protein Engineering, 1997, vol. 10, No. I, Oxford University Press, pp. 1-6.
Nieto, C., et al., "Cloning Vectors, Derived From a Naturally Occurring Plasmid of *Pseudomonas savastanoi*, Specifically Tailored for Genetic Manipulation in *Pseudomonas*," Gene, 1990, vol. 87, Elsevier, pp. 145-149.
Nishihara, et al., "Chaperone coexpression plasmids: differential and synergistic roles of DnaK-DnaJ-GrpE and GroE1-GroES in assisting folding of an allergen of Japanese cedar pollen, Cryj2, in *Escherichia coli*," 1998, Appl. Environ. Microbiol., 64:1694.
Niwa, et al., "An Efficient Gene-Trap Method Using Poly a Trap Vectors and Characterization of Gene-Trap Events," 1993, J. Biochem 113:343-349.
Niwa, et al., "Bimodal protein solubility distribution revealed by an aggregation analysis of the entire ensemble of *Escherichia coli* proteins," PNAS 106(11):4201-4206 (2009).
Nomine, Yves, et al., "Formation of Soluble Inclusion Bodies by HPV E6 Oncoprotein Fused to Maltose-Binding Protein, Protein Expression and Purification," 2001, vol. 23, Academic Press, pp. 22-32.
Nossal and Heppel, "The Release of Enzymes by Osmotic Shock from *Escherichia coli* in exponential phase," 1966, J. Biol. Chem., 241: 3055-3062.
Novak, et al., "Bacterial growth properties at low optical densities," Antonie Van Leeuwenhoek 96(3):267-274 (2009).
Olekhnovich, Igor N., el al., "Controlled-Expression Shuttle Vector for Pseudomonads Based on the trpIBA genes of *Pseudomonas putida*," Gene, 1994, vol. 140, Elsevier Science, pp. 63-65.
Opdenakker, G., et al., Interaction of Interferon With Other Cytokines, Experientia, 1989, vol. 45, Birkhauser Verlag, Switzerland, pp. 513-520.
Orr, et al., "Expression and Immunogenecity of a Mutant Diphtheria Toxin Molecule, CRM 197, and Its Fragments in *Salmonella typhi* Vaccine Strain CVD 908-htrA," Infection and Immunity 67(8):4290-4294 (1999).
Papini, et al., "Cell Penetration of Diphtheria Toxin," J Biol Chem 268(3):1567-1574 (1993).
Park, S., et al., "Secretory production of recombinant protein by a high density culture of a protease negative mutant *Escherichia coli* strain," 1999, Biotechnol. Progr 15, pp. 164-167.
Patra, Ashok K., et al., "Optimization of Inclusion Body Solubilization and Renaturation of Recombinant Human Growth Hormone from *Escherichia coli*," Protein Expression and Purification, 2000, vol. 18, Academic Press, pp. 182-192.
Pearson, William R., et al., "Improved Tools for Biological Sequence Comparison," Proc. Natl. Acad. Sci., Apr. 1988, vol. 85, pp. 2444-2448.
Peluso, P., et al., "Optimizing antibody immobilization strategies for the construction of protein microarrays," 2003, Anal Biochem 312:113-124.
Perussia, Bice, et al., "Immune Interferon Induces the Receptor for Monomeric IgG1 on Human Monocytic and Myeloid Cells," J. Exp. Med., 1983, vol. 158, Rockefeller University Press, pp. 1092-1113.
Pestka, Sidney, et al., "Interferons and Their Actions," Annu. Rev. Biochem., 1987, vol. 56, Annual Reviews, Inc., pp. 727-777.
Pierce, et al., "Exp+A310ression and Recovery of Recombinant Periplasmically Secreted α Amylase derived from *Streptomyces thermoviolaceus*," 1995, Icheme Research Event 2: 995-997.
Pighetti, Gina M., et al., Specific Immune Responses of Dairy Cattle After Primary Inoculation with Recombinant Bovine Interferon-γ as an Adjuvant When Vaccinating Against Mastitis, American Journal of Veterinary Research, 1996, vol. 57, No. 6, pp. 819-824.
Pilon, et al., "High-Level expression and efficient recovery of ubiquitin fusion proteins from *Escherichia coli*," Biotechnol Prog., 1996, vol. 12, No. 3, pp. 331-337.
Puehler, et al., 1984, Advanced Molecular Genetics New York, Heidelberg, Berlin, Tokyo, Springer Verlag.
Quevillon, et al., "InterProScan: protein domains identifier," 2005, Nucleic Acids Research 33: W116-W120.
Radding, C.M., "Homologous pairing and strand exchange in genetic recombination," 1982, Ann. Rev. Genet. 16: 405.
Ralph, Peter, "Human B Cell-Inducing Factor(s) for Production of IgM, IgG and 19A; Independence From IL 2(1)," The Journal of Immunology, Apr. 1984, vol. 132, No. 4, The American Society of Immunologists, pp. 1858-1862.
Randolph, et al., "Amino acid sequence of fibrolase, a direct-acting fibrinolytic enzyme from *Agkistrodon contortrix* contortrix venom," Protein Science 1:590-600 (1992).
Ranson, et al., "Chaperonins," 1998, BioChem. J. 333, 233-242.
Rao, et al., "Stable three-stranded DNA made by RecA protein," 1991, PNAS 88: pp. 2984-2988.
Rawlings et al., "MEROPS: the peptidase database," 2006, Nucleic Acids Res., vol. 34, D270-D272, Database issue doi:10.1093/nar/gkj089.
Retallack, Diane, et al., "Reliable protein production in a *Pseudomonas fluorescens* expression system," Protein Expression and Purification, 2012, vol. 81, No. 2, pp. 157-165.
Retallack, Diane, et al., "*Pseudomonas fluorescens*—a robust expression platform for pharmaceutical protein production," Microbial Cell Factories, 2006, vol. 5 (Suppl. 1), BioMed Central, p. S28.
Retallack, Diane, et al., "Transport of heterologous proteins to the periplasmic space of *Pseudomonas fluorescens* using a variety of native signal sequences," Biotechnology Letters, 2007, vol. 29, Springer Science+Business Media B.V., pp. 1483-1491.
Riesenberg, D., et al., "High Cell Density Cultivation of *Escherichia coli* at Controlled Specific Growth Rate," Journal of Biotechnology, 1991, vol. 20, Elsevier Science Publishers, B.V, pp. 17-28.
Rosenberg, et al., "Vectors for selective expression of cloned DNAs by T7 RNA polymerase," 1987, Gene, 56(1): 125-35.
Ruiz-Taylor, LA, et al., "Monolayers of derivatized poly(L-lysine)-grafted poly(ethylene glycol) on metal oxides as a class of biomolecular interfaces," 2001, Proc Natl Acad Sci USA, 98:852-857.
Ruiz-Taylor, LA, et al., "X-ray photoelectron spectroscopy and radiometry studies of biotin-derivatized poly(L-lysine)-grafted-poly(ethylene glycol) monolayers on metal oxides," 2001, Langmuir, 7313-7322.

(56) References Cited

OTHER PUBLICATIONS

Sabina J., et al., "Interfering with Different Steps of Protein Synthesis Explored by Transcriptional Profiling of *Escherichia coli* K-12," 2003, J. Bacteriol 185, pp. 6158-6170.
Saiki, Osamu, et al., Induction of Human Immunoglobulin Secretion-I. Synergistic Effect of B Cell Mitogen Cowan I Plus T Cell Mitogens or Factors, The Journal of Immunology, Sep. 1981, vol. 127, No. 3, The American Association of Immunologists, pp. 1044-1047.
Sanchez-Romero & V. De Lorenzo, Manual of Industrial Microbiology and Biotechnology, 1999, A. Demain & J. Davies, eds., pp. 460-474.
Schein, C.H., "Production of Soluble recombinant Proteins in Bacteria," Bio/Technology, 1989, 7:1141-1149.
Schena, M. et al., "Quantitative monitoring of gene expression patterns with a complementary DNA microarray," 1995, Science 270:467-70.
Schiavo, et al., "An intact interchain disulfide bond is required for the neurotoxicity of tetanus toxin," 1990, Infection and Immunity 58(12):4136-4141.
Schneider et al., (2005) "Auxotrophic markers pyrF and proC can replace antibiotic markers on protein productions plasmids in high-cell-density *Pseudomonas fluorescens* fermentation," 2005a, Biotechnology Progress 21(2): 343-348.
Schweizer, Herbert P., et al., Vector Design and Development of Host Systems for *Pseudomonas*, Genetic Engineering, 2001, vol. 23, Kluwer Academic/Plenum Publishers, pp. 69-81.
Schweizer, Herbert P., Vectors to Express Foreign Genes and Techniques to Monitor Gene Expression in Pseudomonads, Current Opinion in Biotechnology, 2001, vol. 12, Elsevier Science Ltd., pp. 439-445.
Service, R.F. et al., "Tapping DNA for structures produces a trickle," 2002, Science 298:948-950.
SG200906987-3 Exam Report dated Sep. 26, 2011.
Shine and Dalgarno, "The 3'-terminal sequence of *Escherichia coli* ribosomal RNA: complementarity to nonsense triplets and ribosome binding sites," 1974, Proc. Natl. Sci. USA 71:1342-1346.
Shokri, et al., "Growth rate-dependent changes in *Escherichia coli* membrane structure and protein leakage," 2002, App. Microbiol. Biotechnol 58:386-392.
Shu, et al., "The structure of spider toxin huwentoxin-II with unique disulfide linkage: Evidence for structural evolution," Protein Science 11:245-252 (2002).
Simmons, et al., "Expression of full-length immunoglobins in *Escherichia coli*: rapid and efficient production of aglycosylated antibodies," 2002, J. Immun Meth. 263:133-147.
Singleton, et al., 2000, "Cloning, expression, and characterization of pyrrolidone carboxyl peptidase from the archaeon *Thermococcus litoralis*" Extremophiles 4(5):297-303.
Singleton, Paul & Sainsbury, Diana: "Dictionary of Microbiology," 1978, John Wiley & Sons Ltd., Chichester, UK, XP002667935, pp. 332-333.
Slater, Robert J., and Williams,Ross, "The Expression of Foreign DNA in Bacteria," 2000, Molecular Biology and Biotechnology, Fourth Edition, Chapter 4, The Royal Society of Chemistry, Cambridge, UK, pp. 125-154.
Smialowski, et al., "Protein solubility: sequence based prediction and experimental verification," Bioinformatics 23(19):2536-2542 (2007).
Smith & Waterman, Michael S., Comparison of Biosequences, 1981, Adv. Appl. Math 2:482-489.
Smits, et al., "New Alkane-responsive expression vectors for *Escherichia coli* and *Pseudomonas*," Plasmid, 2001, vol. 46, pp. 16-24.
Song, K.Y., et al., "Accurate modification of a chromosomal plasmid by homologous recombination in human cells," 1987, Proc. Natl. Acad. Sci. USA 84:6820-6824.
Sordillo, L.M., Controlling Acute *Escherichia coli* Mastitis During the Periparturient Period with Recombinant Bovine Interferon-Gamma, Veterinary Microbiology, 1991, vol. 28, pp. 189-198.
Southern, P. and P. Berg, "Transformation of mammalian cells to antibiotic resistance with a bacterial gene under control of the SV40 early region promoter," 1982, J. Mol. Appl. Genet. 1:327-341.
Squires, et al., "Heterologous protein production in *P. fluorescens*," Bioprocess International, 2004, vol. 2, No. 11, pp. 54-56, 58-59.
Stabel, et al., "Periplasmic location of *Brucella abortus* Cu/Zn superoxide dismutase," 1994, Veterinary Microbiol. 38: 307-314.
Stauber, et al., "Development and applications of enhanced green fluorescent protein mutants." (1998) Biotechniques 24(3):462-471.
Steidler, L., et al., Mucosal Delivery of Murine Interleukin-2 (IL-2) and IL-6 by Recombinant Strains of *Lactococcus lactis* Coexpressing Antigen and Cytokine, Infection and Immunity, 1998, vol. 66, No. 7, pp. 3183-3189.
Steidler, L., In Situ Delivery of Cytokines by Genetically Engineered *Lactococcus lactis*, Antonie van Leeuwenhoek, 2002, vol. 82, pp. 323-331.
Steinbeck, M.J., et al., Activation of Bovine Neutrophils by Recombinant Interferon-γ, Cell. Immunol., 1986, vol. 98, pp. 137-144.
Stewart, Russell J., et al., Direction of Microtubule Movement is an Intrinsic Property of the Motor Dotrnins of Kinesin Heavy Chain and *Drosophila* Ned Protein, Proc. Natl. Acad. Sci., 1993, vol. 90, pp. 5209-5213.
Studier, F.W. and B.A. Moffatt, "Use of bacteriophage T7 RNA polymerase to direct selective high-level expression of cloned genes," 1986, Journal of Molecular Biology, 189(1):113-30.
Suzek, Baris E., et al., "A Probabilistic Method for Identifying Start Codons in Bacterial Genomes," Bioinformatics, 2001, vol. 17, No. 12, Oxford University Press, pp. 1123-1130.
Taguchi, et al., "Comparison of secretory expression in *Escherichia coli* and *Streptomyces subtilisin* inhibtor (SSI) gene," 1990, Biochimica Biophysica Acta 1049: 278-85.
Takara Bio Inc., Product Information Bulletin, "Chaperone Plasmid Set," pp. 1-8, Catalog #3340, Version 0401, Mar. 22, 2013.
Tanji, et al., "Controlled Expression of Lysis Genes Encoded in T4 Phage for the Gentle Disruption of *Escherichia coli* cells," 1998, J. Ferment and Bioeng., 85:74-78.
Taub, Dennis D., "Cytokine, growth factor, and chemokine ligand database," Current Protocols in Immunology, 2004, XP002677096, DOI: 10.1002/0471142735.im0629s61, [Retrieved from the Internet: URL:http://onlinelibrary.wiley.com/doi/10.1002/0471142735.im0629s61/full [retrieved on Jun. 1, 2012].
Taylor, J.W. et al., "The use of phosphorothioate-modified DNA in restriction enzyme reactions to prepare nicked DNA," 1985, Nucl. Acids Res. 13, No. 24, pp. 8749-8764.
Te Riele H., et al., "Consecutive inactivation of both alleles of the pim-1 proto-oncogene by homologous recombination in embryonic stem cells," 1990, Nature 348:649-651.
Thomas, J.G, et al., "Molecular chaperones, folding catalysts and the recovery of active recombinant proteins from *E. coli*: to fold or to refold," 1997, Appl Biochem Biotechnol 66, pp. 197-238.
Toogood, H.S., et al., "A thermostable L-aminoacylase from *Thermococcus litoralis*: cloning, overexpression, characterization, and applications in biotransformations," 2002, Extremophiles 6(2), pp. 111-122.
Tsai and Rapoport, "Unfolded cholera toxin is transferred to the ER membrane and released from protein disulfide isomerase upon oxidation by Erol," J Cell Biol 159(2):207-215 (2002).
Tsuda & Nakazawa, "A mutagenesis system utilizing a Tn1722 derivative containing an *Escherichia coli*—specific vector plasmid: application to *Pseudomonas* species," 1993, Gene 136 (1-2): 257-62.
Tsunawaki, et al., "Fungal Metabolite Gliotoxin Inhibits Assembly of the Human Respiratory Burst NADPH Oxidase," Infection and Immunity 72(6):3373-3382 (2004).
Usami, et al., "Primary structure of two-chain botrocetin, a von Willebrand factor modulator purified from the venom of *Bothrops jararaca*," PNAS USA 90:928-932 (1993).
Vad, et al., "Engineering of a *Pichia pastoris* expression system for secretion of high amounts of intact human parathyroid hormone," J Biotechnology 116:251-260 (2005).
Vale, Ronald D., et al., "Identification of a Novel Force-Generating Protein, Kinesin, Involved in Microtubule-Based Motility," Cell, Aug. 1985, vol. 42, MIT, pp. 39-50.

(56) References Cited

OTHER PUBLICATIONS

Vera, Andrea, et al., "The Conformational Quality of Insoluble Recombinant Proteins Is Enhanced at Low Growth Temperatures," Biotechnology and Engineering, Apr. 15, 2007, vol. 96, No. 6, pp. 1101-1106.

Vincentelli, Renaud, et al., "Medium-Scale Structural Genomics: Strategies for Protein Expression and Crystallization," Ace. Chem. Res., 2003, vol. 36, No. 3, pp. 165-172.

Vinogradov, Alexi A, et al., Solubilization and Refolding of Inclusion Body Proteins in Reverse Micelles, Analytical Biochemistry, 2003, Elsevier Science, pp. 234-238.

Wackemagel, et al., "The periplasmic endonuclease I of *Escherichia coli* has amino-acid sequence homology to the extracellular Dnases of *Vibrio cholerae* and *Aeromonas hydrophila*," 1995, Gene 154: 55-59.

Wall, G.J. and Pluckthun, A., "Effects of Overexpressing Folding Modulators on the in vivo Folding of Heterologous Proteins in *Escherichia coli*," Curr. Op. Biotechnol. 6:507-516 (1995).

Wan and Baneyx, "TolAIII Co-overexpression facilitates the recovery of periplasmic recombinant proteins into the growth medium of *Escherichia coli*," 1998, Protein Expression Purif. 14:3-22.

Wang, et al., 1985, "Molecular cloning of the complementary DNA for human tumor necrosis factor," Science 228 (4696), 149-154.

Waterman, Michael. S., Comparison of Biosequences, Advances in Applied Mathematics, 1981, vol. 2, Academic Press, Inc., pp. 482-489.

Wei, Y., et al., "High-density microarray-mediated gene expression profiling of *Escherichia coli*," 2001, J. Bacteriol 183(2), pp. 545-556.

Wesolowski, et al., 2009, "Single domain antibodies: promising experimental and therapeutic tools in infection and immunity," Med Microbiol Immunol. 198(3): 157-174.

Wilson, D.S., et al., "The use of mRNA display to select high-affinity protein-binding peptides," 2001, Proc Nat Acad Sci USA 98:3750-3755.

Witholt, et al., "How does lysozyme penetrate through the bacterial outer membrane?" 1976, Biochim. Biophys. Acta, 443: 534-544.

Wood, David O, et al., "Versatile Cloning Vector for *Pseudomonas aeruginosal*," Journal of Bacteriology, Mar. 1981, vol. 14, No. 3, pp. 1448-1451.

Wu, et al., "Cell-biological applications to transfected-cell microarrays," (2002) TRENDS in Cell Biology, 12(10): 485-488.

Yang, Funmei, et al., Human Transferrin: cDNA Characterization and Chromosomal Localization, Proc. Natl. Acad. Sci. USA, May 1984, vol. 81, pp. 2752-2756.

Yasuda, et al., "Osteoclast differentiation factor is a ligand for osteoprotegerin/osteoclastogenesis-inhibitory factor and is identical to TRANCE/RANKL," 1998, Proc. Natl. Acad. Sci. U.S.A. 95(7), 3597-3602.

Yilma T., et al., Enhancement of Primary and Secondary Immune Responses by Interferon-Gamma, Adv. Exp. Med. Biol., 1989, pp. 145.152, vol. 251.

Yilma, T.K., et al., Expression of an Adjuvant Gene (Interferon-y) an Infectious Vaccinia Virus Recombinants, Vaccines, 1987, vol. 87, pp. 393-396.

Yoshida, et al., "A new strategy of gene trapping in ES cells using 3'RACE," 1995, Transgenic Research 4:277-287.

Yuan, et al., "Discovery of a Distinct Superfamily of Kunitz-Type Toxin (KTT) from Tarantulas," PLoS One 3(10):e3414 (2008).

Zapata, et al., "Engineering linear F(ab')2 fragments for efficient production in *Escherichia coli* and enhanced antiproliferative activity," 1995, Protein Eng. 8(10): 1057-1062.

Zhang, et al., "Enhanced Secretion of Heterologous Proteins in *Pichia pastoris* Following Overexpression of *Saccharomyces cerevisiae* Chaperone Proteins," Biotechnol Prog 22:1090-1095 (2006).

Zhu, H. et al., "Global analysis of protein activities using proteome chips," 2001, Science Express.

Zinder and Arndt, "Production of Protoplasts of *Escherichia coli* by Lysozyme Treatment.," Proc. Mathl. Acad. Sci. USA, 1956, 42: 586-590.

Zuffa, A., et al., Protection of Cattle Vaccinated with Inactivated Oil-Adjuvant Infectious Bovine Rhino Trachetis Vaccine Against Experimental Infection, Zbl. Vet. Med. G., 1989, vol. 27, pp. 725-733.

Korean Patent Application No. 10-2007-7004418 Final Rejection dated Sep. 11, 2012.

\* cited by examiner

A. Plasmid cross-in

B. Tet resistant; FOA sensitive

C. FOA tolerant

```
                        SEQUENCE LISTING

<160> NUMBER OF SEQ ID NOS: 19

<210> SEQ ID NO 1
<211> LENGTH: 20
<212> TYPE: DNA
<213> ORGANISM: artificial sequence
<220> FEATURE:
<223> OTHER INFORMATION: Sense primer HslU gene

<400> SEQUENCE: 1
accgaagtcg gctatgtggg                                               20

<210> SEQ ID NO 2
<211> LENGTH: 20
<212> TYPE: DNA
<213> ORGANISM: artificial sequence
<220> FEATURE:
<223> OTHER INFORMATION: Antisense primer hslU gene

<400> SEQUENCE: 2
aatcgcgctg cacgccttcg                                               20

<210> SEQ ID NO 3
<211> LENGTH: 18
<212> TYPE: DNA
<213> ORGANISM: artificial sequence
<220> FEATURE:
<223> OTHER INFORMATION: forward primer hslF2

<400> SEQUENCE: 3
ttcatcaagg tcgaagcg                                                 18

<210> SEQ ID NO 4
<211> LENGTH: 17
<212> TYPE: DNA
<213> ORGANISM: artificial sequence
<220> FEATURE:
<223> OTHER INFORMATION: reverse primer hslR2

<400> SEQUENCE: 4
tcagtcttga ccatgcc                                                  17

<210> SEQ ID NO 5
<211> LENGTH: 17
<212> TYPE: DNA
<213> ORGANISM: artificial sequence
<220> FEATURE:
<223> OTHER INFORMATION: reverse primer M13R

<400> SEQUENCE: 5
caggaaacag ctatgac                                                  17

<210> SEQ ID NO 6
<211> LENGTH: 15
<212> TYPE: DNA
<213> ORGANISM: artificial sequence
<220> FEATURE:
<223> OTHER INFORMATION: forward primer M13F

<400> SEQUENCE: 6
taaaacgacg gccag                                                    15
```

<210> SEQ ID NO 7
<211> LENGTH: 20
<212> TYPE: DNA
<213> ORGANISM: artificial sequence
<220> FEATURE:
<223> OTHER INFORMATION: overlap extension primer hslUp

<400> SEQUENCE: 7
gtggcagcca ccaaggctgc                                                 20

<210> SEQ ID NO 8
<211> LENGTH: 39
<212> TYPE: DNA
<213> ORGANISM: artificial sequence
<220> FEATURE:
<223> OTHER INFORMATION: overlap extension primer hsl middle up

<400> SEQUENCE: 8
cccacattga gtgaggctta caaggggaga gtctccacg                            39

<210> SEQ ID NO 9
<211> LENGTH: 39
<212> TYPE: DNA
<213> ORGANISM: artificial sequence
<220> FEATURE:
<223> OTHER INFORMATION: overlap extension primer hsl middle down

<400> SEQUENCE: 9
cgtggagact ctccccttgt aagcctcact caatgtggg                            39

<210> SEQ ID NO 10
<211> LENGTH: 20
<212> TYPE: DNA
<213> ORGANISM: artificial sequence
<220> FEATURE:
<223> OTHER INFORMATION: overlap extension primer hsl down

<400> SEQUENCE: 10
ggccaatggt tggccacgcg                                                 20

<210> SEQ ID NO 11
<211> LENGTH: 18
<212> TYPE: DNA
<213> ORGANISM: artificial sequence
<220> FEATURE:
<223> OTHER INFORMATION: overlap extension primer hsl up up

<400> SEQUENCE: 11
tgccgacgcc acaggtgc                                                   18

<210> SEQ ID NO 12
<211> LENGTH: 18
<212> TYPE: DNA
<213> ORGANISM: artificial sequence
<220> FEATURE:
<223> OTHER INFORMATION: overlap extension primer hsl down down

<400> SEQUENCE: 12
gcctggtact gcgactcg                                                   18

<210> SEQ ID NO 13
<211> LENGTH: 42
<212> TYPE: DNA
<213> ORGANISM: artificial sequence
<220> FEATURE:

<223> OTHER INFORMATION: forward primer RC199

<400> SEQUENCE: 13
atatactagt aggaggtaac ttatggctga cgaacagacg ca                42

<210> SEQ ID NO 14
<211> LENGTH: 30
<212> TYPE: DNA
<213> ORGANISM: artificial sequence
<220> FEATURE:
<223> OTHER INFORMATION: reverse primer RC200

<400> SEQUENCE: 14
atattctaga ttacaggtcg ccgaagaagc                              30

<210> SEQ ID NO 15
<211> LENGTH: 1458
<212> TYPE: DNA
<213> ORGANISM: Pseudomonas fluorescens

<400> SEQUENCE: 15

| | | |
|---|---|---|
| atgcactttg gaaatggtt tcacaccagc accctgctgg tcggcttgag ttttgtgctg | 60 |
| ggcggctgcg ccagcgtctc ccaaacctcc accccggcaa ccctggataa gctgttgagc | 120 |
| gacccggcgc tgcaaggcgc caccgtctcg ctgatggtgc gtgatgcccg cacaggcacc | 180 |
| acgctgtatc agcacaaccc acgcaccegg ctggtgcccg cgtccaacct caagctgttg | 240 |
| accacggcgg cagccatgga tgtattgggg ccgcagtacc gcttcgccac gcaactgctg | 300 |
| agcaatggcc tacgccaggg cgaccggctg actggcaacc tgtacctgcg tggcttgggc | 360 |
| gacccgagta ttcagtttgc cgactatcag gcgctcgccg cgcaattggc cagccagggc | 420 |
| gtgcgccagg tgcagggtga cctggtgttc gacgacactt ggttcgatgc cgagcggctg | 480 |
| ggcgtggact ggtcccatga tgatgaaacc acctactacg gcgcgcagat tcagcgctg | 540 |
| accgtggcgc ccaataccga ctttgatgct ggcagcgtgc tggtcaccgc caaggcgccg | 600 |
| ttgcacgtcg gctcgccggt cggcgtggag atctacccgc ccaccgacta cctgcaactg | 660 |
| aataaccgcg ccgtcagcgg gccgggtaac agctatggga tcaaccgtcg ccatggcacc | 720 |
| aacctgctgc agctcagcgg cgcggtggcg cctggccggc agagccagca attgatcagc | 780 |
| gtgtgggagc cgacgcaact ggtgccaac ctgtttgagc aagccttggc gcagcagggc | 840 |
| atcaaggtgc tggggcgtcg ggtgatgggc ggggcaagtc ctgctggggt gacggtgctg | 900 |
| gccgagcacc aatcggcgcc gttgcaggag ctgatcgtgc cgctgctcaa gctctcgaac | 960 |
| aacgccatgt ccgaagccgt gctcaaggcc atgggccgcc agacggccag cagcggcacg | 1020 |
| gcggcggcgg gcgccgtggc ggtggccgac tttctcaagc gccagggggct ggacaccagc | 1080 |
| gctgtgagcc aagtggacgg ctccggcctg tcgcggcgta acctggtgtc gtcgcaaacc | 1140 |
| ctcaccgacc tgctgctggc ggccagcaaa caaccctggt tcgacgcctg gtacaacgcg | 1200 |
| ctgccggttg ccggcaatgc cgaccgtatg accggcggca gctgggtta ccgcctgcgc | 1260 |
| ggcacggctg cggaaaataa cctgcatgcc aagaccggct ccatggccgg cgtgtcgtca | 1320 |
| ttgagcggtt acatcaccga tgctcacggg cgcaagctgg tgttcgcgat gttgaccaac | 1380 |
| aactatgtgg tcgctggcgc gcaggtaaaa gccgtggaaa accgcgtcgc cgtggccctg | 1440 |
| tcccacagcg aagactga | 1458 |

<210> SEQ ID NO 16
<211> LENGTH: 1491

<212> TYPE: DNA
<213> ORGANISM: pseudomonas fluorescens

<400> SEQUENCE: 16

```
atgagtgatc gcaaaaacag ccgcctgatc ctgcccggcc tgatcgccgt caccctgatg      60
gcggccagcg ccgtttactt cttgcgcccc agcgagtcgg tcgccagcca ggccctggac     120
aaggctcaaa cggccagcac cctgcaatcc ctggcggaac tggatggcaa ggcaccgacc     180
aaccgcaagc tcgacgtaca aacctggacc accgccgaag gcgccaaggt gctgttcgtc     240
gaagcccatg agttgccgat gttcgacatg cgcctgctgt cgccgccgg cagcagccag      300
gatggcgacg tgccaggcct ggcgctgatg accaacgcca tgctcaacga aggcgtgccg     360
ggcaaggacg tcagccagat cgccagtggc ttcgaaggcc tggggccga ctttggcaac      420
ggcgcctacc gcgacatggc gctggtgacc ctgcgcagcc tgagcgacag cgccaagcgc     480
gacgccgccc tgtcactgtt caaccaggtg atcggccagc cgactttccc ggcagactca     540
ctggcacgca tcaagaacca gatcctggcc ggtttcgagt accagaagca gaaccccggc     600
aaactggcga gcatcgaact gttcaagcgc ctgtacggcg accaccctta cgcacacccg     660
agcgaaggca cccccgagag cgtgccgaag attaccctgg cgcagttgca ggcgttccac     720
gccaaggcct atgcagcggg taacgcggtg attgcagtgg tgggcgacct gacccgcgcc     780
gaagctgaag ccatgacggc caaggtgtcc gcgtcgctgc caaaggccc ggctatggcc      840
aagatcgccc agccgaccga ccaaaagcc ggcctgagcc gtatcgagtt cccgtccaag      900
caaacccacc tgctgtttgc gcagttgggc atcgaccgtg ccgacccgga ttacgcagcc     960
ttgtccctgg gtaaccagat cctcggcggc ggtggcttcg gcacccgctt gatgagcgaa    1020
gtgcgtgaaa agcgcggcct gacctacggc gtgtattccg gtttctcacc aatgcaggcg    1080
cgcggcccgt tcatgatcaa cctgcagacc cgcgccgaaa tgagcggtgg caccttgcgc    1140
ctggtggagg acgtactggc tgactacctc aagaccggcc gacgcaaaa ggaactggat     1200
gacgccaagc gcgagctggc cggcagcttc ccgctgtcca ccgccagcaa cgccgatatc    1260
gtcgggcagt tgggcgccat gggttttctac aacctgccgc tgagctatct ggaagatttc    1320
atgaaacaat cccaggccct gaccgtcgat caggtcaagg ctgcaatgaa taaacacttg    1380
agcgccgaca agatggtcat cgtgaccgcc ggcccgacga ttgcgcaaaa gccactaccg    1440
cccccactg ataaacctgc cgagcagccg ctcggggttc cggagcatta a             1491
```

<210> SEQ ID NO 17
<211> LENGTH: 1110
<212> TYPE: DNA
<213> ORGANISM: pseudomonas fluorescens

<400> SEQUENCE: 17

```
ttgtcgtgga ttgacgcttt cggcaattcc cctgtcgttt ttgcacccgg ctccgtcggt      60
gcctgggcat atgctggccc caaagcgccg gcagacgatt cggcgcatga atcgccaata     120
agggacgcc tgatgagccc agccgagttg cacgccgaca gcatcgttat cgacggtctg      180
attattgcca agtggaaccg cgacctgttc gaagacatgc gcaaaggtgg cctcaccgcc     240
gccaattgca cggtgtcggt gtgggaaggc ttccaggcca cgatcaataa catcgttgcc     300
agccagaccc tgatccgcga aaacagcgac ctggtgatcc cggtgaaaac caccgccgac     360
atccgccgcg ccaaggagct gggcaagact ggcatcatct tcggcttcca gaatgcccat     420
gcctttgagg accagctcgg ctatgtcgag atcttcaagc agctcggcgt gggcgtggtg    480
```

| | |
|---|---|
| cagatgtgct acaacaccca gaacctggtg ggcaccggtt gctacgagcg cgatggcggc | 540 |
| ctgtcgggtt tcgggcgtga gatcgtcggc gagatgaacc gcgtcggcat catgtgcgac | 600 |
| ctgtcccacg tgggctccaa gaccagcgaa gaggtcatcc tcgaatcgaa aaagccggtg | 660 |
| tgctactccc actgtctgcc gtccgggctt aaagagcacc cgcgcaacaa gtccgatgaa | 720 |
| gagctgaagt tcatcgccga ccatggcgga tttgtcggtg tgaccatgtt cgcgccgttt | 780 |
| ttggccaagg gcatcgactc gactatcgac gactatgccg aagccatcga atacaccatg | 840 |
| aacatcgtcg gcgaagacgc catcggcatc ggcaccgact tcacccaggg ccatggccag | 900 |
| gatttcttcg aaatgctcac cctgacaag gctacgccc gccgcctgac cagcttcggc | 960 |
| aagatcatca acccgctggg catccgcacc gtgggtgagt tccccaacct caccgagacc | 1020 |
| ctgctcaagc gcggccacag cgagcgcgtg gtgcgcaaga tcatgggcga gaactgggtc | 1080 |
| aacgtgctca aggacgtctg gggcgaataa | 1110 |

<210> SEQ ID NO 18
<211> LENGTH: 1149
<212> TYPE: DNA
<213> ORGANISM: pseudomonas fluorescens

<400> SEQUENCE: 18

| | |
|---|---|
| atgacaattt ggcccagggg gcgaacacag ggctatcctg aaaaccgtta cccggacgtt | 60 |
| caccacacgc caaaaggag ccagctcatg tgtgttcgcc aaccgcgcaa cccgatttt | 120 |
| tgcctgatcc cgccgtacat gctcgaccag atcgcacgcc acggcgacaa agcccaacgg | 180 |
| gaagtcgcat tacgcacgcg tgccaaggac agcacgtttc gttcgttgcg catggtcgcg | 240 |
| gtaccgcca aggggccggc ccgcatggca ctggccgtgg gcgccgagaa gcaacgctcg | 300 |
| atctacagtg ccgaaaacac cgacagcctg cccggcaagc tgatccgcgg cgaagggcag | 360 |
| cccgccagtg gcgatgccgc ggtggacgaa gcctatgacg gcctgggcgc gaccttcgat | 420 |
| tttttgacc aggtctttga tcgcaattcc atcgacgatg cgggcatggc gctgacgcc | 480 |
| acggtgcact tcggccagga ctacaacaat gcgttctgga attcgaccca gatggtgttc | 540 |
| ggcgatggcg accagcagtt gttcaaccgc tttaccgtgg cactcgacgt cattgggcat | 600 |
| gagttggccc atggcgtgac tgaggatgag gccaagctga tgtacttcaa ccagtccggt | 660 |
| gcgctgaacg agtcgttgtc ggacgtgttc ggttcgctga tcaagcagta cgcgttaaag | 720 |
| caaacggccg aggatgccga ctggttgatc ggcaaggggt tgtttaccaa aaagatcaag | 780 |
| ggcacggcg tgcgctcgat gaaggcgcca ggcactgcgt tgatgacaa gctgctgggc | 840 |
| aaagacccgc agcctgggca catggatgat tttgtgcaaa cttacgagga caatgggggc | 900 |
| gtgcatatca attccggcat tcccaaccat gcgttctacc aggtggcgat caatataggc | 960 |
| gggttcgcct gggagcgtgc cgggcgtatc tggtatgacg cactgcgcga ttcgcggttg | 1020 |
| cggcccaatt ccgggttctt gcgttttgcg cgcattaccc acgatattgc cggccagctt | 1080 |
| tatgcgtga acaaagctga gcagaaggca gtcaaggaag ctggaaagc ggtgggcata | 1140 |
| aacgtttga | 1149 |

<210> SEQ ID NO 19
<211> LENGTH: 1920
<212> TYPE: DNA
<213> ORGANISM: pseudomonas fluorescens

<400> SEQUENCE: 19

| | |
|---|---|
| ttgaacgata tggcaaagaa tctgatcctg tggttgatca tcgcggctgt cctggtgacg | 60 |

-continued

```
gtgatgaaca acttctccag ccctaacgag ccgcagaccc tcaactattc cgacttcatc    120
cagcaagtta aggatggcaa ggtcgagcgc gtagcggttg atggctacgt gattaccggt    180
aagcgcaacg atggcgacag cttcaagacc attcgtcctg ccattcagga caacggtctc    240
atcggtgacc tggtggataa caaggtcgtt gtggaaggca agcagcctga acagcaaagc    300
atctggaccc agctcctggt ggccagcttc ccgatcctgg tgattatcgc cgtgttcatg    360
ttcttcatgc gccagatgca aggcggtgcg ggaggcaagg gcgggccgat gagcttcggc    420
aaaagcaagg cgcgcctgct ctccgaagac caggtgaaga ccaccctggc tgacgtcgca    480
ggttgcgacg aagccaagga agaagtcggt gagttggtcg agttcctgcg tgatcccggc    540
aagttccagc gcctgggtgg ccgtattcct cgcggtgtgc tgatggtggg gcctccgggt    600
accggtaaaa ccttgctggc caaggcgatt gccggcgaag ccaaggtgcc tttcttcacg    660
atttccggtt ctgacttcgt cgagatgttt gtcggcgtcg gcgccagccg tgttcgcgat    720
atgttcgagc aggccaagaa gcacgcgcca tgcatcatct tcatcgacga aatcgatgcc    780
gttggtcgcc atcgtggcgc gggcatgggg ggtggtcacg atgagcgtga gcagaccctc    840
aaccagttgc tggtagagat ggatggtttc gagatgaatg acggcattat cgtcatcgcc    900
gcaaccaacc gtcccgacgt tctcgaccct gcgttgctgc gtccgggccg tttcgaccgt    960
caggttgtgg tcggcctgcc ggacattcgt ggtcgtgagc agatcctgaa agtacacatg   1020
cgcaaggtgc caatgggtga cgacgtggct ccggctgtga tcgcccgtgg tactcccggt   1080
ttctccggtg ctgatctggc gaacctggtc aacgaggctt cgctgttcgc tgcccgtact   1140
ggcaagcgca tcgttgagat gaaagagttc gaattggcga agacaagat catgatgggc    1200 gccgagcgca aatccatggt catgtccgag aaagagaagc agaacaccgc ttatcacgag   1260
gccggtcacg ccattgtagg tcgcgttgtg cctgagcatg accccgtcta caaagtgtcg   1320
atcattcctc gtggtcgggc actgggtgtg accatgttcc tgccggaaga agatcgctac   1380
agcctctcca agcgtgcgct gatcagccag atctgctcgc tgtatggcgg tcgtattgct   1440
gaggaaatga cccttggctt cgacggtgtg accactggtg cctccaatga catcatgcgt   1500
gccagccaga tcgcacgaaa catggtgacc aagtgggct tgtcggaaaa actcggccca    1560
ttgatgtacg ccgaagagga aggcgaagtg ttcctggggc gtggcggcgg tgggcaaagc   1620
gccagcttct cgggtgagac agccaagctg atcgactccg aagttcgcag catcattgac   1680
cagtgctatg gcacggccaa gcagattttg actgacaacc gtgacaagct ggacgccatg   1740
gctgatgcgt tgatgaagta cgaaaccatc gatgccgacc agatcgacga catcatggcg   1800
ggccgtacgc cgcgtgagcc gcgcgactgg gaaggtggtt cgggtacttc gggcactccg   1860
cctgtggtgc agaatgagcg ccctgaaacg cctatcggcg gcccggcagc tgatcactaa   1920
```

PROCESS FOR IMPROVED PROTEIN EXPRESSION BY STRAIN ENGINEERING

CROSS-REFERENCE

This application is a continuation application of Ser. No. 11/189,375, filed Jul. 26, 2005, which claims the benefit of U.S. Provisional Application No. 60/591,489, filed Jul. 26, 2004, each of which is incorporated herein by reference in its entirety and to which application we claim priority under 35 USC §120.

FIELD OF THE INVENTION

This invention is in the field of protein production, and in particular is a process for improving the production levels of recombinant proteins or peptides or improving the level of active recombinant proteins or peptides expressed in host cells.

BACKGROUND OF THE INVENTION

More than 155 recombinantly produced proteins and peptides have been approved by the U.S. Food and Drug Administration (FDA) for use as biotechnology drugs and vaccines, with another 370 in clinical trials. Unlike small molecule therapeutics that are produced through chemical synthesis, proteins and peptides are most efficiently produced in living cells. In many cases, the cell or organism has been genetically modified to produce or increase the production of the protein.

When a cell is modified to produce large quantities of a target protein, the cell is placed under stress and often reacts by inducing or suppressing other proteins. The stress that a host cell undergoes during production of recombinant proteins can increase expression of, for example, specific proteins or cofactors to cause degradation of the overexpressed recombinant protein. The increased expression of compensatory proteins can be counterproductive to the goal of expressing high levels of active, full-length recombinant protein. Decreased expression or lack of adequate expression of other proteins can cause misfolding and aggregation of the recombinant protein. While it is known that a cell under stress will change its profile of protein expression, it is not known in any given example which specific proteins will be upregulated or down-regulated.

Microarrays

Microarray technology can be used to identify the presence and level of expression of a large number of polynucleotides in a single assay. See for eg. U.S. Pat. No. 6,040,138, filed Sep. 15, 1995, U.S. Pat. No. 6,344,316, filed Jun. 25, 1997, U.S. Pat. No. 6,261,776, filed Apr. 15, 1999, U.S. Pat. No. 6,403,957, filed Oct. 16, 2000, U.S. Pat. No. 6,451,536, filed Sep. 27, 2000, U.S. Pat. No. 6,532,462, filed Aug. 27, 2001, U.S. Pat. No. 6,551,784, filed May 9, 2001, U.S. Pat. No. 6,420,108, filed Feb. 9, 1998, U.S. Pat. No. 6,410,229, filed Dec. 14, 1998, U.S. Pat. No. 6,576,424, filed Jan. 25, 2001, U.S. Pat. No. 6,687,692, filed Nov. 2, 2000, U.S. Pat. No. 6,600,031, filed Apr. 21, 1998, and U.S. Pat. No. 6,567,540, filed Apr. 16, 2001, all assigned to Affymetrix, Inc.

U.S. Pat. No. 6,607,885 to E. I. duPont de Nemours and Co. describes methods to profile and identify gene expression changes after subjecting a bacterial cell to expression altering conditions by comparing a first and second microarray measurement.

Wei et al. used a microarray analysis to investigate gene expression profiles of *E. coli* with lac gene induction (Wei Y., et al. (2001) High-density microarray-mediated gene expression profiling of *Escherichia coli*. *J Bacteriol*. 183(2):545-56). Other groups have also investigated transcriptional profiles regulated after mutation of endogenous genes or deletion of regulatory genes (Sabina, J. et al (2003) Interfering with Different Steps of Protein Synthesis Explored by Transcriptional Profiling of *Escherichia coli* K-12 *J Bacteriol*. 185: 6158-6170; Lee J H (2003) Global analyses of transcriptomes and proteomes of a parent strain and an L-threonine-overproducing mutant strain. *J Bacteriol*. 185(18):5442-51; Kabir M M, et al. (2003) Gene expression patterns for metabolic pathway in pgi knockout *Escherichia coli* with and without phb genes based on RT-PCR *J Biotechnol*. 105(1-2):11-31; Eymann C., et al. (2002) *Bacillus subtilis* functional genomics: global characterization of the stringent response by proteome and transcriptome analysis. *J Bacteriol*. 184(9):2500-20).

Gill et al. disclose the use of microarray technology to identify changes in the expression of stress related genes in *E. coli* after expression of recombinant chloramphenicol acetyltransferase fusion proteins (Gill et al. (2001) Genomic Analysis of High-Cell-Density Recombinant *Escherichia coli* Fermentation and "Cell Conditioning" for Improved Recombinant Protein Yield *Biotech. Bioengin.* 72:85-95). The stress gene transcription profile, comprising only 16% of the total genome, at high cell density was used to evaluate "cell conditioning" strategies to alter the levels of chaperones, proteases, and other intracellular proteins prior to recombinant protein overexpression. The strategies for "conditioning" involved pharmacological manipulation of the cells, including through dithiothreitol and ethanol treatments.

Asai et al. described the use of microarray analysis to identify target genes activated by over-expression of certain sigma factors that are typically induced after cell stresses (Asai K., et al. (2003) DNA microarray analysis of *Bacillus subtilis* sigma factors of extracytoplasmic function family. *FEMS Microbial. Lett.* 220(1):155-60). Cells overexpressing sigma factors as well as reporter genes linked to sigma factor promoters were used to show stress regulated gene induction.

Choi et al. described the analysis and up-regulation of metabolic genes that are down-regulated in high-density batch cultures of *E. coli* expressing human insulin-like growth factor fusion protein (IGF-$I_f$) (Choi et al. (2003) Enhanced Production of Insulin-Like Growth Factor I Fusion Protein in *Escherichia coli* by Coexpression of the Down-Regulated Genes Identified by Transcriptome Profiling *App. Envir. Microbio.* 69:4737-4742). The focus of this work was on the metabolic changes that occur during high-density conditions after protein induction. Genes that were down regulated after induction of recombinant protein production during high density growth conditions were identified and specific metabolic genes that had been down-regulated were expressed in cells producing recombinant IGF-$I_f$. The work showed that increasing metabolic production of certain nucleotide bases and amino acids could increase protein production and that growth rates could be modified by increasing expression of a down-regulated metabolic transporter molecule. These strategies were designed to alter the cellular environment to reduce metabolic stresses associated with the protein production generally or with high density culture.

Protein Degradation

Unwanted degradation of recombinant protein presents an obstacle to the efficient use of certain expression systems. The expression of exogenous proteins often induces stress responses in host cells, which can be, for example, natural defenses to a limited carbon source. All cells contain a large number of genes capable of producing degradative proteins. It is not possible to predict which proteases will be regulated by a given host in response to expression of a particular recombinant protein. For example, the bacteria *P. fluorescens* contains up to 200 proteases and protease related proteins.

In the cytoplasm of *E. coli*, proteolysis is generally carried out by a group of proteases and cofactor molecules. Most early degradation steps are carried out by five ATP-dependent Hsps: Lon/La FtsH/HflB, ClpAP, ClpXP, and ClpYQ/HslUV (Gottesman S (1996), Proteases and their targets in *Escherichia coli. Annu. Rev. Genet.* 30:465-506). Along with FtsH (an inner membrane-associated protease the active site of which faces the cytoplasm), ClpAP and ClpXP are responsible for the degradation of proteins modified at their carboxyl termini by addition of the non-polar destabilizing tail (Gottesman S, et al. (1998). The ClpXP and ClpAP proteases degrade proteins with carboxyl-terminal peptide tails added by the SsrA-tagging system. *Genes Dev.* 12:1338-1347; Herman C, et al. (1998) Degradation of carboxy-terminal-tagged cytoplasmic proteins by the *Escherichia coli* protease HflB (FtsH). *Genes Dev.* 12:1348-1355).

Several approaches have been taken to avoid degradation during recombinant protein production. One approach is to produce host strains bearing mutations in a protease gene. Baneyx and Georgiou, for example, utilized a protease-deficient strain to improve the yield of a protein A-β-lactamase fusion protein (Baneyx F, Georgiou G. (1991) Construction and characterization of *Escherichia coli* strains deficient in multiple secreted proteases: protease III degrades high-molecular-weight substrates in vivo. *J Bacteriol* 173: 2696-2703). Park et al. used a similar mutational approach to improve recombinant protein activity 30% compared with the parent strain of *E. coli* (Park S. et al. (1999) Secretory production of recombinant protein by a high cell density culture of a protease negative mutant *Escherichia coli* strain. *Biotechnol. Progr.* 15:164-167). U.S. Pat. Nos. 5,264,365 and 5,264,365 describe the construction of protease-deficient *E. coli*, particularly multiply protease deficient strains, to produce proteolytically sensitive polypeptides. PCT Publication No. WO 90/03438 describes the production of strains of *E. coli* that include protease deficient strains or strains including a protease inhibitor. Similarly, PCT Publication No. WO 02/48376 describes *E. coli* strains deficient in proteases DegP and Prc.

Protein Folding

Another major obstacle in the production of recombinant proteins in host cells is that the cell often is not adequately equipped to produce either soluble or active protein. While the primary structure of a protein is defined by its amino acid sequence, the secondary structure is defined by the presence of alpha helixes or beta sheets, and the ternary structure by covalent bonds between adjacent protein stretches, such as disulfide bonds. When expressing recombinant proteins, particularly in large-scale production, the secondary and tertiary structure of the protein itself is of critical importance. Any significant change in protein structure can yield a functionally inactive molecule, or a protein with significantly reduced biological activity. In many cases, a host cell expresses folding modulators (FMs) that are necessary for proper production of active recombinant protein. However, at the high levels of expression generally required to produce usable, economically satisfactory biotechnology products, a cell often can not produce enough native folding modulator or modulators to process the recombinant protein.

In certain expression systems, overproduction of exogenous proteins can be accompanied by their misfolding and segregation into insoluble aggregates. In bacterial cells these aggregates are known as inclusion bodies. In *E. coli*, the network of folding modulators/chaperones includes the Hsp70 family. The major Hsp70 chaperone, DnaK, efficiently prevents protein aggregation and supports the refolding of damaged proteins. The incorporation of heat shock proteins into protein aggregates can facilitate disaggregation. However, proteins processed to inclusion bodies can, in certain cases, be recovered through additional processing of the insoluble fraction. Proteins found in inclusion bodies typically have to be purified through multiple steps, including denaturation and renaturation. Typical renaturation processes for inclusion body targeted proteins involve attempts to dissolve the aggregate in concentrated denaturant and subsequent removal of the denaturant by dilution. Aggregates are frequently formed again in this stage. The additional processing adds cost, there is no guarantee that the in vitro refolding will yield biologically active product, and the recovered proteins can include large amounts of fragment impurities.

One approach to reduce protein aggregation is through fermentation engineering, most commonly by reducing the cultivation temperature (see Baneyx F (1999) In vivo folding of recombinant proteins in *Escherichia coli*. In *Manual of Industrial Microbiology and Biotechnology*, Ed. Davies et al. Washington, D.C.: American Society for Microbiology ed. 2:551-565 and references therein). The more recent realization that in vivo protein folding is assisted by molecular chaperones, which promote the proper isomerization and cellular targeting of other polypeptides by transiently interacting with folding intermediates, and by foldases, which accelerate rate-limiting steps along the folding pathway, has provided additional approaches combat the problem of inclusion body formation (see for e.g. Thomas J G et al. (1997). Molecular chaperones, folding catalysts and the recovery of active recombinant proteins from *E. coli*: to fold or to refold. *Appl Biochem Biotechnol*, 66:197-238).

In certain cases, the overexpression of chaperones has been found to increase the soluble yields of aggregation-prone proteins (see Baneyx, F. (1999) Recombinant Protein Expression in *E. coli Curr. Opin. Biotech.* 10:411-421 and references therein). The process does not appear to involve dissolution of preformed recombinant inclusion bodies but is related to improved folding of newly synthesized protein chains. For example, Nishihara et al. coexpressed groESL and dnaJK/grpE in the cytoplasm to improve the stability and accumulation of recombinant Cryj2 (an allergen of Japanese cedar pollen) (Nishihara K, Kanemori M, Kitagawa M, Yanagi H, Yura T. 1998. Chaperone coexpression plasmids: differential and synergistic roles of DnaK-DnaJ-GrpE and GroEL-GroES in assisting folding of an allergen of Japanese cedar pollen, Cryj2, in *Escherichia coli. Appl. Environ. Microbiol.* 64:1694). Lee and Olins also coexpressed GroESL and DnaK and increased the accumulation of human procollagenase by tenfold (Lee S, Olins P. 1992. Effect of overproduction of heat shock chaperones GroESL and DnaK on human procollagenase production in *Escherichia coli. JBC* 267:2849-2852). The beneficial effect associated with an increase in the intracellular concentration of these chaperones appears highly dependent on the nature of the overproduced protein, and success is by no means guaranteed.

A need exists for processes for development of host strains that show improved recombinant protein or peptide production, activity or solubility in order to reduce manufacturing costs and increase the yield of active products.

It is therefore an object of the invention to provide processes for improving recombinant protein expression in a host.

It is a further object of the invention to provide processes that increase expression levels in host cells expressing recombinant proteins or peptides.

It is another object of the invention to provide processes to increase the levels of soluble protein made in recombinant expression systems.

It is yet another object of the invention to provide processes to increase the levels of active protein made in recombinant expression systems.

SUMMARY

A process is provided for improving the expression of a recombinant protein or peptide comprising:
  i) expressing the recombinant protein or peptide in a host cell;
  ii) analyzing a genetic profile of the cell and identifying one or more endogenous gene products that are up-regulated upon expression or overexpression of the recombinant protein or peptide; and
  iii) changing expression of one or more identified endogenous gene products by genetically modifying the cell.

The process can provide improved expression as measured by improved yields of protein, or can improve the recovery of active protein, for example by increasing solubility of the expressed recombinant protein, or a related protein or peptide.

Using this process, it can be determined which of the many cellular proteins are "chosen" by the cell to compensate for the expression of the foreign recombinant protein, and this information can lead to development of more effective protein expression systems. For example, it is known that, typically, a cell will selectively upregulate one or more proteases to degrade an overexpressed recombinant protein. However, it cannot be predicted in advance which protease(s) the cell will upregulate to compensate for the stress caused by any given recombinant protein. Analysis of the cell's genetic profile by microarray or equivalent technology can identify which proteases are upregulated in a given cell in response to exogenous protein production. This information is then used to genetically modify the cell to decrease the expression of these particular proteases, while sparing other proteins that are useful or even necessary for cell homeostasis.

As another example, a cell may selectively upregulate one or more folding modulators or cofactors to increase the folding capability or solubility of the recombinant protein. Again, it cannot be predicted in advance which folding modulators or cofactors will be selected in a given system to assist in the processing of a specific recombinant protein. Analyzing the genetic profile by microarray or equivalent technology allows identification of the folding modulators or cofactors that have been upregulated. Based on this information, the cell is genetically modified to increase the expression of the selected folding modulators or cofactors preferred by the cell for the given recombinant protein. This modification can increase the percent of active protein recovered, while minimizing the detrimental impact on cell homeostasis.

Therefore, the yield and/or activity and/or solubility of the recombinant protein can be increased by modifying the host organism via either increasing or decreasing the expression of a compensatory protein (i.e. a protein that is upregulated in response to given cell stress) in a manner that is selective and that leaves whole other beneficial mechanisms of the cell.

The process can be used iteratively until the expression of active recombinant protein is optimized. For example, using the process described above, the host cell or organism is genetically modified to upregulate, down regulate, knock-in or knock-out one or more identified compensatory proteins. The host cell or organism so modified can then be cultured to express the recombinant protein, or a related protein or peptide, and additional compensatory proteins identified via microarray or equivalent analysis. The modified host cell or organism is then again genetically modified to upregulate, down regulate, knock-in or knock-out the additional selected compensatory proteins. This process can be iterated until a host cell or organism is obtained that exhibits maximum expression of active and/or soluble protein without undue weakening of the host organism or cell. These steps for example can be repeated for example, one, two, three, four, five, six, seven, eight, nine, or ten or more times.

In another embodiment, the process further comprises: iv) expressing the recombinant protein or peptide in a genetically modified cell. In yet another embodiment, the process further comprises: v) analyzing a second genetic profile of the genetically modified cell expressing recombinant protein or peptide and identifying one or more additional gene products that are differentially expressed in the modified cell expressing recombinant protein or peptide. In a further embodiment, the process additionally comprises: vi) changing the expression of one or more identified additional gene products to provide a double modified cell. Optionally, the recombinant protein or peptide, or a related protein or peptide, can be expressed in the double modified cell. The differentially regulated gene products identified in the modified cell can be up- or down-regulated when compared to the host cell or when compared to the modified cell not expressing recombinant protein or peptide.

In yet another embodiment, the process further comprises: iv) analyzing a second genetic profile of a genetically modified cell expressing recombinant protein or peptide and identifying one or more additional gene products that are differentially expressed in the modified cell that is not expressing recombinant protein or peptide. In a further embodiment, the process additionally comprises: v) changing the expression of one or more additional identified gene products in the modified cell to provide a double modified cell. The differentially regulated gene products identified in the modified cell can be up- or down-regulated when compared to the host cell or organism or when compared to the modified cell not expressing recombinant protein or peptide.

In one specific embodiment, a process is provided for improving the expression of a recombinant protein or peptide comprising: i) expressing the recombinant protein or peptide in a host cell; ii) analyzing a genetic profile of the cell and identifying at least one protease that is up-regulated when the recombinant protein or peptide is expressed; and iii) changing expression of an identified protease by genetically modifying the host cell or organism to reduce the expression of the upregulated protease. In a further embodiment, the process comprises changing the expression of at least a second identified protease in the modified cell to provide a double protease modified cell. In another embodiment, the process further comprises: iv) expressing the recombinant protein or peptide, or a related protein or peptide, in a protease modified cell. In another embodiment, the process further comprises analyzing a second genetic profile of the protease modified cell to identify one or more additional gene products that are differentially expressed in the modified cell.

In another embodiment, a process is provided for improving the expression of a recombinant protein or peptide comprising: i) expressing the recombinant protein or peptide in a host cell; ii) analyzing a genetic profile of the cell and identifying at least one up-regulated folding modulator (FM) that is up-regulated after overexpression of the recombinant protein or peptide; and iii) changing expression of at least one identified folding modulator by genetically modifying the cell to provide a FM modified cell. In a further embodiment, the process comprises changing the expression of at least a second identified folding modulator in the modified cell to provide a double FM modified cell. In another embodiment, the process further comprises: iv) expressing the recombinant protein or peptide, or a related protein or peptide, in a FM modified cell. In another embodiment, the process further comprises analyzing a second genetic profile of the FM modified cell to identify one or more additional gene products that are differentially expressed in the modified cell.

The term "genetic profile" as used herein is meant to include an analysis of genes in a genome, mRNA transcribed from genes in the genome (or the equivalent cDNA), transcription products that have been modified by a cell such as splice variants of genes in eukaryotic systems, or proteins or peptides translated from genes in a genome, including proteins that are modified by the cell or translated from splice variants of mRNA translated from the genome. A genetic profile is meant to include more than one gene or gene product, and typically includes a group of at least 5, 10, 50, 100 or more genes or gene products that are analyzed.

In one embodiment, the genetic profile analyzed can be a transcriptome profile, i.e. a profile of the transcription products of genes from the genome. The process can include analyzing the transcriptome profile using a microarray or equivalent technology. In this embodiment, the microarray can include binding partners to at least a portion of the transcriptome of the host cell, and typically includes samples from binding partners to gene products of at least 50% of the genome of the organism. More typically, the microarray includes samples from at least 80%, 90%, 95%, 98%, 99% or 100% of the binding partners to gene products in the genome of the host cell.

In a separate embodiment, the microarray can include a selected subset of binding partners to genes or gene products which represent classes of products that are affected by the recombinant protein expression. Nonlimiting examples include putative or known proteases, co-factors of proteases or protease-like proteins; folding modulators, co-factors of folding modulators or proteins that may improve protein folding or solubility; transcription factors; proteins involved in nucleic acid stability or translational initiation; kinases; extracellular or intracellular receptors; metabolic enzymes; metabolic cofactors; envelope proteins; sigma factors; membrane bound proteins; transmembrane proteins; membrane associated proteins and housekeeping genes. The genetic profile can be analyzed by measuring the binding of the expressed genes of the host cell expressing the recombinant protein or peptide to the microarray. The transcriptome profile can also be analyzed using non-microarray assays such as blot assays, including northern blot assays, or columns coated with binding partners.

In another embodiment, the genetic profile analyzed can be a proteome profile, i.e. a profile of the proteins produced from genes in a given organism. The process can include analyzing the proteome profile using, for example, two-dimensional electrophoresis. Techniques like mass spectrometry in combination with separation tools such as two-dimensional gel electrophoresis or multidimensional liquid chromatography, can also be used in the process. In two dimensional electrophoresis, the proteins separated can include proteins from at least 10% of the proteome of the organism. More typically, proteins from at least 20%, 30%, 40%, 60%, 80% or 90% of the proteins in the proteome of the host cell are separated and analysed by techniques such as staining of proteins and/or mass spectrometry.

In additional embodiment, the proteome profile is analyzed using mass spectrometry. There are several related techniques that use liquid chromatography (LC) coupled to mass spectrometry (MS) and tandem mass spectrometry (MS/MS) to identify proteins and measure their relative abundance. Often, one sample is labeled with a heavy-isotope tag that allows for comparison to another sample without changing the chemical properties. For example, in one sample the amino acid cysteine can be labeled with a tag containing eight hydrogen atoms. The other sample is labeled with a tag that contains eight deuterium ("heavy") atoms instead (+8 Daltons). MS data can be used to find pairs of peptides 8 Daltons apart and quantitate the difference. MS/MS data from the same peptides provides an approximation of primary sequence, and the protein ID. Other experiments label the proteins in vivo by growing cells with "heavy" amino acids. These types of techniques can be used to identify thousands of proteins in a single experiment and estimate relative abundance if present in both samples (see Goodlett D R and Aebersold R H (2001). Mass Spectrometry in Proteomics. Chem. Rev 101:269-295). ICAT is a type of MS/MS, it stands for Isotope Coded Affinity Tags (see Gygi S P, Rist B, Gerber S A, Turecek F, Gelb M H, and Aebersold R H (1999). Quantitative analysis of complex protein mixtures using isotope-coded affinity tags. Nat Biotech 17:994-999).

In another embodiment, the process can include analyzing the proteome profile using, for example, a microarray. In this embodiment, the array can include binding partners to at least a portion of the proteins expressed by the host cell under appropriate growth conditions, and typically includes binding partners to proteins from at least 10% of the proteome of the organism. More typically, the microarray includes binding partners to proteins from at least 20%, 30%, 40%, 60%, 80% or 90% of the proteins in the proteome of the host cell. The binding partners can be antibodies, which can be antibody fragments such as single chain antibody fragments. In a separate embodiment, the microarray can include binding partners for a selected subset of proteins from the proteome, including, for example, putative protease proteins or putative folding modulators. The microarray can typically also include a set of binding partners to proteins that are used as controls. The genetic profile can be analyzed by measuring the binding of the proteins of the host cell expressing the recombinant protein or peptide to the binding partners on the microarray. The proteome profile can also be analyzed in a standard assay format, such as an Elisa assay or a standard western blot assay.

The samples in the genetic profile can be analyzed individually or grouped into clusters. The clusters can typically be grouped by similarity in gene expression. In particular embodiments, the clusters can be grouped as genes that are upregulated to a similar extent or genes that are down-regulated to a similar extent.

The identified up-regulated gene is typically identified by comparing a genetic profile of the host cell expressing the recombinant protein or peptide to a genetic profile of the host cell not expressing the recombinant protein or peptide. In a further embodiment, a host cell expressing a protein homologous to the first recombinant protein is analyzed.

The genome of the host cell expressing the recombinant protein or peptide can be modified by recombination, for example homologous recombination or heterologous recombination. The genome can also be modified by mutation of one or more nucleotides in an open reading frame encoding a gene, particularly an identified protease. In another embodiment, the host cell is modified by including one or more vectors that encode an inhibitor of an identified gene or gene product, such as a protease inhibitor. In another embodiment, the host cell is modified by inhibition of a promoter, which can be a native promoter. In a separate embodiment, the host cell is modified by including one or more vectors that encode a gene, typically a folding modulator or a cofactor of a folding modulator. In another embodiment, the host cell is modified by enhancing a promoter for an identified folding modulator or a cofactor for a folding modulator, including by adding an exogenous promoter to the host cell genome.

The host cell can be any cell capable of producing recombinant protein or peptide. In one embodiment, the host cell is a prokaryote, such as a bacterial cell including, but not limited to an *Escherichia* or a *Pseudomonas* species. The host cell may be a Pseudomonad cell such as a *P. fluorescens* cell. In other embodiments, the host cell is an *E. coli* cell. In another embodiment the host cell is a eukaryotic cell, for example an insect cell, including but not limited to a cell from a *Spodoptera, Trichoplusia Drosophila* or an *Estigmene* species, or a mammalian cell, including but not limited to a murine cell, a hamster cell, a monkey, a primate or a human cell. In another embodiment, the host cell is a plant cell, including, but not limited to, a tobacco cell, corn, a cell from an *Arabidopsis* species, potato or rice cell. In another embodiment, a whole organism is analyzed in the process, including but not limited to a transgenic organism.

In one embodiment, the identified upregulated compensatory genes or gene products are one or more proteases and/or one or more folding modulators. In certain embodiments, an identified gene or gene product can also be a subunit of a protease or a folding modulator or a cofactor of a protease or a cofactor of a folding modulator. In one embodiment, the identified gene can be selected from a serine, threonine, cysteine, aspartic or metallo peptidase. In certain other embodiments, the identified gene or gene product can be selected from hslV, hsIU, clpA, clpB and clpX The identified gene or gene product can also be a cofactor of a protease. In another embodiment, the identified gene or gene product is a folding modulator. In certain embodiments, the identified gene or gene product can be selected from a chaperone protein, a foldase, a peptidyl prolyl isomerase and a disulfide bond isomerase. In one embodiment, the identified gene or gene product can be selected from htpG, cbpA, dnaJ, dnaK and fkbP. In one embodiment, a gene or gene product homologous to the identified up-regulated gene is modified in the genome of the host.

The process can lead to increased production of recombinant protein or peptide in a host cell, by for example, increasing the amount of protein per gram of host protein (total cell protein) in a given amount of time, or increasing the amount of length of time during which the cell or organism is producing the recombinant protein. The increased production may optimize the efficiency of the cell or organism by for example, decreasing the energy expenditure, increasing the use of available resources, or decreasing the requirements for growth supplements in growth media. The increased production may also result in an increased level of recoverable protein or peptide, such as soluble protein, produced per gram of recombinant or per gram of host cell protein.

The invention also includes an improved recombinant host cell that is produced by the claimed process.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
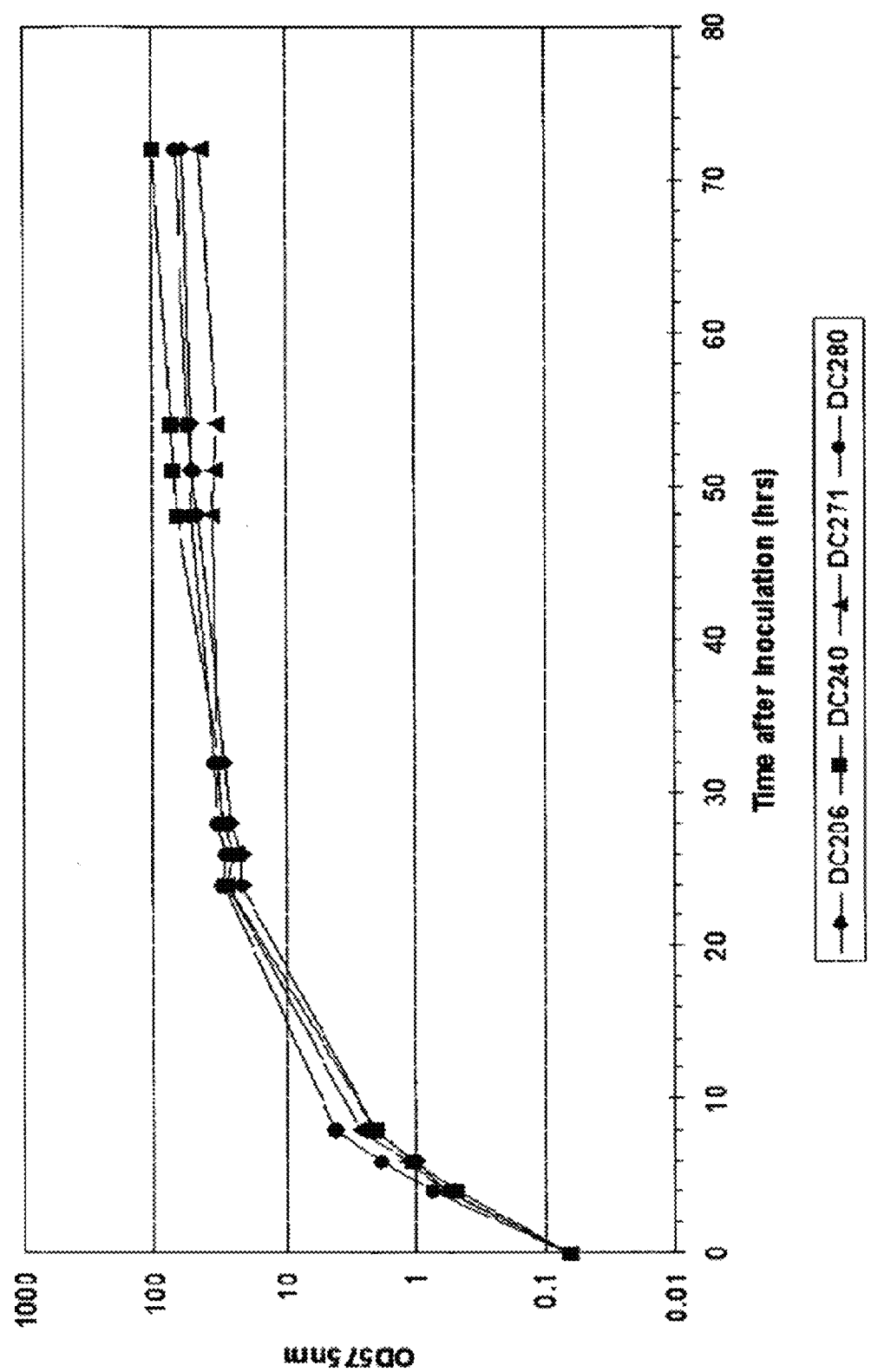
FIG. 1 is a graph of a growth comparison (optical density over time) of different strains of *P. fluorescens*. The cells were induced with 0.3 mM IPTG at 24 hr after inoculation. The strains are: DC280 harboring the empty vector pDOW1339, DC240 that produces the soluble cytoplasmic nitrilase enzyme, and DC271 that produces the partially insoluble periplasmic hGH. DC206, the parental strain of DC280, DC240, and DC271 was included as a control. Samples were taken at 0 and 4 hrs post-IPTG induction for RNA isolation and gene expression profiling.

A process is provided for improving the expression of a recombinant protein or peptide comprising i) expressing the recombinant protein or peptide in a host cell; ii) analyzing a genetic profile of the cell and identifying one or more endogenous up-regulated gene products, including one or more proteases or folding modulators that are up-regulated upon expression of the recombinant protein or peptide; and iii) changing expression of one or more identified gene products by genetically modifying the cell. In another embodiment, the process further comprises expressing the recombinant protein or peptide in a genetically modified cell. In another embodiment, the process further comprises analyzing a second genetic profile of the genetically modified cell to identify one or more additional gene products that are differentially expressed in the modified cell. In a further embodiment, the process comprises changing the expression of at least a second identified gene product in the modified cell to provide a double modified cell. The process can provide improved expression as measured by improved yields of protein, or can improve the recovery of active protein, for example by increasing solubility of the expressed recombinant protein.

More generally, the invention includes a process for improving the expression of a recombinant protein or peptide in a host cell or organism comprising:

i) expressing the recombinant protein or peptide in the recombinant host cell or organism;

ii) analyzing a genetic profile of the recombinant cell to identify a compensatory gene or gene product that is expressed at a higher level in the recombinant cell than in one of either a host cell that has not been modified to express the recombinant protein or a recombinant cell that is not expressing the recombinant protein; and iii) changing expression of the identified compensatory gene or gene product in the recombinant cell by genetic modification to provide a modified recombinant cell that achieves an increase in recombinant protein expression, activity or solubility.

Throughout the specification, when a range is provided, it should be understood that the components are meant to be independent. For example, a range of 1-6 means independently 1, 2, 3, 4, 5 or 6.

The steps of the process are described in more detail below.

Step I: Genetic Modification of Host Cell or Organism to Express a Recombinant Protein or Peptide in a Host Cell In the first step of the process, a host cell is modified to have the capacity to express a recombinant protein or peptide. The host cell can be modified using any techniques known in the art. For example, the recombinant protein can be expressed from an expression vector that is exogenous to the genome of the cell and that is transfected or transformed into the cell. The construction of expression vectors as well as techniques for transfection or transformation are described below. The host cell can also be modified to express a recombinant protein or peptide from a genomic insert as described below. A gene encoding the recombinant protein or peptide can be inserted into the genome of the host cell or organism by techniques such as homologous or heterologous recombination. These techniques are described below.

The recombinant protein or peptide can be expressed under the control of an element that requires further manipulation of the cell. For example, chemical treatment of the cell may be required to initiate or enhance protein or peptide expression. Promoter and repressor elements that govern the expression of recombinant proteins or peptides in host cells are described below and are well known in the art. These can include promoter elements based on the "tac" promoter, responsive to IPTG.

Selection of a Host Cell or Organism

The process of the invention can be used in any given host system, including of either eukaryotic or prokaryotic origin. The process is generally limited only by the availability of enough genetic information for analysis of a genetic profile to identify a identified gene. Although it is generally typical that representative sequences from a large percentage of the genome is available, for example at least 50%, 60%, 70%, 80%, 90%, 95%, 98%, 99% or 100% of the sequences expressed or found in the genome, transcriptome, or proteome, the invention can be practiced using only a portion of the sequences in the genome, transcriptome, or proteome. In particular, in instances when the information available includes information on a group of related sequences, such as a metabolically linked group, only a small portion of representative sequences from the genome can be used for the process of the invention. The process is also not limited to particular recombinant proteins being expressed, as a key aspect of the process is the capacity to rationally and iteratively design expression systems based on techniques for identifying cellular changes that occur in a host cell upon expression of recombinant proteins or peptides and modulating the host cell using procedures known in the art.

The host cell can be any cell capable of producing recombinant protein or peptide. In one embodiment, the host cell is a microbial cell, ie. a cell from a bacteria, fungus, yeast, or other unicellular eukaryotes, prokaryotes and viruses. The most commonly used systems to produce recombinant proteins or peptides include certain bacterial cells, particularly *E. coli*, because of their relatively inexpensive growth requirements and potential capacity to produce protein in large batch cultures. Yeast are also used to express biologically relevant proteins and peptides, particularly for research purposes. Systems include *Saccharomyces cerevisiae* or *Pichia pastoris*. These systems are well characterized, provide generally acceptable levels of total protein expression and are comparatively fast and inexpensive. Insect cell expression systems have also emerged as an alternative for expressing recombinant proteins in biologically active form. In some cases, correctly folded proteins that are post-translationally modified can be produced. Mammalian cell expression systems, such as Chinese hamster ovary cells, have also been used for the expression of recombinant proteins. On a small scale, these expression systems are often effective. Certain biologics can be derived from mammalian proteins, particularly in animal or human health applications. In another embodiment, the host cell is a plant cell, including, but not limited to, a tobacco cell, corn, a cell from an *Arabidopsis* species, potato or rice cell. In another embodiment, a multicellular organism is analyzed or is modified in the process, including but not limited to a transgenic organism. Techniques for analyzing and/or modifying a multicellular organism are generally based on techniques described for modifying cells described below.

In one embodiment, the host cell can be a prokaryote such as a bacterial cell including, but not limited to an *Escherichia* or a *Pseudomonas* species. Typical bacterial cells are described, for example, in "Biological Diversity: Bacteria and Archaeans," a chapter of the On-Line Biology Book, provided by Dr M J Farabee of the Estrella Mountain Community College, Arizona, USA. In certain embodiments, the host cell can be a Pseudomonad cell, and can typically be a *P. fluorescens* cell. In other embodiments, the host cell can also be an *E. coli* cell. In another embodiment the host cell can be a eukaryotic cell, for example an insect cell, including but not limited to a cell from a *Spodoptera, Trichoplusia Drosophila* or an *Estigmene* species, or a mammalian cell, including but not limited to a murine cell, a hamster cell, a monkey, a primate or a human cell.

In certain embodiments, the host cell is a Pseudomonad cell, and can be for example a *P. fluorescens* organism.

In one embodiment, the host cell can be a member of any of the bacterial taxa. The cell can, for example, be a member of any species of eubacteria. The host can be a member any one of the taxa: Acidobacteria, Actinobacteira, Aquificae, Bacteroidetes, Chlorobi, Chlamydiae, Choroflexi, Chrysiogenetes, *Cyanobacteria*, Deferribacteres, *Deinococcus*, Dictyoglomi, Fibrobacteres, Firmicutes, Fusobacteria, Gemmatimonadetes, Lentisphaerae, Nitrospirae, Planctomycetes, Proteobacteria, Spirochaetes, Thermodesulfobacteria, Thermomicrobia, Thermotogae, *Thermus* (Thermales), or Verrucomicrobia. In one embodiment of a eubacterial host cell, the cell can be a member of any species of eubacteria, excluding *Cyanobacteria*.

The bacterial host can also be a member of any species of Proteobacteria. A proteobacterial host cell can be a member of any one of the taxa Alphaproteobacteria, Betaproteobacteria, Gammaproteobacteria, Deltaproteobacteria, or Epsilonproteobacteria. In addition, the host can be a member of any one of the taxa Alphaproteobacteria, Betaproteobacteria, or Gammaproteobacteria, and a member of any species of Gammaproteobacteria.

In one embodiment of a Gammaproteobacterial host, the host will be member of any one of the taxa Aeromonadales, Alteromonadales, Enterobacteriales, Pseudomonadales, or Xanthomonadales; or a member of any species of the Enterobacteriales or Pseudomonadales. In one embodiment, the host cell can be of the order Enterobacteriales, the host cell will be a member of the family Enterobacteriaceae, or a member of any one of the genera *Erwinia, Escherichia*, or *Serratia*; or a member of the genus *Escherichia*. In one embodiment of a host cell of the order Pseudomonadales, the host cell will be a member of the family Pseudomonadaceae, even of the genus *Pseudomonas*. Gamma Proteobacterial hosts include members of the species *Escherichia coli* and members of the species *Pseudomonas fluorescens*.

Other *Pseudomonas* organisms may also be useful. Pseudomonads and closely related species include Gram(−) Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA) (hereinafter "Bergey (1974)"). The following table presents these families and genera of organisms.

| Families and Genera Listed in the Part, "Gram-Negative Aerobic Rods and Cocci" (in Bergey (1974)) | |
|---|---|
| Family I. Pseudomonadaceae | *Gluconobacter* |
|  | *Pseudomonas* |
|  | *Xanthomonas* |
|  | *Zoogloea* |
| Family II. Azotobacteraceae | *Azomonas* |
|  | *Azotobacter* |
|  | *Beijerinckia* |
|  | *Derxia* |
| Family III Rhizobiaceae | *Agrobacterium* |
|  | *Rhizobium* |
| Family IV. Methylomonadaceae | *Methylococcus* |
|  | *Methylomonas* |

-continued

| Families and Genera Listed in the Part, "Gram-Negative Aerobic Rods and Cocci" (in Bergey (1974)) | |
|---|---|
| Family V. Halobacteriaceae | *Halobacterium* |
| | *Halococcus* |
| Other Genera | *Acetobacter* |
| | *Alcaligenes* |
| | *Bordetella* |
| | *Brucella* |
| | *Francisella* |
| | *Thermus* |

"Gram(−) Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia,* and *Stenotrophomonas,* the genus *Sphingomonas* (and the genus *Blastomonas,* derived therefrom), which was created by regrouping organisms belonging to (and previously called species of) the genus *Xanthomonas,* the genus *Acidomonas,* which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciens* (ATCC 19375), and *Pseudomonas putrefaciens* (ATCC 8071), which have been reclassified respectively as *Alteromonas haloplanktis, Alteromonas nigrifaciens,* and *Alteromonas putrefaciens.* Similarly, e.g., *Pseudomonas acidovorans* (ATCC 15668) and *Pseudomonas testosteroni* (ATCC 11996) have since been reclassified as *Comamonas acidovorans* and *Comamonas testosteroni,* respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida.* "Gram(−) Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram(−) Proteobacteria Subgroup 1" include: 1) *Azotobacter* group bacteria of the genus *Azorhizophilus;* 2) Pseudomonadaceae family bacteria of the genera *Cellvibrio, Oligella,* and *Teredinibacter;* 3) Rhizobiaceae family bacteria of the genera *Chelatobacter, Ensifer, Liberibacter* (also called "*Candidatus Liberibacter*"), and *Sinorhizobium;* and 4) Methylococcaceae family bacteria of the genera *Methylobacter, Methylocaldum, Methylomicrobium, Methylosarcina,* and *Methylosphaera.*

In another embodiment, the host cell is selected from "Gram(−) Proteobacteria Subgroup 2." "Gram(−) Proteobacteria Subgroup 2" is defined as the group of Proteobacteria of the following genera (with the total numbers of catalog-listed, publicly-available, deposited strains thereof indicated in parenthesis, all deposited at ATCC, except as otherwise indicated): *Acidomonas* (2); *Acetobacter* (93); *Gluconobacter* (37); *Brevundimonas* (23); *Beijerinckia* (13); *Derxia* (2); *Brucella* (4); *Agrobacterium* (79); *Chelatobacter* (2); *Ensifer* (3); *Rhizobium* (144); *Sinorhizobium* (24); *Blastomonas* (1); *Sphingomonas* (27); *Alcaligenes* (88); *Bordetella* (43); *Burkholderia* (73); *Ralstonia* (33); *Acidovorax* (20); *Hydrogenophaga* (9); *Zoogloea* (9); *Methylobacter* (2); *Methylocaldum* (1 at NCIMB); *Methylococcus* (2); *Methylomicrobium* (2); *Methylomonas* (9); *Methylosarcina* (1); *Methylosphaera; Azomonas* (9); *Azorhizophilus* (5); *Azotobacter* (64); *Cellvibrio* (3); *Oligella* (5); *Pseudomonas* (1139); *Francisella* (4); *Xanthomonas* (229); *Stenotrophomonas* (50); and *Oceanimonas* (4).

Exemplary host cell species of "Gram(−) Proteobacteria Subgroup 2" include, but are not limited to the following bacteria (with the ATCC or other deposit numbers of exemplary strain(s) thereof shown in parenthesis): *Acidomonas methanolica* (ATCC 43581); *Acetobacter aceti* (ATCC 15973); *Gluconobacter oxydans* (ATCC 19357); *Brevundimonas diminuta* (ATCC 11568); *Beijerinckia indica* (ATCC 9039 and ATCC 19361); *Derxia gummosa* (ATCC 15994); *Brucella melitensis* (ATCC 23456), *Brucella abortus* (ATCC 23448); *Agrobacterium tumefaciens* (ATCC 23308), *Agrobacterium radiobacter* (ATCC 19358), *Agrobacterium rhizogenes* (ATCC 11325); *Chelatobacter heintzii* (ATCC 29600); *Ensifer adhaerens* (ATCC 33212); *Rhizobium leguminosarum* (ATCC 10004); *Sinorhizobium fredii* (ATCC 35423); *Blastomonas natatoria* (ATCC 35951); *Sphingomonas paucimobilis* (ATCC 29837); *Alcaligenes faecalis* (ATCC 8750); *Bordetella pertussis* (ATCC 9797); *Burkholderia cepacia* (ATCC 25416); *Ralstonia pickettii* (ATCC 27511); *Acidovorax facilis* (ATCC 11228); *Hydrogenophaga flava* (ATCC 33667); *Zoogloea ramigera* (ATCC 19544); *Methylobacter luteus* (ATCC 49878); *Methylocaldum gracile* (NCIMB 11912); *Methylococcus capsulatus* (ATCC 19069); *Methylomicrobium agile* (ATCC 35068); *Methylomonas methanica* (ATCC 35067); *Methylosarcina fibrata* (ATCC 700909); *Methylosphaera hansonii* (ACAM 549); *Azomonas agilis* (ATCC 7494); *Azorhizophilus paspali* (ATCC 23833); *Azotobacter chroococcum* (ATCC 9043); *Cellvibrio mixtus* (UQM 2601); *Oligella urethralis* (ATCC 17960); *Pseudomonas aeruginosa* (ATCC 10145), *Pseudomonas fluorescens* (ATCC 35858); *Francisella tularensis* (ATCC 6223); *Stenotrophomonas maltophilia* (ATCC 13637); *Xanthomonas campestris* (ATCC 33913); and *Oceanimonas doudoroffii* (ATCC 27123).

In another embodiment, the host cell is selected from "Gram(−) Proteobacteria Subgroup 3." "Gram(−) Proteobacteria Subgroup 3" is defined as the group of Proteobacteria of the following genera: *Brevundimonas; Agrobacterium; Rhizobium; Sinorhizobium; Blastomonas; Sphingomonas; Alcaligenes; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas;* and *Oceanimonas.*

In another embodiment, the host cell is selected from "Gram(−) Proteobacteria Subgroup 4." "Gram(−) Proteobacteria Subgroup 4" is defined as the group of Proteobacteria of the following genera: *Brevundimonas; Blastomonas; Sphingomonas; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas;* and *Oceanimonas.*

In an embodiment, the host cell is selected from "Gram(−) Proteobacteria Subgroup 5." "Gram(−) Proteobacteria Subgroup 5" is defined as the group of Proteobacteria of the following genera: *Methylobacter; Methylocaldum; Methylococcus; Methylomicrobium; Methylomonas; Methylosa-* rcina; Methylosphaera; Azomonas; Azorhizophilus; Azotobacter; Cellvibrio; Oligella; Pseudomonas; Teredinibacter; Francisella; Stenotrophomonas; Xanthomonas; and Oceanimonas.

The host cell can be selected from "Gram(−) Proteobacteria Subgroup 6." "Gram(−) Proteobacteria Subgroup 6" is defined as the group of Proteobacteria of the following genera: Brevundimonas; Blastomonas; Sphingomonas; Burkholderia; Ralstonia; Acidovorax; Hydrogenophaga; Azomonas; Azorhizophilus; Azotobacter; Cellvibrio; Oligella; Pseudomonas; Teredinibacter; Stenotrophomonas; Xanthomonas; and Oceanimonas.

The host cell can be selected from "Gram(−) Proteobacteria Subgroup 7." "Gram(−) Proteobacteria Subgroup 7" is defined as the group of Proteobacteria of the following genera: Azomonas; Azorhizophilus; Azotobacter; Cellvibrio; Oligella; Pseudomonas; Teredinibacter; Stenotrophomonas; Xanthomonas; and Oceanimonas.

The host cell can be selected from "Gram(−) Proteobacteria Subgroup 8." "Gram(−) Proteobacteria Subgroup 8" is defined as the group of Proteobacteria of the following genera: Brevundimonas; Blastomonas; Sphingomonas; Burkholderia; Ralstonia; Acidovorax; Hydrogenophaga; Pseudomonas; Stenotrophomonas; Xanthomonas; and Oceanimonas.

The host cell can be selected from "Gram(−) Proteobacteria Subgroup 9." "Gram(−) Proteobacteria Subgroup 9" is defined as the group of Proteobacteria of the following genera: Brevundimonas; Burkholderia; Ralstonia; Acidovorax; Hydrogenophaga; Pseudomonas; Stenotrophomonas; and Oceanimonas.

The host cell can be selected from "Gram(−) Proteobacteria Subgroup 10." "Gram(−) Proteobacteria Subgroup 10" is defined as the group of Proteobacteria of the following genera: Burkholderia; Ralstonia; Pseudomonas; Stenotrophomonas; and Xanthomonas.

The host cell can be selected from "Gram(−) Proteobacteria Subgroup 11." "Gram(−) Proteobacteria Subgroup 11" is defined as the group of Proteobacteria of the genera: Pseudomonas; Stenotrophomonas; and Xanthomonas. The host cell can be selected from "Gram(−) Proteobacteria Subgroup 12." "Gram(−) Proteobacteria Subgroup 12" is defined as the group of Proteobacteria of the following genera: Burkholderia; Ralstonia; Pseudomonas. The host cell can be selected from "Gram(−) Proteobacteria Subgroup 13." "Gram(−) Proteobacteria Subgroup 13" is defined as the group of Proteobacteria of the following genera: Burkholderia; Ralstonia; Pseudomonas; and Xanthomonas. The host cell can be selected from "Gram(−) Proteobacteria Subgroup 14." "Gram(−) Proteobacteria Subgroup 14" is defined as the group of Proteobacteria of the following genera: Pseudomonas and Xanthomonas. The host cell can be selected from "Gram(−) Proteobacteria Subgroup 15." "Gram(−) Proteobacteria Subgroup 15" is defined as the group of Proteobacteria of the genus Pseudomonas.

The host cell can be selected from "Gram(−) Proteobacteria Subgroup 16." "Gram(−) Proteobacteria Subgroup 16" is defined as the group of Proteobacteria of the following Pseudomonas species (with the ATCC or other deposit numbers of exemplary strain(s) shown in parenthesis): Pseudomonas abietaniphila (ATCC 700689); Pseudomonas aeruginosa (ATCC 10145); Pseudomonas alcaligenes (ATCC 14909); Pseudomonas anguilliseptica (ATCC 33660); Pseudomonas citronellolis (ATCC 13674); Pseudomonas flavescens (ATCC 51555); Pseudomonas mendocina (ATCC 25411); Pseudomonas nitroreducens (ATCC 33634); Pseudomonas oleovorans (ATCC 8062); Pseudomonas pseudoalcaligenes (ATCC 17440); Pseudomonas resinovorans (ATCC 14235); Pseudomonas straminea (ATCC 33636); Pseudomonas agarici (ATCC 25941); Pseudomonas alcaliphila; Pseudomonas alginovora; Pseudomonas andersonii; Pseudomonas asplenii (ATCC 23835); Pseudomonas azelaica (ATCC 27162); Pseudomonas beijerinckii (ATCC 19372); Pseudomonas borealis; Pseudomonas boreopolis (ATCC 33662); Pseudomonas brassicacearum; Pseudomonas butanovora (ATCC 43655); Pseudomonas cellulosa (ATCC 55703); Pseudomonas aurantiaca (ATCC 33663); Pseudomonas chlororaphis (ATCC 9446, ATCC 13985, ATCC 17418, ATCC 17461); Pseudomonas fragi (ATCC 4973); Pseudomonas lundensis (ATCC 49968); Pseudomonas taetrolens (ATCC 4683); Pseudomonas cissicola (ATCC 33616); Pseudomonas coronafaciens; Pseudomonas diterpeniphila; Pseudomonas elongata (ATCC 10144); Pseudomonas flectens (ATCC 12775); Pseudomonas azotoformans; Pseudomonas brenneri; Pseudomonas cedrella; Pseudomonas corrugata (ATCC 29736); Pseudomonas extremorientalis; Pseudomonas fluorescens (ATCC 35858); Pseudomonas gessardii; Pseudomonas libanensis; Pseudomonas mandelii (ATCC 700871); Pseudomonas marginalis (ATCC 10844); Pseudomonas migulae; Pseudomonas mucidolens (ATCC 4685); Pseudomonas orientalis; Pseudomonas rhodesiae; Pseudomonas synxantha (ATCC 9890); Pseudomonas tolaasii (ATCC 33618); Pseudomonas veronii (ATCC 700474); Pseudomonas frederiksbergensis; Pseudomonas geniculata (ATCC 19374); Pseudomonas gingeri; Pseudomonas graminis; Pseudomonas grimontii; Pseudomonas halodenitrificans; Pseudomonas halophile; Pseudomonas hibiscicola (ATCC 19867); Pseudomonas huttiensis (ATCC 14670); Pseudomonas hydrogenovora; Pseudomonas jessenii (ATCC 700870); Pseudomonas kilonensis; Pseudomonas lanceolata (ATCC 14669); Pseudomonas lini; Pseudomonas marginate (ATCC 25417); Pseudomonas mephitica (ATCC 33665); Pseudomonas denitrificans (ATCC 19244); Pseudomonas pertucinogena (ATCC 190); Pseudomonas pictorum (ATCC 23328); Pseudomonas psychrophila; Pseudomonas fulva (ATCC 31418); Pseudomonas monteilii (ATCC 700476); Pseudomonas mosselii; Pseudomonas oryzihabitans (ATCC 43272); Pseudomonas plecoglossicida (ATCC 700383); Pseudomonas putida (ATCC 12633); Pseudomonas reactans; Pseudomonas spinosa (ATCC 14606); Pseudomonas balearica; Pseudomonas luteola (ATCC 43273); Pseudomonas stutzeri (ATCC 17588); Pseudomonas amygdali (ATCC 33614); Pseudomonas avellanae (ATCC 700331); Pseudomonas caricapapayae (ATCC 33615); Pseudomonas cichorii (ATCC 10857); Pseudomonas ficuserectae (ATCC 35104); Pseudomonas fuscovaginae; Pseudomonas meliae (ATCC 33050); Pseudomonas syringae (ATCC 19310); Pseudomonas viridiflava (ATCC 13223); Pseudomonas thermocarboxydovorans (ATCC 35961); Pseudomonas thermotolerans; Pseudomonas thivervalensis; Pseudomonas vancouverensis (ATCC 700688); Pseudomonas wisconsinensis; and Pseudomonas xiamenensis.

The host cell can be selected from "Gram(−) Proteobacteria Subgroup 17." "Gram(−) Proteobacteria Subgroup 17" is defined as the group of Proteobacteria known in the art as the "fluorescent Pseudomonads" including those belonging, e.g., to the following Pseudomonas species: Pseudomonas azotoformans; Pseudomonas brenneri; Pseudomonas cedrella; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis;

*Pseudomonas rhodesiae*; *Pseudomonas synxantha*; *Pseudomonas tolaasii*; and *Pseudomonas veronii*.

The host cell can be selected from "Gram(−) Proteobacteria Subgroup 18." "Gram(−) Proteobacteria Subgroup 18" is defined as the group of all subspecies, varieties, strains, and other sub-special units of the species *Pseudomonas fluorescens*, including those belonging, e.g., to the following (with the ATCC or other deposit numbers of exemplary strain(s) shown in parenthesis): *Pseudomonas fluorescens* biotype A, also called biovar 1 or biovar I (ATCC 13525); *Pseudomonas fluorescens* biotype B, also called biovar 2 or biovar II (ATCC 17816); *Pseudomonas fluorescens* biotype C, also called biovar 3 or biovar III (ATCC 17400); *Pseudomonas fluorescens* biotype F, also called biovar 4 or biovar IV (ATCC 12983); *Pseudomonas fluorescens* biotype G, also called biovar 5 or biovar V (ATCC 17518); *Pseudomonas fluorescens* biovar VI; *Pseudomonas fluorescens* Pf0-1; *Pseudomonas fluorescens* Pf-5 (ATCC BAA-477); *Pseudomonas fluorescens* SBW25; and *Pseudomonas fluorescens* subsp. *cellulosa* (NCIMB 10462).

The host cell can be selected from "Gram(−) Proteobacteria Subgroup 19." "Gram(−) Proteobacteria Subgroup 19" is defined as the group of all strains of *Pseudomonas fluorescens* biotype A. A typical strain of this biotype is *P. fluorescens* strain MB101 (see U.S. Pat. No. 5,169,760 to Wilcox), and derivatives thereof. An example of a derivative thereof is *P. fluorescens* strain MB214, constructed by inserting into the MB101 chromosomal asd (aspartate dehydrogenase gene) locus, a native *E. coli* PlacI-lacI-lacZYA construct (i.e. in which PlacZ was deleted).

Additional *P. fluorescens* strains that can be used in the present invention include *Pseudomonas fluorescens* Migula and *Pseudomonas fluorescens* Loitokitok, having the following ATCC designations: [NCIB 8286]; NRRL B-1244; NCIB 8865 strain CO1; NCIB 8866 strain CO2; 1291 [ATCC 17458; IFO 15837; NCIB 8917; LA; NRRL B-1864; pyrrolidine; PW2 [ICMP 3966; NCPPB 967; NRRL B-899]; 13475; NCTC 10038; NRRL B-1603 [6; IFO 15840]; 52-1C; CCEB 488-A [BU 140]; CCEB 553 REM 15/47]; IAM 1008 [AHH-27]; IAM 1055 [AHH-23]; 1 [IFO 15842]; 12 [ATCC 25323; NIH 11; den Dooren de Jong 216]; 18 [IFO 15833; WRRL P-7]; 93 [TR-10]; 108 [52-22; IFO 15832]; 143 [IFO 15836; PL]; 149 [2-40-40; IFO 15838]; 182 [IFO 3081; PJ 73]; 184 [IFO 15830]; 185 [W2 L-1]; 186 [IFO 15829; PJ 79]; 187 [NCPPB 263]; 188 [NCPPB 316]; 189 [PJ227; 1208]; 191 [IFO 15834; PJ 236; 22/1]; 194 [Klinge R-60; PJ 253]; 196 [PJ 288]; 197 [PJ 290]; 198 [PJ 302]; 201 [PJ 368]; 202 [PJ 372]; 203 [PJ 376]; 204 [IFO 15835; PJ 682]; 205 [PJ 686]; 206 [PJ 692]; 207 [PJ 693]; 208 [PJ 722]; 212 [PJ 832]; 215 [PJ 849]; 216 [PJ 885]; 267 [B-9]; 271 [B-1612]; 401 [C71A; IFO 15831; PJ 187]; NRRL B-3178 [4; IFO 15841]; KY 8521; 3081; 30-21; [IFO 3081]; N; PYR; PW; D946-B83 [BU 2183; FERM-P 3328]; P-2563 [FERM-P 2894; IFO 13658]; IAM-1126 [43F]; M-1; A506 [A5-06]; A505 [A5-05-1]; A526 [A5-26]; B69; 72; NRRL B-4290; PMW6 [NCIB 11615]; SC 12936; A1 [IFO 15839]; F 1847 [CDC-EB]; F 1848 [CDC 93]; NCIB 10586; P17; F-12; AmMS 257; PRA25; 6133D02; 6519E01; N1; SC15208; BNL-WVC; NCTC 2583 [NCIB 8194]; H13; 1013 [ATCC 11251; CCEB 295]; IFO 3903; 1062; or Pf-5.

Other suitable hosts include those classified in other parts of the reference, such as Gram (+) Proteobacteria. In one embodiment, the host cell is an *E. coli*. The genome sequence for *E. coli* has been established for *E. coli* MG1655 (Blattner, et al. (1997) The complete genome sequence of *Escherichia coli* K-12 *Science* 277(5331): 1453-74) and DNA microarrays are available commercially for *E. coli* K12 (MWG Inc, High Point, N.C.). *E. coli* can be cultured in either a rich medium such as Luria-Bertani (LB) (10 g/L tryptone, 5 g/L NaCl, 5 g/L yeast extract) or a defined minimal medium such as M9 (6 g/L $Na_2HPO_4$, 3 g/L $KH_2PO_4$, 1 g/L $NH_4Cl$, 0.5 g/L NaCl, pH 7.4) with an appropriate carbon source such as 1% glucose. Routinely, an over night culture of *E. coli* cells is diluted and inoculated into fresh rich or minimal medium in either a shake flask or a fermentor and grown at 37° C.

A host can also be of mammalian origin, such as a cell derived from a mammal including any human or non-human mammal. Mammals can include, but are not limited to primates, monkeys, porcine, ovine, bovine, rodents, ungulates, pigs, swine, sheep, lambs, goats, cattle, deer, mules, horses, monkeys, apes, dogs, cats, rats, and mice.

A host cell may also be of plant origin. Any plant can be selected for the identification of genes and regulatory sequences. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. In some embodiments, plants useful in the process are *Arabidopsis*, corn, wheat, soybean, and cotton.

For expression of a recombinant protein or peptide, or for modulation of an identified compensatory gene, any plant promoter can be used. A promoter may be a plant RNA polymerase II promoter. Elements included in plant promoters can be a TATA box or Goldberg-Hogness box, typically positioned approximately 25 to 35 basepairs upstream (5') of the transcription initiation site, and the CCAAT box, located between 70 and 100 basepairs upstream. In plants, the CCAAT box may have a different consensus sequence than the functionally analogous sequence of mammalian promoters (Messing et al., In: Genetic Engineering of Plants, Kosuge et al., eds., pp. 211-227, 1983). In addition, virtually all promoters include additional upstream activating sequences or enhancers (Benoist and Chambon, Nature 290:304-310, 1981; Gruss et al., Proc. Nat. Acad. Sci. USA 78:943-947, 1981; and Khoury and Gruss, Cell 27:313-314, 1983) extending from around −100 bp to −1,000 bp or more upstream of the transcription initiation site.

Expression of Recombinant Protein or Peptide

As described below, a host cell or organism can be engineered to express recombinant protein or peptide using standard techniques. For example, recombinant protein can be expressed from a vector or from an exogenous gene inserted into the genome of the host. Vectors that can be used to express exogenous proteins are well known in the art and are described below. Genes for expressing recombinant protein or peptide can also be inserted into the genome using techniques such as homologous or heterologous recombination, as described below.

The recombinant protein or peptide can be expressed after induction with a chemical compound or upon expression of an endogenous gene or gene product. The recombinant protein can also be expressed when the host cell is placed in a particular environment. Specific promoter elements are described below. These include, but are not limited to, promoters that can be induced upon treatment of the cell with chemicals such as IPTG, benzoate or anthranilate.

Recombinant Proteins/Peptides

The host cell has been designed to express a recombinant protein or peptide. These can be of any species and of any size. However, in certain embodiments, the recombinant protein or peptide is a therapeutically useful protein or peptide. In some embodiments, the protein can be a mammalian protein, for example a human protein, and can be, for example, a growth factor, a cytokine, a chemokine or a blood protein. The recombinant protein or peptide can be expressed primarily in an inactive form in the host cell. In certain embodiments, the recombinant protein or peptide is less than 100 kD, less than 50 kD, or less than 30 kD in size. In certain embodiments, the recombinant protein or peptide is a peptide of at least 5, 10, 15, 20, 30, 40, 50 or 100 amino acids.

Expression vectors exist that enable recombinant protein production in *E. coli*. For all these protein expression systems routine cloning procedures as described earlier can be followed (Sambrook, et al. (2000) *Molecular cloning: A laboratory manual, third edition* Cold Spring Harbor, N.Y., Cold Spring Harbor Laboratory Press).

The CHAMPION™ pET expression system provides a high level of protein production. Expression is induced from the strong T7lac promoter. This system takes advantage of the high activity and specificity of the bacteriophage T7 RNA polymerase for high level transcription of the gene of interest. The lac operator located in the promoter region provides tighter regulation than traditional T7-based vectors, improving plasmid stability and cell viability (Studier, F. W. and B. A. Moffatt (1986) Use of bacteriophage T7 RNA polymerase to direct selective high-level expression of cloned genes Journal of Molecular Biology 189(1): 113-30; Rosenberg, et al. (1987) Vectors for selective expression of cloned DNAs by T7 RNA polymerase Gene 56(1): 125-35). The T7 expression system uses the T7 promoter and T7 RNA polymerase (T7 RNAP) for high-level transcription of the gene of interest. High-level expression is achieved in T7 expression systems because the T7 RNAP is more processive than native *E. coli* RNAP and is dedicated to the transcription of the gene of interest. Expression of the identified gene is induced by providing a source of T7 RNAP in the host cell. This is accomplished by using a BL21 *E. coli* host containing a chromosomal copy of the T7 RNAP gene. The T7 RNAP gene is under the control of the lacUV5 promoter which can be induced by IPTG. T7 RNAP is expressed upon induction and transcribes the gene of interest.

The pBAD expression system allows tightly controlled, titratable expression of recombinant protein through the presence of specific carbon sources such as glucose, glycerol and arabinose (Guzman, et al. (1995) Tight regulation, modulation, and high-level expression by vectors containing the arabinose PBAD promote" *Journal of Bacteriology* 177(14): 4121-30). The pBAD vectors are uniquely designed to give precise control over expression levels. Heterologous gene expression from the pBAD vectors is initiated at the araBAD promoter. The promoter is both positively and negatively regulated by the product of the araC gene. AraC is a transcriptional regulator that forms a complex with L-arabinose. In the absence of L-arabinose, the AraC dimer blocks transcription. For maximum transcriptional activation two events are required: (i.) L-arabinose binds to AraC allowing transcription to begin. (ii.) The cAMP activator protein (CAP)-cAMP complex binds to the DNA and stimulates binding of AraC to the correct location of the promoter region.

The trc expression system allows high-level, regulated expression in *E. coli* from the trc promoter. The trc expression vectors have been optimized for expression of eukaryotic genes in *E. coli*. The trc promoter is a strong hybrid promoter derived from the tryptophane (trp) and lactose (lac) promoters. It is regulated by the lacO operator and the product of the lacI$^Q$ gene (Brosius, J. (1984) Toxicity of an overproduced foreign gene product in *Escherichia coli* and its use in plasmid vectors for the selection of transcription terminators *Gene* 27(2): 161-72).

The invention also includes the improved recombinant host cell that is produced by the claimed process. In one embodiment, the invention includes a cell produced by the described process. In another embodiment, the invention includes a host cell or organism that expresses a recombinant protein that has been genetically modified to reduce the expression of at least two proteases. In other embodiments, the invention includes a host cell or organism that expresses a recombinant protein that has been genetically modified to reduce the expression of at least one protease selected from the group consisting of products of hslV, hslU, clpX, clpA and clpB genes, and in certain subembodiments, the cell or organism has been modified to reduce the expression of HslV or HslU. In certain embodiments, the modified host cell or organism expresses a recombinant mammalian derived protein, and may express a recombinant human derived protein, which may be human growth hormone. The cell can be modified by any techniques known in the art, for example by a technique wherein at least one protease gene is knocked out of the genome, or by mutating at least one protease gene to reduce expression of a protease, or by altering at least one promoter of at least one protease gene to reduce expression of a protease.

In another embodiment, a host or organism that expresses a recombinant protein that is presented that has been genetically modified to increase the expression of at least one, at least two folding modulators, or at least three folding modulators. In certain subembodiments, the folding modulators that are not folding modulator subunits. The folding modulator may be selected from the group consisting of products of cbpA, htpG, dnaK, dnaJ, fkbP2, groES and groEL genes, and, in certain subembodiments, can be htpG or cbpA. The host cell or organism can in a non-limiting example, express a mammalian protein, such as a human protein. The protein may be human growth hormone. The folding modulator or modulators can be increased by, for example, including an expression vector as described herein in the cell. The folding modulator expression can also be increased by, for example, mutating a promoter of a folding modulator or folding modulator subunit. A host cell or organism that expresses a recombinant protein can also be genetically modified to increase the expression of at least one folding modulators and decrease the expression of at least one protease or protease protein. Organisms comprising one or more cells produced by the described process are also included in the invention.

Step II: Analyzing a Genetic Profile to Identify a Compensatory Gene or Gene Product that is Expressed at a Higher Level in the Recombinant Cell The process of the invention includes analyzing a genetic profile of the recombinant cell to identify a compensatory gene or gene product that is expressed at a higher level in the recombinant cell than in either a host cell that has not been modified to express the recombinant protein or a recombinant cell that is not expressing the recombinant protein.

A "genetic profile" as used herein can include genes in a genome, mRNA transcribed from genes in the genome or cDNA derived from mRNA transcribed from genes in the genome. A genetic profile can also include transcription products that have been modified by a cell such as splice variants of genes in eukaryotic systems, or proteins translated from genes in a genome, including proteins that are modified by the cell or translated from splice variants of mRNA translated from the genome. A genetic profile is meant to refer solely to the simultaneous analysis of multiple entities, such as in an array or other multiplex system, including multiple simultaneous blot analysis or column chromatography with multiple binding partners attached to the packing. According to the invention, at least 5, 10, 25, 50, 70, 80, 90 or 100 or more genes or gene products that are analyzed simultaneously.

Transcriptome

In one embodiment, the genetic profile analyzed is a transcriptome profile. A complete transcriptome refers to the complete set of mRNA transcripts produced by the genome at any one time. Unlike the genome, the transcriptome is dynamic and varies considerably in differing circumstances due to different patterns of gene expression. Transcriptomics, the study of the transcriptome, is a comprehensive means of identifying gene expression patterns. The transcriptome analyzed can include the complete known set of genes transcribed, i.e. the mRNA content or corresponding cDNA of a host cell or host organism. The cDNA can be a chain of nucleotides, an isolated polynucleotide, nucleotide, nucleic acid molecule, or any fragment or complement thereof that originated recombinantly or synthetically and be double-stranded or single-stranded, coding and/or noncoding, an exon or an intron of a genomic DNA molecule, or combined with carbohydrate, lipids, protein or inorganic elements or substances. The nucleotide chain can be at least 5, 10, 15, 30, 40, 50, 60, 70, 80, 90 or 100 nucleotides in length. The transcriptome can also include only a portion of the known set of genetic transcripts. For example, the transcriptome can include less than 98%, 95, 90, 85, 80, 70, 60, or 50% of the known transcripts in a host. The transcriptome can also be targeted to a specific set of genes.

In one embodiment, the screening process can include screening using an array or a microarray to identify a genetic profile. In another embodiment, the transcriptome profile can be analyzed by using known processes such as hybridization in blot assays such as northern blots. In another embodiment, the process can include PCR-based processes such as RT-PCR that can quantify expression of a particular set of genes. In one embodiment of the invention, an identified gene, for example a folding modulator protein (FM) or protease protein, i.e. a protease, peptidase, or associated polypeptide or cofactor, is identified by a high throughput screening process.

The process can include analyzing the transcriptome profile using a microarray or equivalent technique. In this embodiment, the microarray can include at least a portion of the transcribed genome of the host cell, and typically includes binding partners to samples from genes of at least 50% of the transcribed genes of the organism. More typically, the microarray or equivalent technique includes binding partners for samples from at least 80%, 90%, 95%, 98%, 99% or 100% of the transcribed genes in the genome of the host cell. However, in a separate embodiment, the microarray can include binding partners to a selected subset of genes from the genome, including but not limited to putative protease genes or putative folding modulator genes. A microarray or equivalent technique can typically also include binding partners to a set of genes that are used as controls, such as housekeeper genes. A microarray or equivalent technique can also include genes clustered into groups such as genes coding for degradative proteins, folding modulators and cofactors, metabolic proteins such as proteins involved in glucose metabolism or amino acid or nucleobase synthesis, transcription factors, nucleic acid stabilizing factors, extracellular signal regulated genes such as kinases and receptors or scaffolding proteins.

A microarray is generally formed by linking a large number of discrete binding partners, which can include polynucleotides, aptamers, chemicals, antibodies or other proteins or peptides, to a solid support such as a microchip, glass slide, or the like, in a defined pattern. By contacting the microarray with a sample obtained from a cell of interest and detecting binding of the binding partners expressed in the cell that hybridize to sequences on the chip, the pattern formed by the hybridizing polynucleotides allows the identification of genes or clusters of genes that are expressed in the cell. Furthermore, where each member linked to the solid support is known, the identity of the hybridizing partners from the nucleic acid sample can be identified. One strength of microarray technology is that it allows the identification of differential gene expression simply by comparing patterns of hybridization.

Examples of high throughput screening processes include hybridization of host cell mRNA or substantially corresponding cDNA, to a hybridizable array(s) or micro array(s). The array or microarray can be one or more array(s) of nucleic acid or nucleic acid analog oligomers or polymers. In one embodiment, the array(s) or microarray(s) will be independently or collectively a host-cell-genome-wide array(s) or microarray(s), containing a population of nucleic acid or nucleic acid analog oligomers or polymers whose nucleotide sequences are hybridizable to representative portions of all genes known to encode or predicted as encoding FMs in the host cell strain or all genes known to encode or predicted to encode proteases or protease proteins in the host cell strain. A genome-wide microarray includes sequences that bind to a representative portion of all of the known or predicted open reading frame (ORF) sequences, such as from mRNA or corresponding cDNA of the host.

The oligonucleotide sequences or analogs in the array typically hybridize to the mRNA or corresponding cDNA sequences from the host cell and typically comprise a nucleotide sequence complimentary to at least a portion of a host mRNA or cDNA sequence, or a sequence homologous to the host mRNA or cDNA sequence. Single DNA strands with complementary sequences can pair with each other and form double-stranded molecules. Microarrays generally apply the hybridization principle in a highly parallel format. Instead of one identified, thousands of different potential identifieds can be arrayed on a miniature solid support. Instead of a unique labeled DNA probe, a complex mixture of labeled DNA molecules is used, prepared from the RNA of a particular cell type or tissue. The abundances of individual labeled DNA molecules in this complex probe typically reflect the expression levels of the corresponding genes. In a simplified process, when hybridized to the array, abundant sequences will generate strong signals and rare sequences will generate weak signals. The strength of the signal can represent the level of gene expression in the original sample.

In one embodiment, a genome-wide array or microarray will be used. In one embodiment, the array represents more than 50% of the open reading frames in the genome of the host, or more than 55%, 60%, 65%, 70%, 75%, 80%, 85%, 90%, 91%, 92%, 93%, 94%, 95%, 96%, 97%, 98%, 99% or 100% of the known open reading frames in the genome. The array can also represent at least a portion of at least 50% of the sequences known to encode protein in the host cell. In separate embodiments, the array represents more than 50% of the genes or putative genes of the host cell, or more than 55%, 60%, 65%, 70%, 75%, 80%, 85%, 90%, 91%, 92%, 93%, 94%, 95%, 96%, 97%, 98%, 99% or 100% of the known genes or putative genes. In one embodiment, more than one oligonucleotide or analog can be used for each gene or putative gene sequence or open reading frame. In one embodiment, these multiple oligonucleotide or analogs represent different portions of a known gene or putative gene sequence. For each gene or putative gene sequence, from about 1 to about 10000 or from 1 to about 100 or from 1 to about 50, 45, 40, 35, 30, 25, 20, 15, 10 or less oligonucleotides or analogs can be present on the array.

A microarray or a complete genome-wide array or microarray may be prepared according to any process known in the art, based on knowledge of the sequence(s) of the host cell genome, or the proposed coding sequences in the genome, or based on the knowledge of expressed mRNA sequences in the host cell or host organism.

For different types of host cells, the same type of microarray can be applied. The types of microarrays include complementary DNA (cDNA) microarrays (Schena, M. et al. (1995) Quantitative monitoring of gene expression patterns with a complementary DNA microarray. *Science* 270:467-70) and oligonucleotide microarrays (Lockhart, et al. (1996) Expression monitoring by hybridization to high-density oligonucleotide arrays. *Nat Biotechnol* 14:1675-80). For cDNA microarray, the DNA fragment of a partial or entire open reading frame is printed on the slides. The hybridization characteristics can be different throughout the slide because different portions of the molecules can be printed in different locations. For the oligonucleotide arrays, 20~80-mer oligos can be synthesized either in situ (on-chip) or by conventional synthesis followed by on-chip immobilization, however in general all probes are designed to be similar with regard to hybridization temperature and binding affinity (Butte, A. (2002) The use and analysis of microarray data. *Nat Rev Drug Discov* 1:951-60).

In analyzing the transcriptome profile, the nucleic acid or nucleic acid analog oligomers or polymers can be RNA, DNA, or an analog of RNA or DNA. Such nucleic acid analogs are known in the art and include, e.g.: peptide nucleic acids (PNA); arabinose nucleic acids; altritol nucleic acids; bridged nucleic acids (BNA), e.g., 2'-O,4'-C-ethylene bridged nucleic acids, and 2'-O,4'-C-methylene bridged nucleic acids; cyclohexenyl nucleic acids; 2',5'-linked nucleotide-based nucleic acids; morpholino nucleic acids (nucleobase-substituted morpholino units connected, e.g., by phosphorodiamidate linkages); backbone-substituted nucleic acid analogs, e.g., 2'-substituted nucleic acids, wherein at least one of the 2' carbon atoms of an oligo- or poly-saccharide-type nucleic acid or analog is independently substituted with, e.g., any one of a halo, thio, amino, aliphatic, oxyaliphatic, thio-aliphatic, or aminoaliphatic group (wherein aliphatic is typically $C_1$-$C_{10}$ aliphatic).

Oligonucleotides or oligonucleotide analogs in the array can be of uniform size and, in one embodiment, can be about 10 to about 1000 nucleotides, about 20 to about 1000, 20 to about 500, 20 to about 100, about 20, about 25, about 30, about 40, about 50, about 60, about 70, about 80, about 90 or about 100 nucleotides long.

The array of oligonucleotide probes can be a high density array comprising greater than about 100, or greater than about 1,000 or more different oligonucleotide probes. Such high density arrays can comprise a probe density of greater than about 60, more generally greater than about 100, most generally greater than about 600, often greater than about 1000, more often greater than about 5,000, most often greater than about 10,000, typically greater than about 40,000 more typically greater than about 100,000, and in certain instances is greater than about 400,000 different oligonucleotide probes per $cm^2$ (where different oligonucleotides refers to oligonucleotides having different sequences). The oligonucleotide probes range from about 5 to about 500, or about 5 to 50, or from about 5 to about 45 nucleotides, or from about 10 to about 40 nucleotides and most typically from about 15 to about 40 nucleotides in length. Particular arrays contain probes ranging from about 20 to about 25 oligonucleotides in length. The array may comprise more than 10, or more than 50, or more than 100, and typically more than 1000 oligonucleotide probes specific for each identified gene. In one embodiment, the array comprises at least 10 different oligonucleotide probes for each gene. In another embodiment, the array has 20 or fewer oligonucleotides complementary each gene. Although a planar array surface is typical, the array may be fabricated on a surface of virtually any shape or even on multiple surfaces.

The array may further comprise mismatch control probes. Where such mismatch controls are present, the quantifying step may comprise calculating the difference in hybridization signal intensity between each of the oligonucleotide probes and its corresponding mismatch control probe. The quantifying may further comprise calculating the average difference in hybridization signal intensity between each of the oligonucleotide probes and its corresponding mismatch control probe for each gene.

In some assay formats, the oligonucleotide probe can be tethered, i.e., by covalent attachment, to a solid support. Oligonucleotide arrays can be chemically synthesized by parallel immobilized polymer synthesis processes or by light directed polymer synthesis processes, for example on poly-L-lysine substrates such as slides. Chemically synthesized arrays are advantageous in that probe preparation does not require cloning, a nucleic acid amplification step, or enzymatic synthesis. The array includes test probes which are oligonucleotide probes each of which has a sequence that is complementary to a subsequence of one of the genes (or the mRNA or the corresponding antisense cRNA) whose expression is to be detected. In addition, the array can contain normalization controls, mismatch controls and expression level controls as described herein.

An array may be designed to include one hybridizing oligonucleotide per known gene in a genome. The oligonucleotides or equivalent binding partners can be 5'-amino modified to support covalent binding to epoxy-coated slides. The oligonucleotides can be designed to reduce cross-hybridization, for example by reducing sequence identity to less than 25% between oligonucleotides. Generally, melting temperature of oligonucleotides is analyzed before design of the array to ensure consistent GC content and Tm, and secondary structure of oligonucleotide binding partners is optimized. For transcriptome profiling, secondary structure is typically minimized. In one embodiment, each oligonucleotide is printed at at least two different locations on the slide to increase accuracy. Control oligonucleotides can also be designed based on sequences from different species than the host cell or organism to show background binding.

The samples in the genetic profile can be analyzed individually or grouped into clusters. The clusters can typically be grouped by similarity in gene expression. In one embodiment, the clusters may be grouped individually as genes that are regulated to a similar extent in a host cell. The clusters may also include groups of genes that are regulated to a similar extent in a recombinant host cell, for example genes that are up-regulated or down-regulated to a similar extent compared to a host cell or a modified or an unmodified cell. The clusters can also include groups related by gene or protein structure, function or, in the case of a transcriptome array, by placement or grouping of binding partners to genes in the genome of the host. Groups of binding partners or groups of genes or proteins analyzed can include genes selected from, but not limited to: genes coding for putative or known proteases, co-factors of proteases or protease-like proteins; folding modulators, co-factors of folding modulators or proteins that could improve protein folding or solubility; transcription factors; proteins involved in nucleic acid stability or translational initiation; kinases; extracellular or intracellular receptors; metabolic enzymes; metabolic cofactors; envelope proteins; sigma factors; membrane bound proteins; transmembrane proteins; membrane associated proteins and housekeeping genes.

Proteome

In another embodiment, the genetic profile analyzed is a proteome profile. The proteome of a host is the complete set of proteins produced by the genome at any one time. The proteome is generally much more complex than either the genome or the transcriptome because each protein can be chemically modified after synthesis. Many proteins are cleaved during production, are phosphorylated, acetylated, methylated, or have carbohydrate groups added to them, depending on the host cell. The proteome is also very dynamic. Proteomics, the study of the proteome, can cover a number of different aspects of protein structure, protein expression, and function. The techniques for proteome analysis are not as straightforward as those used in transcriptomics. However, an advantage of proteomics is that the functional molecules of the cell are being studied.

The process can include techniques that measure protein expression levels, protein-protein interactions, protein-small molecule interactions or enzymatic activities. In one embodiment, the proteome is analyzed using a screening process that includes measurement of size of certain proteins, typically using mass spectrometry. In one embodiment, the technique to analyze the proteome profile includes hybridization of an antibody to a protein of interest. For example, the process can include Western blot processes as known in the art or can include column chromatography. The process can also include standard processes such as Elisa screening known in the art. The process can also include binding of nucleic acid modified binding partners, which can be aptamers or can be protein or chemical binding partners for proteins or peptide fragments in the proteome and a screening process can include amplification of the nucleic acids. The process can also include chemical compounds that bind to the proteins or fragments of proteins in a proteome and the process can include measurement of the binding by chemical means. The measurement can also include measurement of reaction products in a chemical reaction, or by activation of a fluorophore. Techniques like mass spectrometry in combination with separation tools such as two-dimensional gel electrophoresis or multidimensional liquid chromatography, can also be used in the process. Typically, the process includes a high throughput screening technique.

The process of the invention can include analyzing the proteome profile using, for example, two-dimensional electrophoresis. This is a method for the separation and identification of proteins in a sample by displacement in two dimensions oriented at right angles to one another. This allows the sample to separate over a larger area, increasing the resolution of each component. The first dimension is typically based on the charge of a particular molecule while the second dimension may be based on the size of a molecule. In the first dimension, proteins are resolved in according to their isoelectric points using immobilized pH gradient electrophoresis (IPGE), isoelectric focusing (IEF), or non-equilibrium pH gradient electrophoresis. Under standard conditions of temperature and urea concentration, the observed focusing points of the great majority of proteins closely approximate the predicted isoelectric points calculated from the proteins' amino acid compositions. Generally, the first step after preparation of a host sample includes running the sample against a pH gradient, a process known as isoelectric focusing. The pH gradients can be generated by adding ampholytes to an acrylamide gel. These are a mixture of amphoteric species with a range of pI values. The pH gradients can also be generated by adding Immobilines, which are similar to ampholytes but have been immobilised within the polyacrylamide gel producing an immobilised pH gradient that does not need to be pre-focused.

The second dimension in two-dimensional electrophoresis may be separation by size of proteins. Proteins may be separated according to their approximate molecular weight using sodium dodecyl sulfate poly-acrylamide-electrophoresis (SDS-PAGE). The technique is widely used and known in the art. The basic idea is to coat proteins with a detergent (SDS), which coats all proteins in a sample and negatively charges them. The proteins are then subjected to gel electrophoresis. The gels can typically be acrylamide gels and can be in a gradient of density. The charge placed on the gel pushes the proteins through the gel based on size. In two dimensional electrophoresis, the proteins separated can include proteins from at least 10% of the proteome of the organism. More typically, proteins from at least 20%, 30%, 40%, 60%, 80% or 90% of the proteins in the proteome of the host cell are separated and analysed by techniques such as staining of proteins and/or mass spectrometry.

The process of the invention can also include analyzing the proteome profile using a microarray. In this embodiment, the microarray can include binding partners to at least a portion of the proteins expressed by the host cell under appropriate growth conditions, and typically includes binding partners to proteins from at least 5% of the proteome of the organism. More typically, the microarray includes binding partners to proteins from at least 10%, 20%, 30%, 40%, 60%, 80% or 90% of the proteins in the proteome of the host cell. The binding partners can be antibodies, which can be antibody fragments such as single chain antibody fragments. The binding partners can also include aptamers, which are molecules including nucleic acids that bind to specific proteins or portions of proteins. In a separate embodiment, the microarray can include binding partners for a selected subset of proteins from the proteome, including, for example, putative protease proteins or putative folding modulators. The microarray can typically also include a set of binding partners to proteins that are used as controls. The genetic profile can be analyzed by measuring the binding of the proteins of the host cell expressing the recombinant protein or peptide to the binding partners on the microarray.

The simplest protein array format generally consists of a large number of protein capture reagents bound to defined spots on a planar support material. This array is then exposed to a complex protein sample. The binding of the specific analyte proteins to the individual spots can then be monitored using different approaches. In cases where the analytes have been pre-labeled with a fluorescent dye, the binding can be monitored directly using a fluorescence scanner. Often the classical antibody sandwich type format is used, in which two protein binding reagents simultaneously bind to the same antigen: one antibody is immobilized onto the surface, and the other one is fluorescently labeled or conjugated to an enzyme that can produce a fluorescent, luminescent or colored product when supplied with the appropriate substrate.

Monoclonal antibodies or their antigen-binding fragments are currently one choice for capture agents due to their high specificity, affinity and stability. They have been used in a variety of classical single analyte protein profiling assays such as enzyme-linked immunosorbent assays (ELISA) since the seventies. Additionally, phage-display libraries of antibody fragments offer the potential for antibody production at proteomic scales. These libraries can be used to isolate high-affinity binding agents against protein identified in a significantly shorter time frame than it is possible with immunization-based processes. Ribosome display and mRNA display are additional, completely in vitro, processes that rely on physically linking the library proteins to their encoding mRNA sequences. Such processes have successfully been used to select high-affinity binding reagents to identified proteins (Wilson, D S, et al. (2001) The use of mRNA display to select high-affinity protein-binding peptides *Proc Natl Acad Sci USA* 98:3750-3755). Several groups have taken a different approach to develop high affinity protein capture reagents for protein biochips. For example, aptamers have been used, which are single stranded RNA or DNA molecules originating from in vitro selection experiments (termed SELEX: systematic evolution of ligands by exponential enrichment) with high affinities to proteins. A further development in aptamer technologies are so called photoaptamers. These molecules have an additional attribute that enhances their utility as protein capture reagents. They carry the photoactivatible crosslinking group 5'-bromodeoxyuridine, which, when activated by UV light, can cause covalent crosslinking with bound identified proteins (Petach, H & Gold, L (2002) Dimensionality is the issue: use of photoaptamers in protein microarrays *Curr Opin Biotechnol* 13:309-314). The photo-crosslinking event provides a second dimension of specificity similar to the binding of a secondary detection antibody in a sandwich immunoassay.

A wide variety of surface substrates and attachment chemistries have been evaluated for the immobilization of capture agents on protein microarrays. One way to immobilize proteins on a solid support relies on non-covalent interactions based on hydrophobic or van der Waals interactions, hydrogen bonding or electrostatic forces. Examples of electrostatic immobilization include the use of materials such as nitrocellulose and poly-lysine- or aminopropyl silane-coated glass slides. Protein microarrays were also fabricated by means of physical adsorption onto plastic surfaces of 96-well plates. An example of covalent attachment of proteins to the surface has been described by MacBeath and Schreiber (MacBeath, G & Schreiber, S L (2000) Printing proteins as microarrays for high-throughput function determination *Science* 289: 1760-1763). Due to the very high affinity of streptavidin to biotin, the immobilization of biotinylated proteins onto streptavidin surfaces can be considered quasi covalent (Peluso, P et al. (2003) Optimizing antibody immobilization strategies for the construction of protein microarrays *Anal Biochem* 312:113-124). Further strategies have been described (Ruiz-Taylor, L A, et al (2001) X-ray photoelectron spectroscopy and radiometry studies of biotin-derivatized poly(L-lysine)-grafted-poly(ethylene glycol) monolayers on metal oxides (Langmuir) 7313-7322; Ruiz-Taylor, L A et al. (2001) Monolayers of derivatized poly(L-lysine)-grafted poly(ethylene glycol) on metal oxides as a class of biomolecular interfaces *Proc Natl Acad Sci USA* 2001, 98:852-857; Espejo A, Bedford M T. (2004) Protein-domain microarrays Processes Mol Biol. 264:173-81; Zhu, H. et al. (2001) Global analysis of protein activities using proteome chips. Science Express).

The samples in the genetic profile can be analyzed individually or grouped into clusters. The clusters can typically be grouped by similarity in gene expression. In one embodiment, the clusters may be grouped individually as proteins that are regulated to a similar extent in a host cell. The clusters may also include groups of proteins that are regulated to a similar extent in a recombinant host cell, for example, that are up-regulated or down-regulated to a similar extent compared to a host cell or a modified or an unmodified cell. The clusters can also include groups related by protein structure, function, or processing. Groups of protein binding partners in an array, or groups of proteins analyzed in a different assay such as two-dimensional electrophoresis can be selected from, but are not limited to: putative or known proteases, co-factors of proteases or protease-like proteins; folding modulators, co-factors of folding modulators or proteins that could improve protein folding or solubility; transcription factors; proteins involved in nucleic acid stability or translational initiation; kinases; extracellular or intracellular receptors; metabolic enzymes; metabolic cofactors; envelope proteins; and house-keeping genes.

Metabolome

Proteomic analysis processes allow the abundance and distribution of many proteins to be determined simultaneously. However, the functional consequences of changes to the proteome are reported only indirectly. Another approach is to measure the levels of these small molecules, or metabolites. A genetic profile analyzed in the process of the invention can thus include a metabolomic profile. Processes for analyzing the metabolome of a specific host include gas chromatography, high-pressure liquid chromatography and capillary electrophoresis to separate metabolites according to various chemical and physical properties. The molecules can then be identified using processes such as mass spectrometry.

Detection/Analysis

The process includes analyzing a genetic profile to identify a compensatory gene or gene product that is expressed at a higher level in the recombinant cell. In general, this step includes the monitoring of the expression (e.g. detecting and or quantifying the expression) of a multitude of genes or gene products. The expression is generally monitored by detecting binding of host cell gene products to a transcriptome, proteome or metabolome profile as described above. The analysis of the binding may involve a comparison of binding between a recombinant host cell expressing recombinant protein or peptide and a naive host cell or a recombinant host cell not expressing the protein or peptide.

Detection

Figure 12:
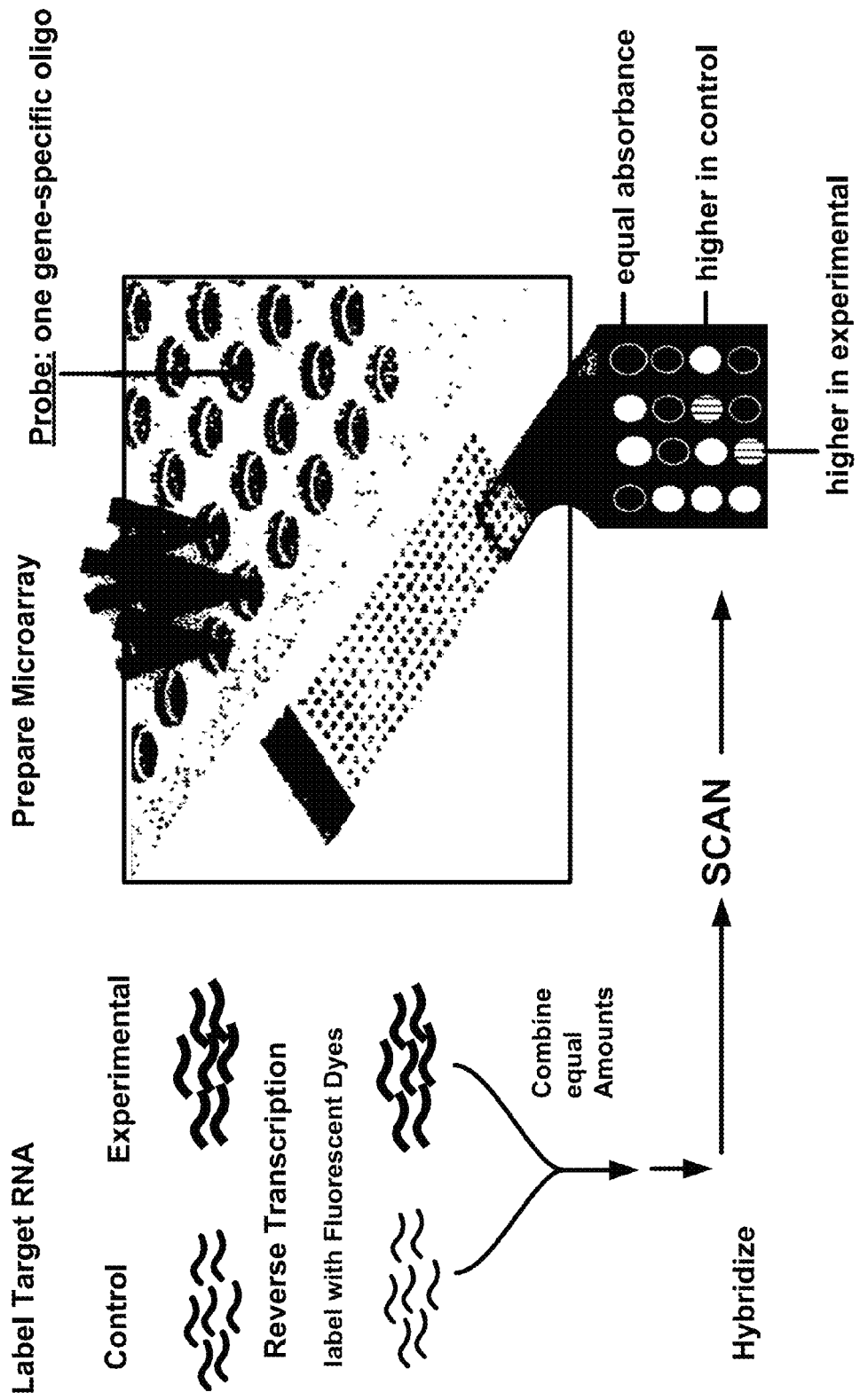
FIG. 12 is a pictoral representation of the process of measuring relative abundance of mRNA between two samples.

This step includes the monitoring of the expression (e.g. detecting and or quantifying the expression) of a multitude of genes or gene products. The expression is generally monitored by detecting binding of host cell gene products to a transcriptome, proteome or metabolome profile as described above. Typically, at least about 10 genes, or at least about 100, or at least about 1000 and or at least about 10,000 different genes can be assayed at one time. The process can involve providing a pool of identified nucleic acids comprising RNA transcripts of one or more of said genes, or nucleic acids derived from the RNA transcripts; hybridizing the pool of nucleic acids to an array of oligonucleotide probes immobilized on a surface, where the array comprises more than 100 different oligonucleotides and each different oligonucleotide is localized in a predetermined region of said surface, each different oligonucleotide is attached to the surface through at least one covalent bond, and the oligonucleotide probes are complementary to the RNA transcripts or nucleic acids derived from the RNA transcripts; and quantifying the hybridized nucleic acids in the array. A pictoral representation of one technique for monitoring expression of a gene product between two samples is depicted in FIG. 12.

The process can also involve providing a pool of cellular proteins. These can be derived from cellular lysates that are made by lysing cells using detergents or surfactants; using osmotic lysis; using thermal changes, such as freeze-thaw cycles; using mechanical means or using pressure changes. Typically chemicals are included in the process of lysing a cell or cell system that inhibit certain proteins, such as proteases, particularly non-specific proteases, to limit degradation of proteins. In addition, cell lysates are typically kept at or below 4° C., and can be kept at or below 0° C. or at or below 20° C. during processing. Cell lysates can be separated before further processing, for example by size exclusion chromatography, ion exchange or affinity matrix chromatography such as by using HPLC.

Typically, the identified genetic product, mRNA, cDNA, protein or metabolite is labeled with a detectable marker or probe. The marker or probe can be one or more fluorescent molecules or fluorophores. These can include commercially available molecules such as Cy3 and Cy5 linked to, for example, particular nucleotides that can be incorporated into a reverse transcribed cDNA to provide detectable molecules for screening. In one embodiment, a first fluorophores is incorporated into a sample from the host and a second fluorophore is incorporated into a sample from a host expressing recombinant protein or peptide. In one embodiment, the first fluorophore and second fluorophore emit different wavelengths of light. In this embodiment, the binding of samples from the host and the host expressing recombinant protein can be monitored in the same assay. In another embodiment, the fluorophores are excited at different wavelengths of light. In another embodiment, the first and second fluorophore are excited or emit light at the same wavelength. In this embodiment, the samples from the host and from the host expressing recombinant protein are typically monitored in different assays.

The process can additionally include a step of quantifying the hybridization of the identified nucleic acids or proteins or chemical metabolites. The quantification can include measurement of the levels of transcription of one or more genes. Typically the pool of identified nucleic acids for example, is one in which the concentration of the identified nucleic acids (pre-mRNA transcripts, mRNA transcripts or nucleic acids derived from the RNA transcripts) is proportional to the expression levels of genes encoding those identified nucleic acids.

For transcriptome analysis, the pool of nucleic acids may be labeled before, during, or after hybridization, although typically the nucleic acids are labeled before hybridization. Fluorescence labels are typically used, often with a single fluorophore, and, where fluorescence labeling is used, quantification of the hybridized nucleic acids can be by quantification of fluorescence from the hybridized fluorescently labeled nucleic acid. Such quantification is facilitated by the use of a confocal laser scanner or fluorescence microscope, such as a confocal fluorescence microscope, which can be equipped with an automated stage to permit automatic scanning of the array, and which can be equipped with a data acquisition system for the automated measurement recording and subsequent processing of the fluorescence intensity information. Devices for reading such arrays include the CLONETRACKER™, IMAGENE™, GENESIGHT™ gene array modules and the GENEDIRECTOR™ gene array database, available from Biodiscovery, Inc., El Segundo, Calif., or the GENECHIP™ gene array reader, available from Affymetrix, Inc. of Santa Clara, Calif. In one embodiment, hybridization occurs at low stringency (e.g. about 20° C. to about 50° C., or about 30° C. to about 40° C., or about 37° C.). Hybridization may include subsequent washes at progressively increasing stringency until a desired level of hybridization specificity is reached.

Quantification of the hybridization signal can be by any means known to one of skill in the art. However, in one embodiment, quantification is achieved by use of a confocal fluorescence scanner. Data is typically evaluated by calculating the difference in hybridization signal intensity between each oligonucleotide probe and its corresponding mismatch control probe. Typically, this difference can be calculated and evaluated for each gene. Certain analytical processes are provided herein.

Techniques have been developed to prepare appropriate bacterial hybridization probes (see for eg. Choi et al. (2003) *App. Envir. Microbio.* 69:4737-4742). For example, cells can be stored in an RNA stabilizing agent such as RNAlater (Ambion, Austin, Tex.). RNA is generally purified in three steps: (1) isolation of the total RNA, (2) removal of contaminating DNA and (3) clean-up of the total RNA. Total RNA can be isolated and then mixed with random hexamer primers and reverse transcriptase to make cDNA. Typically at least one fluorescent probe is incorporated into the cDNA. In one embodiment, one fluorescent probe is incorporated, in another embodiment more than one probe, for example 2, 3, 4, 5 or more fluorescent probes are incorporated into the same or different samples of cDNA. In a eukaryotic host, the pool of identified nucleic acids can also be the total polyA$^+$ mRNA isolated from a biological sample, or cDNA made by reverse transcription of the RNA or second strand cDNA or RNA transcribed from the double stranded cDNA intermediate.

Fluorescent dyes are typically incorporated into cDNA molecules during the reverse transcription reaction. Due to the different mRNA structure between prokaryotes (bacteria) and eukaryotes (yeast, mammalian cells, etc.), different primers can be used, however random primers can be used in both cases, and oligo-dT primers can be used in eukaryots, which have polyA tails. An alternative process is amino-allyl labeling to increase the signal intensity. This process incorporates nucleotide analogs featuring a chemically reactive group to which a fluorescent dye may be attached after the reverse transcription reaction (Manduchi, E. et al. (2002) Comparison of different labeling processes for two-channel high-density microarray experiments. *Physiol Genomics* 10:169-79).

The pool of identified nucleic acids can be treated to reduce the complexity of the sample and thereby reduce the background signal obtained in hybridization. The terms "background" or "background signal" refer to hybridization signals resulting from non-specific binding, or other interactions, between the labeled identified nucleic acids and components of the oligonucleotide array (e.g., the oligonucleotide probes, control probes, the array substrate, etc.). In one approach, a pool of mRNAs, derived from a biological sample, is hybridized with a pool of oligonucleotides comprising the oligonucleotide probes present in the array. The pool of hybridized nucleic acids is then treated with RNase A which digests the single stranded regions. The remaining double stranded hybridization complexes are then denatured and the oligonucleotide probes are removed, leaving a pool of mRNAs enhanced for those mRNAs complementary to the oligonucleotide probes in the array.

In another approach to background reduction, a pool of mRNAs derived from a biological sample is hybridized with paired identified specific oligonucleotides where the paired identified specific oligonucleotides are complementary to regions flanking subsequences of the mRNAs complementary to the oligonucleotide probes in the array. The pool of hybridized nucleic acids is treated with RNase H which digests the hybridized (double stranded) nucleic acid sequences. The remaining single stranded nucleic acid sequences which have a length about equivalent to the region flanked by the paired identified specific oligonucleotides are then isolated (e.g. by electrophoresis) and used as the pool of nucleic acids for monitoring gene expression.

A third approach to background reduction involves eliminating or reducing the representation in the pool of particular preselected identified mRNA messages (e.g., messages that are characteristically overexpressed in the sample). This process involves hybridizing an oligonucleotide probe that is complementary to the preselected identified mRNA message to the pool of polyA$^+$ mRNAs derived from a biological sample. The oligonucleotide probe hybridizes with the particular preselected polyA$^+$ mRNA to which it is complementary. The pool of hybridized nucleic acids is treated with RNase H which digests the double stranded (hybridized) region thereby separating the message from its polyA$^+$ tail. Isolating or amplifying (e.g., using an oligo dT column) the polyA$^+$ mRNA in the pool then provides a pool having a reduced or no representation of the preselected identified mRNA message.

Analysis

The identified gene is typically identified by comparing a genetic profile of the host cell expressing the recombinant protein or peptide to a genetic profile of the host cell not expressing the recombinant protein or peptide. In iterative embodiments, the identified gene to be modified is identified by comparing a genetic profile of the cell that is to be modified (the second cell) to the cell that it was modified from (the first cell). The identified gene is identified by comparing a genetic profile of the second cell to a genetic profile of the first cell and identifying one or more genes the expression of which is increased in the second cell.

cDNA microarrays measure the relative mRNA abundance between two samples. A series of post-induction time point samples can be compared to the pre-induction sample for the same strain (temporal expression profile), or post-induction samples can be compared with different strains at the same time point. The comparison can be through the use of a computer program, such as GENESIGHT™ gene array. For example, when using a microarray using a fluorescent tag, a spot intensity can be measured for each sample attached to the array (for example a DNA sequence). The spot intensity can then be corrected for background and the ratio of the intensity for samples from the host versus the host expressing the recombinant protein or peptide, or for the host expressing the recombinant protein or peptide compared to the modified host expressing the recombinant protein or peptide can be measured. The ratio provides a measure to identify the genes that are up-regulated or the expression of which is increased upon expression of the recombinant protein or peptide, or upon modification of the host cell to allow identification of an identified gene.

To identify whether a gene is up-regulated, a standard or "cut off" ratio is established. The cut off ratio may be designed to overcome the effects of background noise associated with a particular assay. In general, any ratio of greater than 1 between the measurements can designate an up-regulated gene. However, variation between assays can require a ratio higher than 1, for example 1.5, or more than 2, or more than 2.5, or more than 3, or more than 3.5 or more than 4 or more than 4.5, or more than 5 or more than 6, or more than 7, or more than 8, or more than 9 or more than 10. The standard may be established before the process, relying on standards known in the art, or may be established during measurements by comparing ratios of levels of control genes or gene products, such as housekeeper genes.

Step III: Changing Expression of the Identified Compensatory Gene or Gene Product by Genetically Modifying the Cell to Provide a Modified Recombinant Cell that Achieves an Increase in Recombinant Protein Expression, Activity or Solubility Identified Compensatory Genes The compensatory genes or gene products that are identified in step ii), or homologous analogues, cofactors or subunits thereof, are used to design strategies to genetically modify the cell to either increase, decrease, knock in or knock out expression of one or more identified genes. The gene sequences identified in public databases can be used to design strategies, particularly to design constructs to modulate expression of a gene by techniques described above. Such techniques are well known.

In one embodiment, the identified gene or genes is at least one putative protease, a protease-like protein, a cofactor or subunit of a protease. In other embodiments, the identified gene or genes is at least one folding modulator, putative folding modulator, cofactor or subunit of a folding modulator. In certain embodiments, a identified gene is a subunit of a protease. In one embodiment, the identified gene or genes can be a serine, threonine, cysteine, aspartic or metallo peptidase. In one embodiment, the identified gene or genes can be selected from hslV, hslU, clpA, clpB and clpX The identified gene can also be a cofactor of a protease. In another embodiment, the identified gene or genes is a folding modulator. In some embodiments, the identified gene or genes can be selected from a chaperone protein, a foldase, a peptidyl prolyl isomerase and a disulfide bond isomerase. In some embodiments, the identified gene or genes can be selected from htpG, cbpA, dnaJ, dnaK and fkbP.

Bacterial genes are organized into operons, which are gene clusters that encode the proteins necessary to perform coordinated function, such as biosynthesis of a given amino acid. Therefore, in one embodiment, the identified gene is part of an operon. In a particular embodiment, the identified gene is in an operon that encodes for one or more proteins with protease activity alone or in combination, or is an operon that encodes for one or more proteins with folding modulator activity, including foldases, chaperones, and isomerases.

Proteases

In one embodiment of the invention, the host cell is modified by reducing expression of, inhibiting or removing at least one protease from the genome. The modification can also be to more than one protease in some embodiments. In a related embodiment, the cell is modified by reducing expression of a protease cofactor or protease protein. In another embodiment, the host cell is modified by inhibition of a promoter for a protease or related protein, which can be a native promoter. The gene modification can be to modulate a protein homologous to the identified identified gene.

In the MEROPS database, peptidases are grouped into clans and families. The families are groups of closely related functionally similar peptidases. Families are grouped by their catalytic type: S, serine; T, threonine; C, cysteine; A, aspartic; M, metallo and U, unknown. Over 20 families (denoted S1-S27) of serine protease have been identified, these being grouped into 6 clans (SA, SB, SC, SE, SF and SG) on the basis of structural similarity and other functional evidence. Structures are known for four of the clans (SA, SB, SC and SE). Threonine peptidases are characterized by a threonine nucleophile at the N terminus of the mature enzyme. The type example for this clan is the archaean proteasome beta component of *Thermoplasma acidophilum*. Cysteine peptidases have characteristic molecular topologies and are peptidases in which the nucleophile is the sulphydryl group of a cysteine residue. Cysteine proteases are divided into clans (proteins which are evolutionary related), and further sub-divided into families, on the basis of the architecture of their catalytic dyad or triad:

Clan CA contains the families of papain (C1), calpain (C2), streptopain (C10) and the ubiquitin-specific peptidases (C12, C19), as well as many families of viral cysteine endopeptidases.

Clan CD contains the families of clostripain (C11), gingipain R(C25), legumain (C13), caspase-1 (C14) and separin (C50). These enzymes have specificities dominated by the interactions of the S1 subsite.

Clan CE contains the families of adenain (C5) from adenoviruses, the eukaryotic Ulp1 protease (C48) and the bacterial YopJ proteases (C55).

Clan CF contains only pyroglutamyl peptidase I (C15).

Clan PA contains the picornains (C3), which have probably evolved from serine peptidases and which form the majority of enzymes in this clan.

Clans PB and CH contain the autolytic cysteine peptidases.

Aspartic endopeptidases of vertebrate, fungal and retroviral origin have been characterised. Aspartate peptidases are so named because Asp residues are the ligands of the activated water molecule in all examples where the catalytic residues have been identifed, although at least one viral enzyme is believed to have as Asp and an Asn as its catalytic dyad. All or most aspartate peptidases are endopeptidases. These enzymes have been assigned into clans (proteins which are evolutionary related), and further sub-divided into families, largely on the basis of their tertiary structure.

Metalloproteases are the most diverse of the four main types of protease, with more than 30 families identified to date. In these enzymes, a divalent cation, usually zinc, activates the water molecule. The metal ion is held in place by amino acid ligands, usually three in number. The known metal ligands are His, Glu, Asp or Lys and at least one other residue is required for catalysis, which may play an electrophillic role. Of the known metalloproteases, around half contain an HEXXH motif, which has been shown in crystallographic studies to form part of the metal-binding site. The HEXXH motif is relatively common, but can be more stringently defined for metalloproteases as abXHEbbHbc, where 'a' is most often valine or threonine and forms part of the S1' subsite in thermolysin and neprilysin, 'b' is an uncharged residue, and 'c' a hydrophobic residue. Proline is never found in this site, possibly because it would break the helical structure adopted by this motif in metalloproteases.

The peptidases associated with clan U- have an unknown catalytic mechanism as the protein fold of the active site domain and the active site residues have not been reported.

Certain proteases (e.g. OmpT) can adsorb to the surface of inclusion bodies and may degrade the desired protein while it is being refolded. Therefore, certain identified proteins can be proteases or protease proteins that adhere to inclusion bodies and these can be modified to, for example, reduce attachment.

Proteases or protease proteins can also be classified as Aminopeptidases; Dipeptidases; Dipeptidyl-peptidases and tripeptidyl peptidases; Peptidyl-dipeptidases; Serine-type carboxypeptidases; Metallocarboxypeptidases; Cysteine-type carboxypeptidases; Omegapeptidases; Serine proteinases; Cysteine proteinases; Aspartic proteinases; Metallo proteinases; or Proteinases of unknown mechanism.

Aminopeptidases include cytosol aminopeptidase (leucyl aminopeptidase), membrane alanyl aminopeptidase, cystinyl aminopeptidase, tripeptide aminopeptidase, prolyl aminopeptidase, arginyl aminopeptidase, glutamyl aminopeptidase, x-pro aminopeptidase, bacterial leucyl aminopeptidase, thermophilic aminopeptidase, clostridial aminopeptidase, cytosol alanyl aminopeptidase, lysyl aminopeptidase, x-trp aminopeptidase, tryptophanyl aminopeptidase, methionyl aminopeptidas, d-stereospecific aminopeptidase, aminopeptidase ey. Dipeptidases include x-his dipeptidase, x-arg dipeptidase, x-methyl-his dipeptidase, cys-gly dipeptidase, glu-glu dipeptidase, pro-x dipeptidase, x-pro dipeptidase, met-x dipeptidase, non-stereospecific dipeptidase, cytosol non-specific dipeptidase, membrane dipeptidase, beta-ala-his dipeptidase. Dipeptidyl-peptidases and tripeptidyl peptidases include dipeptidyl-peptidase i, dipeptidyl-peptidase ii, dipeptidyl peptidase iii, dipeptidyl-peptidase iv, dipeptidyl-dipeptidase, tripeptidyl-peptidase I, tripeptidyl-peptidase II. Peptidyl-dipeptidases include peptidyl-dipeptidase a and peptidyl-dipeptidase b. Serine-type carboxypeptidases include lysosomal pro-x carboxypeptidase, serine-type D-ala-D-ala carboxypeptidase, carboxypeptidase C, carboxypeptidase D. Metallocarboxypeptidases include carboxypeptidase a, carboxypeptidase B, lysine(arginine) carboxypeptidase, gly-X carboxypeptidase, alanine carboxypeptidase, muramoylpentapeptide carboxypeptidase, carboxypeptidase h, glutamate carboxypeptidase, carboxypeptidase M, muramoyltetrapeptide carboxypeptidase, zinc d-ala-d-ala carboxypeptidase, carboxypeptidase A2, membrane pro-x carboxypeptidase, tubulinyl-tyr carboxypeptidase, carboxypeptidase t. Omegapeptidases include acylaminoacyl-peptidase, peptidyl-glycinamidase, pyroglutamyl-peptidase I, beta-aspartyl-peptidase, pyroglutamyl-peptidase II, n-formylmethionyl-peptidase, pteroylpoly-[gamma]-glutamate carboxypeptidase, gamma-glu-X carboxypeptidase, acylmuramoyl-ala peptidase. Serine proteinases include chymotrypsin, chymotrypsin c, metridin, trypsin, thrombin, coagulation factor Xa, plasmin, enteropeptidase, acrosin, alpha-lytic protease, glutamyl, endopeptidase, cathepsin G, coagulation factor viia, coagulation factor ixa, cucumisi, prolyl oligopeptidase, coagulation factor xia, brachyurin, plasma kallikrein, tissue kallikrein, pancreatic elastase, leukocyte elastase, coagulation factor xiia, chymase, complement component clr55, complement component cls55, classical-complement pathway c3/c5 convertase, complement factor I, complement factor D, alternative-complement pathway c3/c5 convertase, cerevisin, hypodermin C, lysyl endopeptidase, endopeptidase la, gamma-reni, venombin ab, leucyl endopeptidase, tryptase, scutelarin, kexin, subtilisin, oryzin, endopeptidase k, thermomycolin, thermitase, endopeptidase SO, T-plasminogen activator, protein C, pancreatic endopeptidase E, pancreatic elastase ii, IGA-specific serine endopeptidase, U-plasminogen, activator, venombin A, furin, myeloblastin, semenogelase, granzyme A or cytotoxic T-lymphocyte proteinase 1, granzyme B or cytotoxic T-lymphocyte proteinase 2, streptogrisin A, treptogrisin B, glutamyl endopeptidase II, oligopeptidase B, *limulus* clotting factor c, *limulus* clotting factor, *limulus* clotting enzyme, omptin, repressor lexa, bacterial leader peptidase I, togavirin, flavirin. Cysteine proteinases include cathepsin B, papain, ficin, chymopapain, asciepain, clostripain, streptopain, actinide, cathepsin 1, cathepsin H, calpain, cathepsin t, glycyl, endopeptidase, cancer procoagulant, cathepsin S, picornain 3C, picornain 2A, caricain, ananain, stem bromelain, fruit bromelain, legumain, histolysain, interleukin 1-beta converting enzyme. Aspartic proteinases include pepsin A, pepsin B, gastricsin, chymosin, cathepsin D, neopenthesin, renin, retropepsin, proopiomelanocortin converting enzyme, aspergillopepsin I, aspergillopepsin II, penicillopepsin, rhizopuspepsin, endothiapepsin, mucoropepsin, candidapepsin, saccharopepsin, rhodotorulapepsin, physaropepsin, acrocylindropepsin, polyporopepsin, pycnoporopepsin, scytalidopepsin a, scytalidopepsin b, xanthomonapepsin, cathepsin e, barrierpepsin, bacterial leader peptidase I, pseudomonapepsin, plasmepsin. Metallo proteinases include atrolysin a, microbial collagenase, leucolysin, interstitial collagenase, neprilysin, envelysin, iga-specific metalloendopeptidase, procollagen N-endopeptidase, thimet oligopeptidase, neurolysin, stromelysin 1, meprin A, procollagen C-endopeptidase, peptidyl-lys metalloendopeptidase, astacin, stromelysin, 2, matrilysin gelatinase, aeromonolysin, pseudolysin, thermolysin, bacillolysin, aureolysin, coccolysin, mycolysin, betalytic metalloendopeptidase, peptidyl-asp metalloendopeptidase, neutrophil collagenase, gelatinase B, leishmanolysin, saccharolysin, autolysin, deuterolysin, serralysin, atrolysin B, atrolysin C, atroxase, atrolysin E, atrolysin F, adamalysin, horrilysin, ruberlysin, bothropasin, bothrolysin, ophiolysin, trimerelysin I, trimerelysin II, mucrolysin, pitrilysin, insulysin, O-syaloglycoprotein endopeptidase, russellysin, mitochondrial, intermediate, peptidase, dactylysin, nardilysin, magnolysin, meprin B, mitochondrial processing peptidase, macrophage elastase, choriolysin, toxilysin. Proteinases of unknown mechanism include thermopsin and multicatalytic endopeptidase complex.

Certain proteases of *P. fluorescens* are listed in Table A.

TABLE A

| Class | Family | RXF | Curated Function | Gene | Physiology |
|---|---|---|---|---|---|
| MEROPS Homologs | | | | | |
| Aspartic Peptidases | | | | | |
| | A8 (signal peptidase II family) | | | | |
| | | RXF05383 | Lipoprotein signal peptidase (ec 3.4.23.36) | | Processing of numerous bacterial secreted lipoproteins. |
| | A24 (type IV prepilin peptidase family) | | | | |
| | | RXF05379 | type 4 prepilin peptidase pild (ec 3.4.99.—) | | This membrane-bound peptidase cleaves a specialized leader peptide from type 4 prepilin during its secretion from many bacterial species. Once secreted, the processed proteins are required for functions including type 4 pilus formation, toxin and other enzyme secretion, gene transfer, and biofilm formation. |
| Cysteine Peptidases | | | | | |
| | C15 (pyroglutamyl peptidase I family) | | | | |
| | | RXF02161 | Pyrrolidone-carboxylate peptidase (ec 3.4.19.3) | | Removal of pyroglutamyl groups from peptides in protein catabolism. |
| | C40 | | | | |
| | | RXF01968 | invasion-associated protein, P60 | | |
| | | RXF04920 | invasion-associated protein, P60 | | |
| | | RXF04923 | phosphatase-associated protein papq | | |
| | C56 (PfpI endopeptidase family) | | | | |
| | | RXF01816 | protease I (ec 3.4.—.—) | | |
| Metallopeptidases | | | | | |
| | M1 | | | | |
| | | RXF08773 | Membrane alanine aminopeptidase (ec 3.4.11.2) | | |
| | M3 | | | | |
| | | RXF00561 | Oligopeptidase A (ec 3.4.24.70) | prlC | Degradation of lipoprotein signal peptides, and other Intracellular oligopeptides. Role in maturation of bacteriophage P22 gp7 precursor. |
| | | RXF04631 | Zn-dependent oligopeptidases | | |
| | M4 (thermolysin family) | | | | |
| | | RXF05113 | Extracellular metalloprotease precursor (ec 3.4.24.—) | | |
| | M41 (FtsH endopeptidase family) | | | | |
| | | RXF05400 | Cell division protein ftsH (ec 3.4.24.—) | | Proposed role in proteolytic quality control of regulatory molecules and membrane proteins, in yeast. |
| | M10 | | | | |
| | | RXF04304 | Serralysin (ec 3.4.24.40) | | |

TABLE A-continued

| Class | Family | RXF | Curated Function | Gene | Physiology |
|---|---|---|---|---|---|
| | | RXF04500 | Serralysin (ec 3.4.24.40) | | |
| | | RXF01590 | Serralysin (ec 3.4.24.40) | | |
| | | RXF04495 | Serralysin (ec 3.4.24.40) | | |
| | | RXF02796 | Serralysin (ec 3.4.24.40) | | |
| | M14 (carboxypeptidase A family) | | | | |
| | | RXF09091 | Zinc-carboxypeptidase precursor (ec 3.4.17.—) | | |
| | M16 (pitrilysin family) | | | | |
| | | RXF03441 | Coenzyme pqq synthesis protein F (ec 3.4.99.—) | | |
| | | RXF01918 | zinc protease (ec 3.4.99.—) | | |
| | | RXF'01919 | zinc protease (ec 3.4.99.—) | | |
| | | RXF03699 | processing peptidase (ec 3.4.24.64) | | |
| | M17 (leucyl aminopeptidase family) | | | | |
| | | RXF00285 | Cytosol aminopeptidase (ec 3.4.11.1) | | Contributes to bacterial nutrition. |
| | M18 | | | | |
| | | RXF07879 | Aspartyl aminopeptidase (ec 3.4.11.21) | | |
| | M20 | | | | |
| | | RXF00811 | Succinyl-diaminopimelate desuccinylase (ec 3.5.1.18) | dapE | |
| | | RXF04052 | Xaa-His dipeptidase (ec 3.4.13.3) | | |
| | | RXF01822 | Carboxypeptidase G2 precursor (ec 3.4.17.11) | | |
| | | RXF04892 | N-acyl-L-amino acid amidohydrolase (ec 3.5.1.14) | | |
| | M28 (aminopeptidase Y family) | | | | |
| | | RXF03488 | Alkaline phosphatase isozyme conversion protein precursor (ec 3.4.11.—) | | |
| | M42 (glutamyl aminopeptidase family) | | | | |
| | | RXF05615 | Deblocking aminopeptidase (ec 3.4.11.—) | | |
| | M22 | | | | |
| | | RXF05817 | O-sialoglycoprotein endopeptidase (ec 3.4.24.57) | | |
| | | RXF03065 | Glycoprotease protein family | | |
| | M23 | | | | |
| | | RXF01291 | Cell wall endopeptidase, family M23/M37 | | |
| | | RXF03916 | Membrane proteins related to metalloendopeptidases | | |
| | | RXF09147 | Cell wall endopeptidase, family M23/M37 | | |
| | M24 | | | | |
| | | RXF04693 | Methionine aminopeptidase (ec 3.4.11.18) | | Probable role in cotranslational removal of N-terminal methionine. |
| | | RXF03364 | Methionine aminopeptidase (ec 3.4.11.18) | | Probable role in cotranslational removal of N-terminal methionine. |
| | | RXF02980 | Xaa-Pro aminopeptidase (ec 3.4.11.9) | | Involved in intracellular protein turnover, in bacteria. |

TABLE A-continued

| Class | Family | RXF | Curated Function | Gene | Physiology |
|---|---|---|---|---|---|
| | | RXF06564 | Xaa-Pro aminopeptidase (ec 3.4.11.9) | | |
| | M48 (Ste24 endopeptidase family) | | | | |
| | | RXF05137 | Heat shock protein HtpX | | |
| | | RXF05081 | Zinc metalloprotease (ec 3.4.24.—) | | |
| | M50 (S2P protease family) | | | | |
| | | RXF04692 | Membrane metalloprotease | | |
| Serine Peptidases | | | | | |
| | S1 (chymotrypsin family) | | | | |
| | | RXF01250 | protease do (ec 3.4.21.—) | | |
| | | RXF07210 | protease do (ec 3.4.21.—) | | |
| | S8 (subtilisin family) | | | | |
| | | RXF06755 | serine protease (ec 3.4.21.—) | | |
| | | RXF08517 | serine protease (ec 3.4.21.—) | | |
| | | RXF08627 | extracellular serine protease (ec 3.4.21.—) | | |
| | | RXF06281 | Extracellular serine protease precursor (ec 3.4.21.—) | | |
| | | RXF08978 | extracellular serine protease (ec 3.4.21.—) | | |
| | | RXF06451 | serine protease (ec 3.4.21.—) | | |
| | S9 (prolyl oligopeptidase family) | | | | |
| | | RXF02003 | Protease ii (ec 3.4.21.83) | | |
| | | RXF00458 | Hydrolase | | |
| | S11 (D-Ala-D-Ala carboxypeptidase A family) | | | | |
| | | RXF04657 | D-alanyl-D-alanine-endopeptidase (ec 3.4.99.—) | | |
| | | RXF00670 | D-alanyl-D-alanine carboxypeptidase (ec 3.4.16.4) | | |
| | S13 (D-Ala-D-Ala peptidase C family) | | | | |
| | | RXF00133 | D-alanyl-meso-diaminopimelate endopeptidase (ec 3.4.—.—) | | Acts in synthesis and remodelling of bacterial cell walls. |
| | | RXF04960 | D-alanyl-meso-diaminopimelate endopeptidase (ec 3.4.—.—) | | |
| | S14 (ClpP endopeptidase family) | | | | |
| | | RXF04567 | atp-dependent Clp protease proteolytic subunit (ec 3.4.21.92) | clpP | Thought to contribute to elimination of damaged proteins in heat shock. |
| | | RXF04663 | atp-dependent Clp protease proteolytic subunit (ec 3.4.21.92) | clpP | Thought to contribute to elimination of damaged proteins in heat shock. |
| | S16 (lon protease family) | | | | |
| | | RXF04653 | atp-dependent protease La (ec 3.4.21.53) | | Thought to contribute to elimination of damaged proteins in heat shock. |
| | | RXF08653 | atp-dependent protease La (ec 3.4.21.53) | | |
| | | RXF05943 | atp-dependent protease La (ec 3.4.21.53) | | |
| | S24 (LexA family) | | | | |
| | | RXF00449 | LexA repressor (ec 3.4.21.88) | | |
| | | RXF03397 | LexA repressor (ec 3.4.21.88) | | |
| | S26 (signal peptidase I family) | | | | |
| | | R3CF01181 | Signal peptidase I (ec 3.4.21.89) | | Cleaves signal peptides from secreted proteins. |
| | S33 | | | | |
| | | RXF05236 | Proline iminopeptidase (ec 3.4.11.5) | pip3 | |
| | | RXF04802 | Proline iminopeptidase (ec 3.4.11.5) | pip1 | |
| | | RXF04808 | Proline iminopeptidase (ec 3.4.11.5) | pip2 | |

TABLE A-continued

| Class | Family | RXF | Curated Function | Gene | Physiology |
|---|---|---|---|---|---|
| | S41 (C-terminal processing peptidase family) | | | | |
| | | RXF06586 | Tail-specific protease (ec 3.4.21.—) | | |
| | | RXF01037 | Tail-specific protease (ec 3.4.21.—) | | |
| | S45 | | | | |
| | | RXF07170 | Penicillin acylase (ec 3.5.1.11) | pacB2 | |
| | | RXF06399 | Penicillin acylase ii (ec 3.5.1.11) | pacB1 | |
| | S49 (protease IV family) | | | | |
| | | RXF06993 | possible protease sohb (ec 3.4.—.—) | | |
| | | RXF01418 | protease iv (ec 3.4.—.—) | | |
| | S58 (DmpA aminopeptidase family) | | | | |
| | | RXF06308 | D-aminopeptidase (ec 3.4.11.19) | | |
| Threonine Peptidases | | | | | |
| | T1 (proteasome family) | | | | |
| | | RXF01961 | atp-dependent protease hslV (ec 3.4.25.—) | hslV | Thought to contribute to elimination of damaged proteins in heat shock. |
| | T3 (gamma-glutamyltransferase family) | | | | |
| | | RXF02342 | Gamma-glutamyltranspeptidase (ec 2.3.2.2) | ggt1 | |
| | | RXF04424 | Gamma-glutamyltranspeptidase (ec 2.3.2.2) | ggt2 | |
| Unclassified Peptidases | | | | | |
| | U32 | | | | |
| | | RXF00428 | protease (ec 3.4.—.—) | | |
| | | RXF02151 | protease (ec 3.4.—.—) | | |
| | U61 | | | | |
| | | RXF04715 | Muramoyltetrapeptide carboxypeptidase (ec 3.4.17.13) | | |
| | U62 | | | | |
| | | RXF04971 | PmbA protein | pmbA | The product of the PmbA gene ({*Escherichia coli*}) facilitates the secretion of the antibiotic peptide microcin B17, removing an N-terminal, 26-amino acid leader peptide (Madison et al., 1997). |
| | | RXF04968 | TldD protein | | |
| Non MEROPS Proteases | | | | | |
| | | RXF00325 | Repressor protein C2 | | |
| | | RXF02689 | Microsomal dipeptidase (ec 3.4.13.19) | | |
| | | RXF02739 | membrane dipeptidase (3.4.13.19) | | |
| | | RXF03329 | Hypothetical Cytosolic Protein | | |
| | | RXF02492 | Xaa-Pro dipeptidase (ec 3.4.13.9) | | |
| | | RXF04047 | caax amino terminal protease family | | |
| | | RXF08136 | protease (transglutaminase-like protein) | | |
| | | RXF09487 | Zinc metalloprotease (ec 3.4.24.—) | | |

Certain proteases of *E. coli* origin are listed in Table B.

TABLE B

| Class | Family | Code | Peptidase or homologue (subtype) | Gene |
|---|---|---|---|---|
| Aspartic Peptidases | A8 | A08.001 | signal peptidase II | lspA |
| | A24A | A24.001 | type IV prepilin peptidase 1 (EtpN protein (plasmid p0157)) | etpN |
| | | A24.001 | type IV prepilin peptidase 1 (CofP protein) | cofP |

TABLE B-continued

| Class | Family | Code | Peptidase or homologue (subtype) | Gene |
|---|---|---|---|---|
| | | A24.001 | type IV prepilin peptidase 1 (HofD protein) | hofD/hopD/hopO |
| | | A24.003 | type IV prepilin peptidase 2 (HopD protein) | hopD/ECs4188 |
| | | A24 unassigned | family A24A unassigned peptidases (ORF_F310 protein) | pppA/ORF_F310 |
| | | A24 unassigned | family A24A unassigned peptidases (PilU protein (plasmid R721)) | pilU |
| | | A24 unassigned | family A24A unassigned peptidases (BfpP protein (plasmid pMAR2)) | bfpP/bfpG |
| | | A24 unassigned | family A24A unassigned peptidases (PilU protein) | PILU |
| | A26 | A26.001 | omptin | ompT/ECS1663/B0565 |
| | | A26.005 | proteinase SopA | sopA |
| Cysteine Peptidases | C26 | C26 unassigned | family C26 unassigned peptidases | YCJL/Z2490/ECS1875 |
| | C40 | C40.004 | spr g.p. (*Escherichia*-type) (spr protein) | spr |
| | | C40 unassigned | family C40 unassigned peptidases (NlpC protein) | nlpC/C2104//Z2737/ECS2415 |
| | | C40 unassigned | family C40 unassigned peptidases (YafL protein) | YafL |
| | | C40 unassigned | family C40 unassigned peptidases (chitinase 3) | |
| | | C40 unassigned | family C40 unassigned peptidases (YdhO protein) | ydhO |
| | C39 | C39.005 | colicin V processing peptidase (CvaB protein) | cvaB |
| | | C39.005 | colicin V processing peptidase (MtfB protein) | mtfB |
| | | C39 unassigned | family C39 unassigned peptidases (microcin H47 secretion protein MchF) | mchF/MCLB |
| | C56 | C56 unassigned | family C56 unassigned peptidases (YhbO protein) | yhbo |
| | | C56 unassigned | family C56 unassigned peptidases (c4536 protein) | c4536 |
| Metallopeptidases | M1 | M01.005 | alanyl aminopeptidase (proteobacteria) | pepN |
| | M3A | M03.004 | oligopeptidase A | prlC/opdA |
| | | M03.005 | peptidyl-dipeptidase Dcp | dcp/Z2160/ECS2147 |
| | | M03.005 | peptidyl-dipeptidase Dcp | dcp |
| | M41 | M41.001 | FtsH endopeptidase | hflB/ftsH/ECS4057 |
| | M66 | M66.001 | StcE protease | stcE |
| | M15D | M15 unassigned | subfamily M15D unassigned peptidases (VanX protein) | ddpX/vanX/B1488/Z2222/ECS2092 |
| | M16A | M16.001 | pitrilysin | ptr/ECs3678 |
| | M16B | M16 unassigned | subfamily M16B unassigned peptidases (PqqL protein) | pqqL/yddC |
| | M17 | M17.003 | aminopeptidase A (bacteria) | pepA/xerB |
| | | M17.004 | PepB aminopeptidase | pepB/Z3790/ECS3389 |
| | M24A | M24.001 | methionyl aminopeptidase 1 | map |
| | M24B | M24.003 | X-Pro dipeptidase (bacteria) | pepQ/ECs47 75 |
| | | M24.004 | aminopeptidase P (bacteria) | pepP |
| | | M24 unassigned | subfamily M24B unassigned peptidases (YqhT protein) | yqhT/ypdF/B2385/c2924 |
| | M20A | M20.010 | DapE peptidase (succinyl-diaminopimelate desuccinylase) | dapE/msgB/C2999 |
| | | M20 unassigned | subfamily M20A unassigned peptidases (YgeY protein) | ygey |
| | M20B | M20.003 | peptidase T | pepT/Z1832/ECS1572 |
| | M20C | M20.007 | X-His dipeptidase | pepD/pepH/ECs0264 |
| | M20D | M20 unassigned | family M2OD unassigned peptidases (YdaJ protein) | ydaJ/ECs1922 |
| | M28A | M28 unassigned | subfamily M28A unassigned peptidases (YfbL protein) | yfbL |
| | M28C | M28.005 | TAP aminopeptidase | iap |
| | M42 | M42 unassigned | family M42 unassigned peptidases (YjhO protein) | yjhO |
| | | M42 unassigned | family M42 unassigned peptidases (FrvX protein) | frvX |
| | | M42 unassigned | family M42 unassigned peptidases (FrvX protein) | frvX/b2384/ypdE |
| | M38 | M38.001 | beta-aspartyl dipeptidase | iadA |
| | M22 | M22.001 | O-sialoglycoprotein endopeptidase | ygjD |
| | | M22.002 | yeaZ protein | yeaZ/C2211/Z2850/ECS2516 |
| | M23B | M23.006 | YibP peptidase (YibP protein) | yibP |
| | | M23 unassigned | subfamily M23B unassigned peptidases (YebA protein) | yebA |

TABLE B-continued

| Class | Family | Code | Peptidase or homologue (subtype) | Gene |
|---|---|---|---|---|
| | M48B | M48.002 | HtpX endopeptidase | HtpX |
| | | M48 unassigned | subfamily M48B unassigned peptidases | YGGG/C3521 |
| | | M48 unassigned | subfamily M48B unassigned peptidases | YFGC/C3011 |
| | | M48 unassigned | subfamily M48B unassigned peptidases (YggG protein) | YggG/Z4280/ECS3811 |
| | | M48 unassigned | subfamily M48B unassigned peptidases (YcaL protein) | ycaL/C1047/Z1255/ECS0992 |
| | M50A | M50.004 | YaeL protease (YAEL protein) | ecfE/YAEL/B0176/Z0187/ECS0178/C0213 |
| | M52 | M52.001 | HybD endopeptidase (HybD protein) | hybD/ECS3878 |
| | | M52.002 | HyaD endopeptidase (HyaD protein) | hyaD |
| | | M52.003 | HycI endopeptidase (HycI protein) | hycI/C3277 |
| Serine Peptidases | S1B | S01.260 | B1598 endopeptidase | b1598 |
| | S1C | S01.273 | protease Do | htrA/degP |
| | | S01.274 | DegQ | hhoA/degQ/ECS4107/Z4593 |
| | | S01.275 | DegS | hhoB/degS |
| | S6 | S06.002 | EspP g.p. (*Escherichia coli*) | espP/pssA |
| | | S06.003 | Tsh peptidase (*Escherichia coli*) (Tsh protein) | tsh/hbp |
| | | S06.003 | Tsh peptidase (*Escherichia coli*) | c0393 |
| | | S06.004 | Pet endopeptidase | sat |
| | | S06.004 | Pet endopeptidase | |
| | | S06.005 | Pic endopeptidase (*Shigella flexneri*) | she/pic |
| | | S6 unassigned | family S6 unassigned peptidases (eatA protein) | eatA |
| | | S6 unassigned | family S6 unassigned peptidases (c0350 protein) | c0350 |
| | | S6 unassigned | family S6 unassigned peptidases (EspC protein) | espC |
| | | S6 unassigned | family S6 unassigned peptidases (epeA protein) | epeA |
| | | S6 unassigned | family S6 unassigned peptidases | |
| | S8A | S8 unassigned | subfamily S8A unassigned peptidases | |
| | S9A | S09.010 | oligopeptidase B | ptrB |
| | | S09.010 | oligopeptidase B | ptrB/C2255 |
| | S9X | S9 unassigned | family S9 unassigned peptidases | YFHR/C3060/b2534/Z3802 |
| | S11 | S11.002 | murein-DD-endopeptidase | pbpG |
| | | S11.003 | penicillin-binding protein 6 | dacC/Z1066/ECS0919 |
| | | S11.003 | penicillin-binding protein 6 (penicillin-binding protein pbp-6B) | dacD/phsE/ECs2812 |
| | | S11.003 | penicillin-binding protein 6 | dacA |
| | S12 | S12 unassigned | family S12 unassigned peptidases (c2452 protein) | c2452 |
| | | S12 unassigned | family S12 unassigned peptidases (YaiH protein) | yaiH/C0480 |
| | S13 | S13.001 | D-Ala-D-Ala peptidase C | dacB/ECs4061 |
| | S14 | S14.001 | endopeptidase Clp (type 1) | clpP/lopP/ECS0491 |
| | | S14 unassigned | family S14 unassigned peptidases (ECs0829 protein) | Z0967/ECS0829 |
| | | S14 unassigned | family S14 unassigned peptidases (ECs2960 protein) | H0022/Z2112/ECS2960/L34 |
| | S16 | S16.001 | lon protease | lon/deg/ECs0493 |
| | | S16 unassigned | family S16 unassigned peptidases (ECS1039 protein) | lonB/Z1305/ECS1039 |
| | | S16 unassigned | family S16 unassigned peptidases (c 1091 protein) | c1091 |
| | S24 | S24.001 | repressor LexA (LexA protein) | lexA/exrA |
| | | S24.003 | UmuD protein | |
| | | S24.003 | UmuD protein | umuD/C1631 |
| | S26 | S26A S26.001 | | signal peptidase I |
| | | S26.014 | traF plasmid-transfer protein (TraF protein) | traF |
| | S33 | S33 unassigned | family S33 unassigned peptidases (BioH protein) | bioH/C4189//Z4767/ECS4255 |
| | S41A | S41.001 | C-terminal processing protease-1 | prc/tsp/ECS2540/Z2877//C2239 |
| | S45 | S45.001 | penicillin G acylase precursor | pac |
| | S49 | S49.001 | protease IV | sppA/ECs2472//C2170 |
| | | S49.002 | sohB endopeptidase | sohB/ECS1844/Z2538//C1737 |
| | S51 | S51.001 | dipeptidase E | pepE |

TABLE B-continued

| Class | Family | Code | Peptidase or homologue (subtype) | Gene |
|---|---|---|---|---|
| | S54 | S54 unassigned | family S54 unassigned peptidases (c0741 protein) | c0741 |
| | | S54 unassigned | family S54 unassigned peptidases (glycerophosphate dehydrogenase) | glpG/C4201//Z4784/ECS4267 |
| Threonine Peptidases | T1B | T01.006 | HslV component of HslUV peptidase | hslV |
| | T2 | T02.002 | asparaginase | ybiK/Z1051m/C0913 |
| | T3 | T03.001 | gamma-glutamyltransferase 1 (bacterial) | ggt/C4236 |
| | S41A | S41.001 | C-terminal processing protease-1 | prc/tsp/ECS2540/Z2877//C2239 |
| Unclassified Peptidases | U6 | U06.001 | murein endopeptidase | mepA/ECs3212//C2874 |
| | | U32 | U32 unassigned | family U32 unassigned peptidases (YdcP protein) |
| | | U32 unassigned | family U32 unassigned peptidases (YegQ protein) | yegQ/C2611 |
| | | U32 unassigned | family U32 unassigned peptidases (YhbU protein) | YHBU/C3911/Z4519/ECS4039 |
| | | U35 | U35 unassigned | family U35 unassigned peptidases |
| | | U35 unassigned | family U35 unassigned peptidases (ECs4973 protein) | ECs4973 |
| | | U49 | U49.001 | Lit protease (*Escherichia coli*) |
| | | U61 | U61.001 | muramoyl-tetrapeptide carboxypeptidase |
| | | U61 unassigned | family U61 unassigned peptidases (MccF protein) | mccF |
| | | U62 | U62.001 | microcin-processing peptidase 1 |
| | | | U62.002 | microcin-processing peptidase 2 | tldD/ECs4117 |
| | | | M9G.035 | endopeptidase ECP 32 (*Escherichia coli*) |

Certain proteases of *S. cerevisiae* origin are listed in Table C.

TABLE C

| Class | Family | Code | Peptidase or homologue (subtype) | Gene |
|---|---|---|---|---|
| Aspartic Peptidases | A1 | A01.015 | barrierpepsin | bar1 |
| | | A01.018 | saccharopepsin | pep4/pho9 |
| | | A01.030 | yapsin 1 | yap3 |
| | | A01.031 | yapsin 2 | mkc7 |
| | | A01.035 | yapsin 3 | YPS3 |
| | | A01.UPW | family A1 unassigned peptidases | YPS7/D9476.8/YDR349C |
| | | A01.UPW | family A1 unassigned peptidases (YIR039C protein) | YIR039C |
| | A2D | A02.022 | Ty3 transposon (*Saccharomyces cerevisiae*) endopeptidase (retrotransposon Ty3-1) | POL3/TY3-2 orfB/TY3B |
| | A11B | A11.003 | Ty1 transposon (*Saccharomyces cerevisiae*) endopeptidase (transposon Ty1-17 protein B) | Ty1B |
| | | A11.003 | Ty1 transposon (*Saccharomyces cerevisiae*) endopeptidase (transposon Ty1 protein B) | Ty1B |
| | | A11.003 | Ty1 transposon (*Saccharomyces cerevisiae*) endopeptidase (transposon Ty1 protein B)' | Ty1B |
| | A11X | A11.UPW | family A11 unassigned peptidases (retrotransposon Ty4) | |
| | A22B | A22.008 | YKL100c protein (*Saccharomyces cerevisiae*) | YKL100c |
| Cysteine Peptidases | C1B | C01.085 | bleomycin hydrolase (yeast) | GAL6/YCP1/LAP3 |
| | C2 | C02.008 | calpain-7 | YMR154C/Cpl1/Rim13 |
| | C12 | C12.002 | ubiquitinyl hydrolase YUH1 | yuh1 |
| | C13 | C13.005 | glycosylphosphatidylinositol:protein transamidase | d9798.2 |

TABLE C-continued

| Class | Family | Code | Peptidase or homologue (subtype) | Gene |
|---|---|---|---|---|
| | C19 | C19.002 | Ubp1 ubiquitin peptidase | ubp1 |
| | | C19.003 | Ubp2 ubiquitin peptidase | ubp2 |
| | | C19.004 | Ubp3 ubiquitin peptidase | ubp3 |
| | | C19.005 | Doa4 ubiquitin peptidase | DOA4 |
| | | C19.006 | Ubp5 ubiquitin peptidase | ubp5 |
| | | C19.079 | UBP6 (*Saccharomyces cerevisiae*) (YFROlOW protein) | yfr010w |
| | | C19.UPW | family C19 unassigned peptidases (YNL186W protein) | YNL186W |
| | | C19.UPW | family C19 unassigned peptidases (UBP9) | ubp9 |
| | | C19.UPW | family C19 unassigned peptidases (YBL067C protein) | YBL067C |
| | | C19.UPW | family C19 unassigned peptidases (YBRO58C protein) | UBP12/YBR058C |
| | | C19.UPW | family C19 unassigned peptidases (ubiquitin carboxy-terminal hydrolase 16) | UBP16/YPL072W/ LPF12W |
| | | C19.UPW | family C19 unassigned peptidases (YMR304W protein) | YMR304W/ ym9952.06 |
| | | C19.UPW | family C19 unassigned peptidases (YMR223W protein) | YMR223W/ ym9959.05 |
| | | C19.UPW | family C19 unassigned peptidases (UBP7) | ubp7 |
| | | C19.UPW | family C19 unassigned peptidases (UBP13) | ubp13 |
| | C44 | C44.971 | glucosamine-fructose-6-phosphate aminotransferase | |
| | | C44.971 | glucosamine-fructose-6-phosphate aminotransferase (glucosamine-fructose-6-phosphate aminotransferase) | gfa1 |
| | C48 | C48.001 | Ulp1 endopeptidase | YPL020c |
| | | C48.005 | Ulp2 endopeptidase (Smt4p protein) | SMT4 |
| | C50 | C50.001 | separase | ESP1/YGR098C |
| | C54 | C54.001 | ATG4 peptidase (*Saccharomyces cerevisiae*) | Apg4/Aut2 |
| | C56 | C56.004 | YDR533C g.p. (*Saccharomyces cerevisiae*) | YDR533C/D9719.36 |
| | | C56.UPW | family C56 unassigned peptidases (YPL280W protein) | YPL280W |
| | | C56.UPW | family C56 unassigned peptidases (YOR391C protein) | YOR391C |
| | I34 | I34.001 | saccharopepsin inhibitor | PAI3/YMR174C/YM8010 |
| Metallopeptidases | M1 | M01.006 | Ape2 aminopeptidase | lap1/ape2 |
| | | M01.007 | Aap1' aminopeptidase | AAP1 |
| | | M01.007 | Aap1' aminopeptidase | |
| | | M01.017 | Yin7 g.p. (*Saccharomyces cerevisiae*) | yil137C |
| | | M01.UPW | family M1 unassigned peptidases (ynl045w protein) | ynl045w |
| | M3A | M03.003 | saccharolysin | prd1 |
| | | M03.006 | mitochondrial intermediate peptidase | MIP1 |
| | M16A | M16.007 | Axl1 peptidase | axl1 |
| | | M16.008 | Ste23 peptidase | ste23 |
| | | M16.UPA | subfamily M16A unassigned peptidases (orf1 protein) | orf1 |
| | M16B | M16.003 | mitochondrial processing peptidase beta-subunit (beta) | mas1/mif1 |
| | M16C | M16.UPC | subfamily M16C unassigned peptidases (YDR430C protein) | YDR430C |
| | | M16.UPC | subfamily M16C unassigned peptidases (YOL098C protein) | YOL098C |
| | M16X | M16.971 | mitochondrial processing peptidase non-peptidase alpha subunit (alpha) | mas2/mif2 |
| | | M16.974 | UCR2_HUMAN (ubiquinol-cytochrome c reductase core protein 2) | ucr2/cor2/qcr2 |
| | M18 | M18.001 | aminopeptidase I | ape1/lap4 |
| | | M18.UPW | family M18 unassigned peptidases (YHR113W protein) | YHR113W |
| | M20A | M20.005 | cytosolic nonspecific dipeptidase | YFR044C |
| | M20E | M20.002 | Gly-X carboxypeptidase | cps1/cps |
| | | M20.002 | Gly-X carboxypeptidase (pseudogene; deduced from nucleotide sequence by MEROPS) | AOE110, AOE264, AOE130 |
| | M22 | M22.003 | Mername-AA017 peptidase (YKR038C protein) | YKR038C |
| | | M22.UPW | family M22 unassigned peptidases (QRI7 protein) | QRI7 |

TABLE C-continued

| Class | Family | Code | Peptidase or homologue (subtype) | Gene |
|---|---|---|---|---|
| | M24A | M24.001 | methionyl aminopeptidase 1 | map1 |
| | | M24.002 | methionyl aminopeptidase 2 | ybl091c |
| | M24B | M24.009 | aminopeptidase P1 | YLL029w |
| | | M24.026 | aminopeptidase P homologue (YER078C protein) | YER078C |
| | | M24.UPB | subfamily M24B unassigned peptidases (YFR006W protein) | yfr006w |
| | M28A | M28.001 | aminopeptidase Y | ape3 |
| | M28E | M28.006 | Mername-AA063 peptidase (YDR415c protein) | YDR415c |
| | M28X | M28.974 | glutaminyl cyclase | YFR018C |
| | | M28.UPW | family M28 unassigned peptidases (YBRO74W protein) | YBR074W |
| | M41 | M41.002 | Afg3 g.p. (*Saccharomyces cerevisiae*) (AGF3 protein) | agf3/yta10 |
| | | M41.003 | m-AAA protease (RCA1 protein) | rca1/yta12 |
| | | M41.004 | i-AAA protease | yme1/yta11/osd1 |
| | M48A | M48.001 | Ste24 endopeptidase | STE24 |
| | M48B | M48.018 | Omal endopeptidase (*Saccharomyces cerevisiae*) (YKR087C protein) | YKR087C/YKR407 |
| | M49 | M49.001 | dipeptidyl-peptidase HI | YOL057W |
| | | M49.UPW | family M49 unassigned peptidases | |
| | M67A | M67.001 | Poh1 peptidase | RPN11/MPR1/YFR004W |
| | | M67.002 | Jab1/MPN domain metalloenzyme | YDL216c/D0888 |
| | | M67.973 | 26S proteasome non-ATPase regulatory subunit 7 | RPN8/YOR261C |
| Serine Peptidases | S1C | 501.434 | Nma111 endopeptidase (*Saccharomyces cerevisiae*) (YNL123W protein) | ynl123w |
| | S8A | 508.052 | cerevisin | prb1 |
| | | S08.UPA | subfamily S8A unassigned peptidases (YSP3 protein) | YSP3 |
| | | S08.UPA | subfamily S8A unassigned peptidases (YCR54C protein) | YCR54C |
| | S8B | S08.070 | kexin | kex2 |
| | S9B | S09.005 | dipeptidyl aminopeptidase A | ste13/ycil |
| | | S09.006 | dipeptidyl aminopeptidase B (fungus) | dap2 |
| | S9X | S09.UPW | family S9 unassigned peptidases (Ynl320w protein) | YNL320W |
| | S10 | S10.001 | carboxypeptidase Y | prc1 |
| | | S10.007 | kex carboxypeptidase | kex1 |
| | | S10.UPW | family S10 unassigned peptidases (YBR139W protein) | ybr139W |
| | S16 | S16.002 | PIM1 endopeptidase | lon/pim1 |
| | S26A | S26.002 | mitochondrial inner membrane protease 1 (1) | imp1 |
| | | S26.012 | mitochondrial inner membrane protease 2 (2) | imp2 |
| | S26B | S26.010 | signalase (eukaryote) 21 kDa component | sec11 |
| | | S33.UPW | family S33 unassigned peptidases | ECM18/YDR125C |
| | | S33.UPW | family S33 unassigned peptidases | ECM18/YDR125C |
| | S54 | 554.007 | Pcpl protein (*Saccharomyces cereviseae*) (YGR101W protein) | YGR101W |
| | S59 | S59.001 | nucleoporin 145 | Nup145 |
| Threonine Peptidases | T1A | T01.010 | proteasome catalytic subunit 1 | pre3 |
| | | T01.011 | proteasome catalytic subunit 2 | pup1 |
| | | T01.012 | proteasome catalytic subunit 3 | pre2/prg1 |
| | | T01.983 | proteasome subunit beta 3 | pup3 |
| | | T01.984 | proteasome subunit beta 2 | pre1 |
| | | T01.986 | proteasome subunit beta 1 | pre7/prs3 |
| | | T01.987 | proteasome subunit beta 4 | pre4 |
| | T1X | T01.971 | proteasome subunit alpha 6 | prs2/prc2 |
| | | T01.972 | proteasome subunit alpha 2 | pre8/prs4 |
| | | T01.973 | proteasome subunit alpha 4 | pre9/prs5 |
| | | T01.974 | proteasome subunit alpha 7 | pre6 |
| | | T01.975 | proteasome subunit alpha 5 | pup2 |
| | | T01.976 | proteasome subunit alpha 1 | pre5 |
| | | T01.977 | proteasome subunit alpha 3 | pre10/prs1/prc1 |
| | T3 | T03.012 | gamma-glutamyltransferase (*Saccharomyces*) (YLR299w protein) | L8003.4 |
| | T5 | T05.001 | ornithine acetyltransferase precursor | arg7/emc40/YMR062C |
| Unclassified Peptidases | U48 | U48.001 | prenyl protease 2 | rcel |

Folding Modulators

The identified up-regulated genes or gene products can be one or more folding modulator. Folding modulators can for example be HSP70 proteins, HSP110/SSE proteins, HSP40 (DNAJ-related) proteins, GRPE-like proteins, HSP90 proteins, CPN60 and CPN10 proteins, Cytosolic chaperonins, HSP100 proteins, Small HSPs, Calnexin and calreticulin, PDI and thioredoxin-related proteins, Peptidyl-prolyl isomerases, Cyclophilin PPIases, FK-506 binding proteins, Parvulin PPIases, Individual chaperonins, Protein specific chaperones, or intramolecular chaperones. Folding modulators are generally described in "Guidebook to Molecular Chaperones and Protein-Folding Catalysts" (1997) ed. M. Gething, Melbourne University, Australia.

The best characterized molecular chaperones in the cytoplasm of E. coli are the ATP-dependent DnaK-DnaJ-GrpE and GroEL-GroES systems. Based on in vitro studies and homology considerations, a number of additional cytoplasmic proteins have been proposed to function as molecular chaperones in E. coli. These include ClpB, HtpG and IbpA/B, which, like DnaK-DnaJ-GrpE and GroEL-GroES, are heat-shock proteins (Hsps) belonging to the stress regulon. The trans conformation of X-Pro bonds is energetically favored in nascent protein chains; however, ~5% of all prolyl peptide bonds are found in a cis conformation in native proteins. The trans to cis isomerization of X-Pro bonds is rate limiting in the folding of many polypeptides and is catalyzed in vivo by peptidyl prolyl cis/trans isomerases (PPIases). Three cytoplasmic PPIases, SlyD, SlpA and trigger factor (TF), have been identified to date in E. coli. TF, a 48 kDa protein associated with 50S ribosomal subunits that has been postulated to cooperate with chaperones in E. coli to guarantee proper folding of newly synthesized proteins. At least five proteins (thioredoxins 1 and 2, and glutaredoxins 1, 2 and 3, the products of the trxA, trxC, grxA, grxB and grxC genes, respectively) are involved in the reduction of disulfide bridges that transiently arise in cytoplasmic enzymes. Thus, identified genes can be disulfide bond forming proteins or chaperones that allow proper disulfide bond formation.

Certain folding modulators in P. fluorescens are listed in Table D.

TABLE D

| RXF | gene | function | Family |
|---|---|---|---|
| GroES/EL | | | |
| rxf1712095 | groES | chaperone | Hsp10 |
| ncfl)6767::rxf0209 0 | groEL | chaperone | Hsp60 |
| RXF01748 | ibpA | Small heat-shock protein (sHSP) IbpA PA3126; Acts as a holder for GroESL folding | Hsp20 |
| RXF03385 | hscB | Chaperone protein hscB | Hsp20 |
| Hsp70 (DnaK/J) | | | |
| rxfD5399 | dnaK | chaperone | Hsp70 |
| RXF06954 | dnaK | chaperone | Hsp70 |
| RXF03376 | hscA | chaperone | Hsp70 |
| RXF03987 | cbpA | Curved dna-binding protein, dnaJ like activity | Hsp40 |
| RXF05406 | dnaJ | Chaperone protein dnaJ | Hsp40 |
| RXF03346 | dnaJ | Molecular chaperones (DnaJ family) | Hsp40 |
| Hsp100 (Clp/Hsl) | | | |
| RXF04587 | clpA | atp-dependent clp protease atp-binding subunit clpA | Hsp100 |
| RXF08347 | clpB | ClpB protein | Hsp 100 |
| RXF04654 | clpX | atp-dependent clp protease atp-binding subunit clpX | Hsp100 |
| RXF01957 | hslU | atp-dependent hsl protease atp-binding subunit hslU | Hsp100 |
| RXF01961 | hslV | atp-dependent hsl protease atp-binding subunit hslV | Hsp100 |
| Hsp33 | | | |
| RXF04254 | ytfI | 33 kDa chaperonin (Heat shock protein 33 homolog) (HSP33). | Hsp33 |
| Hsp90 | | | |
| RXF05455 | htpG | Chaperone protein htpG | Hsp90 |
| SecB | | | |
| RXF02231 | secB | secretion specific chaperone SecB | SecB |
| Disulfide Bond Isomerases | | | |
| RXF07017 | dsbA | disulfide isomerase | DSBA oxidoreductase |
| RXF08657 | dsbA/ dsbC/ dsbG/ fernA | disulfide isomerase | DSBA oxidoreductase |
| rxf01002 | dsbA/ dsbC | disulfide isomerase | DSBA oxidoreductase/ Thioredoxin |
| rxf03307 | dsbC | disulfide isomerase | glutaredoxin/ Thioredoxin |
| rxf04890 | dsbG | disulfide isomerase | glutaredoxin/ Thioredoxin |

TABLE D-continued

| RXF | gene | function | Family |
|---|---|---|---|
| Peptidyl-prolyl cis-trans isomerases | | | |
| RXF03768 | ppiA | Peptidyl-prolyl cis-trans isomerase A (ec 5.2.1.8) | PPIase: cyclophilin type |
| RXF05345 | ppiB | Peptidyl-prolyl cis-trans isomerase B. | PPIase: cyclophilin type |
| RXF06034 | fklB | Peptidyl-prolyl cis-trans isomerase Fk1B. | PPIase: FKBP type |
| RXF06591 | fldB/ fkbP | fk506 binding protein Peptidyl-prolyl cis-trans isomerase (EC 5.2.1.8) | PPIase: FKBP type |
| RXF05753 | fldB, fkbP | Peptidyl-prolyl cis-trans isomerase (ec 5.2.1.8) | PPIase: FKBP type |
| RXF01833 | slyD | Peptidyl-prolyl cis-trans isomerase SlyD. | PPIase: FKBP type |
| RXF04655 | tig | Trigger factor, ppiase (ec 5.2.1.8) | PPIase: FKBP type |
| RXF05385 | yaad | Probable FKBP-type 16 kDa peptidyl-prolyl cis-trans isomerase (EC 5.2.1.8) (PPiase) (Rotamase). | PPIase: FKBP type |
| RXF00271 | | Peptidyl-prolyl cis-trans isomerase (ec 5.2.1.8) | PPIase: FKBP type |
| pili assembly chaperones (papD like) | | | |
| RXF06068 | cup | Chaperone protein cup | pili assembly papD |
| RXF05719 | ecpD | Chaperone protein ecpD | pili assembly papD |
| RXF03406 | ecpD; csuC | Chaperone protein ecpD | pili assembly papD |
| RXF04296 | ecpD; cup | Chaperone protein ecpD | pili assembly papD |
| RXF04553 | ecpD; cup | Chaperone protein ecpD | pili assembly papD |
| RXF04554 | ecpD; cup | Chaperone protein ecpD | pili assembly papD |
| RXF05310 | ecpD; cup | Chaperone protein ecpD | pili assembly papD |
| RXF05304 | ecpD; cup | Chaperone protein ecpD | pili assembly papD |
| RXF05073 | gltF | Gram-negative pili assembly chaperone periplasmic function | pili assembly papD |

Certain folding modulators in *E. coli* are listed in Table E.

TABLE E

| Uniprot Accession | Uniprot ID | Annotation | Family |
|---|---|---|---|
| GroES/EL | | | |
| P05380 | CH10_ECOLI | 10 kDa chaperonin | Hsp10 |
| P06139 | CH60_ECOLI | 60 kDa chaperonin | Hsp60 |
| Hsp70 (DnaK/J) | | | |
| P04475 | DNAK_ECOLI | Chaperone protein dnaK | Hsp70 |
| P77319 | HSCC_ECOLI | Chaperone protein hscC | Hsp70 |
| P36659 | CBPA_ECOLI | Curved DNA-binding protein cbpA | Hsp40 |
| P31680 | DJLA_ECOLI | DnaJ-like protein dj1A, rscG | Hsp40 |
| P08622 | DNAJ_ECOLI | Chaperone protein dnaJ | Hsp40 |
| P29131 | FTSN_ECOLI | Cell division protein ftsN | Hsp40 |
| P09372 | GRPE ECOLI | GrpE protein | GrpE |
| P31658 | HCHA_ECOLI | Chaperone protein hchA | Hsp31 |
| Hsp100 (Clp/Hsl) | | | |
| P15716 | CLPA_ECOLI | ATP-dependent Clp protease ATP-binding subunit clpA | Hsp100 |
| P03815 | CLPB_ECOLI | C1pB protein | Hsp100 |
| P33138 | CLPX_ECOLI | ATP-dependent Clp protease ATP-binding subunit clpX | Hsp100 |
| P32168 | HSLU_ECOLI | ATP-dependent hsl protease ATP-binding subunit hslU, cipY | Hsp100 |

TABLE E-continued

| Uniprot Accession | Uniprot ID | Annotation | Family |
|---|---|---|---|
| | | Small Heat Shock Proteins | |
| P29209 | IBPA_ECOLI | 16 kDa heat shock protein A. | Hsp16 |
| P29210 | IBPB_ECOLI | 16 kDa heat shock protein B. | Hsp16 |
| | | Not Part of a Larger Group | |
| P36662 | TORD_ECOLI | Chaperone protein torD | TorD |
| P15040 | SECB_ECOLI | Protein-export protein secB | SecB |
| P45803 | HSLO_ECOLI | 33 kDa chaperonin | Hsp33 |
| P10413 | HTPG_ECOLI | Chaperone protein htpG | Hsp90 |
| | | HscAB | |
| P36541 | HSCA_ECOLI | Chaperone protein hscA | Hsp66 |
| P36540 | HSCB ECOLI | Co-chaperone protein hscB | Hsp20 |
| | | Lipoprotein Carrier Protein | |
| P61316 | LOLA_ECOLI | Outer-membrane lipoprotein carrier protein precursor | LolA |
| P61320 | LOLB_ECOLI | Outer-membrane lipoprotein lolB precursor | LolB |
| | | Disulfide Bond Isomerases | |
| P24991 | DSBA_ECOLI | Thiol: disulfide interchange protein dsbA precursor. | |
| P30018 | DSBB_ECOLI | Disulfide bond formation protein B | Disulfide Bond Oxidoreductase |
| P21892 | DSBC_ECOLI | Thiol: disulfide interchange protein dsbC precursor. | |
| P36655 | DSBD_ECOLI | Thiol: disulfide interchange protein dsbD precursor (EC 1.8.1.8) (Protein-disulfide reductase) | |
| P33926 | DSBE_ECOLI | Thiol: disulfide interchange protein dsbE (Cytochrome c biogenesis protein ccmG). | |
| P77202 | DSBG_ECOLI | Thiol: disulfide interchange protein dsbG precursor | Disulfide Bond Oxidoreductase |
| | | Peptidyl-prolyl cis-trans isomerases | |
| P22257 | TIG_ECOLI | Trigger factor | PPIase: FKBP type |
| P45523 | FKBA_ECOLI | FKBP-type peptidyl-prolyl cis-trans isomerase fkpA precursor | PPIase: FKBP type |
| P39311 | FKBB_ECOLI | FKBP-type 22 kDa peptidyl-prolyl cis-trans isomerase | PPIase: FKBP type |
| P22563 | FKBX_ECOLI | FKBP-type 16 kDa peptidyl-prolyl cis-trans isomerase | PPIase: FKBP type |
| P30856 | SLYD_ECOLI | FKBP-type peptidyl-prolyl cis-trans isomerase slyD | PPIase: FKBP type |
| P20752 | PPIA_ECOLI | Peptidyl-prolyl cis-trans isomerase A precursor | PPIase: Cyclophilin type |
| P23869 | PPIB_ECOLI | Peptidyl-prolyl cis-trans isomerase B | PPIase: Cyclophilin type |
| P39159 | PPIC_ECOLI | Peptidyl-prolyl cis-trans isomerase C | PPIase: PPIC type |
| P77241 | PPID_ECOLI | Peptidyl-prolyl cis-trans isomerase D | PPIase: PPIC type |
| P21202 | SURA_ECOLI | Survival protein surA precursor | PPIase: Parvulin type |
| | | pili assembly chaperones (papD like) | |
| P53516 | AFAB_ECOLI | Chaperone protein afaB precursor | Pili Assembly PapD |
| P33128 | ECPD_ECOLI | Chaperone protein ecpD precursor | Pili Assembly PapD |
| P31697 | FIIVIC_ECOLI | Chaperone protein fimC precursor | Pili Assembly PapD |
| P77249 | SFMC_ECOLI | Chaperone protein sfmC precursor | Pili Assembly PapD |
| P75749 | YBGP_ECOLI | Hypothetical fimbrial chaperone ybgP precursor | Pili Assembly PapD |
| P40876 | YCBF_ECOLI | Hypothetical fimbrial chaperone ycbF precursor | Pili Assembly PapD |
| P75856 | YCBR_ECOLI | Hypothetical fimbrial chaperone ycbR precursor | Pili Assembly PapD |
| P33342 | YEHC_ECOLI | Hypothetical fimbrial chaperone yehC precursor | Pili Assembly PapD |
| P77599 | YFCS_ECOLI | Hypothetical fimbrial chaperone yfcS precursor | Pili Assembly PapD |
| P28722 | YHCA_ECOLI | Hypothetical fimbrial chaperone yhcA precursor | Pili Assembly PapD |
| P77616 | YQIH_ECOLI | Hypothetical fimbrial chaperone yqiH precursor | Pili Assembly PapD |
| P42914 | YRAI_ECOLI | Hypothetical fimbrial chaperone yraI precursor | Pili Assembly PapD |

Certain folding modulators of *S. cervisia* are shown in table F.

TABLE F

| Uniprot Accession GroES/EL | Uniprot ID | GO Source | Annotation | Family |
|---|---|---|---|---|
| P19882 | HS6O__YEAST | GOA:interpro | Heat shock protein 60, mitochondrial precursor | Hsp60 |
| P38228 | TC62__YEAST | GOA:interpro | Mitochondrial chaperone TCM62 | Hsp60 |
| P38910 | CH10 'YEAST | GOA:interpro | 10 kDa heat shock protein, mitochondrial | Hsp10 |
| Hsp70 (DnaK/J) | | | | |
| P25491 | MASS YEAST | GOA:interpro | Mitochondrial protein import protein MASS, Ydj 1 | Hsp40 |
| P10591 | HS71__YEAST | PMID:9789005 | Heat shock protein SSA1 | Hsp70 |
| P10592 | HS72__YEAST | PMID:9448096 | Heat shock protein SSA2 | Hsp70 |
| P11484 | HS75__YEAST | | Heat shock protein SSB1 | Hsp70 |
| P40150 | HS76__YEAST | | Heat shock protein SSB2 | Hsp70 |
| P09435 | HS73__YEAST | PMID:7867784 | Heat shock protein SSA3 | Hsp70 |
| P22202 | HS74__YEAST | | Heat shock protein SSA4 | Hsp70 |
| P25294 | SIS1 YEAST | GOA:interpro | SIS1 protein | Hsp40 |
| P32527 | ZUO1__YEAST | GO:0003754 | Zuotin | Hsp40 |
| P35191 | MDJ1__YEAST | GOA:interpro | MDJ1 protein, mitochondrial precursor | Hsp40 |
| P12398 | HS77__YEAST | PM-D:8654364 | Heat shock protein SSC1, mitochondrial precursor | Hsp70 |
| P38523 | GRPE__YEAST | GOA:interpro | GrpE protein homolog, mitochondrial precursor, MGE1 | GrpE |
| P14906 | SC63__YEAST | GOA: spkw | Translocation protein SEC63 | Hsp40 |
| P16474 | GR78__YEAST | | GRP 78, BIP, Kart | Hsp70 |
| P25303 | SCJ1__YEAST | GOA:interpro | DnaJ-related protein SCJ1 | Hsp40 |
| P39101 | CAJ1__YEAST | GOA:interpro | CAJ1 protein | Hsp40 |
| P48353 | HLJ1__YEAST | GOA:interpro | HLJ1 protein | Hsp40 |
| P39102 | XDJ1__YEAST | GOA:interpro | XDJ1 protein | Hsp40 |
| P52868 | YGM8__YEAST | GOA:interpro | Hypothetical 41.0 lcDa protein in CEG1-SOH1 intergenic region | Hsp40 |
| P53940 | YNH7__YEAST | GOA:interpro | Hypothetical 58.9 lcDa protein in TPM1-MKS1 intergenic region | Hsp40 |
| P38353 | SSH1__YEAST | | Sec sixty-one protein homolog. | Hsp70 |
| P36016 | LHS1 YEAST | GOA:spkw | Heat shock protein 70 homolog LHS1, SSI1 | Hsp70 |
| P38788 | YHM4__YEAST | PMID:11054575 | Heat shock protein 70 homolog YHR064C | Hsp70 |
| Hsp110/Sse | | | | |
| P32589 | HS78__YEAST | PMID:10480867 | Heat shock protein homolog SSE1 | SSE |
| P32590 | HS79__YEAST | | Heat shock protein homolog SSE2 | SSE |
| Hsp100 (Clp/Hsl) | | | | |
| P31539 | H104__YEAST | GOA:interpro | Heat shock protein 104 | Hsp100 |
| P33416 | HSP7__YEAST | GOA: spkw | Heat shock protein 78, mitochondrial precursor | Hsp100 |
| P38323 | MCX1__YEAST | GOA:interpro | Mitochondrial clpX-like chaperone MCX1 | Hsp100 |
| Small Heat Shock Proteins | | | | |
| P15992 | HS26__YEAST | PMID:10581247 | Heat shock protein 26 | Small Hsp |
| Prefoldin | | | | |
| P48363 | PFD3__YEAST | GOA:interpro | Probable prefoldin subunit 3 | Prefoldin |
| Q04493 | PFD5 YEAST | GOA:interpro | Prefoldin subunit 5 | Prefoldin |
| P43573 | YFC3__YEAST | GOA: interpro | Hypothetical 91.4 lcDa protein in STE2-FRS2 intergenic region | Prefoldin |
| P46988 | PFD1__YEAST | GOA: spkw | Prefoldin subunit 1 | KE2 |
| P40005 | PFD2__YEAST | GOA: spkw | Prefoldin subunit 2 | KE2 |
| P53900 | PFD4__YEAST | GOA: spkw | Prefoldin subunit 4 | KE2 |
| P52553 | PFD6__YEAST | GOA: spkw | Prefoldin subunit 6 | KE2 |
| Hsp90 | | | | |
| P02829 | HS82__YEAST | GOA:interpro | Heat shock protein HSP82 | Hsp90 |
| P15108 | HS83__YEAST | GOA:interpro | Heat shock cognate protein HSC82 | Hsp90 |
| P06101 | CC37__YEAST | GOA:spkw | Hsp90 co-chaperone Cdc37 | Cdc37 |

TABLE F-continued

| Uniprot Accession GroES/EL | Uniprot ID | GO Source | Annotation | Family |
|---|---|---|---|---|
| P33313 | CNS1_YEAST | GOA:spkw | Cyclophilin seven suppressor 1 | CNS1 |
| P15705 | STI1_YEAST | PMID:8972212 | Heat shock protein STI | |
| *Calnexin* | | | | |
| P27825 | CALX_YEAST | GOA: spkw | Calnexin homolog precursor | Calnexin |
| *Cytosolic Chaperonins T-com plex* | | | | |
| P12612 | TCPA_YEAST | GOA:interpro | T-complex protein 1, alpha subunit | TCP-1, Hsp60 |
| P39076 | TCPB_YEAST | GOA:interpro | T-complex protein 1, beta subunit | TCP-1, Hsp60 |
| P39078 | TCPD_YEAST | GOA:interpro | T-complex protein 1, delta subunit | TCP-1, Hsp60 |
| P40413 | TCPE_YEAST | GOA:interpro | T-complex protein 1, epsilon subunit | TCP-1, Hsp60 |
| P39077 | TCPG YEAST | GOA:interpro | T-complex protein 1, gamma subunit | TCP-1, Hsp60 |
| P42943 | TCPH_YEAST | GOA:interpro | T-complex protein 1, eta subunit | TCP-1, Hsp60 |
| P47079 | TCPQ_YEAST | GOA:interpro | T-complex protein 1, theta subunit | TCP-1, Hsp60 |
| P39079 | TCPZ_YEAST | GOA:interpro | T-complex protein 1, zeta subunit | TCP-1, Hsp60 |
| *Protein Specific* | | | | |
| P48606 | TBCA_YEAST | GOA: spkw | Tubulin-specific chaperone A | protein specific |
| P53904 | TBCB YEAST | GOA: spkw | Tubulin-specific chaperone B | protein specific |
| P46670 | CIN2_YEAST | GOA:spkw | Tubulin-folding cofactor C Cin2 | protein specific |
| P40987 | CIN1_YEAST | | Tubulin-folding cofactor D Cin1 | protein specific |
| P39937 | PAC2_YEAST | GOA: spkw | Tubulin-folding cofactor E PAC2 | protein specific |
| P21560 | CBP3_YEAST | GOA:spkw | CBP3 protein, mitochondrial precursor | protein specific |
| Q12287 | COXS_YEAST | GOA:spkw | Cytochrome c oxidase copper chaperone | protein specific |
| P40202 | LYS7 YEAST | GOA:interpro | Superoxide dismutase 1 copper chaperone | |
| Q02774 | SHR3_YEAST | PMID: 10564255 | Secretory component protein SHR3 | protein specific |
| P38293 | UMP1_YEAST | GOA:spkw | Proteasome maturation factor UMP1 | protein specific |
| P38784 | VM22_YEAST | PMID:7673216 | Vacuolar ATPase assembly protein VMA22 | protein specific |
| P38072 | SCO2_YEAST | GOA: spkw | SCO2 protein, mitochondrial precursor | protein specific |
| P53266 | SHY1_YEAST | PMID:11389896 | SHY1 protein | protein specific |
| P40046 | VTC1_YEAST | GOA:spkw | Vacuolar transporter chaperone 1 | protein specific |
| P38958 | PT00_YEAST | PMID:11498004 | PET 100 protein, mitochondrial precursor | protein specific |
| *Disulfide Bond Isomerases* | | | | |
| P17967 | PDI_YEAST | PMID:11157982 | Protein disulfide isomerase precursor | Disulfide bond oxidoreductase |
| P32474 | EUG1_YEAST | PMID:11157982 | Protein disulfide isomerase EUG1 precursor | Disulfide bond oxidoreductase |
| Q12404 | MPD1_YEAST | PM1D:11157982 | Disulfide isomerase MPD1 precursor | Disulfide bond oxidoreductase |
| Q99316 | MPD2_YEAST | PMID:11157982 | Protein disulfide isomerase MPD2 precursor (EC 5.3.4.1) | Disulfide bond oxidoreductase |
| Q03103 | ERO1_YEAST | PMID:9659913 | Endoplasmic oxidoreductin 1 precursor (EC 1.8.4.—) (Endoplasmic oxidoreductase protein 1). | Disulfide bond oxidoreductase |
| P38866 | FMO1_YEAST | PM1D:10077572 | Thiol-specific monooxygenase (EC 1.14.13.—) (Flavin-dependent monooxygenase). | Disulfide bond oxidoreductase |
| *Peptidyl-prolyl cis-trans isomerases* | | | | |
| P14832 | CYPH_YEAST | GOA:interpro | Peptidyl-prolyl cis-trans isomerase cyclophilin ***A/Cpr1/Cyp1/CPH1/Sccl | PPIase: Cyclophilin Type |
| P23285 | CYPB_YEAST | GOA:interpro | Peptidyl-prolyl cis-trans isomerase cyclophilin B/Cpr2/Cyp2 | PPIase: Cyclophilin Type |

TABLE F-continued

| Uniprot Accession GroES/EL | Uniprot ID | GO Source | Annotation | Family |
|---|---|---|---|---|
| P25719 | CYPC_YEAST | GOA:interpro | Peptidyl-prolyl cis-trans isomerase C/CYP3/CPR3, mitochondrial | PPIase: Cyclophilin Type |
| P25334 | CYPR_YEAST | GOA:interpro | Peptidyl-prolyl cis-trans isomerase CPR4/Scc3 | PPIase: Cyclophilin Type |
| P35176 | CYPD_YEAST | GOA:interpro | Peptidyl-prolyl cis-trans isomerase D CypD/CprS | PPIase: Cyclophilin Type |
| P53691 | CYP6_YEAST | PMID:10942767 | Peptidyl-prolyl cis-trans isomerase CPR6 | PPIase: Cyclophilin Type |
| P47103 | CYP7_YEAST | PMID: 10942767 | Peptidyl-prolyl cis-trans isomerase CYP7 | PPIase: Cyclophilin Type |
| P53728 | CYP8_YEAST | GOA:interpro | Peptidyl-prolyl cis-trans isomerase CYP8 | PPIase: Cyclophilin Type |
| Q02770 | Q02770 | GOA:interpro | Yp1064cp | PPIase: Cyclophilin Type |
| P20081 | FKBP_YEAST | GOA:interpro | FK506-binding protein 1 FKB1/RBP1 | PPIase: FKBP Type |
| P32472 | FKB2_YEAST | GOA:interpro | FK506-binding protein 2, FKBP-13/FKBP-15/FKB2, FPR2 | PPIase: FKBP Type |
| P38911 | FKB3_YEAST | GOA:interpro | FK506-binding nuclear protein FKBP-70/Npi46/Fpr3/ | PPIase: FKBP Type |
| Q06205 | FKB4_YEAST | GOA:interpro | FK506-binding protein 4 FPR4 | PPIase: FKBP Type |
| P22696 | ESS1_YEAST | GOA:spkw | ESS1 protein | PPIase: Parvulin Type |
| Miscellaneous poorly characterised |
| P27697 | ABC1_YEAST | GOA: spkw | ABC1 protein, mitochondrial precursor | ABC1 |
| P53193 | YGB8_YEAST | GOA:interpro | Hypothetical 21.8 kDa protein in CKB1-ATE1 intergenic region | Hsp20 |
| P28707 | YKL7_YEAST | PMID:9632755 | 24.1 kDa protein in VMA12-APN1 intergenic region | p23/wos2 |
| P38932 | VP45_YEAST | PMID:11432826 | Vacuolar protein sorting-associated protein 45 | SEC1 like |
| Q12019 | MDN1_YEAST | GOA:spkw | Midasin | |

Genetic Manipulation

In step iii), the process includes changing expression of the identified compensatory gene or gene product in the recombinant cell by genetic modification to provide a modified recombinant cell. After identification of one or more up-regulated genes, proteins or metabolic processes, the genome of the host may be modified. Certain genes or gene products, although identified as up-regulated, may not be available for modulation because they are essential to the cell or are known to affect other processes that may be essential to the cell or organism.

The genome may be modified by including an exogenous gene or promoter element in the genome or in the host with an expression vector, by enhancing the capacity of an identified gene to produce mRNA or protein, or by deleting or disrupting a gene or promoter element, or by reducing the capacity of a gene to produce mRNA or protein. The genetic code can be altered, thereby affecting transcription and/or translation of a gene, for example through substitution, deletion ("knock-out"), co-expression or insertion ("knock-in") techniques. Additional genes for a desired protein or regulatory sequence that modulate transcription of an existing sequence can also be inserted.

Recombination

The genome of the host cell expressing recombinant protein or peptide can be modified via a genetic targeting event, which can be by insertion or recombination, for example homologous recombination. Homologous recombination refers to the process of DNA recombination based on sequence homology. Homologous recombination permits site-specific modifications in endogenous genes and thus novel alterations can be engineered into a genome. One step in homologous recombination is DNA strand exchange, which involves a pairing of a DNA duplex with at least one DNA strand containing a complementary sequence to form an intermediate recombination structure containing heteroduplex DNA (see, for example Radding, C. M. (1982) Ann. Rev. Genet. 16: 405; U.S. Pat. No. 4,888,274). The heteroduplex DNA can take several forms, including a three DNA strand containing triplex form wherein a single complementary strand invades the DNA duplex (Hsieh, et al., Genes and Development 4: 1951 (1990); Rao, et al., (1991) PNAS 88:2984)) and, when two complementary DNA strands pair with a DNA duplex, a classical Holliday recombination joint or chi structure (Holliday, R., Genet. Res. 5: 282 (1964)) can form, or a double-D loop ("Diagnostic Applications of Double-D Loop Formation" U.S. Ser. No. 07/755,462, filed Sep. 4, 1991). Once formed, a heteroduplex structure can be resolved by strand breakage and exchange, so that all or a portion of an invading DNA strand is spliced into a recipient DNA duplex, adding or replacing a segment of the recipient DNA duplex. Alternatively, a heteroduplex structure can result in gene conversion, wherein a sequence of an invading strand is transferred to a recipient DNA duplex by repair of mismatched bases using the invading strand as a template (Genes, 3$^{rd}$ Ed. (1987) Lewin, B., John Wiley, New York, N.Y.; Lopez, et al., *Nucleic Acids Res.* 15: 5643 (1987)). Whether by the mechanism of breakage and rejoining or by the mechanism(s) of gene conversion, formation of heteroduplex DNA at homologously paired joints can serve to transfer genetic sequence information from one DNA molecule to another.

In homologous recombination, the incoming DNA interacts with and integrates into a site in the genome that contains a substantially homologous DNA sequence. In non-homologous ("random" or "illicit") integration, the incoming DNA integrates not at a homologous sequence in the genome but elsewhere, at one of a large number of potential locations. A number of papers describe the use of homologous recombination in mammalian cells.

Various constructs can be prepared for homologous recombination at a identified locus. Usually, the construct can include at least 10 bp, 20 bp, 30 bp, 40 bp, 50 bp, 70 bp, 100 bp, 500 bp, 1 kbp, 2 kbp, 4 kbp, 5 kbp, 10 kbp, 15 kbp, 20 kbp, or 50 kbp of sequence homologous with the identified locus. Various considerations can be involved in determining the extent of homology of identified DNA sequences, such as, for example, the size of the identified locus, availability of sequences, relative efficiency of double cross-over events at the identified locus and the similarity of the identified sequence with other sequences.

The targeting DNA can include a sequence in which DNA substantially isogenic flanks the desired sequence modifications with a corresponding identified sequence in the genome to be modified. The substantially isogenic sequence can be at least about 95%, 9798%, 99.0-99.5%, 99.6-99.9%, or 100% identical to the corresponding identified sequence (except for the desired sequence modifications). The targeting DNA and the identified DNA can share stretches of DNA at least about 10, 20, 30, 50, 75, 150 or 500 base pairs that are 100% identical.

The DNA constructs can be designed to modify the endogenous, identified gene product. The homologous sequence for identifiedying the construct can have one or more deletions, insertions, substitutions or combinations thereof designed to disrupt the function of the resultant gene product. In one embodiment, the alteration can be the insertion of a selectable marker gene fused in reading frame with the upstream sequence of the identified gene.

The genome can also be modified using insertional deletion. In this embodiment, the genome is modified by recombining a sequence in the gene that inhibits gene product formation. This insertion can either disrupt the gene by inserting a separate element, or remove an essential portion of the gene. In one embodiment, the insertional deletion includes insertion of a gene coding for resistance to a particular stressor, such as an antibiotic, or for growth in a particular media, for example for production of an essential amino acid.

The genome can also be modified by use of transposons, which are genetic elements capable of inserting at sites in prokaryote genomes by mechanisms independant of homologous recombination. Transposons can include, for example, Tn7 in *E. coli*, Tn554 in *S. aureus*, 1S900 in *M. paratuberculosis*, IS492 from *Pseudomonas atlantica*, 1S116 from *Streptomyces* and 1S900 from *M. paratuberculosis*. Steps believed to be involved in transposition include cleavage of the end of the transposon to yield 3' OH; strand transfer, in which transposase brings together the 3'OH exposed end of transposon and the identified sequence; and a single step transesterification reaction to yield a covalent linkage of the transposon to the identified DNA. The key reaction performed by transposase is generally thought to be nicking or strand exchange, the rest of the process is done by host enzymes.

In one embodiment, a process is provided to increase the level of a identified gene or homologue thereof by incorporating a genetic sequence encoding the gene or homologue into the genome by recombination. In another embodiment, a promoter is inserted into the genome to enhance the expression of the identified gene or homologue. In a separate embodiment, a process is provided for decreasing the expression of a identified gene or homologue thereof by recombination with an inactive gene. In another embodiment, a sequence that encodes a different gene, which can have a separate function in the cell or can be a reporter gene such as a resistance marker or an otherwise detectable marker gene can be inserted into a genome through recombination. In yet another embodiment, a copy of at least a portion of the identified gene that has been mutated at one or more locations is inserted into the genome through recombination. The mutated version of the identified gene can not encode a protein, or the protein encoded by the mutated gene can be rendered inactive, the activity can be modulated (either increased or decreased), or the mutant protein can have a different activity when compared to the native protein.

There are strategies to knock out genes in bacteria, which have been generally exemplified in *E. coli*. One route is to clone a gene-internal DNA fragment into a vector containing an antibiotic resistance gene (e.g. ampicillin). Before cells are transformed via conjugative transfer, chemical transformation or electroporation (Puehler, et al. (1984) *Advanced Molecular Genetics* New York, Heidelberg, Berlin, Tokyo, Springer Verlag), an origin of replication, such as the vegetative plasmid replication (the oriV locus) is excised and the remaining DNA fragment is re-ligated and purified (Sambrook, et al. (2000) *Molecular cloning: A laboratory manual, third edition* Cold Spring Harbor, N.Y., Cold Spring Harbor Laboratory Press). Alternatively, antibiotic-resistant plasmids that have a DNA replication origin can be used. After transformation, the cells are plated onto e.g. LB agar plates containing the appropriate antibiotics (e.g. 200 μg/mL ampicillin). Colonies that grow on the plates containing the antibiotics presumably have undergone a single recombination event (Snyder, L., W. Champness, et al. (1997) *Molecular Genetics of Bacteria* Washington D.C., ASM Press) that leads to the integration of the entire DNA fragment into the genome at the homologous locus. Further analysis of the antibiotic-resistant cells to verify that the desired gene knock-out has occurred at the desired locus is e.g. by diagnostic PCR (McPherson, M. J., P. Quirke, et al. (1991) *PCR: A Practical Approach* New York, Oxford University Press). Here, at least two PCR primers are designed: one that hybridizes outside the DNA region that was used for the construction of the gene knock-out; and one that hybridizes within the remaining plasmid backbone. Successful PCR amplification of the DNA fragment with the correct size followed by DNA sequence analysis will verify that the gene knock-out has occurred at the correct location in the bacterial chromosome. The phenotype of the newly constructed mutant strain can then be analyzed by e.g. SDS polyacrylamide gel electrophoresis (Simpson, R. J. (2003) *Proteins and Proteomics—A Laboratory Manual*. Cold Spring Harbor, N.Y., Cold Spring Harbor Laboratory Press).

An alternate route to generate a gene knock-out is by use of a temperature-sensitive replicon, such as the pSC101 replicon to facilitate gene replacement (Hamilton, et al. (1989) New process for generating deletions and gene replacements in *Escherichia coli. Journal of Bacteriology* 171(9): 4617-22). The process proceeds by homologous recombination between a gene on a chromosome and homologous sequences carried on a plasmid temperature sensitive for DNA replication. After transformation of the plasmid into the appropriate host, it is possible to select for integration of the plasmid into the chromosome at 44° C. Subsequent growth of these cointegrates at 30° C. leads to a second recombination event, resulting in their resolution. Depending on where the second recombination event takes place, the chromosome will either have undergone a gene replacement or retain the original copy of the gene.

Other strategies have been developed to inhibit expression of particular gene products. For example, RNA interference (RNAi), particularly using small interfering RNA (siRNA), has been extensively developed to reduce or even eliminate expression of a particular gene product. siRNAs are short, double-stranded RNA molecules that can target complementary mRNAs for degradation. RNAi is the phenomenon in which introduction of a double-stranded RNA suppresses the expression of the homologous gene. dsRNA molecules are reduced in vivo to 21-23 nt siRNAs which are the mediators of the RNAi effect. Upon introduction, double stranded RNAs get processed into 20-25 nucleotide siRNAs by an RNase III-like enzyme called Dicer (initiation step). Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effecter step). Cleavage of cognate RNA takes place near the middle of the region bound by the siRNA strand. RNAi has been successfully used to reduce gene expression in a variety of organisms including zebrafish, nematodes (*C. elegans*), insects (*Drosophila melanogaster*), planaria, cnidaria, trypanosomes, mice and mammalian cells.

Mutation

The genome can also be modified by mutation of one or more nucleotides in a open reading frame encoding an identified gene, particularly an identified protease. Techniques for genetic mutation, for instance site directed mutagenesis are well known in the art. Some approaches focus on the generation of random mutations in chromosomal DNA such as those induced by X-rays and chemicals. Mutagenesis targeted to a defined region of DNA includes many techniques, some more popular than others. In vitro approaches to site-directed mutagenesis can be grouped generally into three categories: i) processes that restructure fragments of DNA, such as cassette mutagenesis; ii) localized random mutagenesis; and iii) oligonucleotide-directed mutagenesis.

Oligonucleotide-directed mutagenesis is based on the concept that an oligonucleotide encoding a desired mutation(s) is annealed to one strand of the DNA of interest and serves as a primer for initiation of DNA synthesis. In this manner, the mutagenic oligonucleotide is incorporated into the newly synthesized strand. Mutagenic oligonucleotides incorporate at least one base change but can be designed to generate multiple substitutions, insertions or deletions. Examples include PCR-based processes and practically all of the non-PCR-based processes in use today. These techniques include positive antibiotic selection (Lewis, M. K. and Thompson, D. V. (1990) *Nucl. Acids Res.* 18, 3439; Bohnsack, R. N. (1996) *Meth. Mol. Biol.* 57, 1; Vavra, S. and Brondyk, W. H. (1996) *Promega Notes* 58, 30; *AlteredSites® II in vitro Mutagenesis Systems Technical Manual* #TM001, Promega Corporation), unique restriction site selection (Deng, W. P. and Nickoloff, J. A. (1992) *Anal. Biochem.* 200, 81), uracil incorporation (Kunkel, T. A. (1985) *Proc. Natl. Acad. Sci. USA* 82, 488; Kunkel, T. A., Roberts, J. D. and Zakour, R. A. (1987) *Meth. Enzymol.* 154, 367), and phosphorothioate incorporation (Taylor, J. W., Ott, J. and Eckstein, F. (1985) *NucL Acids Res.* 13, 8764; Nakamaye, K. and Eckstein, F. (1986) *NucL Acids Res.* 14, 9679). Oligonucleotides can also encode a library of mutations by randomizing the base composition at sites during chemical synthesis resulting in degenerate or "doped" oligonucleotides. The ability to localize and specify mutations is greatly enhanced by the use of synthetic oligonucleotides hybridized to the DNA insert-containing plasmid vector.

The general format for site-directed mutagenesis is: denaturation of plasmid DNA containing the template of interest (cDNA, promoter, etc.) to produce single-stranded regions; annealing of a synthetic mutant oligonucleotide to the identified strand; synthesis of a new complementary strand using, for example, T4 DNA Polymerase; and sealing the resulting nick between the end of the new strand and the oligonucleotide, for example using T4 DNA Ligase. The resulting heteroduplex is propagated by transformation, for example in *E. coli*. Selection and enrichment processes have been incorporated into mutagenesis processes to greatly improve the efficiency of mutant strand recovery and rates approaching 80-90% are possible. Numerous processes exist to generate different types of mutations and to enhance for the selection of the mutant. Examples of processes to enhance for the selection of the mutant include positive antibiotic selection of the mutant strand, using a uracil-containing DNA strand which can be selectively degraded in vivo, and dNTP analog incorporation, which can render one strand of heteroduplex DNA impervious to digestion. Some approaches can be combined, such as cassette mutagenesis and the use of "doped" oligonucleotides to create a library of random mutations in a small, defined region.

An extension of the so-called "standard" processes of site-directed mutagenesis includes those that rely on DNA amplification, specifically the polymerase chain reaction (PCR). The major commonality in site-directed mutagenesis is the use of a mutagenic oligonucleotide. The mutagenic oligonucleotide should hybridize efficiently to the template. For efficient hybridization, there can be, for example, 100% base pairing at either end of the identified sequence without secondary structure formation, but can also be less than 100% identify, such as 98%, 95%, 92%, 90%, 85%, 80%, 70% or only a portion of the sequence can be identical. For small substitutions, 10-15 bases hybridizing on either side of the mismatch are usually sufficient. The composition of the 3'-end of the primer is particularly important as polymerases do not typically extend from a mismatched or poorly hybridized 3'-end.

The basis for site-directed mutagenesis by positive antibiotic selection is that a selection oligonucleotide or oligonucleotides are simultaneously annealed, with the mutagenic oligonucleotide, to repair an antibiotic resistance gene (10-13). Selection for the mutant strand is enabled by antibiotic resistance of the mutated DNA and sensitivity of the nonmutated strand. This approach offers a very efficient means to generate an indefinite number of the desired mutations with little hands-on time.

Site-directed mutagenesis by the use of a unique restriction site is based on the processes of Deng and Nickoloff (Deng, W. P. and Nickoloff, J. A. (1992) *Anal. Biochem.* 200, 81). In this approach, a selection oligonucleotide containing a mutated sequence for a unique restriction site is annealed simultaneously with the mutagenic oligonucleotide. The selection oligonucleotide renders the nonessential site immune to restriction by the corresponding enzyme. Selection for the mutant strand is enhanced by digesting the resulting pool of plasmids with the unique restriction enzyme. The digestion linearizes the parental plasmid thereby effectively decreasing its ability to transform bacteria.

Site-directed mutagenesis by deoxyuridine incorporation relies on the ability of a host strain to degrade template DNA that contains uracil (U) in place of thymidine (T). A small number of dUTPs are incorporated into the template strand in place of dTTP in a host that lacks dUTPase (dut-) and uracil N-deglycosidase (ung-) activities. (Uracil per se is not mutagenic and it base pairs with adenine.) Normally, dUTPase degrades deoxyuridine and uracil N-deglycosidase removes any incorporated uracil. Post-mutation replication in a dut+ ung+ strain is used then to degrade nonidentified strand DNA. This approach requires that single-stranded DNA be used so that only one strand contains the Us which are susceptible to degradation.

The phosphorothioate incorporation approach to site-directed mutagenesis rests on the ability of a dNTP analog containing a thiol group to render heteroduplex DNA resistant to restriction enzyme digestion. The mutant strand is extended from the mutagenic oligonucleotide and synthesized in the presence of dCTPalphaS. Unused template DNA is removed by digestion with an exonuclease. Theoretically, only circular, heteroduplex DNA remains. The heteroduplex is then nicked, but not cut, at the restriction site(s). Exonuclease III is used to digest the nicked strand and the remaining fragment then acts as a primer for repolymerization, creating a mutant homoduplex.

In the polymerase chain reaction (PCR) based approach to generate a mutation in DNA, a template is amplified using a set of gene-specific oligonucleotide primers except that one oligonucleotide, or more in protocols that use multiple amplifications, contains the desired mutation. Variations include altering the hybridization site of the oligonucleotides to produce multiple, overlapping PCR fragments with the mutation in the overlap and the "megaprimer" approach, which uses three oligonucleotides and two rounds of amplification wherein a product strand from the first amplification serves as a primer in the second amplification.

In the overlap extension approach, complementary oligodeoxyribonucleotide (oligo) primers and the polymerase chain reaction are used to generate two DNA fragments having overlapping ends. These fragments are combined in a subsequent 'fusion' reaction in which the overlapping ends anneal, allowing the 3' overlap of each strand to serve as a primer for the 3' extension of the complementary strand. The resulting fusion product is amplified further by PCR. Specific alterations in the nucleotide (nt) sequence can be introduced by incorporating nucleotide changes into the overlapping oligo primers.

Vector Constructs

In a separate embodiment, the host cell is modified by including one or more vectors that encode a identified gene, typically a folding modulator or a cofactor of a folding modulator. In another embodiment, the host cell is modified by enhancing a promoter for a folding modulator or a cofactor for a folding modulator, including by adding an exogenous promoter to the host cell genome.

In another embodiment, the host cell is modified by including one or more vectors that encode an inhibitor of an identified compensatory gene, such as a protease inhibitor. Such an inhibitor can be an antisense molecule that limits the expression of the identified compensatory gene, a cofactor of the identified gene or a homologue of the identified gene. Antisense is generally used to refer to a nucleic acid molecule with a sequence complementary to at least a portion of the identified gene. In addition, the inhibitor can be an interfering RNA or a gene that encodes an interfering RNA. In Eukaryotic organisms, such an interfering RNA can be a small interfering RNA or a ribozyme, as described, for example, in Fire, A. et al. (1998) *Nature* 391:806-11, Elbashir et al. (2001) *Genes & Development* 15(2):188-200, Elbashir et al. (2001) *Nature* 411(6836):494-8, U.S. Pat. No. 6,506,559 to Carnegie Institute, U.S. Pat. No. 6,573,099 to Benitec, U.S. Patent Application Nos. 2003/0108923 to the Whitehead Inst., and 2003/0114409, PCT Publication Nos. WO03/006477, WO03/012052, WO03/023015, WO 03/056022, WO 03/064621 and WO 03/070966. The inhibitor can also be another protein or peptide. The inhibitor can, for example, be a peptide with a consensus sequence for the protease or protease protein. The inhibitor can also be a protein or peptide that can produce a direct or indirect inhibitory molecule for the protease or protease protein in the host. Protease inhibitors can include Amastatin, E-64, Antipain, Elastatinal, APMSF, Leupeptin, Bestatin, Pepstatin, Benzamidine, 1,10-Phenanthroline, Chymostatin, Phosphoramidon, 3,4-dichloroisocoumarin, TLCK, DFP, TPCK. Over 100 naturally occurring protein protease inhibitors have been identified so far. They have been isolated in a variety of organisms from bacteria to animals and plants. They behave as tight-binding reversible or pseudo-irreversible inhibitors of proteases preventing substrate access to the active site through steric hindrance. Their size are also extremely variable from 50 residues (e.g BPTI: Bovine Pancreatic Trypsin Inhibitor) to up to 400 residues (e.g alpha-1PI: alpha-1 Proteinase Inhibitor). They are strictly class-specific except proteins of the alpha-macroglobulin family (e.g alpha-2 macroglobulin) which bind and inhibit most proteases through a molecular trap mechanism.

An exogenous vector or DNA construct can be transfected or transformed into the host cell. Techniques for transfecting and transforming eukaryotic and prokaryotic cells respectively with exogenous nucleic acids are well known in the art. These can include lipid vesicle mediated uptake, calcium phosphate mediated transfection (calcium phosphate/DNA co-precipitation), viral infection, particularly using modified viruses such as, for example, modified adenoviruses, microinjection and electroporation. For prokaryotic transformation, techniques can include heat shock mediated uptake, bacterial protoplast fusion with intact cells, microinjection and electroporation. Techniques for plant transformation include *Agrobacterium* mediated transfer, such as by *A. tumefaciens*, rapidly propelled tungsten or gold microprojectiles, electroporation, microinjection and polyethelyne glycol mediated uptake. The DNA can be single or double stranded, linear or circular, relaxed or supercoiled DNA. For various techniques for transfecting mammalian cells, see, for example, Keown et al. (1990) *Processes in Enzymology* Vol. 185, pp. 527-537.

For recombination events, the constructs can include one or more insertion sequences, which can insert or transpose one or more nucleic acid sequence into a different sequence. However, the construct can be designed for exogenous expression of an identified compensatory gene or homologue thereof without incorporation into the existing cellular DNA/genome.

The constructs can contain one, or more than one, internal ribosome entry site (IRES). The construct can also contain a promoter operably linked to the nucleic acid sequence encoding at least a portion of the identified gene, or a cofactor of the identified gene, a mutant version of at least a portion of the identified compensatory gene, or in the case of proteases, an inhibitor of the identified gene. Alternatively, the construct can be promoterless. In cases in which the construct is not designed to incorporate into the cellular DNA/genome, the vector typically contains at least one promoter element. In addition to the nucleic acid sequences the expression vector can contain selectable marker sequences. The expression constructs can further contain sites for transcription initiation, termination, and/or ribosome binding sites. The identified constructs can be inserted into and can be expressed in any prokaryotic or eukaryotic cell, including, but not limited to bacterial cells, such as *P. fluorescens* or *E. coli*, yeast cells, mammalian cells, such as CHO cells, or plant cells.

Cloning vectors can include e.g. plasmid pBR322 (Bolivar, Rodriguez et al. 1977), the pUC series of plasmids (Vieira and Messing 1982), pBluescript (Short, Fernandez et al. 1988), pACYC177 and pACYC184 (Chang and Cohen 1978). Exogenous promoters for use in such constructs, include, but are not limited to, the phage lambda PL promoter, *E. coli* lac, *E. coli* trp, *E. coli* phoA, *E. coli* tac promoters, SV40 early, SV40 late, retroviral LTRs, PGKI, GALI, GALIO genes, CYCI, PH05, TRPI, ADHI, ADH2, forglymaldehyde phosphate dehydrogenase, hexokinase, pyruvate decarboxylase, phosphofructokinase, triose phosphate isomerase, phosphoglucose isomerase, glucokinase alpha-mating factor pheromone, PRBI, GUT2, GPDI promoter, metallothionein promoter, and/or mammalian viral promoters, such as those derived from adenovirus and vaccinia virus. Other promoters will be known to one skilled in the art.

Promoters for exogenous vectors, or exogenous promoters designed to be inserted into the genome can be based on specific response elements in a cell. For example, promoters can be responsive to chemical compounds, for example to anthranilate or benzoate, as described in PCT Publication No. WO 2004/005221. The constructs can include one or more promoters. These can be independent, or can be in tandem. For example the promoters can be designed so that a identified compensatory gene is up- or down-regulated in a particular time frame with the recombinant protein or peptide. For example, in a case in which the identified gene is a folding modulator, the folding modulator or cofactor can be induced shortly before induction of the recombinant protein or peptide. Promoters can include, but are not limited to the following:

| Promoter | source | regulation | induction |
|---|---|---|---|
| lac | *E. coli* | lacI, lacI$^q$ | IPTG |
| lacUV5 | *E. coli* | lacI, lacI$^q$ | IPTG |
| lacUV5 | *E. coli* | lacI, lacI$^q$ | IPTG |
| tac (hybrid) | *E. coli* | lacI, lacI$^q$ | IPTG |
| trc (hybrid) | *E. coli* | | IPTG |
| tac (hybrid) | *E. coli* | lacI, lacI$^q$ | IPTG |
| P$_{syn}$ (synthetic) | *E. coli* | | IPTG |
| trp | *E. coli* | araC | tryptophan starvation |
| araBAD | *E. coli* | | 1-arabinose |
| lpp$^a$ | *E. coli* | | IPTG, lactose |
| lpp-lac (hybrid) | *E. coli* | lacI | IPTG |
| phoA | *E. coli* | phoB (positive) phoR (negative) | phosphate starvation |
| recA | *E. coli* | lexA | nalidixic acid |
| proU | *E. coli* | | osmolarity |
| cst-1 | *E. coli* | | glucose starvation |
| tetA | *E. coli* | | tetracyclin |
| cadA | *E. coli* | cadR | pH |
| nar | *E. coli* | fnr | anaerobic conditions |
| PL | λ | λ cIts857 | thermal (shift to 42° C.) |

-continued

| Promoter | source | regulation | induction |
|---|---|---|---|
| cspA | *E. coli* | | thermal (shift to below 20° C.) |
| T7 | T7 | λ cIts857 | thermal |
| T7-lac operator | T7 | lacI$^q$ | IPTG |
| T3-lac operator | T3 | lacI$^q$ | IPTG |
| T5-lac operator | T5 | lad, lacI$^q$ | IPTG |
| T4 gene 32 | T4 | | T4 infection |
| nprM-lac operator | *Bacillus* | lacI$^q$ | IPTG |
| VHb | *Vitreoscilla* | | oxygen |
| Protein A | *S. aureus* | | |

Constructs can include selection markers to identify modified cells. Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). See, for example, Song, K-Y., et al. (1987) *Proc. Nat'l Acad. Sci. U.S.A.* 84:6820-6824; Sambrook, J., et al. (1989) *Molecular Cloning—A Laboratory Manual*, Cold Spring Harbor Laboratory, Cold Spring Harbor, N.Y., Chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo) (Southern, P., and P. Berg, (1982) *J. Mol. Appl. Genet.* 1:327-341); and the hygromycin resistance gene (hyg) ((1983) *Nucleic Acids Research* 11:6895-6911, and Te Riele, H., et al. (1990) *Nature* 348:649-651). Other selectable marker genes include: acetohydroxy acid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Additional selectable marker genes useful in this invention, for example, are described in U.S. Pat. Nos. 6,319,669; 6,316,181; 6,303,373; 6,291,177; 6,284,519; 6,284,496; 6,280,934; 6,274,354; 6,270,958; 6,268,201; 6,265,548; 6,261,760; 6,255,558; 6,255,071; 6,251,677; 6,251,602; 6,251,582; 6,251,384; 6,248,558; 6,248,550; 6,248,543; 6,232,107; 6,228,639; 6,225,082; 6,221,612; 6,218,185; 6,214,567; 6,214,563; 6,210,922; 6,210,910; 6,203,986; 6,197,928; 6,180,343; 6,172,188; 6,153,409; 6,150,176; 6,146,826; 6,140,132; 6,136,539; 6,136,538; 6,133,429; 6,130,313; 6,124,128; 6,110,711; 6,096,865; 6,096,717; 6,093,808; 6,090,919; 6,083,690; 6,077,707; 6,066,476; 6,060,247; 6,054,321; 6,037,133; 6,027,881; 6,025,192; 6,020,192; 6,013,447; 6,001,557; 5,994,077; 5,994,071; 5,993,778; 5,989,808; 5,985,577; 5,968,773; 5,968,738; 5,958,713; 5,952,236; 5,948,889; 5,948,681; 5,942,387; 5,932,435; 5,922,576; 5,919,445; and 5,914,233.

Deletions can be at least about 5 bp, 10 bp, 20 bp, 30 bp, 40 bp or 50 bp, commonly at least about 100 bp, and generally not more than about 20 kbp, where the deletion can normally include at least a portion of the coding region including a portion of or one or more exons, a portion of or one or more introns, and can or can not include a portion of the flanking non-coding regions, particularly the 5'-non-coding region (transcriptional regulatory region). Thus, the homologous region can extend beyond the coding region into the 5'-non-coding region or alternatively into the 3'-non-coding region. Insertions can generally not exceed 10 kbp, usually not exceed 5 kbp, generally being at least 50 bp, more usually at least 200 bp.

The region(s) of homology can include mutations, where mutations can further inactivate the identified gene, in providing for a frame shift, or changing a key amino acid, or the mutation can correct a dysfunctional allele, etc. Usually, the mutation can be a subtle change, not exceeding about 5% of the homologous flanking sequences.

The construct can be prepared in accordance with processes known in the art, various fragments can be brought together, introduced into appropriate vectors, cloned, analyzed and then manipulated further until the desired construct has been achieved (see, for example FIGS. 5-11). Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed. Processes for the incorporation of antibiotic resistance genes and negative selection factors will be familiar to those of ordinary skill in the art (see, e.g., WO 99/15650; U.S. Pat. No. 6,080,576; U.S. Pat. No. 6,136,566; Niwa, et al., *J. Biochem.* 113:343-349 (1993); and Yoshida, et al., *Transgenic Research,* 4:277-287 (1995)).

The construct can be prepared using a bacterial vector, including a prokaryotic replication system, e.g. an origin recognizable by a prokaryotic cell such as *P. fluorescens* or *E. coli*. A marker, the same as or different from the marker to be used for insertion, can be employed, which can be removed prior to introduction into the identified cell. Once the vector containing the construct has been completed, it can be further manipulated, such as by deletion of certain sequences, linearization, or introducing mutations, deletions or other sequences in the homologous sequence. After final manipulation, the construct can be introduced into the cell.

The process can be iterative. In one embodiment, after modification of the host and expression of the recombinant protein in the modified host, a genetic profile of the modified host cell is analyzed to identify one or more further identified genes the expression of which is changed in the modified host cell. In particular, compensatory genes can be those that show increased expression in the modified host expressing recombinant protein when compared to a modified host cell not expressing the recombinant protein or peptide, or when compared to an unmodified host cell. The process further includes changing the expression of the further identified gene or genes and expressing the protein or peptide in the doubly modified cell. These steps can be iterated to improve protein expression and can be repeated one, two, three, four, five, six, seven, eight, nine, or at least ten times.

Production of Protein

The process of the invention optimally leads to increased production of recombinant protein or peptide in a host cell. The increased production can include an increased amount of protein per gram of host protein in a given amount of time, or can include an increase in the length of time the host cell is producing recombinant protein or peptide. The increased production can also include an improvement in the requirements for growth of the recombinant host cell. The increased production can be an increased production of full length protein or peptide. If the improvement is in increased levels of protein, the protein or peptide can be produced in one or more inclusion bodies in a host cell.

The increased production alternatively can be an increased level of active protein or peptide per gram of protein produced, or per gram of host protein. The increased production can also be an increased level of recoverable protein or peptide, such as soluble protein, produced per gram of recombinant or per gram of host cell protein. The increased production can also be any combination of increased total level and increased active or soluble level of protein.

Increased production is typically measured by comparing the level of production after a certain period of induction in a modified cell to the same induction in the unmodified cell.

Soluble/Insoluble

The improved expression of recombinant protein can be an increase in the solubility of the protein. The recombinant protein or peptide can be produced and recovered from the cytoplasm, periplasm or extracellular medium of the host cell. The protein or peptide can be insoluble or soluble. The protein or peptide can include one or more targeting sequences or sequences to assist purification.

In certain embodiments, the invention provides a process for improving the solubility of a recombinant protein or peptide in a host cell. The term "soluble" as used herein means that the protein is not precipitated by centrifugation at between approximately 5,000 and 20,000× gravity when spun for 10-30 minutes in a buffer under physiological conditions. Soluble, active proteins are capable of exhibiting function, and are not part of an inclusion body or other precipitated mass.

The invention can also improve recovery of active recombinant proteins or peptides. For example, the interaction between a identified and a parent polypeptide, polypeptide variant, segment-substituted polypeptide and/or residue-substituted polypeptide can be measured by any convenient in vitro or in vivo assay. Thus, in vitro assays can be used to determine any detectable interaction between a identified and polypeptide, e.g. between enzyme and substrate, between hormone and hormone receptor, between antibody and antigen, etc. Such detection can include the measurement of colorimetric changes, changes in radioactivity, changes in solubility, changes in molecular weight as measured by gel electrophoresis and/or gel exclusion processes, etc. In vivo assays include, but are not limited to, assays to detect physiological effects, e.g. weight gain, change in electrolyte balance, change in blood clotting time, changes in clot dissolution and the induction of antigenic response. Generally, any in vivo assay can be used so long as a variable parameter exists so as to detect a change in the interaction between the identified and the polypeptide of interest. See, for example, U.S. Pat. No. 5,834,250.

Cytoplasmic/Periplasmic/Secreted

In certain embodiments, the protein can also be secreted into the periplasm if fused to an appropriate signal secretion sequence. In one embodiment, the signal sequence can be a phosphate binding protein, a Lys-Arg-Orn binding protein (LAObp or KRObp) secretion signal peptide, an Outer Membrane Porin E (OprE) secretion signal peptide, an azurin secretion signal peptide, an iron (III) binding protein [Fe(III) bp] secretion signal peptide, or a lipoprotein B (LprB) secretion signal peptide.

In one embodiment, no additional disulfide-bond-promoting conditions or agents are required in order to recover disulfide-bond-containing identified polypeptide in active, soluble form from the modified host cell or doubly or multiply modified cell. In one embodiment, the transgenic peptide, polypeptide, protein, or fragment thereof has a folded intramolecular conformation in its active state. It has been found that complex mammalian proteins soluble in the cytoplasm can configure appropriately with the proper positioning of the thiol groups for later disulfide bond formation in the periplasm. In one embodiment, the transgenic peptide, polypeptide, protein, or fragment contains at least one intramolecular disulfide bond in its active state; and perhaps up to 2, 4, 6, 8, 10, 12, 14, 16, 18, or 20 or more disulfide bonds.

In one embodiment, more than 50% of the expressed, transgenic peptide, polypeptide, protein, or fragment thereof produced will be produced as single, functional peptides, polypeptides, proteins, or fragments thereof in soluble, active form or insoluble easily renatured form in the cytoplasm or periplasm. In another embodiment about 60%, 70%, 75%, 80%, 85%, 90%, 95% of the expressed protein is obtained in or easily renatured into active form.

EXAMPLES

The bacterial strains used in the current study are listed in Table 1. Strains of *P. fluorescens* were grown in shake-flasks at 30° C. OD575 was recorded for each strain at various time points.

TABLE 1

Overview of bacterial strains

| Strain | Relevant Strain Genotype | Plasmid | Recombinant Protein |
|---|---|---|---|
| MB214 | *P. flourescens* host strain | | |
| DC206 | pyrF | | |
| DC240 | pyrF | pDOW2415 | nitrilase |
| DC271 | pyrF | pDOW1323 | pbp: hGH |
| DC280 | pyrF | pDOW1339 | vector only plasmid |
| DC369 | pyrF | pDOW1426 | hGH |
| DC462 | pyrF | pDOW3501 | GrpE,DnaKJ |
| DC463 | pyrF | pDOW3501, pDOW1426 | GrpE, DnaKJ, hGH |
| HJ104 | pyrE | pDOW1349 | hGH-COP |
| DC370 | pyrF, hslU | | |
| DC372 | pyrE, hslU | pDOW1426 | hGH |
| DC373 | pyrF, hslU | pDOW1323 | pbp: hGH |
| HJ105 | pyrF, hslU | pDOW1349 | hGH-COP |
| DC417 | pyrE, hslUV | | |
| HJ115 | pyrF, hslUV | pDOW1426 | hGH |
| HJ117 | pyrF, hslUV | pDOW1349 | hGH-COP |

Plasmids used in the following experiments are listed in Table 2.

TABLE 2

Overview of plasmids

| Plasmids | Relevance |
|---|---|
| PDOW2236 | cloning vector |
| pDOW2240 | Ptac grpE-dnaKJ, pyrF+ |
| pDOW2247 | Pmtl no recombinant gene; empty vector |
| pDOW3501 | Pmtl grpE-dnaKJ, pyrF+ |
| pDOW1349 | pyrF+, hGH::COP |
| pDOW1426 | pyrF+, hGH |
| pDOW1261-2 | suicide vector, pyrF+ |
| pDOW2050 | used for construction of the hslUV deletion strains |

Sample Collection and RNA Isolation

All samples were collected from a 200 ml standard shake flasks experiments. Samples were taken at different time points as indicated in the figures. At each time point, 10 ml of cell culture from the shake flasks was collected and mixed with 10 ml of RNAlater (Ambion, Austin, Tex.) reagent to stabilize RNA.

Microarray Hybridization and Data Analysis

For each RNA sample, the fluorescent nucleotides Cy3-dUTP or Cy5-dUTP (Amersham Pharmacia, Piscataway, N.J.) were incorporated into cDNA in a reverse transcription (RT) reaction using random hexamer primer (Amersham). The two labeled cDNA pools were combined and applied to a microarray slide. The microarray slides contains 50mer amino-modified oligodeoxyribonucleotides (oligos) representing each ORF of *P. fluorescens*. Each oligo was printed twice for duplicate spots at different location using the SDDC-2 robot (Virtek, Toronto, Canada—now distributed through Bio-Rad Laboratories, Hercules, Calif.) and SMP3 pins (TeleChem International Inc., Sunnyvale, Calif.). The microscope slides used were coated with a positively charged epoxy resin for efficient DNA binding (MWG Inc, Alameda, Calif.). After printing, the slides were post-processed according to MWG's specifications. A software package from Bio-Discovery Inc. (El Segundo, Calif.) was used to facilitate the data analysis. This package consists of CLONETRACKER™, IMAGENE™, GENESIGHT™ gene array modules and the GENEDIRECTOR™ gene array database. Each hybridized slide was scanned using ScanArray 5000 (Packard BioScience, Billerica, Mass.) to measure fluorescence of the Cy3- and Cy5-labeled cDNA bound to the microarray. The acquired images were quantified in IMAGENE™ gene array module and raw data was processed in GENESIGHT™ gene module. During the data preparation, the spot intensity for each gene was background-corrected; the signal for the Cy5 channel was normalized to the Cy3 channel using the total signal intensity for the entire array; the normalized ratio of Cy5 to Cy3 for each gene was log 2 transformed, and replicates were combined.

Protein Expression Analysis by SDS-PAGE

Culture aliquots were harvested at various time points after IPTG induction, normalized to $OD_{600}$ of 10. Cell lysates were separated into soluble and insoluble fractions by centrifugation at 11000 g for 5 min. Aliquots of 2.5 ul were combined with 5 ul 2× NuPAGE LDS sample buffer (Invitrogen, San Diego, Calif.), 50 uM DTT, and $H_2O$ to 10 µl, then heated at 95° C. for 5 min. The proteins were separated and visualized on 12% Nupage gels stained with Coomassie Blue using Simply Blue Safestain (Invitrogen, San Diego, Calif.).

Fluorescence Activity Measurement

Protein yield was also measured by fluorescence activity of the fusion of green fluorescence protein (COP) and human growth hormone (hGH). The hgh::COP fusion construct was transformed into wild-type or hslU mutant strains and selected on the M9 glucose agar plate without uracil. The IPTG-induced cell culture were normalized to $OD_{600}$ of five. Relative fluorescence (RF) activity was measured using the Spectramax Gemini microplate spectrofluorimeter (Molecu-

Example 1

Gene Expression Analysis of Strains Producing Cytoplasmic and Periplasmic Proteins—Comparison of Different Timepoints To study the FMs and protease gene expression during the production of heterologous protein, *P. fluorescens* strains DC206, 280, 240 and 271 were used in the initial microarray experiments. DC206 is the host strain and was used as a control for cell growth; DC280 has a vector-only plasmid and was used as a control for the microarray experiments; DC240 is DC206 with a plasmid encoding cytoplasmic nitrilase enzyme that is soluble; DC271 is DC206 with a plasmid encoding the periplasmic human growth hormone (pbp:: hGH) that is partly insoluble. Strains were grown in 200 ml of shake flask medium and cell growth was monitored by measuring $OD_{575}$. IPTG induction was performed 24 hrs after inoculation. All strains grew similarly and culture samples were taken just before (0 hr) and 4 hrs after induction for RNA isolation and transcriptional profiling (TxP) using DNA microarrays (FIG. 1).

Figure 2:
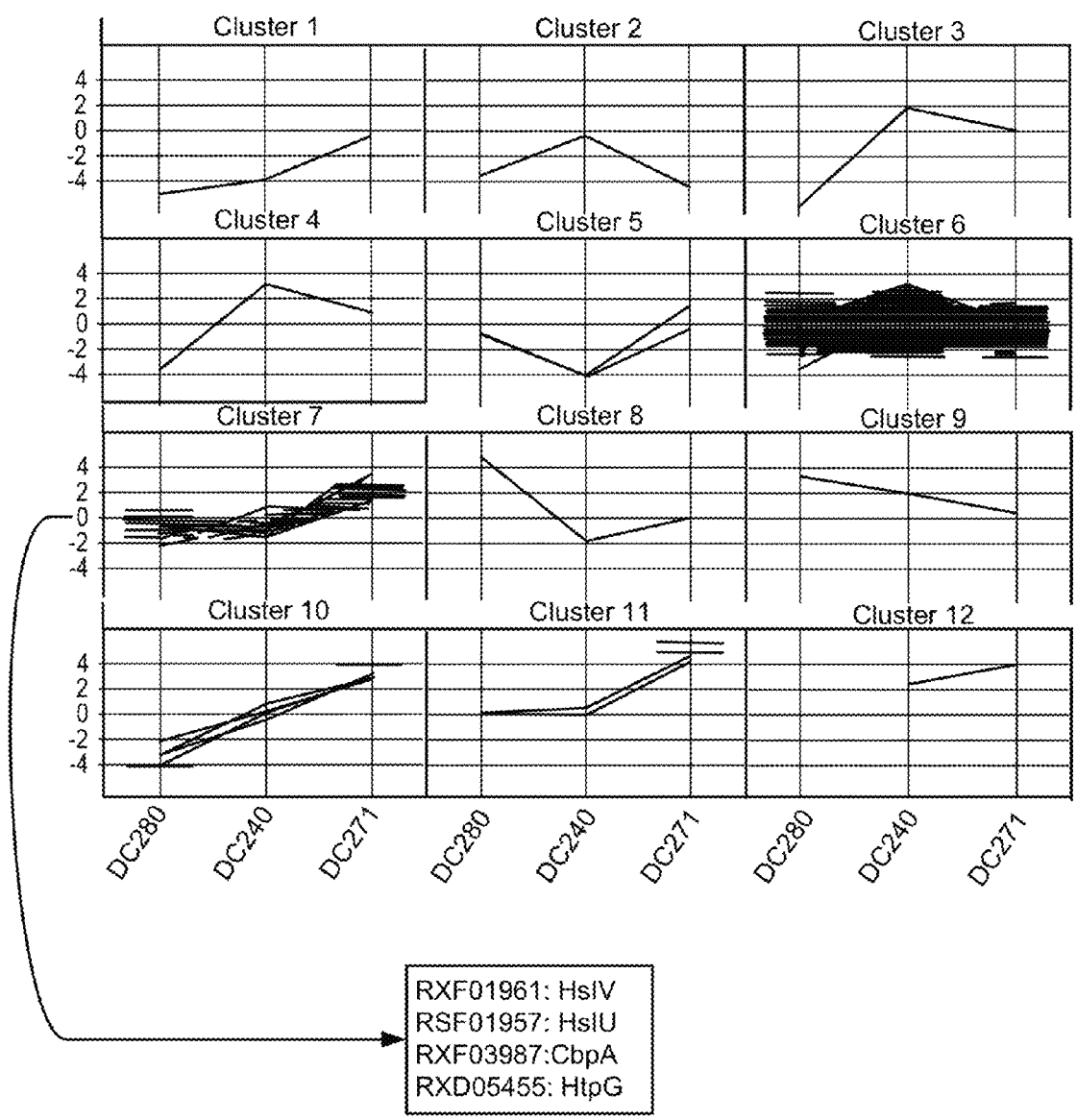
FIG. 2 is as graph of hierarchical clustering of all genes from *P. fluorescens* strains DC280, DC240 and DC271 into 12 clusters at 4 hr after IPTG when compared to 0 hr IPTG. Based on the value and trend, genes were clustered and grouped using the hierarchical clustering algorithm from Spotfire DecisionSite. Broken lines indicate data points that were filtered out due to poor spots quality or low level of expression. The x-axis represents the comparison of each strain; the y-axis represents the relative expression value 4 hrs after induction compared to at the time of IPTG induction. All the identified FMs are highlighted. Cluster 7 shows 2 FM and 2 protease subunit genes that are highly expressed in strain DC271, which overproduces the periplasmic hGH protein. The remaining FM genes are grouped in cluster 6.

The genetic profiles, ie. transcriptional profiles were based on the comparison of the 4 hrs after induction time point sample with that of 0 hr sample, the two samples were labeled with fluorescent dyes, either Cy3-dUTP or Cy5-dUTP, and co-hybridized to the same slide for each strain. Each hybridization was duplicated with dye-swap experiments (i.e., samples were labeled with either Cy3-dUTP or Cy5-dUTP) (Table 3, slides 1 to 6). The hybridized slides were scanned using a confocal laser scanner. Signal intensity for each gene was determined and processed using the microarray software package from Biodiscovery (El Segundo, Calif.). The expression ratio of the two time points for each gene was calculated and ratios for all the genes across the strains were clustered based on the ratio value and trend among the three strains (DC280, DC240 and DC271) (FIG. 2).

TABLE 3

Summary of microarray experiments performed in Examples 1-3

| Experiment | Slide | Cy3 | Cy5 |
|---|---|---|---|
| DC280 | 1 | 4 hr sample | 0 hr sample |
|  | 2 | 0 hr sample | 4 hr sample |
| DC240 | 3 | 4 hr sample | 0 hr sample |
|  | 4 | 0 hr sample | 4 hr sample |
| DC271 | 5 | 4 hr sample | 0 hr sample |
|  | 6 | 0 hr sample | 4 hr sample |
| 0 hr | 7 | DC240 | DC271 |
|  | 8 | DC271 | DC240 |
| 4 hr | 9 | DC240 | DC271 |
|  | 10 | DC271 | DC240 |
| DC369 | 11 | 4 hr sample | 0 hr sample |
|  | 12 | 0 hr sample | 4 hr sample |

To focus on FM and protease gene expression in *P. fluorescens* under the stress imposed by high level recombinant protein production, a list of FM and protease genes was compared to the cluster analysis. After hierarchical clustering analysis of all the genes from DC280, DC240 and DC271, FMs and proteases were identified in two clusters (lines in clusters 6 and 7; FIG. 2).

Four genes in cluster 7 show significant higher expression in DC271 expressing mainly insoluble periplasmic human growth hormone as compared to DC240 producing soluble cytoplasmic nitrilase or DC280, which does not overproduce any protein. The four genes are rxfD1961 encoding HslV, rxf01957 encoding HslU, rxf03987 encoding CbpA and rxf05455 encoding HtpG. The *E. coli* HslV (ClpQ) and HslU (ClpY) together form a cytoplasmic protease. The small subunit, HslV, is a peptidase related to the proteasomal a-subunits of eukaryotes. The large subunit, HslU, is an ATPase with homology to other Clp family ATPases such as ClpA and ClpX. CbpA of *E. coli* is an analogue of the well-characterized co-chaperone DnaJ as judged from not only its structure but also its function. The phenotype of lesions in DnaJ, such as temperature sensitivity for growth, are restored upon introduction of the cbpA gene on a multicopy plasmid. HtpG of *E. coli* functions as an ATP-independent molecular chaperone in vitro. It recognizes and transiently binds normative folding intermediates, reducing their free concentration in solution and thus preventing unspecific aggregation.

Figure 3:
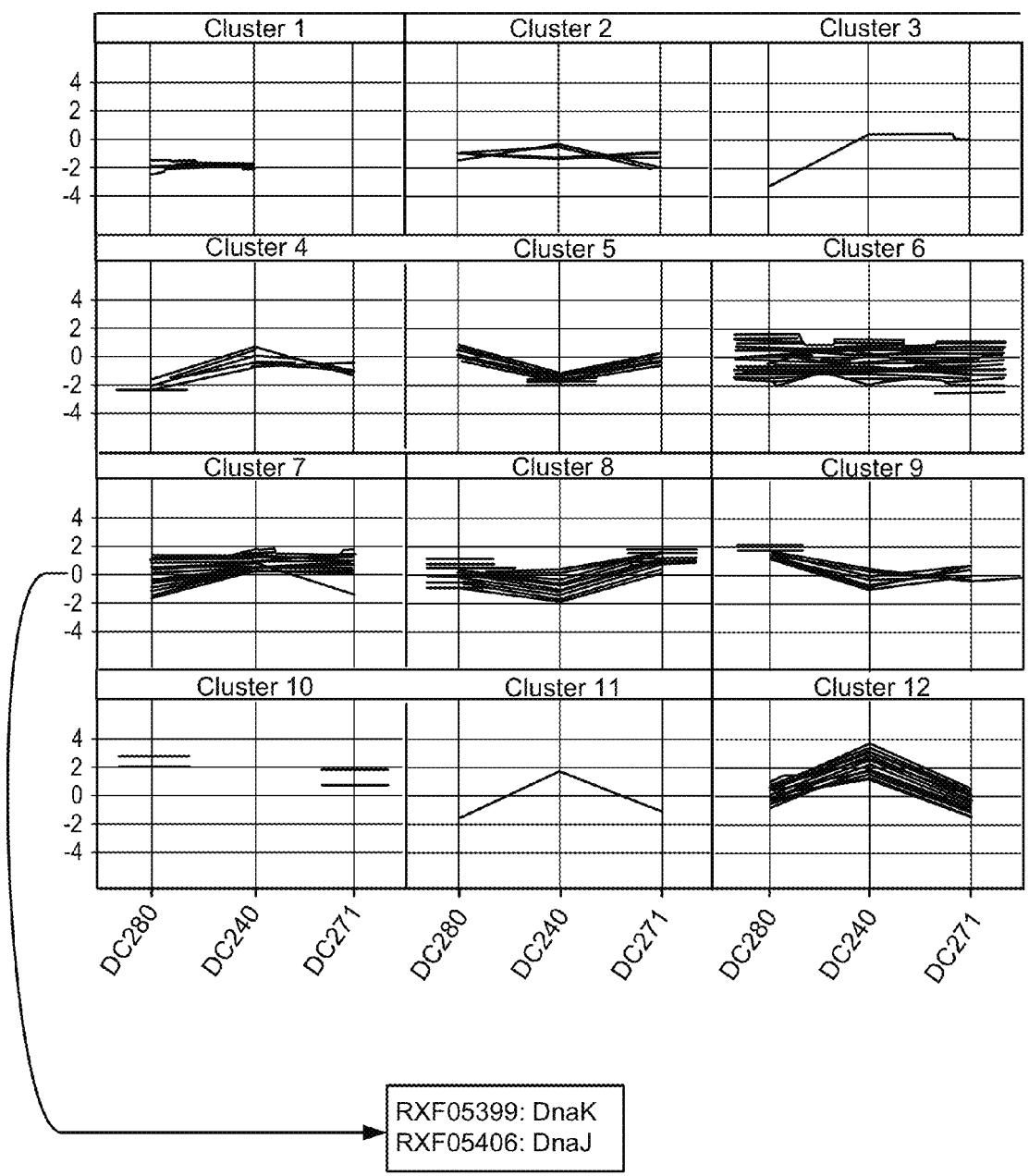
FIG. 3 is a hierarchical cluster analysis of cluster 6 from FIG. 2. In the new cluster 8, two folding modulators, DnaK and DnaJ, were identified both of which showed higher expression levels for periplasmic recombinant protein production similar to the previously identified HslVU, CbpA, and HtpG. Cluster 6 shows where the rest of the FMs are grouped.

The genes in cluster 6 of FIG. 2 were clustered again using hierarchical clustering to identify less pronounced effects. FIG. 3 shows that FMs and proteases were identified in two main clusters (lines in cluster 6 and 8). The two FMs in cluster 8 are DnaK and DnaJ, two main chaperones that are well known to work together to fold numerous proteins. Further analysis of expression values of genes from cluster 6 identified an additional FM, ClpX that is higher expressed in DC271 producing pbp::hGH as compared to DC240 producing nitrilase or DC280, which does not overproduce any protein. The *E. coli* ClpX heat shock protein is homologous to members of prokaryotic and eukaryotic HSP100/Clp ATPases family. ClpX of *E. coli* was isolated as a specific component of the ATP-dependent Clp proteases, which maintain certain polypeptides in a form competent for proteolysis by the ClpP protease subunit. ClpX can act as a molecular chaperone, in the absence of ClpP, by activating the initiation proteins involved in DNA replication. Identified FMs and proteases important for periplasmic hGH production are listed in Table 4.

TABLE 4

List of FM and protease genes whose steady-state mRNA ratio levels are higher in DC271 as compared to DC240 and DC280. The values listed are the ratio of 4 hr after IPTG induction to 0 hr.

| Gene ID | DC280 (4 hr vs. 0hr) | DC240 (4 hr vs. 0hr) | DC271 (4 hr vs.0hr) | Gene | Function |
|---|---|---|---|---|---|
| RXF05455_1 | 0.8 | 0.6 | 5.3 | htpG | Chaperone protein HtpG |
| RXF03987_1 | 1.0 | 0.5 | 5.2 | cbpA | Curved DNA-binding protein |
| RXF01961_1 | 0.9 | 0.4 | 5.0 | hslV | ATP-dependent protease HslV (ec 3.4.25.—) |

TABLE 4-continued

List of FM and protease genes whose steady-state mRNA ratio levels are higher in DC271 as compared to DC240 and DC280. The values listed are the ratio of 4 hr after IPTG induction to 0 hr.

| Gene ID | DC280 (4 hr vs. 0hr) | DC240 (4 hr vs. 0hr) | DC271 (4 hr vs.0hr) | Gene | Function |
|---|---|---|---|---|---|
| RXF01957_1 | 1.0 | | 4.8 | hslU | ATP-dependent Hsl protease, ATP-binding subunit HslU |
| RXF05399 | 1.0 | 0.6 | 3.3 | dnaK* | Chaperone protein DnaK |
| RXF05399_1 | 1.3 | 0.6 | 3.0 | dnaK* | Chaperone protein DnaK |
| RXF05406_1 | 1.2 | 0.7 | 3.0 | dnaJ | Chaperone protein DnaJ |
| RXF04654_1 | 1.1 | 0.9 | 2.0 | clpX | ATP-dependent Clp protease, ATP-binding subunit clpX |

*For dnaK two probes are present on the microarray chip and thus two gene expression values are provided.

Example 2

Gene Expression Analysis of Strains Producing Cytoplasmic and Periplasmic Proteins—Ph-eel Comparison gfaifftereza" Strains In order to confirm the results obtained above, additional microarray experiments were performed by direct comparison of the two strains DC271 and DC240 (slides 7 to 10 in Table 3). The comparison of the two strains at the 4 hrs after induction time point confirmed that an almost identical set of FM and protease genes were up-regulated in cells expressing partially soluble pbp::hGH (Table 5). All genes listed in Table 5 are significantly (i.e. >2-fold) higher expressed in strains producing the partly insoluble hGH as compared to cells producing fully soluble nitrilase. In the direct comparison of DC271 to DC240, a few additional proteins were identified as compared to the time point comparison (see Table 4) that showed significantly higher gene expression values during partially insoluble hGH production. Those genes included rxf08347 encoding ClpB, rxf04587 encoding ClpA, and rxf05753 encoding FkbP. The *E. coli* ClpB homologue is involved in reactivation of inclusion bodies together with DnaKJ-GrpE. ClpA from *E. coli* has a chaperone function or, when together with ClpP, degrades proteins. In *E. coli*, FkbP functions as a peptidyl-prolyl isomerase.

Example 3

Gene Expression Analysis of a Strain Producing an Insoluble Cytoplasmic Protein Since DC271 expresses partially periplasmic human growth hormone (pbp::hGH), it was investigated if similar or different FMs and protease genes were up-regulated in a strain expressing mainly insoluble cytoplasmic hGH. DC369 was used in this experiment. The 4 hrs after induction sample was compared with that of the 0 hr time point sample, and microarray experiments were performed as shown in Table 3 (slides 11 and 12). Again, similar FM and protease genes were found to be up-regulated indicating that the identified genes are involved in cytoplasmic rather than periplasmic folding and protein degradation (Table 6). A summary of which genes were identified in which experiment along with the fold up-regulation is shown in the Venn diagram of FIG. 4.

TABLE 5

List of FM and protease genes whose steady-state mRNA levels are higher in DC271 as compared to DC240. The values listed are the ratio of DC271 to DC240 at 4 hr after IPTG induction.

| Gene ID | DC271 vs. DC240 at 0hr | DC271 vs. DC240 at 4 hr | Gene | Function |
|---|---|---|---|---|
| RXF03987_1 | 0.8 | 10.8 | cbpA | Curved DNA-binding protein |
| RXF01957_1 | 0.9 | 10.0 | hslU | ATP-dependent Hsl protease, ATP-binding subunit HslU |
| RXF01961_1 | 0.7 | 10.0 | hslV | ATP-dependent protease HslV (ec 3.4.25.—) |
| RXF05455_1 | 0.7 | 7.8 | htpG | Chaperone protein HtpG |
| RXF05406_1 | 1.0 | 4.7 | dnaJ | Chaperone protein DnaJ |
| RXF08347_1 | 0.6 | 3.8 | clpB | ClpB protein |
| RXF05399_1 | 1.0 | 3.7 | dnaK* | Chaperone protein DnaK |
| RXF05399 | 0.9 | 2.9 | dnaK* | Chaperone protein DnaK |
| RXF04587_1 | 0.9 | 2.8 | clpA | ATP-dependent Clp protease, ATP-binding subunit ClpA |
| RXF05753_1 | 1.1 | 2.1 | fkbP | Peptidyl-prolyl cis-trans isomerase (ec 5.2.1.8) |
| RXF04654_1 | 1.2 | 2.0 | clpX | ATP-dependent Clp protease, ATP-binding subunit ClpX |

*For dnaK, two probes are present on the microarray chip and thus two gene expression values are provided.

TABLE 6

List of FM and protease genes whose steady-state mRNA levels are higher in DC369 at 4 hrs after induction as compared to time zero. The values listed are the ratio of 4 hr after IPTG induction to 0 hr (just before induction).

| Gene ID | DC369 (4 hr vs. 0hr) | Gene | Function |
|---|---|---|---|
| RXF01961_1 | 4.8 | hslV | ATP-dependent protease HslV (ec 3.4.25.—) |
| RXF01957_1 | 4.3 | hslU | ATP-dependent Hsl protease, ATP-binding subunit HslU |
| RXF03987_1 | 4.1 | cbpA | Curved DNA-binding protein |
| RXF05455_1 | 3.3 | htpG | Chaperone protein HtpG |
| RXF05406_1 | 2.3 | dnaJ | Chaperone protein DnaJ |
| RXF08347_1 | 2.2 | clpB | C1pB protein |
| RXF05399_1 | 2.1 | dnaK* | Chaperone protein DnaK |
| RXF02095_1 | 2.0 | groES | 10 lcDa Chaperonin GroES |
| RXF06767_1 | 2.0 | groEL | 10 kDa Chaperonin GroEL |
| RXF05399 | 1.8 | dnaK* | Chaperone protein DnaK |
| RXF04587_1 | 1.7 | clpA | ATP-dependent Clp protease, ATP-binding subunit ClpA |

*For dnaK two probes are present on the microarray chip and thus two gene expression values are provided.

Example 4

Generation of an hslU Mutant Strain in *P. fluorescens* DC206

The two genes hslVU were found to be among the most highly up-regulated identified genes. HslU is a cytoplasmic ATPase. The homologous protein in *E. coli* can act in combination with a second protein to promote energy dependent protein degradation in *E. coli*. HslU interacts with HslV, a protein with homology to the a subunits of proteasome. The *E. coli* HslVU homologues were reported to be involved in overall proteolysis of misfolded proteins in Missiakas, D., et al. (1996) Identification and characterization of HsIV HsIU (ClpQ ClpY) proteins involved in overall proteolysis of misfolded proteins in *Escherichia coli*. Embo J 15:6899-909.

Figure 5:
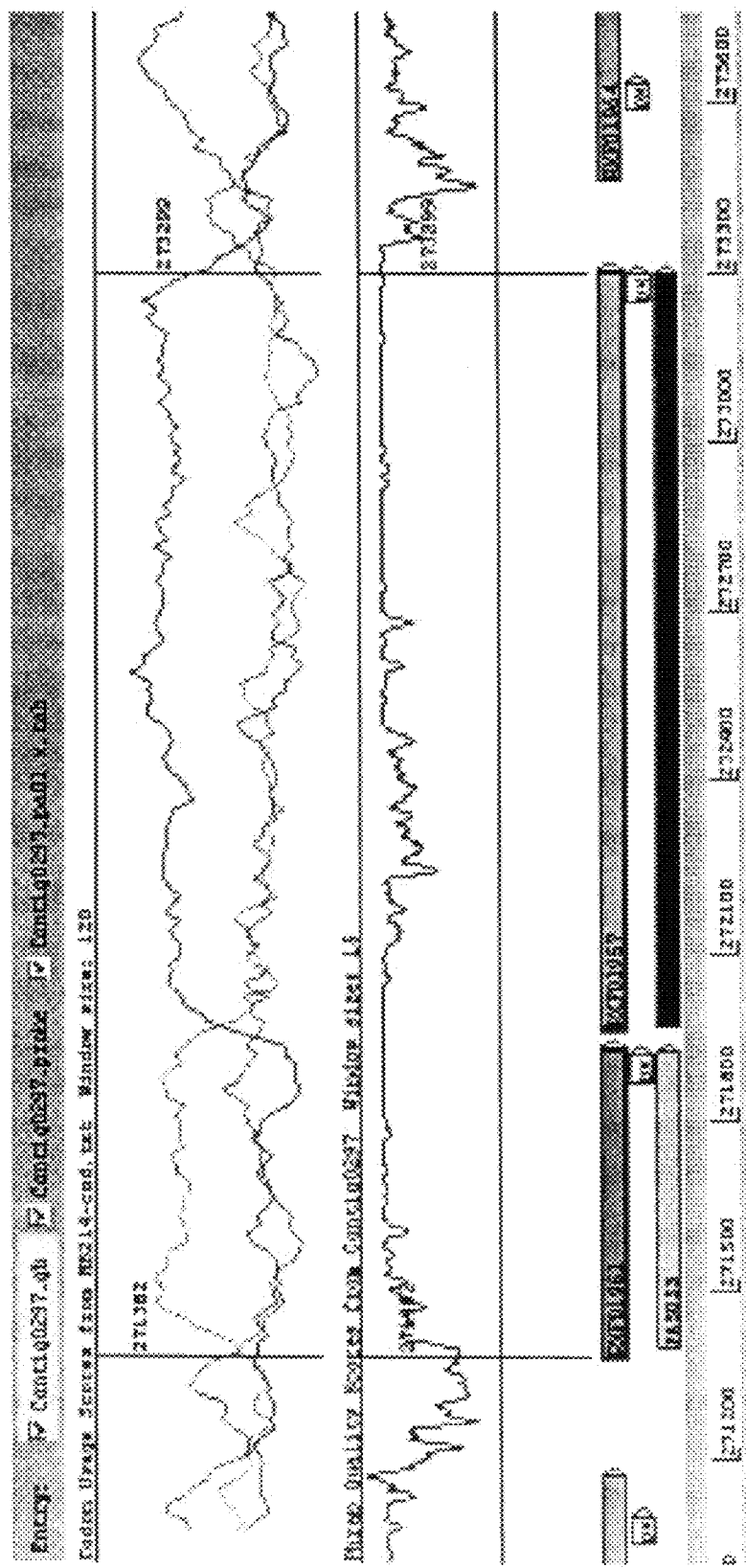
FIG. 5 is a graph of the sequence analysis of the hslV (RXF01961) and hslU (RXF01957) genes from *P. fluorescens* generated by Artemis. The codon usage plot (top panel) indicates that the gene boundary are correct. This is corroborated by the best homologues of HslV and HslU protein sequences to *P. aeruginosa* as indicated beneath the genes of RXF01961 and RXF01957. The Phrap quality score plot shows that the sequence quality is good, i.e. the score line is above the horizontal line indicating a better quality than 1 error in 10 kb (middle panel). The open white pointed boxes below the genes show the location of the probes generated for use in the DNA microarray experiments.

DNA sequence analysis suggested that the *P. fluorescens* hslVU genes are likely to be part of a bicistronic operon (FIG. 5).

Figure 6:
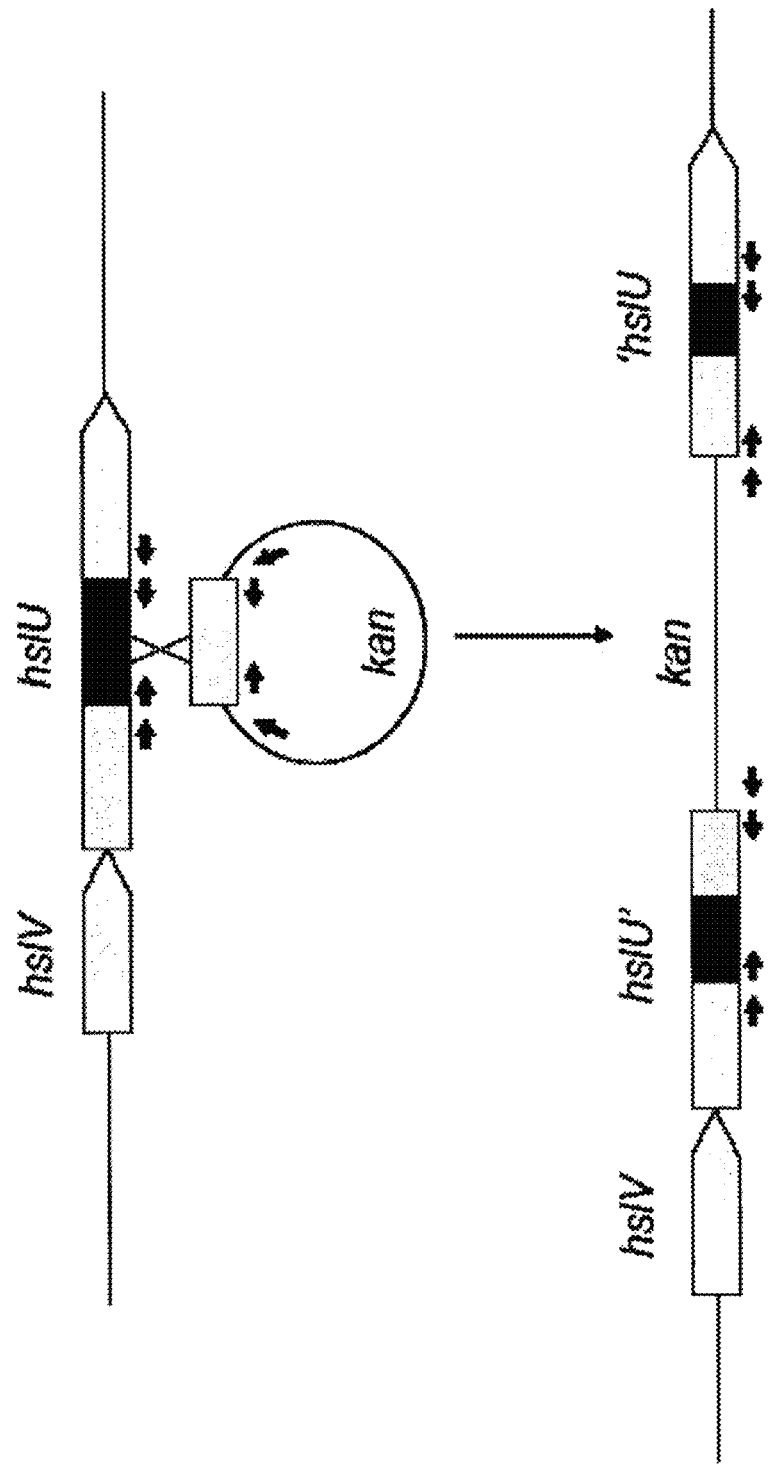
FIG. 6 is a schematic illustration of an hslU mutant construction where an approximately 550 bp PCR product of hslU (light blue box) was ligated into TOPO TA2.1 cloning vector (circle). The resulting plasmid was transformed into competent *P. fluorescens* cells and kanamycin (kan)-resistant colonies were analyzed in diagnostic PCR to confirm the construction of an insertion mutation in the hslU gene.

In order to verify that HslVU are indeed involved in the degradation of hGH, an hslU knockout strain was constructed. Such a strain was generated by insertional inactivation of hslU (FIG. 6). An approximately 550 bp DNA fragment internal to hslU was cloned into the kanamycin-resistant pCR2.1-TOPO vector. Since this vector has an origin of replication (ColE1) that is functional in *E. coli* but not in *P. fluorescens*, the constructed plasmids will integrate into the chromosome of DC206 through homologous recombination in order to confer kanamycin resistance. The correct insertion site for the kanamycin resistant colonies was confirmed by diagnostic colony PCR using primers that hybridize to the outside of the originally amplified region and within the plasmid backbone (Table 3). The constructed hslU mutant strain was designated DC370.

Primers were designed that would amplify a—550 bp internal region of the hslU gene (Table 7). The internal fragment was amplified using Taq Polymerase (Promega), purified, and cloned into pCR2.1-TOPO vector (Invitrogen, San Diego, Calif.). The plasmids were transformed into competent *P. fluorescens* DC206 and selected on the M9 glucose agar plates supplemented with 250 μg/ml uracil and 50 μg/ml kanamycin.

TABLE 7

Primers

| Primers | Sequence | Purpose |
|---|---|---|
| hslU_sens | accgaagtcggctatgtggg (SEQ ID NO: 1) | used in PCR amplification of the internal hslU fragment |
| hslU_antis | aatcgcgctgcacgccttcg (SEQ ID NO: 2) | |
| hsl_F2 | ttcatcaaggtcgaagcg (SEQ ID NO: 3) | used in diagnostic PCR |
| hsl_R2 | tcagtcttgaccatgcc (SEQ ID NO: 4) | |
| M13_R | caggaaacagctatgac (SEQ ID NO: 5) | |
| M13_F | taaaacgacggccag (SEQ ID NO: 6) | |
| hsl-Up | gtggcagccaccaaggctgc (SEQ ID NO: 7) | used in SOE PCR the up- and down- DNA fragment of hslUV |
| hsl_middleUp | cccacattgagtgaggcttacaaggggagagtctccacg (SEQ ID NO: 8) | |
| hsl_middleDown | cgtggagactctcccttgtaagcctcactcaatgtggg (SEQ ID NO: 9) | |
| hsl_down | ggccaatggttggccacgcg (SEQ ID NO: 10) | |
| hsl_UpUp | tgccgacgccacaggtgc (SEQ ID NO: 11) | used in diagnostic PCR |
| hsl_DownDown | gcctggtactgcgactcg (SEQ ID NO: 12) | |
| RC199 | atatactagtaggaggtaacttatggctgacgaacagacgca (SEQ ID NO: 13) | used in cloning the grpE-DnaKI |
| RC200 | atattctagattacaggtcgccgaagaagc (SEQ ID NO: 14) | |

Protein Expression Comparison by SDS-PAGE Analysis

To study the effect of the hslU gene knockout, two exogenous protein expression were compared between the parent strain DC206 and the newly constructed mutant strain DC370. The plasmids harboring the gene encoding pbp::hGH (pDOW1323), and hGH (pDOW1426) were each transformed into competent DC370 cells and resulted in strains DC373 and DC372, respectively. Standard shake-flask growth experiments were performed with the four strains.

Figure 7:
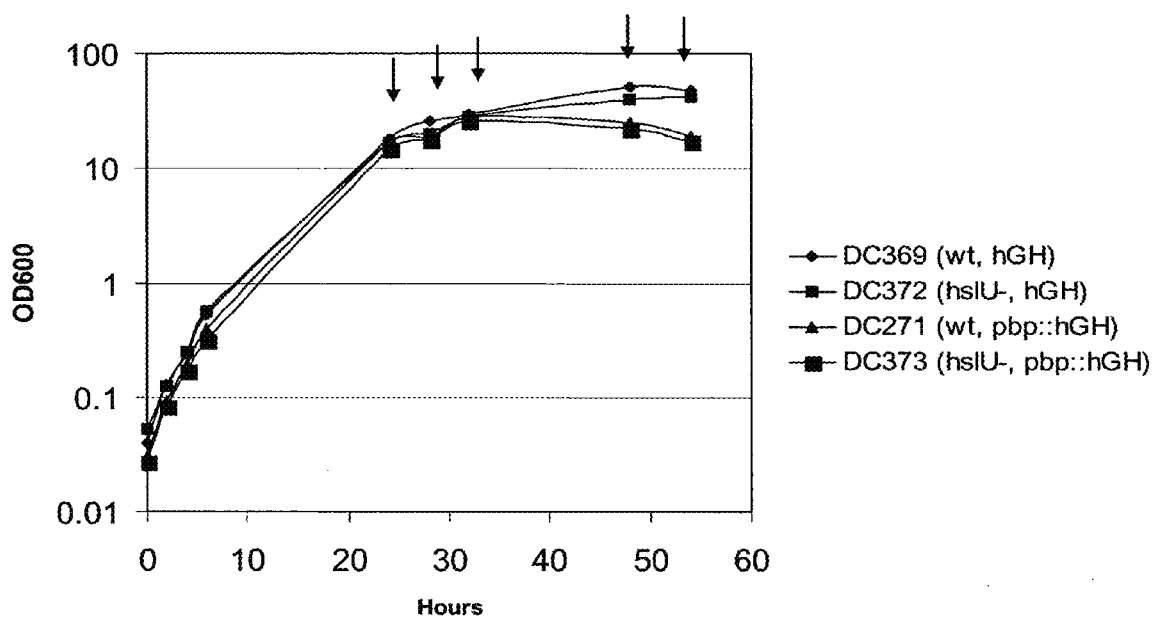
FIG. 7 is a graph of a growth curve assays comparing wild type with hslU mutant strain overproducing hGH or pbp::hGH in shake flask production medium. The arrows indicate time points where samples were taken.
Figure 8:
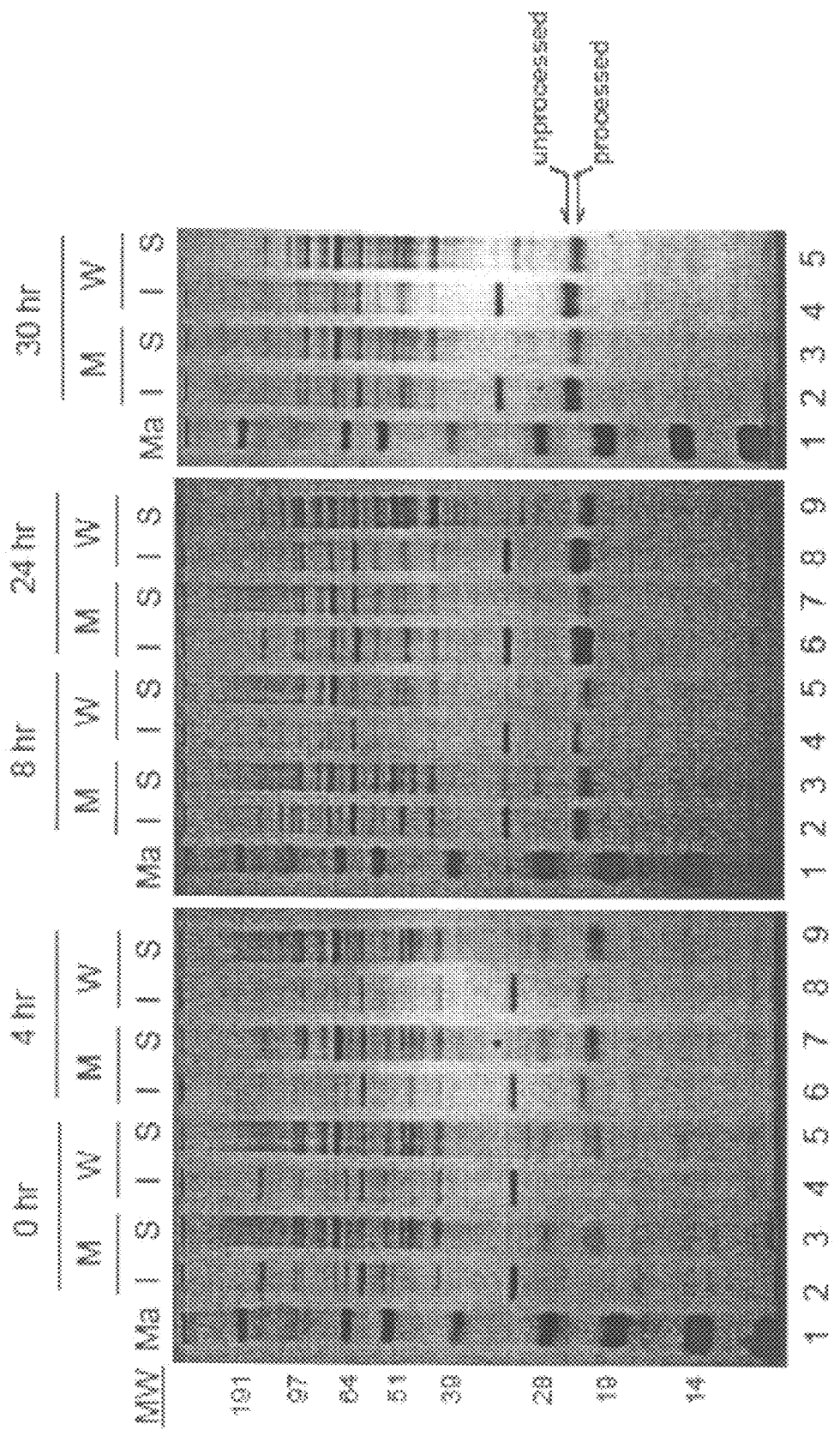
FIG. 8 is an image of SDS-PAGE analysis of strains DC271 and DC373 expressing pbp::hGH. Samples were taken from DC271 (wild-type, W) and DC373 (hslU mutant, M) just before protein induction (0 hr) and then 4 hr, 8 hr, 24 hr, and 30 hr after IPTG addition. Soluble (S) and insoluble (I) fractions were prepared for each sample analyzed. The production of unprocessed and processed hGH is indicated by arrows. The molecular weight (MW) marker (Ma) is shown on the right hand side of the gels.
Figure 9:
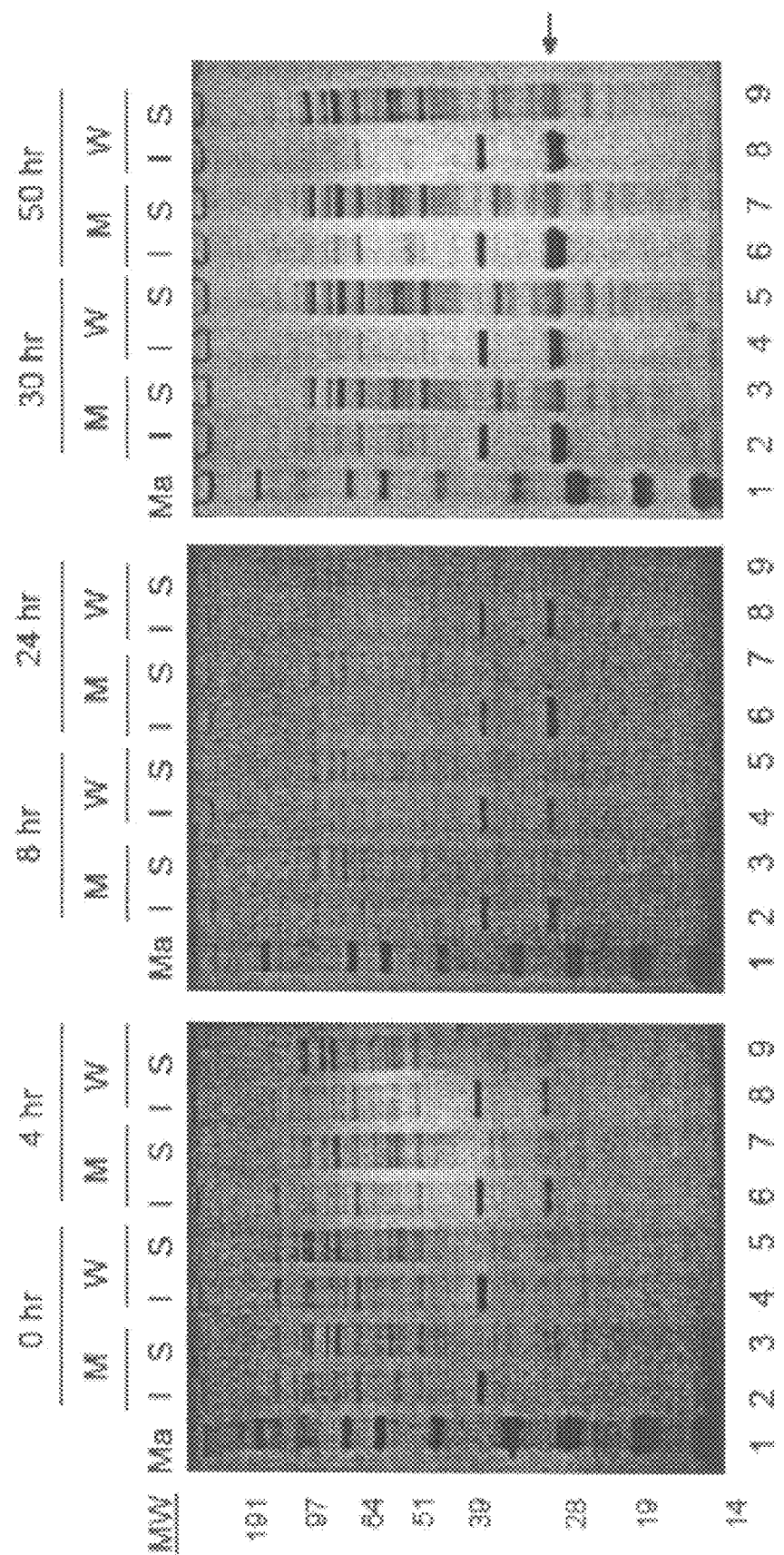
FIG. 9 is an image of the SDS-PAGE analysis of strains DC369 and DC372 expressing hGH in the cytoplasm. Samples were taken from DC369 (wild-type, W) and DC372 (hslU mutant, M) just before protein induction (0 hr) and then 4 hrs, 8 hrs, 24 hrs, 30 hrs, and 50 hrs after IPTG addition. Soluble (S) and insoluble (I) fractions were prepared for each sample analyzed. The production of hGH is indicated by an arrow. The molecular weight (MW) marker (Ma) is shown on the right hand side of the gels.

FIG. 7 shows that the wild-type and mutant strains have similar growth rates. Samples were run on SDS-PAGE gels (FIGS. 8 and 9). The results suggest that the mutant produced higher amounts of proteins due to the deletion of the protease subunit HslU.

Protein Expression Comparison by Fluorescence Activity

Figure 10:
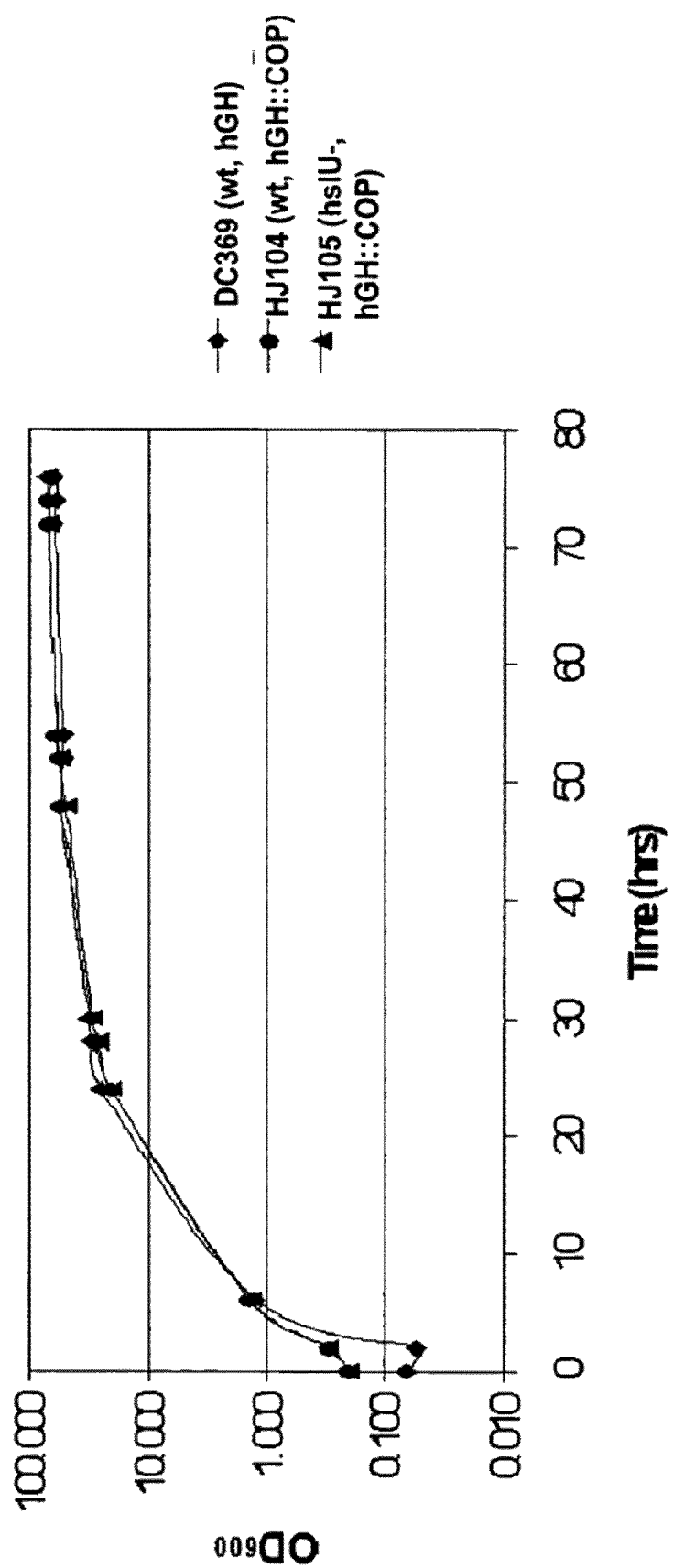
FIG. 10 is a graph of growth curves of strains expressing the hGH::COP fusion protein. The strains include: DC369 expressing hGH only (not fused to COP) as a negative control; HJ104, the wild type expressing hGH::COP; HJ105, the hslU mutant expressing hGH::COP.
Figure 11:
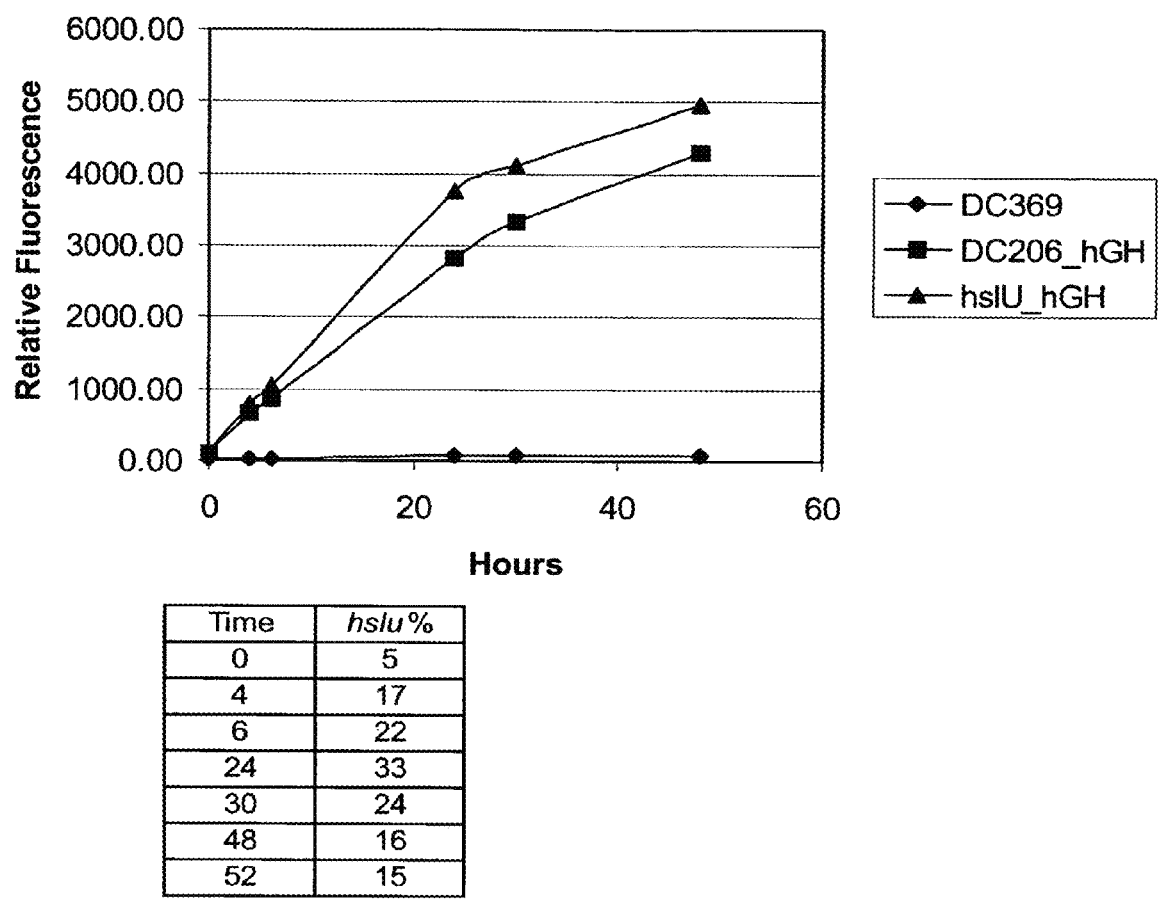
FIG. 11 is a graph of the green fluorescence activity measurements for strains expressing the hGH::COP fusion protein using a fluorimeter. Five OD600 of cell culture were sampled for each strain harboring hGH or hGH::COP at different time points after IPTG induction. The strains tested include: DC369 expressing hGH only (not fused to COP) as a negative control; HJ104, the wild type expressing hGH::COP; HJ105, the hslU mutant expressing hGH::COP. The inserted table shows percent increase of relative fluorescence in the hslU mutant compared to the wild type at different time points after IPTG induction.

Since the observed effect of the lack of HslU on the yield of hGH is difficult to quantitate using SDS-PAGE analyses, the temporal profile of protein production was monitored by the fluorescence of a fusion protein between COP green fluorescent protein and hGH. A plasmid containing an hGH::COP fusion was constructed and transformed into the parent strain DC206 and the hslU gene deletion strain DC370 resulting in strains HJ104 and HJ105 (Table 1). Standard shake flask experiments were performed and samples were taken at various time points for fluorescence measurements (FIG. 10). The readings from the fluorimeter clearly showed that the hslU protease mutant strain had significantly higher protein expression levels compared to that of the parental strain (FIG. 11). This finding corroborates the results obtained by SDS-PAGE analysis. Comparing to the wild type strain, the hslU mutant increased 33.05% of the relative fluorescence at 24 hrs after induction (see insert in FIG. 11).

Example 5

Construction of an hslUV Knockout Strain

The Hsl protease consists of two subunits: an ATP-binding subunit encoded by hslU, and a protease subunit encoded by hslV. The previously constructed Hsl protease knock-out strain is an insertional inactivation of the hslU gene. To remove the concern that HslV might still function as a protease by being able to couple with an ATP-binding subunit of another protease, a deletion strain was constructed that had both the hslU and hslV genes removed from the chromosome.

Figure 13:
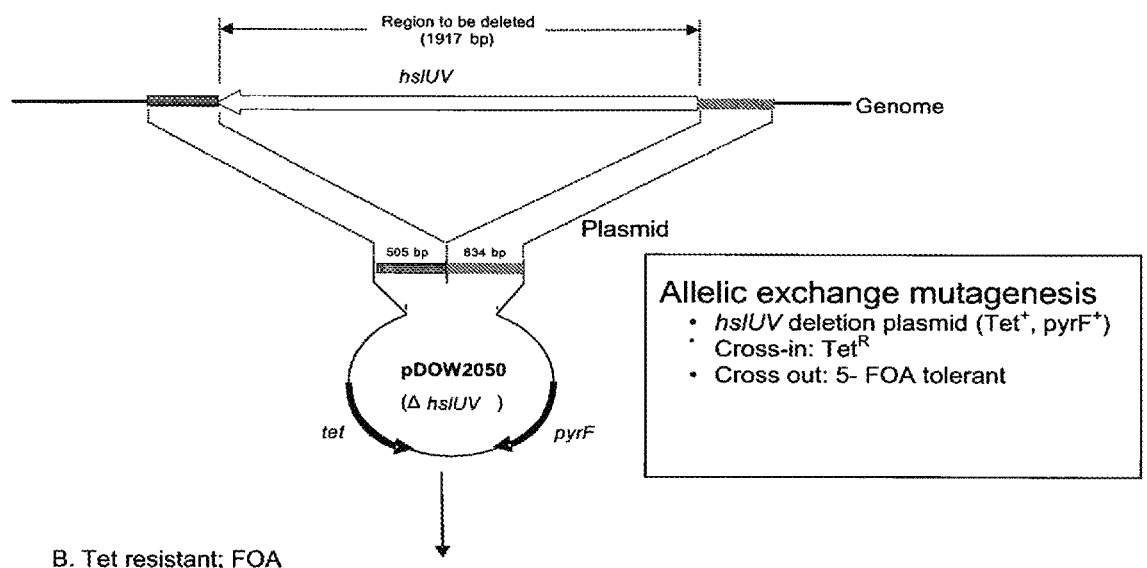
FIG. 13 is a representation of the construction of chromosomal deletion of hslUV gene in pyrF-negative strain. A. Plasmid pDOW2050 contains 505 bp and 634 bp DNA fragments flanking the hslUV gene. Since suicide plasmid pDOW2050 can not replicate in *P. fluorescens*, tetracycline-resistant cells will only be generated after a single recombination event at one of the homologous regions that integrates the entire plasmid into the genome. B. Tetracycline-resistant cells contains the entire plasmid integrated into the genome. These cells also contain the pyrF gene encoded from the plasmid. Selection for cells that has the second recombinant event occurred by plating cells on agar plates supplemented with FOA, which in pyrF-positive strains, is converted into a toxic compound. C. The chromosomal deletion strain was confirmed by sequencing analysis
Figure 13:
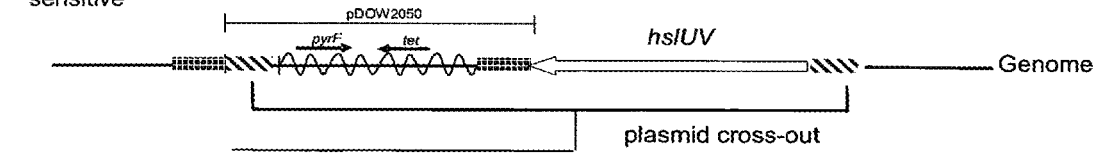
Figure 13:

As shown in FIG. 13, plasmid pDOW2050 was constructed by PCR amplification of two DNA fragments flanking the hslUV region, the two fragments were subsequently fused using the Splicing by Overlap Extension (SOE) PCR method (see U.S. Pat. No. 5,023,171, Ho, S. N. (1991) Method for gene splicing by overlap extension using the polymerase chain reaction. The fused DNA fragments were then ligated into the SrfI site of vector pDOW1261-2. The deletion plasmid was named pDOW2050 after the insert was confirmed by DNA sequencing.

Plasmid pDOW2050 was electroporated in DC206 and plated onto M9 agar plates supplemented with 1% glucose and 15 µg/ml tetracycline. Tetracycline-resistance is due to an integration event that recombines the entire plasmid into the chromosome at one of the two homologous regions within the genome (FIG. 13). To select for cells that have a deletion of the hslUV genes resulting from a second homologous recombination between the integrated plasmid and the homologous DNA region in the chromosome, the tetracycline resistant colonies were grown to stationary phase in LB medium supplemented with 250 µg/ml uracil. Cells are then plated onto LB agar plates supplemented with 500 µg/ml 5-fluoro-orotic acid (5-FOA). Cells that lost the integrated plasmid by a second recombination event also have lost the pyrF gene and thus are resistant to 5-FOA, resulting in the desired chromosomal hslUV deletion strain, called DC417.

Phenotypic Analysis of hslUV Deletion Strain

SDS-PAGE analysis of the hslUV deletion strain expressing hGH protein (strain HJ115) showed much higher protein yield than the wild-type strain DC369, similar to what was observed earlier using the hslU insertional mutant strain DC372 (data not shown).

Figure 14:
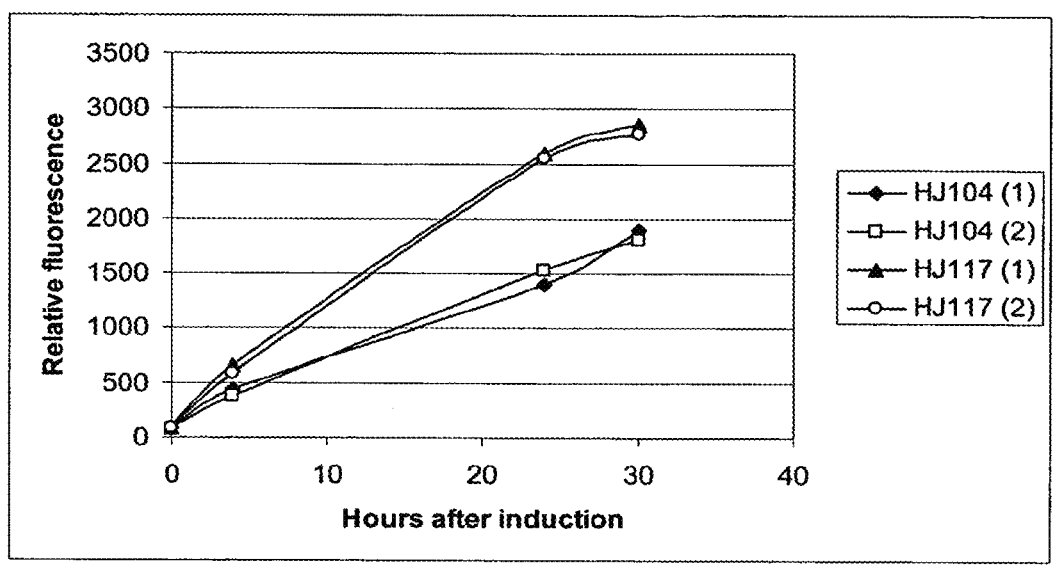
FIG. 14 is a graph of relative fluorescence over time for green fluorescence activity measurements for the strains expressing the hGH::COP fusion protein using a fluorimeter. Duplicates were used for both the wild type (HJ104) and hslUV deletion strain (HJ117).

Protein yield was also measured by fluorescence activity of the hGH::COP fusion using the same method described earlier. Plasmid pDOW1349 containing the hGH::COP fusion was transformed into wild-type and mutant strains resulting in strains HJ104 and HJ117, respectively. Standard shake flask experiments were performed and samples were taken at various time points for relative fluorescence measurements (FIG. 14). The readings from the fluorimeter indicated that the hslUV protease deletion strain had significantly higher proteins expression levels (about 50% yield increase) as compared to that of the wild-type strain. This result is similar to what was observed previously with the hslU knock-out strain.

Example 6

Iterative Target Identification Using DNA Microarray Technology

To investigate if a new set of proteases are up-regulated in the hslUV protease deletion strain, DNA microarray experiments were conducted. Standard shake flask experiments were performed using the wild type (DC369) and mutant strain (HJ115) expressing hGH. For each strain, the 4 hrs after induction samples were compared to that of the 0 hr time point sample (just before heterologous protein induction) and DNA microarray experiments were performed. Comparing the ratio of the two time points between the wild-type and mutant strains, a new list of protease genes that are up-regulated in the hslUV protease deletion strain was identified (Table 8). These newly identified genes encoding proteases can now be the targets for a second round of gene deletion events to further improve the yield of heterologous protein production.

TABLE 8

Protease genes whose steady-state mRNA levels arc higher in the hslUV protease deletion strain (HJ115) as compared to the wild type strain (DC369), based on the ratio of 4 hr after IPTG induction to 0 hr (just before induction).

| OrFID | Curated Function | Sequence |
|---|---|---|
| rxf000133 | D-alanyl-meso-diamino-pimelate endopep-tidase (ec3.4.-.-) | atgcactttggaaaatggtttcacaccagcaccctgctggtcggcttgagatgtgctgggcggctgcgccagc<br>gtctcccaaacctccaccccggcaaccctggataagctgttgagcgaccggcgctgcaaggcgccaccgt<br>ctcgctgatggtgcgtgatgcccgcacaggcaccacgctgtatcagcacaacccacgcacccggctggtgcc<br>cgcgtccaacctcaagctgttgaccacggcggcagccatggatgtattggggccgcagtaccgcttcgccac<br>gcaactgctgagcaatggcctacgccagggcgaccggctgactggcaacctgtacctgcgtggcttgggcg<br>acccgagtattcagtttgccgactatcaggcgctcgccgcgcaattggccagccagggcgtgcgccaggtgc<br>agggtgacctggtgttcgacgacacttggttcgatgccgagcggctgggcgtggactggtcccatgatgatga<br>aaccacctactacgcgcgcagatttcagcgctgaccgtggcgcccaataccgactttgatgctggcagcgtg<br>ctggtcaccgccaaggcgccgttgcacgtcggctcgccggtcggcgtggagatctacccgcccaccgacta |

TABLE 8-continued

Protease genes whose steady-state mRNA levels are higher in the hslUV protease deletion strain (HJ115) as compared to the wild type strain (DC369), based on the ratio of 4 hr after IPTG induction to 0 hr (just before induction).

| OrFID | Curated Function | Sequence |
|---|---|---|
| | | cctgcaactgaataaccgcgccgtcagcgggccgggtaacagctatgggatcaaccgtcgccatggcacca acctgctgcagctcagcggcgcggtggcgcctggccggcagagcgcaattgatcagcgtgtgggagcc gacgcaactggtggccaacctgttgagcaagccttggcgcagcagggcatcaaggtgctgggcgtcggg tgatgggcggggcaagtcctgctggggtgacggtgctggccgagcaccaatcggcgccgttgcaggagctg atcgtgccgctgctcaagctctcgaacaacgccatgtccgaagccgtgctcaaggccatgggccgccagacg gccagcagcggcacggccggcggcgccgtggcgtggccgactttctcaagcgccagggggctggac accagcgctgtgagccaagtggacggctccggcctgtcgcggcgtaacctggtgtcgtcgcaaaccctcacc gacctgctgctggcggccagcaaacaaccctggttcgacgcctggtacaacgcgctgccggttgccggcaat gccgaccgtatgaccggcggcagcctgggttaccgcctgcgcggcacggctgcggaaaataacctgcatgc caagaccggctccatggccggcgtgtcgtcattgaugggttacatcaccgatgctcacgggcgcaagctggtg ttcgcgatgttgaccaacaactatgtggtcgctggcgcgcaggtaaaagccgtggaaaaccgcgtcgccgtg gccctgtcccacagcgaagactga |
| rxf01918 | zinc protease ec 3.4.99.-) | atgagtgatcgcaaaaacagccgcctgatcctgcccggcctgatcgccgtcaccctgatggcggccagcgcc gtttactcttcgcgccccagcgagtcggtcgccagccaggccctggacaaggctcaaacggccagcaccctg caatcccctggcggaactggatggcaaggcaccgaccaaccgcaagctcgacgtacaaacctggaccaccg ccgaaggcgccaaggtgctgttcgtcgaagccatgagttgccgatgttcgacatgcgcctgctgttcgccgc cggcagcagccaggatggcgacgtgccaggccgtgcgatgaccaacgccatgctcaacgaaggcgtg ccgggcaaggacgtcagccagatcgccagtggctcgaaggcctgggggccgactttggcaacggcgcct accgcgacatggcgctggtgaccctgcgcagcctgagcgacagcgccaagcgcgacgccgccctgtcact gttcaaccaggtgatcggccagccgactttccggcagactcactggcacgcatcaagaaccagatcctggc cggtttcgagtaccagaagcagaaccccggcaaactggcgagcatcgaactgttcaagcgcctgtacgcg accacccttacgcacacccgagcgaaggcaccccgagagcgtgccgaagattaccctggcgcagttgcag gcgttccacgccaaggcctatgcagcgggtaacgcggtgattgcagtggtgggcgacctgacccgcgccga agctgaagccatgacggccaaggtgtccgcgtcgctgcccaaaggcccggctatggccaagatcgcccagc cgaccgagccaaaagccggcctgagccgtatcgagttcccgtccaagcaaacccacctgtgtgtttgcgcagf tgggcatcgaccgtgccgaaccggattacgcagecttgtccctgggtaaccagatcctcggcggcggtggctt cggcaccgcttgatgagcgaagtgcgtgaaaagcgcggcctgacctacggcgtgtattccggtttctcacca atgcaggcgcgggccgttcatgatcaacctgcagaccgcgccgaaatgagcggtggcaccttgcgcct ggtggaggacgtactggctgactacctcaagaccggcccgacgcaaaaggaactggatgacgccaagcgc gagctggccggcagcttcccgctgtccaccgccagcaacgccgatatcgtcgggcagttgggcgccatggg tttctacaacctgccgctgagctatctggaagatttcatgaaacaatccaggccctgaccgtcgatcaggtcaa ggctgcaatgaataaacacttgagcgccgacaagatggtcatcgtgaccgccggcccgacgattgcgcaaaa gccactaccgccccccactgataaacctgccgagcagccgctcggggttccggagcattaa |
| rxf02689 | Microsomal dipeptidase (ec 3.4.13.19) | ttgtcgtggattgacgctttcggcaattcccctgtcgttttcgcacccggctccgtcggtgcctgggcatatgctg gccccaaagcgccggcagacgattcggcgcatgaatcgccaataaggggacgcctgatgagcccagccga gttgcacgccgacagcatcgttatcgacggctgattattgccaagtggaaccgcgaccgttcgaagacatgc gcaaaggtggcctcaccgccgccaattgcacggtgtcggtgtgggaaggcttccaggccacgatcaataaca tcgttgccagccagaccctgatccgcgaaaacagcgaccctggtgatcccggtgaaaaccaccgccgacatcc gccgcgccaaggagagggcaagactggcatcatcttcggccttccagaatgcccatgcctttgaggaccagct cggctatgtcgagatcttcaagcagctcggcgtgggcgtggtgcagatgtgctacaacacccagaacctggtg ggcaccggttgctacgagccgcagtgatggcggcctgtcgggttcggggcgtgagatcgtcgggcgagatgaaccg cgtcggcatcatgtgccgacctgtcccacgtgggctccaagaccagcgaagaggtcatcctcgaatcgaaaa gccggtgtgctactcccactgtctgccgtccgggcttaaagagcacccgcgcaacaagtccgatgaagagct gaagttcatcgccgaccatggcggatttgtcggtgtgaccatgttcgcgccgttttttggccaagggcatcgactc gactatcgacgactatgccgaagccatcgaatacaccatgaacatcgtcggcgaagacgccatcggcatcgg caccgacttcacccagggccatggccaggatttctttcgaaatgctcacccatgacaagggctacgcccgccg cctgaccagcttcggcaagatcatcaaccgctgggcatccgcaccgtgggtgagttccccaacctcaccga gaccctgctcaagcgcggcacagcgagcgcgtggtgcgcaagatcatgggcgagaactgggtcaacgtg ctcaaggacgtctgggcgaataa |
| rxf05113 | Extra-cellular metallo-protease precursor (ec 3.4.24.-) | atgacaatttggcccaggggcgaacacagggctatcctgaaaaccgttaccggacgttcaccacacgcca aaaaggagccagctcatgtgtgttcgccaaccgcgcaaccgattattgcctgatccccgcctacatgtcga ccagatcgcacgccacggcgacaaagcccaacgggaagtcgcattacgcacgcgtgccaaggacagcac gtttcgttcgttgcgcatggtcgcggttaccgccaaggggccggccgcatggcactggccgtgggcgcg agaagcaacgctcgatctacagtgccgaaaacaccgacagcctgcccggcaagctgatccgcggcgaagg gcagcccgccagtggccgatgccgcggtggacgaagcctatgacggcctgggcgcgaccttcgatttttttga ccaggtctttgatcgcaattccatcgacgatgcgggcatggcgctggacgccacggtgcacttcggccagga ctacaacaatgcgttctggaattcgaccaagatggtgttcggcgatggcgaccagcagttgttcaaccgattac cgtggcactcgacgtcattgggcatgagttggcccatggcgtgactgaggatgaggccaagctgatgtacttc aaccagtccggtgcgctgaacgagtcgttgtcggacgtgttcggttcgctgatcaagcagtacgcgttaaagc aaacggccgaggatgccgactggttgatcggcaaggggttgttaccaaaaagatcaagggcacggcgctg cgctcgatgaaggcgccaggcactgcgtttgatgacaagctgtgggcaaagacccgcagcctgggcacat ggatgattttgtgcaaacttacgaggacaatgggggcgtgcatatcaattccggcattcccaaccatgcgttcta ccaggtggcgatcaatataggcgggttcgcctgggagcgtgccgggcgtatctggtatgacgcactgcgcga ttcgcggttgccggccaattccgggttcttcgttttgcgcgcattacccacgatatgccggccagctttatggc gtgaacaaagctgagcagaaggcagtcaaggaaggctggaaagcggtgggcataaacgtttga |
| rxf05400 | Cell division protein | ttgaacgatatggcaaagaatctgatcctgtggttgatcatcgcggctgtcctggtgacggtgatgaacaacttct ccagccctaacgagccgcagaccctcaactattccgacttcatccagcaagttaaggatggcaaggtcgagc gcgtagcggttgatggctacgtgattaccggtaagcgcaacgatggcgacagcttcaagaccattcgtcctgc |

TABLE 8-continued

Protease genes whose steady-state mRNA levels are higher in the hslUV protease deletion strain (HJ115) as compared to the wild type strain (DC369), based on the ratio of 4 hr after IPTG induction to 0 hr (just before induction).

| OrFID | Curated Function | Sequence |
|---|---|---|
| | FtsH (ec 3.4.24.-) | cattcaggacaacggtctcatcggtgacctggtggataacaaggtcgttgtggaaggcaagcagcctgaaca gcaaagcatctggacccagctcctggtggcagcttcccgatcctggtgattatcgccgtgttcatgttcttcatg cgccagatgcaaggeggtgegggaggcaagggegggccgatgagcttcggcaaaagcaaggcgcgcct gctctccgaagaccaggtgaagaccaccctggctgacgtcgcaggttgcgacgaagccaaggaagaagtc ggtgagttggtcgagttcctgcgtgatccgggcaagttccagcgcctgggtggccgtattcctcgcggtgtgct gatggtggggcctccgggtaccggtaaaacctt gctggccaaggcgattgccggcgaagccaaggtgcctt ettcacgatttccggttctgacttcgtcgagatgtttgteggcgtoggcgccagccgtgttcgcgatatgttcgag caggccaagaagcacgcgccatgcatcatcttcatcgacgaaatcgatgccgttggtcgccatcgtggcgcg ggcatggggggtggtcacgatgagcgtgagcagaccctcaaccagttgctggtagagatggatggtttcgag atgaatgacggcattatcgtcatcgccgcaaccaaccgteccgacgttctcgaccctgcgttgctgcgtccggg ccgtttcgaccgtcaggttgtggtcggcctgccggacattcgtggtcgtgagcagatcctgaaagtacacatgc gcaaggtgccaatgggtgacgacgtggctccggctgtgatcgcccgtggtactcccggtttctccggtgctga tctggcgaacctggtcaacgaggcttcgtgttcgctgcccgtactggcaagcgcatcgttgagatgaaagag ttcgaattggcgaaagacaagatcatgatgggcgccgagcgcaaatccatggtcatgtccgagaaagagaag cagaacaccgcttatcacgaggccggtcacgccattgtaggtcgcgttgtgcctgagcatgacccgtctaca aagtgtcgatcattcctcgtggtcgggcactgggtgtgaccatgttcctgccggaagaagatcgctacagcctc tccaagcgtgcgctgatcagccagatctgctcgctgtatggcggtcgtattgctgaggaaatgacccttggcttc gacggtgtgaccactggtgcctccaatgacatcatgcgtgccagccagatcgcacgaaacatggtgaccaag tggggettgteggaaaaactcggcccattgatgtacgccgaagaggaaggcgaagtgttcctggggcgtggc ggcggtgggcaaagcgccagcttctcgggtgagacagccaagctgatcgactccgaagttcgcagcatcatt gaccagtgctatggcacggccaagcagattttgactgacaaccgtgacaagctggacgccatggctgatgcg ttgatgaagtacgaaaccatcgatgccgaccagatcgacgacatcatggcgggccgtacgccgcgtgagcc gcgcgactgggaaggtggttcgggtacttcgggcactccgcctgtggtgcagaatgagcgccctgaaacgc ctatcggcggcccggcagctgatcactaa |

Example 7

Figure 4:
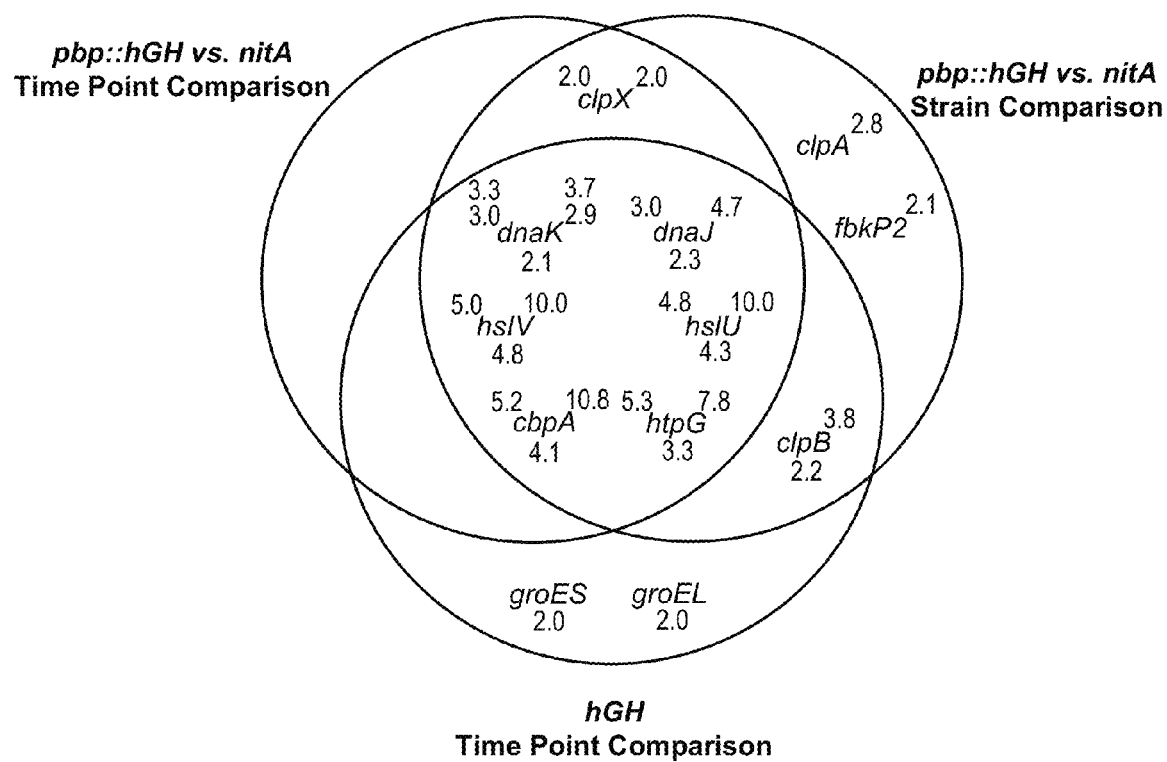
FIG. 4 is a Venn diagram showing the up-regulated protease and FMs from the three sets of experiments in Table 5, 6 and 7. As summarized in Table 5, 6 and 7, the list of genes were organized in Venn diagram to highlight the overlap of the gene list among the three sets of experiments indicated at the corner. For each gene, the ratio of each experiment was shown with 2 as a cut off.

Co-Overexpression of Folding Modulators Increases Solubility of Target Protein hGH Based on the transcriptional profiling data shown in FIG. 4, expression of folding modulators (FMs) DnaK and DnaJ was increased in strains producing recombinant protein compared to control strains (see Tables 4 and 5). A strain that co-overexpressed GrpE, DnaK and DnaJ along with hGH was produced and tested to identify if this resulted in the accumulation of increased levels of soluble hGH.

Construction of grpE-dnaKJ-Containing Plasmid for Co-Overexpression with hGH

The *P. fluorescens* grpE-dnaKf genes were amplified using chromosomal DNA isolated from MB214 (DNeasy; Qiagen, Valencia, Calif.) as a template, RC199 (5'-ATAT<u>ACTAGT</u>AGGAGGTAACTTATGGCTGACGAACAGACGCA-3') and RC200 (5'-ATAT<u>TCTAGA</u>TTACAGGTCGCCGAAGAAGC-3') as primers, PfuTurbo (Stratagene, La Jolla, Calif.) was used following the manufacturer's recommendations. The resulting PCR product (4 kb) was digested with SpeI and XbaI (restriction sites underlined in the primers above) and ligated to pDOW2236 to create pDOW2240 containing the grpE-dnaKf genes under the control of the tac promoter. Plasmid pDOW2240 was digested with SpeI and HindIII and the resulting grpE dnaKJ-containing 4.0 kb fragment was gel-purified using Qiaquick (Qiagen) and ligated to pDOW2247 also digested with SpeI and HindIII. The resulting plasmid, pDOW3501, containing grpE-dnaKJ under the control of the mannitol promoter, was transformed into DC388 by selecting on M9 glucose plates supplemented with 250 µg/ml uracil. Finally, pDOW1426 was electroporated into the above strain (DC462) and selected on M9 glucose plates, resulting in strain DC463 with two inducible plasmids: 1) pDOW1426 carrying $P_{tac}$ hGH and 2) pDOW3501 carrying $P_{mtl}$ grpE-dnaKJ.

Shake Flask Fermentation, Sample Collection and Analysis

Figure 15:
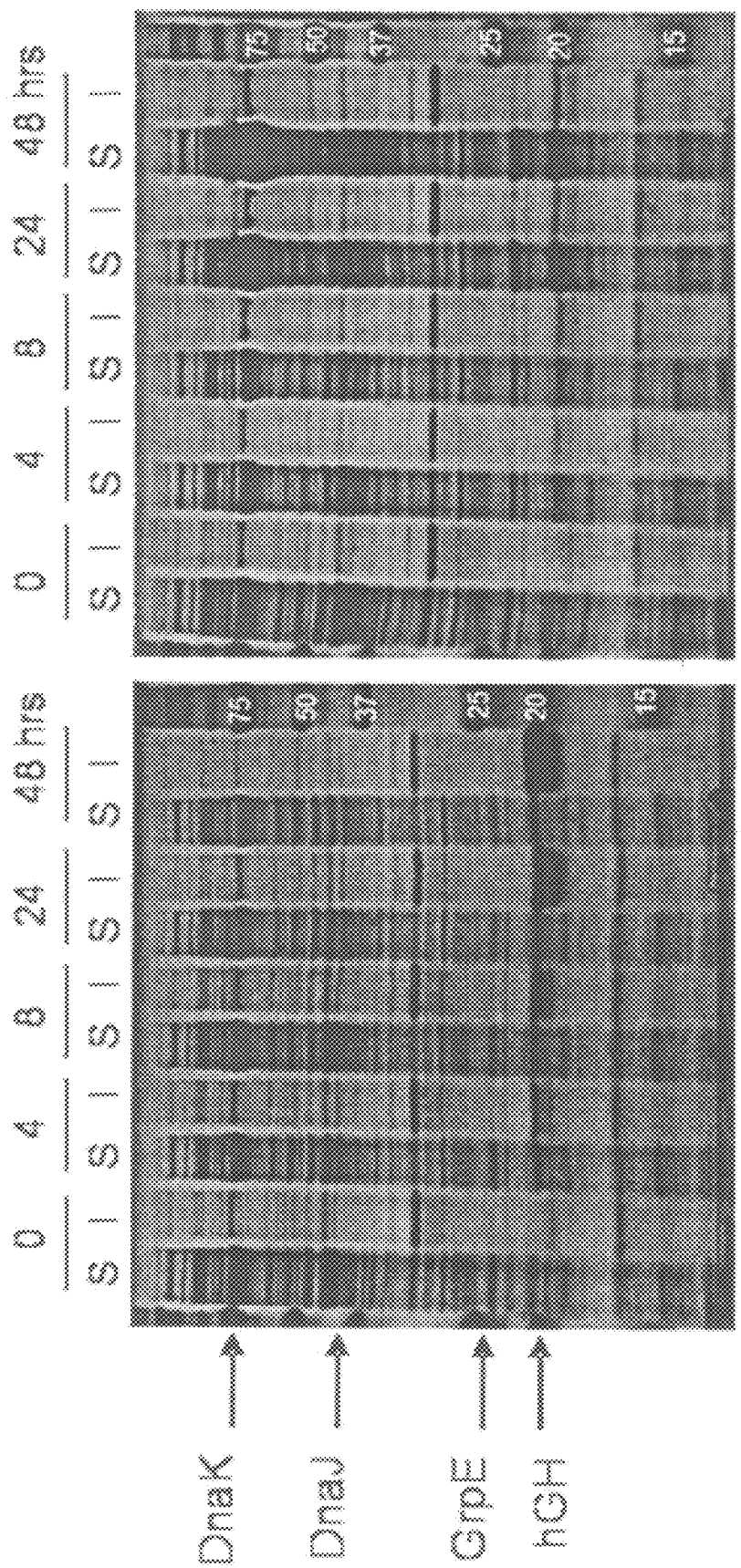
FIG. 15 is images of SDS-PAGE gels of strains expressing hGH with or without folding modulators GrpE-DnakJ. Samples were removed at various times after induction by IPTG (0, 4, 8, 24 and 48 hr), normalized to OD600 of 20 and lysed using EasyLyse. The soluble (S) insoluble (I) fractions were separated on a BioRad Criterion 15% Tris HCl SDS-PAGE gel and stained with Coomassie.

Duplicate cultures of DC463 were grown in shake flasks. Protein induction was accomplished by addition of 0.1 mM IPTG for hGH and 0.5% mannitol for GrpE-DnaKJ at 24 hrs after inoculation. Samples were collected at 0, 4, 8, 24 and 48 hours after induction. At each time point, 20 $OD_{600}$ cells normalized in 1 mL were harvested, lysed using EASYL-YSE™ lysis reagent (Epicentre, Madison, Wis.) and separated into soluble and insoluble fractions by centrifugation at 14000 rpm for 30 minutes. Equal volumes of samples were combined with BioRad (Hercules, Calif.) 2× Laemmli buffer, heated at 95° C. for 5 minutes with 30 µL loaded onto a BioRad 15% Tris HCl Criterion gel using 1× Tris Glycine SDS running buffer (BioRad). The proteins were visualized with SIMPLY BLUE™ Safestain staining solution (Invitrogen, Carlsbad, Calif.) as shown in FIG. 15. The resulting Coomassie-stained gels were scanned using a Molecular Devices Personal Densitometer (Molecular Devices, Sunnyvale, Calif.) with analyses performed using ImageQuant and Excel. As shown in FIG. 15, co-overexpression of GrpE, DnaKJ significantly increased the solubility of hGH, converting almost 100% of the target protein into the soluble fraction, albeit at a lower total protein yield. Additional experiments repeating growth and induction of DC463 using the simultaneous addition of IPTG and mannitol closely mimicked the results shown here, although with a varying degree of hGH solubility (between 50-100%; data not shown), when GrpE DnaKJ were co-overproduced. These findings further demonstrate that targeted strain engineering based on transcriptional profiling can lead to a rational strain design to increase solubility and/or yield of a recombinant protein.

The invention has been described with reference to certain embodiments and non-limiting examples. It will be clear to one of skill in the art that other embodiments of the invention are also possible.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A process for engineering a recombinant bacterial cell for expression of a recombinant protein or peptide, the process comprising:

i) obtaining a bacterial cell;

ii) transforming the bacterial cell with an expression vector comprising a nucleic acid encoding the recombinant protein or peptide operably linked to an expression control sequence operable in said bacterial cell, to make a recombinant bacterial host cell;

iii) expressing the recombinant protein or peptide in the recombinant bacterial host cell of step (ii);

iv) analyzing a genetic profile of the recombinant bacterial host cell of step (iii), wherein said genetic profile comprises at least one gene encoding a protease and at least one gene encoding a folding modulator, to identify at least one protease and at least one folding modulator that are upregulated in the recombinant bacterial host cell of step (iii) relative to a gene product of the at least one protease gene and a gene product of the at least one folding modulator gene, in either a bacterial cell that has not been modified to express the recombinant protein or peptide, or a recombinant bacterial host cell that does not express the recombinant protein or peptide, wherein the genetic profile is a transcriptome profile;

v) modifying the bacterial cell of step (i) to increase the expression of the at least one upregulated folding modulator identified in step (iv) and to decrease the expression of the at least one upregulated protease identified in step (iv), by genetic modification to produce a modified bacterial cell, wherein increasing the expression of the at least one upregulated folding modulator identified in step (iv) comprises introducing into the bacterial cell of step (i) a DNA encoding the at least one upregulated folding modulator identified in step (iv), wherein the DNA encoding the at least one upregulated folding modulator is operably linked to an expression control sequence operable in the bacterial cell into which it is introduced, and expressing the DNA encoding the at least one upregulated folding modulator identified in step (iv);

vi) transforming the modified bacterial host cell with an expression vector comprising a nucleic acid encoding the recombinant protein or peptide operably linked to an expression control sequence operable in said modified bacterial cell to make a modified recombinant bacterial host cell;

vii) expressing the recombinant protein or peptide in the modified recombinant bacterial host cell of step (vi);

viii) analyzing a genetic profile of the modified recombinant bacterial host cell of step (vii), wherein the genetic profile of the modified recombinant bacterial host cell of step (vii) comprises at least one gene encoding a protease and at least one gene encoding a folding modulator, to identify at least one protease and at least one folding modulator that are upregulated in the modified recombinant bacterial host cell of step (vii) relative to a gene product of the at least one protease gene and a gene product of the at least one folding modulator gene in a bacterial cell that has not been modified to express the recombinant protein or peptide, a recombinant bacterial host cell that does not express the recombinant protein or peptide, or a modified recombinant bacterial host cell that does not express the recombinant protein or peptide, wherein the genetic profile is a transcriptome profile;

ix) modifying the modified bacterial cell of step (v) to increase the expression of the at least one upregulated folding modulator identified in step (viii) and to decrease the expression of the at least one upregulated protease identified in step (viii), in the modified bacterial cell to produce a multiply modified bacterial cell;

x) transforming the multiply modified bacterial host cell with an expression vector comprising a nucleic acid encoding the recombinant protein or peptide operably linked to an expression control sequence operable in said multiply modified bacterial cell to make a multiply modified recombinant bacterial host cell;

xi) expressing the recombinant protein or peptide in the multiply modified recombinant bacterial host cell of step (x);

xii) measuring the amount of soluble and active recombinant protein or peptide in the multiply modified recombinant bacterial host cell of step (xi) and in the recombinant bacterial host cell of step (iii); and, xiii) comparing the amount of soluble and active recombinant protein or peptide measured in the multiply modified recombinant bacterial host cell of step (xi) to the amount of soluble and active recombinant protein or peptide measured in the recombinant bacterial host cell of step (iii); wherein a. the measured amount of soluble and active recombinant protein or peptide in the multiply modified recombinant bacterial host cell of step (xi) is increased relative to the measured amount of soluble and active recombinant protein or peptide in the recombinant bacterial host cell of step (iii); or b. the measured amount of soluble and active recombinant protein or peptide in the multiply modified recombinant bacterial host cell of step (xi) is not increased relative to the measured amount of soluble and active recombinant protein or peptide in the recombinant bacterial host cell of step (iii), and wherein steps (vii) through (xii) are repeated until the amount of soluble and active recombinant protein or peptide is increased relative to the measured amount of soluble and active recombinant protein or peptide in the recombinant bacterial host cell of step (iii);

wherein a cell comprising the increased amount of the soluble and active recombinant protein or peptide is the engineered recombinant bacterial cell.

2. The process of claim 1 wherein the analysis of claim 1, step (iv), claim 1, step (viii), or both, further comprises identifying an upregulated gene product selected from the group consisting of: a subunit of a protease, a homologous analog of a protease, a cofactor of a protease, a cellular modulator affecting expression of a protease, and a genetic modulator affecting expression of a protease, and wherein the modification of step (v) and step (ix) requires increasing the level of the further identified upregulated gene product.

3. The process of claim 1 wherein the at least one protease that is encoded by the at least one protease gene in step (iv), step (viii), or both is a D alanyl-meso-diaminopimelate endopeptidase, a zinc protease, a microsomal dipeptidase, an extracellular metalloprotease precursor, a protease expressed from the gene hslV, a protease expressed from the gene hslU, a protease expressed from the gene clpX, a protease expressed from the gene clpA, or a protease expressed from the gene clpB.

4. The process of claim 1 wherein step (iv), step (viii), or both comprises analyzing the level(s) of the at least one protease cDNA to determine whether the at least one protease cDNA level is upregulated when the recombinant protein or peptide is expressed.

5. The process of claim 1 wherein decreasing the expression of the at least one protease in step (v), step (ix), or both, comprises removing a sequence encoding all or part of the at least one protease from the genome of the bacterial cell of step (i), the modified bacterial cell of step (v), or both.

6. The process of claim 5 wherein the sequence encoding all or part of the protease is removed by homologous recombination.

7. The process of claim 1 wherein the analysis of claim 1, step (iv), step (viii) or both further comprises identifying an upregulated gene product selected from the group consisting of: a subunit of a folding modulator, a putative folding modulator, a cofactor of a folding modulator, a cellular modulator affecting the expression of a folding modulator, and a genetic modulator affecting the expression of a folding modulator, and wherein the modification of step (v) and step (ix) requires increasing the level of the further identified upregulated gene product.

8. The process of claim 1 wherein the at least one folding modulator that is encoded by the at least one folding modulator gene in step (iv), step (viii), or both is a chaperone protein.

9. The process of claim 1 wherein the at least one folding modulator that is encoded by the at least one folding modulator gene in step (iv), step (viii), or both, is a folding modulator expressed from the gene cbpA, the gene htpG, the gene dnaK, the gene dnaJ, the gene fkbP2, the gene groES, or the gene groEL.

10. The process of claim 1 wherein increasing the expression of the at least one upregulated folding modulator in step (ix) comprises:
   a) introducing into the modified bacterial cell of step (v) a DNA encoding the at least one upregulated folding modulator identified in step (viii), wherein the DNA encoding the at least one upregulated folding modulator identified in step (viii) is operably linked to an expression control sequence operable in the recombinant bacterial host cell into which it is introduced; and
   b) expressing from the introduced DNA the at least one upregulated folding modulator identified in step (viii).

11. The process of claim 1 wherein increasing the expression of the at least one upregulated folding modulator in step (v), step (ix), or both, comprises insertion of a promoter into the genome of the bacterial cell of step (i) the modified bacterial cell of step (v), or both, respectively, wherein the promoter is operable in the bacterial cell or modified bacterial cell into which it is introduced, and wherein the promoter is inserted in a genomic location sufficient to control expression of said at least one folding modulator of step (v), (ix), or both.

12. The process of claim 1 wherein increasing the expression of the at least one upregulated folding modulator in step (v), (ix), or both, comprises:
   a) introducing into the bacterial cell of step (i), the modified bacterial cell of step (v), or both, an exogenous vector comprising a nucleotide sequence encoding said at least one folding modulator operably linked to an expression control sequence operable in the bacterial cell or modified bacterial cell into which it is introduced; and
   b) expressing from the nucleotide sequence encoding the at least one folding modulator on the introduced exogenous vector said at least one upregulated folding modulator.

13. The process of claim 1 wherein the genetic profile in step (iv), step (viii), or both, is a profile of genes in a gene family.

14. The process of claim 1 wherein the transcriptome profile(s) is determined through a microarray.

15. The process of claim 14 wherein the microarray comprises: binding partners for at least 50% of a genome of the bacterial cell of step (i); binding partners for at least 80% of a genome of the bacterial cell of step (i); binding partners for at least 90% of a genome of the bacterial cell of step (i); or binding partners for at least 95% of a genome of the bacterial cell of step (i).

16. The process of claim 1 wherein the bacterial cell of step (i) is a Pseudomonad cell.

17. The process of claim 16 wherein the bacterial cell of step (i) is a *Pseudomonas* cell.

18. The process of claim 17, wherein the bacterial cell of step (i) is a *Pseudomonas fluorescens* cell.

19. The process of claim 1 wherein the bacterial cell of step (i) is an *E. coli* cell.

20. The process of claim 1 wherein the bacterial cell of step (i) is a Pseudomonad cell.

21. The process of claim 16 wherein the bacterial cell of step (i) is a *Pseudomonas* cell.

22. The process of claim 17, wherein the bacterial cell of step (i) is a *Pseudomonas fluorescens* cell.

23. The process of claim 1 wherein the bacterial cell of step (i) is an *E. coli* cell.

24. A process for engineering a recombinant bacterial cell for expression of a recombinant protein or peptide, the process comprising:
   i) obtaining a bacterial cell;
   ii) transforming the bacterial cell with an expression vector comprising a nucleic acid encoding the recombinant protein or peptide operably linked to an expression control sequence operable in said bacterial cell, to make a recombinant bacterial host cell;
   iii) expressing the recombinant protein or peptide in the recombinant bacterial host cell of step (ii);
   iv) analyzing a genetic profile of the recombinant bacterial host cell of step (iii), wherein said genetic profile comprises at least one gene encoding a folding modulator, to identify at least one folding modulator that is upregulated in the recombinant bacterial host cell of step (iii) relative to a gene product of the at least one folding modulator gene, in either a bacterial cell that has not been modified to express the recombinant protein or peptide, or a recombinant bacterial host cell that does not express the recombinant protein or peptide, wherein the genetic profile is a transcriptome profile;
   v) modifying the bacterial cell of step (i) to increase the expression of the at least one upregulated folding modulator identified in step (iv), by genetic modification to produce a modified bacterial cell, wherein increasing the expression of the at least one upregulated folding modulator identified in step (iv) comprises introducing into the bacterial cell of step (i) a DNA encoding the at least one upregulated folding modulator identified in step (iv), wherein the DNA encoding the at least one upregulated folding modulator is operably linked to an expression control sequence operable in the bacterial cell into which it is introduced; and expressing the DNA encoding the at least one upregulated folding modulator identified in step (iv);
   vi) transforming the modified bacterial host cell with an expression vector comprising a nucleic acid encoding the recombinant protein or peptide operably linked to an expression control sequence operable in said modified bacterial cell to make a modified recombinant bacterial host cell;
   vii) expressing the recombinant protein or peptide in the modified recombinant bacterial host cell of step (vi);
   viii) analyzing a genetic profile of the modified recombinant bacterial host cell of step (vii), wherein the genetic profile of the modified recombinant bacterial host cell of step (vi) comprises at least one gene encoding a folding modulator, to identify at least one folding modulator that is upregulated in the modified recombinant bacterial host cell of step (vi) relative to a gene product of the at least one folding modulator gene, in a bacterial cell that has not been modified to express the recombinant protein or peptide, a recombinant bacterial host cell that does not express the recombinant protein or peptide, or a modified recombinant bacterial host cell that does not express the recombinant protein or peptide, wherein the genetic profile is a transcriptome profile;
   ix) modifying the modified bacterial cell of step (v) to increase the expression of the at least one upregulated folding modulator identified in step (vii), in the modified bacterial cell to produce a multiply modified bacterial host cell;
   x) transforming the multiply modified bacterial host cell with an expression vector comprising a nucleic acid encoding the recombinant protein or peptide operably linked to an expression control sequence operable in said multiply modified bacterial cell to make a multiply modified recombinant bacterial host cell;

xi) expressing the recombinant protein or peptide in the multiply modified recombinant bacterial host cell of step (x);

xii) measuring the amount of soluble and active recombinant protein or peptide in the multiply modified recombinant bacterial host cell of step (x) and in the recombinant bacterial host cell of step (ii); and, xii) comparing the amount of soluble and active recombinant protein or peptide measured in the multiply modified recombinant bacterial host cell of step (xi) to the amount of soluble and active recombinant protein or peptide measured in the recombinant bacterial host cell of step (iii); wherein a. the measured amount of soluble and active recombinant protein or peptide in the multiply modified recombinant bacterial host cell of step (xi) is increased relative to the measured amount of soluble and active recombinant protein or peptide in the recombinant bacterial host cell of step (iii); or b. the measured amount of soluble and active recombinant protein or peptide in the multiply modified recombinant bacterial host cell of step (xi) is not increased relative to the measured amount of soluble and active recombinant protein or peptide in the recombinant bacterial host cell of step (iii), and wherein steps (vii) through (xii) are repeated until the amount of soluble and active recombinant protein or peptide is increased relative to the measured amount of soluble and active recombinant protein or peptide in the recombinant bacterial host cell of step (iii);

wherein a cell comprising the increased amount of the soluble and active recombinant protein or peptide is the engineered recombinant bacterial cell.

25. The process of claim 24 wherein increasing the expression of the at least one upregulated folding modulator in step (is) comprises:

a) introducing into the modified bacterial cell of step (v) a DNA encoding the at least one upregulated folding modulator identified in step (vii), wherein the DNA encoding the at least one upregulated folding modulator is operably linked to an expression control sequence operable in the modified bacterial cell into which it is introduced; and b) expressing from the introduced DNA the at least one upregulated folding modulator identified in step (vii).

26. The process of claim 24 wherein the analysis of claim 24, step (iv), step (viii) or both further comprises identifying an upregulated gene product selected from the group consisting of: a subunit of a folding modulator, a putative folding modulator, a cofactor of a folding modulator, a cellular modulator affecting the expression of a folding modulator, and a genetic modulator affecting the expression of a folding modulator, and wherein the modification of step (v) and step (ix) requires increasing the level of the further identified upregulated gene product.

27. The process of claim 24 wherein the at least one folding modulator that is encoded by the at least one folding modulator gene in step (iv), step (viii), or both, is a chaperone protein.

28. The process of claim 24 wherein the at least one folding modulator that is encoded by the at least one folding modulator gene in step (iv), step (viii), or both, is a folding modulator expressed from the gene cbpA, the gene htpG, the gene dnaK, the gene dnaJ, the gene fkbP2, the gene groES, or the gene groEL.

29. The process of claim 24 wherein increasing the expression of the at least one upregulated folding modulator in step (v), step (ix), or both, comprises insertion of a promoter into the genome of the bacterial cell of step (i), the modified bacterial cell of step (v), or both, respectively, wherein the promoter is operable in the bacterial cell or the recombinant bacterial cell into which it is introduced, and wherein the promoter is inserted in a genomic location sufficient to control expression of said at least one folding modulator of step (v), (ix), or both.

30. The process of claim 24 wherein increasing the expression of the at least one upregulated folding modulator in step (v), step (ix), or both, comprises:

a) introducing into the bacterial cell of step (i), the modified bacterial cell of step (v), or both, an exogenous vector comprising a nucleotide sequence encoding said at least one folding modulator operably linked to an expression control sequence operable in the bacterial cell or modified bacterial cell into which it is introduced; and b) expressing from the nucleotide sequence encoding the at least one upregulated folding modulator on the introduced exogenous vector said at least one upregulated folding modulator.

* * * * *